(12) United States Patent
Artero Allepuz et al.

(10) Patent No.: US 12,116,575 B2
(45) Date of Patent: Oct. 15, 2024

(54) OLIGONUCLEOTIDES CONJUGATED TO OLEIC ACID AND USES THEREOF

(71) Applicants: Universitat de València, Valencia (ES); ARTHEX BIOTECH S.L., Paterna (ES)

(72) Inventors: Rubén Artero Allepuz, Valencia (ES); Nerea Moreno Cervera, Valencia (ES); Irene González Martínez, Valencia (ES); Estefanía Cerro Herreros, Valencia (ES); Eric G. Marcusson, San Francisco, CA (US); María Beatriz Llamusí Troisi, Paterna (ES)

(73) Assignees: UNIVERSITAT DE VALENCIA, Valencia (ES); ARTHEX BIOTECH S.L., Paterna (ES)

( * ) Notice: Subject to any disclaimer, the term of this patent is extended or adjusted under 35 U.S.C. 154(b) by 0 days.

(21) Appl. No.: 18/322,487

(22) Filed: May 23, 2023

(65) Prior Publication Data
US 2023/0407305 A1 Dec. 21, 2023

(30) Foreign Application Priority Data
May 23, 2022 (EP) .................................. 22 382 493

(51) Int. Cl.
*C12N 15/113* (2010.01)
*A61P 21/00* (2006.01)

(52) U.S. Cl.
CPC ............ *C12N 15/113* (2013.01); *A61P 21/00* (2018.01); *C12N 2310/141* (2013.01); *C12N 2310/31* (2013.01)

(58) Field of Classification Search
None
See application file for complete search history.

(56) References Cited

U.S. PATENT DOCUMENTS

| | | | |
|---|---|---|---|
| 2019/0231809 A1* | 8/2019 | Artero Allepuz .... | C12N 15/113 |
| 2021/0340533 A1 | 11/2021 | Khvorova et al. | |
| 2022/0133774 A1 | 5/2022 | Artero Allepuz et al. | |

OTHER PUBLICATIONS

Grossi, Ilaria, et al. "Functional role of microRNA-23b-3p in cancer biology." Microrna 7.3 (2018): 156-166.*
Aviñó, Anna, et al. ("Synthesis and structural properties of oligonucleotides covalently linked to acridine and quindoline derivatives through a threoninol linker." Bioorganic & medicinal chemistry 18.21 (2010): 7348-7356.*
Romero-López, Manuel Joaquín, et al. ("miR-23b-3p, miR-124-3p and miR-218-5p Synergistic or Additive Effects on Cellular Processes That Modulate Cervical Cancer Progression? A Molecular Balance That Needs Attention." International Journal of Molecular Sciences 23.21 (2022): 13551).*
Lennox, K. A., and M. A. Behlke. "Chemical modification and design of anti-miRNA oligonucleotides." Gene therapy 18.12 (2011): 1111-1120.*
Liu, Lijun, Ziping Cheng, and Jie Yang. "miR-23 regulates cell proliferation and apoptosis of vascular smooth muscle cells in coronary heart disease." Pathology-Research and Practice 214.11 (2018): 1873-1878.*
Cerro-Herreros, Estefania, et al. "miR-23b and miR-218 silencing increase Muscleblind-like expression and alleviate myotonic dystrophy phenotypes in mammalian models." Nature Communications 9.1 (2018): 2482.*
Theadom, Alice, et al. "Prevalence of muscular dystrophies: a systematic literature review." Neuroepidemiology 43.3-4 (2015): 259-268.*
Mastaglia, F. L. ("Inflammatory muscle diseases." Neurology India 56.3 (2008): 263-270).*
Agrawal et al., "Mixed-backbone oligonucleotides as second generation antisense oligonucleotides: In vitro and in vivo studies," *Proceedings of the National Academy of Sciences* 94:2620-2625, Mar. 1997. (6 pages).
Agrawal et al., "Novel enzymatic and immunological responses to oligonucleotides," *Toxicology Letters* 82/83:431-434, Dec. 1995. (4 pages).
Arandel et al., "Immortalized human myotonic dystrophy muscle cell lines to assess therapeutic compounds," *Disease Models & Mechanisms* 10:487-497, Apr. 2017. (11 pages).
Cerro-Herreros et al., "miR-23b and miR-218 silencing increase Muscleblind-like expression and alleviate myotonic dystrophy phenotypes in mammalian models," *Nature Communications* 9:2482, Jun. 2018. (13 pages).
Cho et al., "miRGator v3.0: a microRNA portal for deepm sequencing, expression profiling and mRNA targeting," *Nucleic Acids Research* 41:D252-D257, Nov. 2012. (6 pages).

(Continued)

*Primary Examiner* — Kimberly Chong
(74) *Attorney, Agent, or Firm* — SEED INTELLECTUAL PROPERTY LAW GROUP LLP

(57) ABSTRACT

The invention provides oligonucleotide and/or oligonucleotide analogue molecules that are antagonists of a microRNA, preferably antagonists of human microRNAs hsa-miR-23b-3p and hsa-miR-218-5p, that comprise a mixture of phosphorothioate and phosphodiester linkages, and that are conjugated to at least one oleic acid molecule. Inhibiting these microRNAs allows to increase the endogenous levels of the corresponding proteins MBNL1 and/or MBNL2. The present invention further provides compositions comprising said oligonucleotides and/or oligonucleotide analogue molecules and their uses for the treatment and prevention of DM in a subject in need thereof.

17 Claims, 33 Drawing Sheets
Specification includes a Sequence Listing.

(56) References Cited

OTHER PUBLICATIONS

Hu et al., "Therapeutic siRNA: state of the art," *Signal Transduction and Targeted Therapy* 5:101, Jun. 2020. (25 pages).
Kanadia et al., "Reversal of RNA missplicing and myotonia after muscleblind overexpression in a mouse poly(CUG) model for myotonic dystrophy," *Proceedings of the National Academy of Sciences* 103(31):11748-11753, Aug. 2006. (6 pages).
Lee et al., "Compound loss of muscleblind-like function in myotonic dystrophy," EMBO *Molecular Medicine* 5:1887-1900, Dec. 2013. (14 pages).
Mankodi et al., "Myotonic Dystrophy in Transgenic Mice Expressing an Expanded CUG Repeat," *Science* 289:1769-1772, Sep. 2000. (5 pages).
Maruyama et al., "Directed aggregation and fusion of lipid vesicles induced by DNA-surfactants," *Colloids and Surfaces B: Biointerfaces* 66:119-124, Oct. 2008. (6 pages).
McKenzie et al., "Recent Progress in Non-Native Nucleic Acid Modifications," *Chemical Society Reviews* 50(8):5126-5164, Apr. 2021. (41 pages).
Rump et al., "Preparation of Conjugates of Oligodeoxynucleotides and Lipid Structures and Their Interaction with Low-Density Lipoprotein," *Bioconjugate Chemistry* 9:341-349, Apr. 1998. (9 pages).
Sarmiento et al., "In Vivo Toxicological Effects of rel A Antisense Phosphorothioates in CD-1 Mice," *Antisense Research and Development* 4:99-107, 1994 (published online Apr. 2009).
Senn et al., "Non-CpG-Containing Antisense 2'-Methoxyethyl Oligonucleotides Activate a Proinflammatory Response Independent of Toll-Like Receptor 9 or Myeloid Differentiation Factor 88," *Journal of Pharmacology and Experimental Therapeutics* 314(3):972-979, Sep. 2005. (8 pages).
Smith et al., "Therapeutic Oligonucleotides: State of the Art," *Annual Review of Pharmacology and Toxicology* 59:605-630, 2019 (published in advance Oct. 2018).
Wan et al., "The Medicinal Chemistry of Therapeutic Oligonucleotides," *Journal of Medicinal Chemistry* 59:9645-9667, Jul. 2016. (24 pages).
Zhang et al., "In Vivo Stability, Disposition and Metabolism of a "Hybrid" Oligonucleotide Phosphorothioate in Rats," *Biochemical Pharmacology* 50(4):545-556, Aug. 1995. (12 pages).

* cited by examiner

A

A

B

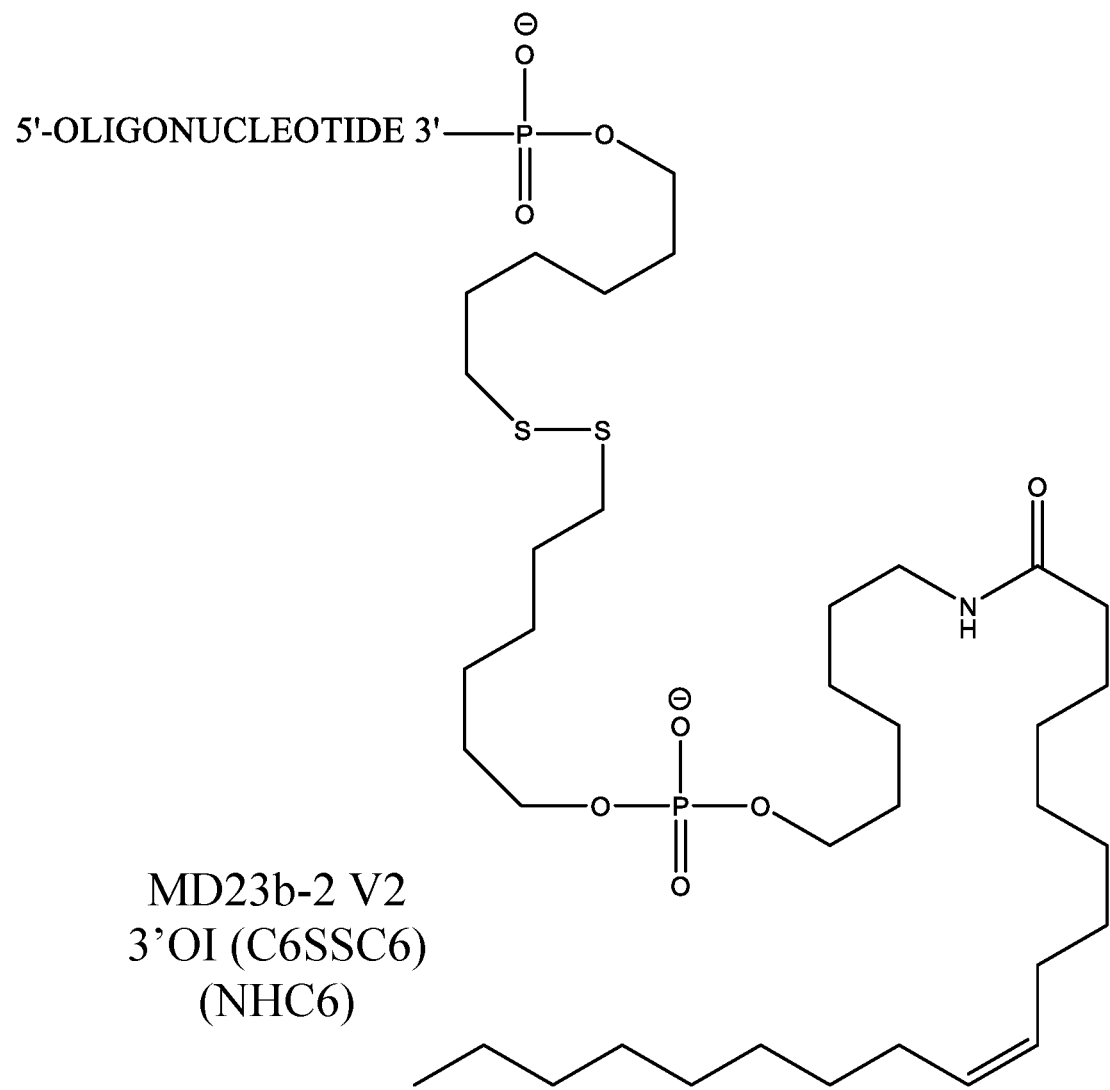
FIG. 8 *(continued)*

SEQUENCE LISTING

```
Sequence total quantity: 160
SEQ ID NO: 1            moltype = DNA  length = 15
FEATURE                 Location/Qualifiers
misc_feature            1..15
                        note = Antagonist of the human hsa-miR-218-5p
source                  1..15
                        mol_type = other DNA
                        organism = synthetic construct
SEQUENCE: 1
ttagatcaag cacaa                                                   15

SEQ ID NO: 2            moltype = DNA  length = 16
FEATURE                 Location/Qualifiers
misc_feature            1..16
                        note = Antagonist of the human hsa-miR-23b-3p
source                  1..16
                        mol_type = other DNA
                        organism = synthetic construct
SEQUENCE: 2
atccctggca atgtga                                                  16

SEQ ID NO: 3            moltype = DNA  length = 16
FEATURE                 Location/Qualifiers
misc_feature            1..16
                        note = MD23b-2 V2 3'Ol
```

| | |
|---|---|
| misc_feature | 1<br>note = /note="LNA modified base" |
| misc_feature | 1<br>note = /note="nucleotide bond by a Phosphorothioate linkage" |
| misc_feature | 2<br>note = /note="LNA modified base" |
| misc_feature | 2<br>note = /note="nucleotide bond by a Phosphorothioate linkage" |
| misc_feature | 3<br>note = /note="nucleotide bond by a Phosphorothioate linkage" |
| misc_feature | 3<br>note = /note="5-Methyl-2'-O-Methyl cytidine " |
| misc_feature | 4<br>note = /note="nucleotide bond by a Phosphorothioate linkage" |
| misc_feature | 4<br>note = /note="5-Methyl-2'-O-Methyl cytidine " |
| misc_feature | 5<br>note = /note="2'-O-MOE RNA nucleotide" |
| misc_feature | 6<br>note = /note="LNA modified base" |
| misc_feature | 7<br>note = /note="nucleotide bond by a Phosphorothioate linkage" |
| misc_feature | 7<br>note = /note="2'-O-MOE RNA nucleotide" |
| misc_feature | 8<br>note = /note="nucleotide bond by a Phosphorothioate linkage" |
| misc_feature | 8<br>note = /note="2 -O-Methyl-nucleotide" |
| misc_feature | 9<br>note = /note="nucleotide bond by a Phosphorothioate linkage" |
| misc_feature | 9<br>note = /note="2'-O-MOE RNA nucleotide" |
| misc_feature | 10<br>note = /note="LNA modified base" |
| misc_feature | 11<br>note = /note="2'-O-MOE RNA nucleotide" |
| misc_feature | 12<br>note = /note="LNA modified base" |
| misc_feature | 13<br>note = /note="LNA modified base" |
| misc_feature | 14<br>note = /note="nucleotide bond by a Phosphorothioate linkage" |
| misc_feature | 14<br>note = /note="2'-O-MOE RNA nucleotide" |
| misc_feature | 15<br>note = /note="LNA modified base" |
| misc_feature | 15<br>note = /note="nucleotide bond by a Phosphorothioate linkage" |
| misc_feature | 16<br>note = /note="nucleotide conjugated to NHC6 conjugated to oleic acid" |
| misc_feature | 16<br>note = /note="LNA modified base" |
| source | 1..16<br>mol_type = other DNA<br>organism = synthetic construct |
| SEQUENCE: 3 | |
| atccctggca atgtga | 16 |
| SEQ ID NO: 4<br>FEATURE | moltype = DNA  length = 16<br>Location/Qualifiers |
| misc_feature | 1..16<br>note = MD23b-2-PS/PO 3'OI |
| misc_feature | 1<br>note = /note="nucleotide bond by a Phosphorothioate linkage" |
| misc_feature | 1<br>note = /note="LNA nucleotide" |
| misc_feature | 2<br>note = /note="2'-O-MOE RNA nucleotides " |
| misc_feature | 2<br>note = /note="nucleotide bond by a Phosphorothioate linkage" |
| misc_feature | 3<br>note = /note="5-Methyl-2'-O-Methyl cytidine" |
| misc_feature | 3<br>note = /note="nucleotide bond by a Phosphorothioate linkage" |
| misc_feature | 4<br>note = /note="5-Methyl-2'-O-Methyl cytidine" |
| misc_feature | 5<br>note = /note="5-Methyl-2'-O-Methyl cytidine" |

| | |
|---|---|
| misc_feature | 6 |
| | note = /note="LNA modified base" |
| misc_feature | 7 |
| | note = /note="2 -O-Methyl-nucleotide" |
| misc_feature | 7 |
| | note = /note="nucleotide bond by a Phosphorothioate linkage" |
| misc_feature | 8 |
| | note = /note="2 -O-Methyl-nucleotide" |
| misc_feature | 8 |
| | note = /note="nucleotide bond by a Phosphorothioate linkage" |
| misc_feature | 9 |
| | note = /note="5-Methyl-2'-O-Methyl cytidine" |
| misc_feature | 9 |
| | note = /note="nucleotide bond by a Phosphorothioate linkage" |
| misc_feature | 10 |
| | note = /note="LNA nucleotide" |
| misc_feature | 11 |
| | note = /note="2'-O-MOE RNA nucleotides " |
| misc_feature | 12 |
| | note = /note="LNA nucleotide" |
| misc_feature | 13 |
| | note = /note="LNA nucleotide" |
| misc_feature | 13 |
| | note = /note="nucleotide bond by a Phosphorothioate linkage" |
| misc_feature | 14 |
| | note = /note="2'-O-MOE RNA nucleotides " |
| misc_feature | 14 |
| | note = /note="nucleotide bond by a Phosphorothioate linkage" |
| misc_feature | 15 |
| | note = /note="nucleotide bond by a Phosphorothioate linkage" |
| misc_feature | 15 |
| | note = /note="LNA nucleotide" |
| misc_feature | 16 |
| | note = /note="LNA nucleotide" |
| misc_feature | 16 |
| | note = /note="nucleotide conjugated to NHC6 conjugated to oleic acid" |
| source | 1..16 |
| | mol_type = other DNA |
| | organism = synthetic construct |
| SEQUENCE: 4 | |
| atccctggca atgtga | 16 |
| | |
| SEQ ID NO: 5 | moltype = DNA  length = 16 |
| FEATURE | Location/Qualifiers |
| misc_feature | 1..16 |
| | note = MD23b-2-PS/PO 5'OI |
| misc_feature | 1 |
| | note = /note="nucleotide conjugated to NHC6 conjugated to oleic acid" |
| misc_feature | 1 |
| | note = /note="nucleotide bond by a Phosphorothioate linkage" |
| misc_feature | 1 |
| | note = /note="LNA nucleotide" |
| misc_feature | 2 |
| | note = /note="2'-O-MOE RNA nucleotides " |
| misc_feature | 3 |
| | note = /note="5-Methyl-2'-O-Methyl cytidine" |
| misc_feature | 4 |
| | note = /note="5-Methyl-2'-O-Methyl cytidine" |
| misc_feature | 5 |
| | note = /note="5-Methyl-2'-O-Methyl cytidine" |
| misc_feature | 6 |
| | note = /note="nucleotide bond by a Phosphorothioate linkage" |
| misc_feature | 6 |
| | note = /note="LNA nucleotide" |
| misc_feature | 7 |
| | note = /note="2 -O-Methyl-nucleotide" |
| misc_feature | 8 |
| | note = /note="2 -O-Methyl-nucleotide" |
| misc_feature | 9 |
| | note = /note="nucleotide bond by a Phosphorothioate linkage" |
| misc_feature | 9 |
| | note = /note="5-Methyl-2'-O-Methyl cytidine" |
| misc_feature | 10 |
| | note = /note="LNA nucleotide" |
| misc_feature | 11 |
| | note = /note="nucleotide bond by a Phosphorothioate linkage" |
| misc_feature | 11 |

|  |  |
|---|---|
| | note = /note="2'-O-MOE RNA nucleotides " |
| misc_feature | 12 |
| | note = /note="nucleotide bond by a Phosphorothioate linkage" |
| misc_feature | 12 |
| | note = /note="LNA nucleotide" |
| misc_feature | 13 |
| | note = /note="LNA nucleotide" |
| misc_feature | 14 |
| | note = /note="nucleotide bond by a Phosphorothioate linkage" |
| misc_feature | 14 |
| | note = /note="2'-O-MOE RNA nucleotides " |
| misc_feature | 15 |
| | note = /note="nucleotide bond by a Phosphorothioate linkage" |
| misc_feature | 15 |
| | note = /note="LNA nucleotide" |
| misc_feature | 16 |
| | note = /note="LNA nucleotide" |
| source | 1..16 |
| | mol_type = other DNA |
| | organism = synthetic construct |
| SEQUENCE: 5 | |
| atccctggca atgtga | 16 |
| | |
| SEQ ID NO: 6 | moltype = DNA  length = 16 |
| FEATURE | Location/Qualifiers |
| misc_feature | 1..16 |
| | note = MD23b-2-PS/PO |
| misc_feature | 1 |
| | note = /note="nucleotide bond by a Phosphorothioate linkage" |
| misc_feature | 1 |
| | note = /note="LNA nucleotide" |
| misc_feature | 2 |
| | note = /note="2'-O-MOE RNA nucleotides " |
| misc_feature | 3 |
| | note = /note="5-Methyl-2'-O-Methyl cytidine" |
| misc_feature | 4 |
| | note = /note="5-Methyl-2'-O-Methyl cytidine" |
| misc_feature | 5 |
| | note = /note="5-Methyl-2'-O-Methyl cytidine" |
| misc_feature | 6 |
| | note = /note="nucleotide bond by a Phosphorothioate linkage" |
| misc_feature | 6 |
| | note = /note="LNA nucleotide" |
| misc_feature | 7 |
| | note = /note="2 -O-Methyl-nucleotide" |
| misc_feature | 8 |
| | note = /note="2 -O-Methyl-nucleotide" |
| misc_feature | 9 |
| | note = /note="nucleotide bond by a Phosphorothioate linkage" |
| misc_feature | 9 |
| | note = /note="5-Methyl-2'-O-Methyl cytidine" |
| misc_feature | 10 |
| | note = /note="LNA nucleotide" |
| misc_feature | 11 |
| | note = /note="nucleotide bond by a Phosphorothioate linkage" |
| misc_feature | 11 |
| | note = /note="2'-O-MOE RNA nucleotides " |
| misc_feature | 12 |
| | note = /note="nucleotide bond by a Phosphorothioate linkage" |
| misc_feature | 12 |
| | note = /note="LNA nucleotide" |
| misc_feature | 13 |
| | note = /note="LNA nucleotide" |
| misc_feature | 14 |
| | note = /note="nucleotide bond by a Phosphorothioate linkage" |
| misc_feature | 14 |
| | note = /note="2'-O-MOE RNA nucleotides " |
| misc_feature | 15 |
| | note = /note="nucleotide bond by a Phosphorothioate linkage" |
| misc_feature | 15 |
| | note = /note="LNA nucleotide" |
| misc_feature | 16 |
| | note = /note="LNA nucleotide" |
| source | 1..16 |
| | mol_type = other DNA |
| | organism = synthetic construct |
| SEQUENCE: 6 | |
| atccctggca atgtga | 16 |

-continued

| | |
|---|---|
| SEQ ID NO: 7 | moltype = DNA   length = 15 |
| FEATURE | Location/Qualifiers |
| misc_feature | 1..15 |
| | note = 218 MOE Oleic 3' |
| misc_feature | 1 |
| | note = /note="nucleotide bond by a Phosphorothioate linkage" |
| misc_feature | 1 |
| | note = /note="LNA modified base" |
| misc_feature | 2 |
| | note = /note="nucleotide bond by a Phosphorothioate linkage" |
| misc_feature | 2 |
| | note = /note="LNA modified base" |
| misc_feature | 3 |
| | note = /note="nucleotide bond by a Phosphorothioate linkage" |
| misc_feature | 3 |
| | note = /note="2'-O-MOE RNA nucleotides" |
| misc_feature | 4 |
| | note = /note="nucleotide bond by a Phosphorothioate linkage" |
| misc_feature | 4 |
| | note = /note="LNA modified base" |
| misc_feature | 5 |
| | note = /note="nucleotide bond by a Phosphorothioate linkage" |
| misc_feature | 5 |
| | note = /note="2'-O-MOE RNA nucleotides" |
| misc_feature | 6 |
| | note = /note="nucleotide bond by a Phosphorothioate linkage" |
| misc_feature | 6 |
| | note = /note="2'-O-MOE RNA nucleotides" |
| misc_feature | 7 |
| | note = /note="LNA modified base" |
| misc_feature | 8 |
| | note = /note="nucleotide bond by a Phosphorothioate linkage" |
| misc_feature | 8 |
| | note = /note="2'-O-MOE RNA nucleotides" |
| misc_feature | 9 |
| | note = /note="2'-O-MOE RNA nucleotides" |
| misc_feature | 10 |
| | note = /note="LNA modified base" |
| misc_feature | 11 |
| | note = /note="2'-O-MOE RNA nucleotides" |
| misc_feature | 12 |
| | note = /note="nucleotide bond by a Phosphorothioate linkage" |
| misc_feature | 12 |
| | note = /note="LNA modified base" |
| misc_feature | 13 |
| | note = /note="nucleotide bond by a Phosphorothioate linkage" |
| misc_feature | 13 |
| | note = /note="2'-O-MOE RNA nucleotides" |
| misc_feature | 14 |
| | note = /note="nucleotide bond by a Phosphorothioate linkage" |
| misc_feature | 14 |
| | note = /note="LNA modified base" |
| misc_feature | 15 |
| | note = /note="LNA modified base" |
| misc_feature | 15 |
| | note = /note="nucleotide conjugated to NHC6 conjugated to oleic acid" |
| source | 1..15 |
| | mol_type = other DNA |
| | organism = synthetic construct |
| SEQUENCE: 7 | |
| ttagatcaag cacaa | 15 |
| | |
| SEQ ID NO: 8 | moltype = DNA   length = 15 |
| FEATURE | Location/Qualifiers |
| misc_feature | 1..15 |
| | note = 218 MOE DD Oleic 3' |
| misc_feature | 1 |
| | note = /note="LNA modified base" |
| misc_feature | 1 |
| | note = /note="nucleotide bond by a Phosphorothioate linkage" |
| misc_feature | 2 |
| | note = /note="LNA modified base" |
| misc_feature | 2 |
| | note = /note="nucleotide bond by a Phosphorothioate linkage" |
| misc_feature | 3 |
| | note = /note="nucleotide bond by a Phosphorothioate linkage" |
| misc_feature | 3 |
| | note = /note="2'-O-MOE RNA nucleotides" |

| | |
|---|---|
| misc_feature | 4 |
| | note = /note="LNA modified base" |
| misc_feature | 4 |
| | note = /note="nucleotide bond by a Phosphorothioate linkage" |
| misc_feature | 5 |
| | note = /note="nucleotide bond by a Phosphorothioate linkage" |
| misc_feature | 5 |
| | note = /note="2'-O-MOE RNA nucleotides" |
| misc_feature | 6 |
| | note = /note="nucleotide bond by a Phosphorothioate linkage" |
| misc_feature | 6 |
| | note = /note="2'-O-MOE RNA nucleotides" |
| misc_feature | 7 |
| | note = /note="LNA modified base" |
| misc_feature | 8 |
| | note = /note="nucleotide bond by a Phosphorothioate linkage" |
| misc_feature | 8 |
| | note = /note="2'-O-MOE RNA nucleotides" |
| misc_feature | 9 |
| | note = /note="nucleotide bond by a Phosphorothioate linkage" |
| misc_feature | 9 |
| | note = /note="2'-O-MOE RNA nucleotides" |
| misc_feature | 10 |
| | note = /note="LNA modified base" |
| misc_feature | 11 |
| | note = /note="2'-O-MOE RNA nucleotides" |
| misc_feature | 12 |
| | note = /note="LNA modified base" |
| misc_feature | 12 |
| | note = /note="nucleotide bond by a Phosphorothioate linkage" |
| misc_feature | 13 |
| | note = /note="nucleotide bond by a Phosphorothioate linkage" |
| misc_feature | 13 |
| | note = /note="2'-O-MOE RNA nucleotides" |
| misc_feature | 14 |
| | note = /note="nucleotide bond by a Phosphorothioate linkage" |
| misc_feature | 14 |
| | note = /note="2'-O-Methyl-2,6-diaminopurine " |
| misc_feature | 15 |
| | note = /note="2'-O-Methyl-2,6-diaminopurine " |
| misc_feature | 15 |
| | note = /note="nucleotide conjugated to NHC6 conjugated to oleic acid" |
| source | 1..15 |
| | mol_type = other DNA |
| | organism = synthetic construct |

SEQUENCE: 8
ttagatcaag cacaa        15

| | |
|---|---|
| SEQ ID NO: 9 | moltype = DNA  length = 15 |
| FEATURE | Location/Qualifiers |
| misc_feature | 1..15 |
| | note = 218 OME/MOE oleic 3' |
| misc_feature | 1 |
| | note = /note="nucleotide bond by a Phosphorothioate linkage" |
| misc_feature | 1 |
| | note = /note="LNA modified base" |
| misc_feature | 2 |
| | note = /note="nucleotide bond by a Phosphorothioate linkage" |
| misc_feature | 2 |
| | note = /note="2'-O-MOE RNA nucleotides" |
| misc_feature | 3 |
| | note = /note="nucleotide bond by a Phosphorothioate linkage" |
| misc_feature | 3 |
| | note = /note="2 O-Methyl-nucleotides" |
| misc_feature | 4 |
| | note = /note="nucleotide bond by a Phosphorothioate linkage" |
| misc_feature | 4 |
| | note = /note="LNA modified base" |
| misc_feature | 4 |
| | note = /note="2 O-Methyl-nucleotides" |
| misc_feature | 5 |
| | note = /note="nucleotide bond by a Phosphorothioate linkage" |
| misc_feature | 6 |
| | note = /note="nucleotide bond by a Phosphorothioate linkage" |
| misc_feature | 6 |
| | note = /note="2 -OMe-5-methyluridine or 2 -OMe-ribothymidine " |
| misc_feature | 7 |

```
                        note = /note="LNA modified base"
misc_feature            8
                        note = /note="nucleotide bond by a Phosphorothioate linkage"
misc_feature            8
                        note = /note="2'-O-MOE RNA nucleotides"
misc_feature            9
                        note = /note="2'-O-MOE RNA nucleotides"
misc_feature            10
                        note = /note="LNA modified base"
misc_feature            11
                        note = /note="2'-O-MOE RNA nucleotides"
misc_feature            12
                        note = /note="nucleotide bond by a Phosphorothioate linkage"
misc_feature            12
                        note = /note="LNA modified base"
misc_feature            13
                        note = /note="nucleotide bond by a Phosphorothioate linkage"
misc_feature            13
                        note = /note="2'-O-MOE RNA nucleotides"
misc_feature            14
                        note = /note="nucleotide bond by a Phosphorothioate linkage"
misc_feature            14
                        note = /note="2'-O-MOE RNA nucleotides"
misc_feature            15
                        note = /note="LNA modified base"
misc_feature            15
                        note = /note="nucleotide conjugated to NHC6 conjugated to
                         oleic acid"
source                  1..15
                        mol_type = other DNA
                        organism = synthetic construct
SEQUENCE: 9
ttagatcaag cacaa                                                      15

SEQ ID NO: 10           moltype = RNA  length = 21
FEATURE                 Location/Qualifiers
misc_feature            1..21
                        note = hsa-miR-218-5p
source                  1..21
                        mol_type = other RNA
                        organism = synthetic construct
SEQUENCE: 10
ttgtgcttga tctaaccatg t                                               21

SEQ ID NO: 11           moltype = RNA  length = 23
FEATURE                 Location/Qualifiers
misc_feature            1..23
                        note = hsa-miR-23b-3p
source                  1..23
                        mol_type = other RNA
                        organism = synthetic construct
SEQUENCE: 11
atcacattgc cagggattac cac                                             23

SEQ ID NO: 12           moltype =    length =
SEQUENCE: 12
000

SEQ ID NO: 13           moltype =    length =
SEQUENCE: 13
000

SEQ ID NO: 14           moltype = DNA  length = 15
FEATURE                 Location/Qualifiers
misc_feature            1..15
                        note = 218 OME/MOE oleic 3'2
misc_feature            1
                        note = /note="nucleotide bond by a Phosphorothioate linkage"
misc_feature            1
                        note = /note="LNA modified base"
misc_feature            2
                        note = /note="nucleotide bond by a Phosphorothioate linkage"
misc_feature            2
                        note = /note="LNA modified base"
misc_feature            3
                        note = /note="nucleotide bond by a Phosphorothioate linkage"
misc_feature            3
                        note = /note="2'-O-Methyl-nucleotides"
misc_feature            4
```

|   |   |   |
|---|---|---|
| misc_feature | 4 | |
| | note = /note="LNA modified base" | |
| misc_feature | 5 | |
| | note = /note="nucleotide bond by a Phosphorothioate linkage" | |
| misc_feature | 5 | |
| | note = /note="2´-O-Methyl-nucleotides" | |
| misc_feature | 6 | |
| | note = /note="nucleotide bond by a Phosphorothioate linkage" | |
| misc_feature | 6 | |
| | note = /note="2´-OMe-5-methyluridine or 2´-OMe-ribothymidine" | |
| misc_feature | 7 | |
| | note = /note="LNA modified base" | |
| misc_feature | 8 | |
| | note = /note="nucleotide bond by a Phosphorothioate linkage" | |
| misc_feature | 8 | |
| | note = /note="2'-O-MOE RNA nucleotides" | |
| misc_feature | 9 | |
| | note = /note="2'-O-MOE RNA nucleotides" | |
| misc_feature | 10 | |
| | note = /note="LNA modified base" | |
| misc_feature | 11 | |
| | note = /note="2'-O-MOE RNA nucleotides" | |
| misc_feature | 12 | |
| | note = /note="nucleotide bond by a Phosphorothioate linkage" | |
| misc_feature | 12 | |
| | note = /note="LNA modified base" | |
| misc_feature | 13 | |
| | note = /note="nucleotide bond by a Phosphorothioate linkage" | |
| misc_feature | 13 | |
| | note = /note="2'-O-MOE RNA nucleotides" | |
| misc_feature | 14 | |
| | note = /note="nucleotide bond by a Phosphorothioate linkage" | |
| misc_feature | 14 | |
| | note = /note="2'-O-MOE RNA nucleotides" | |
| misc_feature | 15 | |
| | note = /note="LNA modified base" | |
| misc_feature | 15 | |
| | note = /note="nucleotide conjugated to NHC6 conjugated to oleic acid" | |
| source | 1..15 | |
| | mol_type = other DNA | |
| | organism = synthetic construct | |

SEQUENCE: 14
ttagatcaag cacaa                                                          15

|   |   |   |
|---|---|---|
| SEQ ID NO: 15 | moltype = DNA length = 15 | |
| FEATURE | Location/Qualifiers | |
| misc_feature | 1..15 | |
| | note = 218 MOE | |
| misc_feature | 1 | |
| | note = /note="nucleotide bond by a Phosphorothioate linkage" | |
| misc_feature | 1 | |
| | note = /note="nucleotide bond by a Phosphorothioate linkage" | |
| misc_feature | 1 | |
| | note = /note="LNA modified base" | |
| misc_feature | 1 | |
| | note = /note="LNA modified base" | |
| misc_feature | 2 | |
| | note = /note="nucleotide bond by a Phosphorothioate linkage" | |
| misc_feature | 2 | |
| | note = /note="nucleotide bond by a Phosphorothioate linkage" | |
| misc_feature | 2 | |
| | note = /note="LNA modified base" | |
| misc_feature | 2 | |
| | note = /note="LNA modified base" | |
| misc_feature | 3 | |
| | note = /note="nucleotide bond by a Phosphorothioate linkage" | |
| misc_feature | 3 | |
| | note = /note="nucleotide bond by a Phosphorothioate linkage" | |
| misc_feature | 3 | |
| | note = /note="2'-O-MOE RNA nucleotides" | |
| misc_feature | 3 | |
| | note = /note="2'-O-MOE RNA nucleotides" | |
| misc_feature | 4 | |
| | note = /note="nucleotide bond by a Phosphorothioate linkage" | |
| misc_feature | 4 | |
| | note = /note="nucleotide bond by a Phosphorothioate linkage" | |

| | | |
|---|---|---|
| misc_feature | 4 | |
| | note = /note="LNA modified base" | |
| misc_feature | 4 | |
| | note = /note="LNA modified base" | |
| misc_feature | 5 | |
| | note = /note="nucleotide bond by a Phosphorothioate linkage" | |
| misc_feature | 5 | |
| | note = /note="nucleotide bond by a Phosphorothioate linkage" | |
| misc_feature | 5 | |
| | note = /note="2'-O-MOE RNA nucleotides" | |
| misc_feature | 5 | |
| | note = /note="2'-O-MOE RNA nucleotides" | |
| misc_feature | 6 | |
| | note = /note="nucleotide bond by a Phosphorothioate linkage" | |
| misc_feature | 6 | |
| | note = /note="nucleotide bond by a Phosphorothioate linkage" | |
| misc_feature | 6 | |
| | note = /note="2'-O-MOE RNA nucleotides" | |
| misc_feature | 6 | |
| | note = /note="2'-O-MOE RNA nucleotides" | |
| misc_feature | 7 | |
| | note = /note="LNA modified base" | |
| misc_feature | 7 | |
| | note = /note="LNA modified base" | |
| misc_feature | 8 | |
| | note = /note="nucleotide bond by a Phosphorothioate linkage" | |
| misc_feature | 8 | |
| | note = /note="nucleotide bond by a Phosphorothioate linkage" | |
| misc_feature | 8 | |
| | note = /note="2'-O-MOE RNA nucleotides" | |
| misc_feature | 8 | |
| | note = /note="2'-O-MOE RNA nucleotides" | |
| misc_feature | 9 | |
| | note = /note="2'-O-MOE RNA nucleotides" | |
| misc_feature | 9 | |
| | note = /note="2'-O-MOE RNA nucleotides" | |
| misc_feature | 10 | |
| | note = /note="LNA modified base" | |
| misc_feature | 10 | |
| | note = /note="LNA modified base" | |
| misc_feature | 11 | |
| | note = /note="2'-O-MOE RNA nucleotides" | |
| misc_feature | 11 | |
| | note = /note="2'-O-MOE RNA nucleotides" | |
| misc_feature | 12 | |
| | note = /note="nucleotide bond by a Phosphorothioate linkage" | |
| misc_feature | 12 | |
| | note = /note="nucleotide bond by a Phosphorothioate linkage" | |
| misc_feature | 12 | |
| | note = /note="LNA modified base" | |
| misc_feature | 12 | |
| | note = /note="LNA modified base" | |
| misc_feature | 13 | |
| | note = /note="nucleotide bond by a Phosphorothioate linkage" | |
| misc_feature | 13 | |
| | note = /note="nucleotide bond by a Phosphorothioate linkage" | |
| misc_feature | 13 | |
| | note = /note="2'-O-MOE RNA nucleotides" | |
| misc_feature | 13 | |
| | note = /note="2'-O-MOE RNA nucleotides" | |
| misc_feature | 14 | |
| | note = /note="nucleotide bond by a Phosphorothioate linkage" | |
| misc_feature | 14 | |
| | note = /note="nucleotide bond by a Phosphorothioate linkage" | |
| misc_feature | 14 | |
| | note = /note="LNA modified base" | |
| misc_feature | 14 | |
| | note = /note="LNA modified base" | |
| misc_feature | 15 | |
| | note = /note="LNA modified base" | |
| misc_feature | 15 | |
| | note = /note="LNA modified base" | |
| source | 1..15 | |
| | mol_type = other DNA | |
| | organism = synthetic construct | |
| SEQUENCE: 15 | | |
| ttagatcaag cacaa | | 15 |
| | | |
| SEQ ID NO: 16 | moltype = DNA  length = 16 | |

| FEATURE | Location/Qualifiers |
|---|---|
| misc_feature | 1..16<br>note = MD23b-2 V2 3 Pal |
| misc_feature | 1<br>note = /note="LNA modified base" |
| misc_feature | 1<br>note = /note="nucleotide bond by a Phosphorothioate linkage" |
| misc_feature | 2<br>note = /note="LNA modified base" |
| misc_feature | 2<br>note = /note="nucleotide bond by a Phosphorothioate linkage" |
| misc_feature | 3<br>note = /note="nucleotide bond by a Phosphorothioate linkage" |
| misc_feature | 3<br>note = /note="5-Methyl-2'-O-Methyl cytidine " |
| misc_feature | 3<br>note = /note="2 -O-Methyl-nucleotide" |
| misc_feature | 4<br>note = /note="nucleotide bond by a Phosphorothioate linkage" |
| misc_feature | 4<br>note = /note="5-Methyl-2'-O-Methyl cytidine " |
| misc_feature | 4<br>note = /note="2 -O-Methyl-nucleotide" |
| misc_feature | 5<br>note = /note="2'-O-MOE RNA nucleotide" |
| misc_feature | 6<br>note = /note="LNA modified base" |
| misc_feature | 7<br>note = /note="nucleotide bond by a Phosphorothioate linkage" |
| misc_feature | 7<br>note = /note="2'-O-MOE RNA nucleotide" |
| misc_feature | 8<br>note = /note="nucleotide bond by a Phosphorothioate linkage" |
| misc_feature | 8<br>note = /note="2 -O-Methyl-nucleotide" |
| misc_feature | 9<br>note = /note="LNA modified base" |
| misc_feature | 9<br>note = /note="nucleotide bond by a Phosphorothioate linkage" |
| misc_feature | 9<br>note = /note="2'-O-MOE RNA nucleotide" |
| misc_feature | 11<br>note = /note="LNA modified base" |
| misc_feature | 11<br>note = /note="2'-O-MOE RNA nucleotide" |
| misc_feature | 12<br>note = /note="LNA modified base" |
| misc_feature | 14<br>note = /note="LNA modified base" |
| misc_feature | 14<br>note = /note="nucleotide bond by a Phosphorothioate linkage" |
| misc_feature | 14<br>note = /note="2'-O-MOE RNA nucleotide" |
| misc_feature | 15<br>note = /note="LNA modified base" |
| misc_feature | 15<br>note = /note="nucleotide bond by a Phosphorothioate linkage" |
| misc_feature | 16<br>note = /note="nucleotide conjugated to NHC6 conjugated to palmitic acid" |
| source | 1..16<br>mol_type = other DNA<br>organism = synthetic construct |

SEQUENCE: 16
atccctggca atgtga                              16

| SEQ ID NO: 17 | moltype = DNA   length = 16 |
|---|---|
| FEATURE | Location/Qualifiers |
| misc_feature | 1..16<br>note = MD23b-2 V2 |
| misc_feature | 1<br>note = /note="LNA modified base" |
| misc_feature | 1<br>note = /note="nucleotide bond by a Phosphorothioate linkage" |
| misc_feature | 2<br>note = /note="LNA modified base" |
| misc_feature | 2<br>note = /note="nucleotide bond by a Phosphorothioate linkage" |
| misc_feature | 3 |

| | | |
|---|---|---|
| misc_feature | 3 | |
| | note = /note="5-Methyl-2'-O-Methyl cytidine " | |
| misc_feature | 3 | |
| | note = /note="2 -O-Methyl-nucleotide" | |
| misc_feature | 4 | |
| | note = /note="nucleotide bond by a Phosphorothioate linkage" | |
| misc_feature | 4 | |
| | note = /note="5-Methyl-2'-O-Methyl cytidine " | |
| misc_feature | 4 | |
| | note = /note="2 -O-Methyl-nucleotide" | |
| misc_feature | 5 | |
| | note = /note="2'-O-MOE RNA nucleotide" | |
| misc_feature | 6 | |
| | note = /note="LNA modified base" | |
| misc_feature | 7 | |
| | note = /note="nucleotide bond by a Phosphorothioate linkage" | |
| misc_feature | 7 | |
| | note = /note="2'-O-MOE RNA nucleotide" | |
| misc_feature | 8 | |
| | note = /note="nucleotide bond by a Phosphorothioate linkage" | |
| misc_feature | 8 | |
| | note = /note="2 -O-Methyl-nucleotide" | |
| misc_feature | 9 | |
| | note = /note="LNA modified base" | |
| misc_feature | 9 | |
| | note = /note="nucleotide bond by a Phosphorothioate linkage" | |
| misc_feature | 9 | |
| | note = /note="2'-O-MOE RNA nucleotide" | |
| misc_feature | 11 | |
| | note = /note="LNA modified base" | |
| misc_feature | 11 | |
| | note = /note="2'-O-MOE RNA nucleotide" | |
| misc_feature | 12 | |
| | note = /note="LNA modified base" | |
| misc_feature | 14 | |
| | note = /note="LNA modified base" | |
| misc_feature | 14 | |
| | note = /note="nucleotide bond by a Phosphorothioate linkage" | |
| misc_feature | 14 | |
| | note = /note="2'-O-MOE RNA nucleotide" | |
| misc_feature | 15 | |
| | note = /note="LNA modified base" | |
| misc_feature | 15 | |
| | note = /note="nucleotide bond by a Phosphorothioate linkage" | |
| source | 1..16 | |
| | mol_type = other DNA | |
| | organism = synthetic construct | |
| SEQUENCE: 17 | | |
| atccctggca atgtga | | 16 |
| | | |
| SEQ ID NO: 18 | moltype = DNA length = 16 | |
| FEATURE | Location/Qualifiers | |
| misc_feature | 1..16 | |
| | note = MD23 MOE | |
| misc_feature | 1 | |
| | note = /note="nucleotide bond by a Phosphorothioate linkage" | |
| misc_feature | 1 | |
| | note = /note="LNA modified base" | |
| misc_feature | 2 | |
| | note = /note="nucleotide bond by a Phosphorothioate linkage" | |
| misc_feature | 2 | |
| | note = /note="LNA modified base" | |
| misc_feature | 3 | |
| | note = /note="nucleotide bond by a Phosphorothioate linkage" | |
| misc_feature | 3 | |
| | note = /note="2'-O-MOE RNA nucleotides" | |
| misc_feature | 4 | |
| | note = /note="2'-O-MOE RNA nucleotides" | |
| misc_feature | 5 | |
| | note = /note="nucleotide bond by a Phosphorothioate linkage" | |
| misc_feature | 5 | |
| | note = /note="2'-O-MOE RNA nucleotides" | |
| misc_feature | 6 | |
| | note = /note="nucleotide bond by a Phosphorothioate linkage" | |
| misc_feature | 6 | |
| | note = /note="2'-O-MOE RNA nucleotides" | |
| misc_feature | 7 | |
| | note = /note="2'-O-MOE RNA nucleotides" | |

| | | |
|---|---|---|
| misc_feature | 8 | |
| | note = /note="nucleotide bond by a Phosphorothioate linkage" | |
| misc_feature | 8 | |
| | note = /note="2'-O-MOE RNA nucleotides" | |
| misc_feature | 9 | |
| | note = /note="2'-O-MOE RNA nucleotides" | |
| misc_feature | 10 | |
| | note = /note="2'-O-MOE RNA nucleotides" | |
| misc_feature | 11 | |
| | note = /note="nucleotide bond by a Phosphorothioate linkage" | |
| misc_feature | 11 | |
| | note = /note="2'-O-MOE RNA nucleotides" | |
| misc_feature | 12 | |
| | note = /note="LNA modified base" | |
| misc_feature | 13 | |
| | note = /note="nucleotide bond by a Phosphorothioate linkage" | |
| misc_feature | 13 | |
| | note = /note="2'-O-MOE RNA nucleotides" | |
| misc_feature | 14 | |
| | note = /note="2'-O-MOE RNA nucleotides" | |
| misc_feature | 15 | |
| | note = /note="nucleotide bond by a Phosphorothioate linkage" | |
| misc_feature | 15 | |
| | note = /note="LNA modified base" | |
| misc_feature | 16 | |
| | note = /note="LNA modified base" | |
| source | 1..16 | |
| | mol_type = other DNA | |
| | organism = synthetic construct | |

SEQUENCE: 18
atccctggca atgtga                                                            16

| | | |
|---|---|---|
| SEQ ID NO: 19 | moltype = RNA  length = 97 | |
| FEATURE | Location/Qualifiers | |
| misc_feature | 1..97 | |
| | note = The microRNA precursor (pre-microRNA) of hsa-miR-23b-3p | |
| source | 1..97 | |
| | mol_type = other RNA | |
| | organism = synthetic construct | |

SEQUENCE: 19
ctcaggtgct ctggctgctt gggttcctgg catgctgatt tgtgacttaa gattaaaatc    60
acattgccag ggattaccac gcaaccacga ccttggc                              97

| | | |
|---|---|---|
| SEQ ID NO: 20 | moltype = RNA  length = 110 | |
| FEATURE | Location/Qualifiers | |
| misc_feature | 1..110 | |
| | note = Pre-hsa-miR-218-5p-1(chr4:20529898-20530007) | |
| source | 1..110 | |
| | mol_type = other RNA | |
| | organism = synthetic construct | |

SEQUENCE: 20
gtgataatgt agcgagattt tctgttgtgc ttgatctaac catgtggttg cgaggtatga    60
gtaaacatg gttccgtcaa gcaccatgga acgtcacgca gctttctaca               110

| | | |
|---|---|---|
| SEQ ID NO: 21 | moltype = RNA  length = 110 | |
| FEATURE | Location/Qualifiers | |
| misc_feature | 1..110 | |
| | note = Pre-miR-218-2 (chr5:1681951 SI- 168195260) | |
| source | 1..110 | |
| | mol_type = other RNA | |
| | organism = synthetic construct | |

SEQUENCE: 21
gaccagtcgc tgcggggctt tcctttgtgc ttgatctaac catgtggtgg aacgatggaa    60
acggaacatg gttctgtcaa gcaccgcgga aagcaccgtg ctctcctgca               110

| | | |
|---|---|---|
| SEQ ID NO: 22 | moltype = DNA  length = 16 | |
| FEATURE | Location/Qualifiers | |
| misc_feature | 1..16 | |
| | note = MD23b-2 V2 3 OI without specific spacer molecule | |
| misc_feature | 1 | |
| | note = /note="LNA modified base" | |
| misc_feature | 1 | |
| | note = /note="nucleotide bond by a Phosphorothioate linkage" | |
| misc_feature | 2 | |
| | note = /note="LNA modified base" | |
| misc_feature | 2 | |
| | note = /note="nucleotide bond by a Phosphorothioate linkage" | |
| misc_feature | 3 | |

| | | |
|---|---|---|
| misc_feature | | 3 |
| | | note = /note="nucleotide bond by a Phosphorothioate linkage" |
| misc_feature | | 3 |
| | | note = /note="5-Methyl-2'-O-Methyl cytidine " |
| misc_feature | | 4 |
| | | note = /note="nucleotide bond by a Phosphorothioate linkage" |
| misc_feature | | 4 |
| | | note = /note="5-Methyl-2'-O-Methyl cytidine " |
| misc_feature | | 5 |
| | | note = /note="2'-O-MOE RNA nucleotide" |
| misc_feature | | 6 |
| | | note = /note="LNA modified base" |
| misc_feature | | 7 |
| | | note = /note="nucleotide bond by a Phosphorothioate linkage" |
| misc_feature | | 7 |
| | | note = /note="2'-O-MOE RNA nucleotide" |
| misc_feature | | 8 |
| | | note = /note="nucleotide bond by a Phosphorothioate linkage" |
| misc_feature | | 8 |
| | | note = /note="2 -O-Methyl-nucleotide" |
| misc_feature | | 9 |
| | | note = /note="nucleotide bond by a Phosphorothioate linkage" |
| misc_feature | | 9 |
| | | note = /note="2'-O-MOE RNA nucleotide" |
| misc_feature | | 10 |
| | | note = /note="LNA modified base" |
| misc_feature | | 11 |
| | | note = /note="2'-O-MOE RNA nucleotide" |
| misc_feature | | 12 |
| | | note = /note="LNA modified base" |
| misc_feature | | 13 |
| | | note = /note="LNA modified base" |
| misc_feature | | 14 |
| | | note = /note="nucleotide bond by a Phosphorothioate linkage" |
| misc_feature | | 14 |
| | | note = /note="2'-O-MOE RNA nucleotide" |
| misc_feature | | 15 |
| | | note = /note="LNA modified base" |
| misc_feature | | 15 |
| | | note = /note="nucleotide bond by a Phosphorothioate linkage" |
| misc_feature | | 16 |
| | | note = /note="nucleotide conjugated to a Spacer conjugated to oleic acid, wherein the spacer molecule is preferably selected from the group consisting of NHC3, NHC5, NHC6, threoninol, or a derivative thereof." |
| misc_feature | | 16 |
| | | note = /note="LNA modified base" |
| source | | 1..16 |
| | | mol_type = other DNA |
| | | organism = synthetic construct |
| SEQUENCE: 22 | | |
| atccctggca atgtga | | 16 |
| | | |
| SEQ ID NO: 23 | | moltype = DNA  length = 16 |
| FEATURE | | Location/Qualifiers |
| misc_feature | | 1..16 |
| | | note = MD23b-2-PS/PO 3 OI without specific spacer molecule |
| misc_feature | | 1 |
| | | note = /note="nucleotide bond by a Phosphorothioate linkage" |
| misc_feature | | 1 |
| | | note = /note="LNA nucleotide" |
| misc_feature | | 2 |
| | | note = /note="2'-O-MOE RNA nucleotides " |
| misc_feature | | 2 |
| | | note = /note="nucleotide bond by a Phosphorothioate linkage" |
| misc_feature | | 3 |
| | | note = /note="5-Methyl-2'-O-Methyl cytidine" |
| misc_feature | | 3 |
| | | note = /note="nucleotide bond by a Phosphorothioate linkage" |
| misc_feature | | 4 |
| | | note = /note="5-Methyl-2'-O-Methyl cytidine" |
| misc_feature | | 5 |
| | | note = /note="5-Methyl-2'-O-Methyl cytidine" |
| misc_feature | | 6 |
| | | note = /note="LNA modified base" |
| misc_feature | | 7 |
| | | note = /note="2 -O-Methyl-nucleotide" |
| misc_feature | | 7 |
| | | note = /note="nucleotide bond by a Phosphorothioate linkage" |
| misc_feature | | 8 |

| | | |
|---|---|---|
| | | note = /note="2 -O-Methyl-nucleotide" |
| misc_feature | 8 | |
| | | note = /note="nucleotide bond by a Phosphorothioate linkage" |
| misc_feature | 9 | |
| | | note = /note="5-Methyl-2'-O-Methyl cytidine" |
| misc_feature | 9 | |
| | | note = /note="nucleotide bond by a Phosphorothioate linkage" |
| misc_feature | 10 | |
| | | note = /note="LNA nucleotide" |
| misc_feature | 11 | |
| | | note = /note="2'-O-MOE RNA nucleotides " |
| misc_feature | 12 | |
| | | note = /note="LNA nucleotide" |
| misc_feature | 13 | |
| | | note = /note="LNA nucleotide" |
| misc_feature | 13 | |
| | | note = /note="nucleotide bond by a Phosphorothioate linkage" |
| misc_feature | 14 | |
| | | note = /note="2'-O-MOE RNA nucleotides " |
| misc_feature | 14 | |
| | | note = /note="nucleotide bond by a Phosphorothioate linkage" |
| misc_feature | 15 | |
| | | note = /note="nucleotide bond by a Phosphorothioate linkage" |
| misc_feature | 15 | |
| | | note = /note="LNA nucleotide" |
| misc_feature | 16 | |
| | | note = /note="LNA nucleotide" |
| misc_feature | 16 | |
| | | note = /note="nucleotide conjugated to a spacer conjugated to oleic acid, wherein the spacer molecule is preferably selected from the group consisting of NHC3, NHC5, NHC6, threoninol, or a derivative thereof." |
| source | 1..16 | |
| | | mol_type = other DNA |
| | | organism = synthetic construct |
| SEQUENCE: 23 | | |
| atccctggca atgtga | | 16 |
| | | |
| SEQ ID NO: 24 | moltype = DNA  length = 16 | |
| FEATURE | Location/Qualifiers | |
| misc_feature | 1..16 | |
| | | note = MD23b-2-PS/PO 5 OI without specific spacer molecule |
| misc_feature | 1 | |
| | | note = /note="nucleotide conjugated to a Spacer molecule conjugated to oleic acid" |
| misc_feature | 1 | |
| | | note = /note="nucleotide bond by a Phosphorothioate linkage" |
| misc_feature | 1 | |
| | | note = /note="LNA nucleotide" |
| misc_feature | 2 | |
| | | note = /note="2'-O-MOE RNA nucleotides " |
| misc_feature | 3 | |
| | | note = /note="5-Methyl-2'-O-Methyl cytidine" |
| misc_feature | 4 | |
| | | note = /note="5-Methyl-2'-O-Methyl cytidine" |
| misc_feature | 5 | |
| | | note = /note="5-Methyl-2'-O-Methyl cytidine" |
| misc_feature | 6 | |
| | | note = /note="nucleotide bond by a Phosphorothioate linkage" |
| misc_feature | 6 | |
| | | note = /note="LNA nucleotide" |
| misc_feature | 7 | |
| | | note = /note="2 -O-Methyl-nucleotide" |
| misc_feature | 8 | |
| | | note = /note="2 -O-Methyl-nucleotide" |
| misc_feature | 9 | |
| | | note = /note="nucleotide bond by a Phosphorothioate linkage" |
| misc_feature | 9 | |
| | | note = /note="5-Methyl-2'-O-Methyl cytidine" |
| misc_feature | 10 | |
| | | note = /note="LNA nucleotide" |
| misc_feature | 11 | |
| | | note = /note="nucleotide bond by a Phosphorothioate linkage" |
| misc_feature | 11 | |
| | | note = /note="2'-O-MOE RNA nucleotides " |
| misc_feature | 12 | |
| | | note = /note="nucleotide bond by a Phosphorothioate linkage" |
| misc_feature | 12 | |
| | | note = /note="LNA nucleotide" |

| | | |
|---|---|---|
| misc_feature | 13 | |
| | note = /note="LNA nucleotide" | |
| misc_feature | 14 | |
| | note = /note="nucleotide bond by a Phosphorothioate linkage" | |
| misc_feature | 14 | |
| | note = /note="2'-O-MOE RNA nucleotides " | |
| misc_feature | 15 | |
| | note = /note="nucleotide bond by a Phosphorothioate linkage" | |
| misc_feature | 15 | |
| | note = /note="LNA nucleotide" | |
| misc_feature | 16 | |
| | note = /note="LNA nucleotide" | |
| source | 1..16 | |
| | mol_type = other DNA | |
| | organism = synthetic construct | |
| SEQUENCE: 24 | | |
| atccctggca atgtga | | 16 |
| | | |
| SEQ ID NO: 25 | moltype = DNA  length = 15 | |
| FEATURE | Location/Qualifiers | |
| misc_feature | 1..15 | |
| | note = 218 MOE Oleic 3  without specific spacer molecule | |
| misc_feature | 1 | |
| | note = /note="nucleotide bond by a Phosphorothioate linkage" | |
| misc_feature | 1 | |
| | note = /note="LNA modified base" | |
| misc_feature | 2 | |
| | note = /note="nucleotide bond by a Phosphorothioate linkage" | |
| misc_feature | 2 | |
| | note = /note="LNA modified base" | |
| misc_feature | 3 | |
| | note = /note="nucleotide bond by a Phosphorothioate linkage" | |
| misc_feature | 3 | |
| | note = /note="2'-O-MOE RNA nucleotides" | |
| misc_feature | 4 | |
| | note = /note="nucleotide bond by a Phosphorothioate linkage" | |
| misc_feature | 4 | |
| | note = /note="LNA modified base" | |
| misc_feature | 5 | |
| | note = /note="nucleotide bond by a Phosphorothioate linkage" | |
| misc_feature | 5 | |
| | note = /note="2'-O-MOE RNA nucleotides" | |
| misc_feature | 6 | |
| | note = /note="nucleotide bond by a Phosphorothioate linkage" | |
| misc_feature | 6 | |
| | note = /note="2'-O-MOE RNA nucleotides" | |
| misc_feature | 7 | |
| | note = /note="LNA modified base" | |
| misc_feature | 8 | |
| | note = /note="nucleotide bond by a Phosphorothioate linkage" | |
| misc_feature | 8 | |
| | note = /note="2'-O-MOE RNA nucleotides" | |
| misc_feature | 9 | |
| | note = /note="2'-O-MOE RNA nucleotides" | |
| misc_feature | 10 | |
| | note = /note="LNA modified base" | |
| misc_feature | 11 | |
| | note = /note="2'-O-MOE RNA nucleotides" | |
| misc_feature | 12 | |
| | note = /note="nucleotide bond by a Phosphorothioate linkage" | |
| misc_feature | 12 | |
| | note = /note="LNA modified base" | |
| misc_feature | 13 | |
| | note = /note="nucleotide bond by a Phosphorothioate linkage" | |
| misc_feature | 13 | |
| | note = /note="2'-O-MOE RNA nucleotides" | |
| misc_feature | 14 | |
| | note = /note="nucleotide bond by a Phosphorothioate linkage" | |
| misc_feature | 14 | |
| | note = /note="LNA modified base" | |
| misc_feature | 15 | |
| | note = /note="LNA modified base" | |
| misc_feature | 15 | |
| | note = /note="nucleotide conjugated to a spacer molecule conjugated to oleic acid, wherein the spacer molecule is preferably selected from the group consisting of NHC3, NHC5, NHC6, threoninol, or a derivative thereof." | |
| source | 1..15 | |
| | mol_type = other DNA | |

|                  |                                                                                      |
|------------------|--------------------------------------------------------------------------------------|
|                  | organism = synthetic construct                                                       |
| SEQUENCE: 25     |                                                                                      |
| ttagatcaag cacaa | 15                                                                                   |
|                  |                                                                                      |
| SEQ ID NO: 26    | moltype = DNA  length = 15                                                           |
| FEATURE          | Location/Qualifiers                                                                  |
| misc_feature     | 1..15                                                                                |
|                  | note = 218 MOE DD Oleic 3  without specific spacer molecule                          |
| misc_feature     | 1                                                                                    |
|                  | note = /note="LNA modified base"                                                     |
| misc_feature     | 1                                                                                    |
|                  | note = /note="nucleotide bond by a Phosphorothioate linkage"                         |
| misc_feature     | 2                                                                                    |
|                  | note = /note="LNA modified base"                                                     |
| misc_feature     | 2                                                                                    |
|                  | note = /note="nucleotide bond by a Phosphorothioate linkage"                         |
| misc_feature     | 3                                                                                    |
|                  | note = /note="nucleotide bond by a Phosphorothioate linkage"                         |
| misc_feature     | 3                                                                                    |
|                  | note = /note="2'-O-MOE RNA nucleotides"                                              |
| misc_feature     | 4                                                                                    |
|                  | note = /note="LNA modified base"                                                     |
| misc_feature     | 4                                                                                    |
|                  | note = /note="nucleotide bond by a Phosphorothioate linkage"                         |
| misc_feature     | 5                                                                                    |
|                  | note = /note="nucleotide bond by a Phosphorothioate linkage"                         |
| misc_feature     | 5                                                                                    |
|                  | note = /note="2'-O-MOE RNA nucleotides"                                              |
| misc_feature     | 6                                                                                    |
|                  | note = /note="nucleotide bond by a Phosphorothioate linkage"                         |
| misc_feature     | 6                                                                                    |
|                  | note = /note="2'-O-MOE RNA nucleotides"                                              |
| misc_feature     | 7                                                                                    |
|                  | note = /note="LNA modified base"                                                     |
| misc_feature     | 8                                                                                    |
|                  | note = /note="nucleotide bond by a Phosphorothioate linkage"                         |
| misc_feature     | 8                                                                                    |
|                  | note = /note="2'-O-MOE RNA nucleotides"                                              |
| misc_feature     | 9                                                                                    |
|                  | note = /note="nucleotide bond by a Phosphorothioate linkage"                         |
| misc_feature     | 9                                                                                    |
|                  | note = /note="2'-O-MOE RNA nucleotides"                                              |
| misc_feature     | 10                                                                                   |
|                  | note = /note="LNA modified base"                                                     |
| misc_feature     | 11                                                                                   |
|                  | note = /note="2'-O-MOE RNA nucleotides"                                              |
| misc_feature     | 12                                                                                   |
|                  | note = /note="LNA modified base"                                                     |
| misc_feature     | 12                                                                                   |
|                  | note = /note="nucleotide bond by a Phosphorothioate linkage"                         |
| misc_feature     | 13                                                                                   |
|                  | note = /note="nucleotide bond by a Phosphorothioate linkage"                         |
| misc_feature     | 13                                                                                   |
|                  | note = /note="2'-O-MOE RNA nucleotides"                                              |
| misc_feature     | 14                                                                                   |
|                  | note = /note="nucleotide bond by a Phosphorothioate linkage"                         |
| misc_feature     | 14                                                                                   |
|                  | note = /note="2'-O-Methyl-2,6-diaminopurine "                                        |
| misc_feature     | 15                                                                                   |
|                  | note = /note="2'-O-Methyl-2,6-diaminopurine "                                        |
| misc_feature     | 15                                                                                   |
|                  | note = /note="nucleotide conjugated to a Spacer molecule                             |
|                  |  conjugated to oleic acid"                                                           |
| source           | 1..15                                                                                |
|                  | mol_type = other DNA                                                                 |
|                  | organism = synthetic construct                                                       |
| SEQUENCE: 26     |                                                                                      |
| ttagatcaag cacaa | 15                                                                                   |
|                  |                                                                                      |
| SEQ ID NO: 27    | moltype = DNA  length = 15                                                           |
| FEATURE          | Location/Qualifiers                                                                  |
| misc_feature     | 1..15                                                                                |
|                  | note = 218 OME/MOE oleic 3  without specific spacer molecule                         |
| misc_feature     | 1                                                                                    |
|                  | note = /note="nucleotide bond by a Phosphorothioate linkage"                         |
| misc_feature     | 1                                                                                    |
|                  | note = /note="LNA modified base"                                                     |
| misc_feature     | 2                                                                                    |
|                  | note = /note="nucleotide bond by a Phosphorothioate linkage"                         |

```
misc_feature      2
                  note = /note="2'-O-MOE RNA nucleotides"
misc_feature      3
                  note = /note="nucleotide bond by a Phosphorothioate linkage"
misc_feature      3
                  note = /note="2 -O-Methyl-nucleotides"
misc_feature      4
                  note = /note="nucleotide bond by a Phosphorothioate linkage"
misc_feature      4
                  note = /note="LNA modified base"
misc_feature      4
                  note = /note="2 -O-Methyl-nucleotides"
misc_feature      5
                  note = /note="nucleotide bond by a Phosphorothioate linkage"
misc_feature      6
                  note = /note="nucleotide bond by a Phosphorothioate linkage"
misc_feature      6
                  note = /note="2 -OMe-5-methyluridine or 2
                   -OMe-ribothymidine "
misc_feature      7
                  note = /note="LNA modified base"
misc_feature      8
                  note = /note="nucleotide bond by a Phosphorothioate linkage"
misc_feature      8
                  note = /note="2'-O-MOE RNA nucleotides"
misc_feature      9
                  note = /note="2'-O-MOE RNA nucleotides"
misc_feature      10
                  note = /note="LNA modified base"
misc_feature      11
                  note = /note="2'-O-MOE RNA nucleotides"
misc_feature      12
                  note = /note="nucleotide bond by a Phosphorothioate linkage"
misc_feature      12
                  note = /note="LNA modified base"
misc_feature      13
                  note = /note="nucleotide bond by a Phosphorothioate linkage"
misc_feature      13
                  note = /note="2'-O-MOE RNA nucleotides"
misc_feature      14
                  note = /note="nucleotide bond by a Phosphorothioate linkage"
misc_feature      14
                  note = /note="2'-O-MOE RNA nucleotides"
misc_feature      15
                  note = /note="LNA modified base"
misc_feature      15
                  note = /note="nucleotide conjugated to a spacer molecule
                   conjugated to oleic acid"
source            1..15
                  mol_type = other DNA
                  organism = synthetic construct
SEQUENCE: 27
ttagatcaag cacaa                                                          15

SEQ ID NO: 28     moltype = DNA  length = 15
FEATURE           Location/Qualifiers
misc_feature      1..15
                  note = 218 OME/MOE oleic 3 2 without specific spacer
                   molecule
misc_feature      1
                  note = /note="nucleotide bond by a Phosphorothioate linkage"
misc_feature      1
                  note = /note="LNA modified base"
misc_feature      2
                  note = /note="nucleotide bond by a Phosphorothioate linkage"
misc_feature      2
                  note = /note="LNA modified base"
misc_feature      3
                  note = /note="nucleotide bond by a Phosphorothioate linkage"
misc_feature      3
                  note = /note="2 -O-Methyl-nucleotides"
misc_feature      4
                  note = /note="nucleotide bond by a Phosphorothioate linkage"
misc_feature      4
                  note = /note="LNA modified base"
misc_feature      5
                  note = /note="nucleotide bond by a Phosphorothioate linkage"
misc_feature      5
                  note = /note="2 -O-Methyl-nucleotides"
```

| | |
|---|---|
| misc_feature | 6<br>note = /note="nucleotide bond by a Phosphorothioate linkage" |
| misc_feature | 6<br>note = /note="2 -OMe-5-methyluridine or 2<br>-OMe-ribothymidine" |
| misc_feature | 7<br>note = /note="LNA modified base" |
| misc_feature | 8<br>note = /note="nucleotide bond by a Phosphorothioate linkage" |
| misc_feature | 8<br>note = /note="2'-O-MOE RNA nucleotides" |
| misc_feature | 9<br>note = /note="2'-O-MOE RNA nucleotides" |
| misc_feature | 10<br>note = /note="LNA modified base" |
| misc_feature | 11<br>note = /note="2'-O-MOE RNA nucleotides" |
| misc_feature | 12<br>note = /note="nucleotide bond by a Phosphorothioate linkage" |
| misc_feature | 12<br>note = /note="LNA modified base" |
| misc_feature | 13<br>note = /note="nucleotide bond by a Phosphorothioate linkage" |
| misc_feature | 13<br>note = /note="2'-O-MOE RNA nucleotides" |
| misc_feature | 14<br>note = /note="nucleotide bond by a Phosphorothioate linkage" |
| misc_feature | 14<br>note = /note="2'-O-MOE RNA nucleotides" |
| misc_feature | 15<br>note = /note="LNA modified base" |
| misc_feature | 15<br>note = /note="nucleotide conjugated to a Spacer molecule<br>conjugated to oleic acid" |
| source | 1..15<br>mol_type = other DNA<br>organism = synthetic construct |
| SEQUENCE: 28 | |
| ttagatcaag cacaa | 15 |
| SEQ ID NO: 29<br>FEATURE | moltype = DNA   length = 16<br>Location/Qualifiers |
| misc_feature | 1..16<br>note = MD23b-2 V2 3 Pal without specific spacer molecule |
| misc_feature | 1<br>note = /note="LNA modified base" |
| misc_feature | 1<br>note = /note="nucleotide bond by a Phosphorothioate linkage" |
| misc_feature | 2<br>note = /note="LNA modified base" |
| misc_feature | 2<br>note = /note="nucleotide bond by a Phosphorothioate linkage" |
| misc_feature | 3<br>note = /note="nucleotide bond by a Phosphorothioate linkage" |
| misc_feature | 3<br>note = /note="5-Methyl-2'-O-Methyl cytidine " |
| misc_feature | 3<br>note = /note="2 -O-Methyl-nucleotide" |
| misc_feature | 4<br>note = /note="nucleotide bond by a Phosphorothioate linkage" |
| misc_feature | 4<br>note = /note="5-Methyl-2'-O-Methyl cytidine " |
| misc_feature | 4<br>note = /note="2 -O-Methyl-nucleotide" |
| misc_feature | 5<br>note = /note="2'-O-MOE RNA nucleotide" |
| misc_feature | 6<br>note = /note="LNA modified base" |
| misc_feature | 7<br>note = /note="nucleotide bond by a Phosphorothioate linkage" |
| misc_feature | 7<br>note = /note="2'-O-MOE RNA nucleotide" |
| misc_feature | 8<br>note = /note="nucleotide bond by a Phosphorothioate linkage" |
| misc_feature | 8<br>note = /note="2 -O-Methyl-nucleotide" |
| misc_feature | 9<br>note = /note="LNA modified base" |
| misc_feature | 9 |

```
misc_feature           note = /note="nucleotide bond by a Phosphorothioate linkage"
                       9
                       note = /note="2'-O-MOE RNA nucleotide"
misc_feature           11
                       note = /note="LNA modified base"
misc_feature           11
                       note = /note="2'-O-MOE RNA nucleotide"
misc_feature           12
                       note = /note="LNA modified base"
misc_feature           14
                       note = /note="LNA modified base"
misc_feature           14
                       note = /note="nucleotide bond by a Phosphorothioate linkage"
misc_feature           14
                       note = /note="2'-O-MOE RNA nucleotide"
misc_feature           15
                       note = /note="LNA modified base"
misc_feature           15
                       note = /note="nucleotide bond by a Phosphorothioate linkage"
misc_feature           16
                       note = /note="nucleotide conjugated to a spacer molecule
                        conjugated to palmitic acid"
source                 1..16
                       mol_type = other DNA
                       organism = synthetic construct
SEQUENCE: 29
atccctggca atgtga                                                         16

SEQ ID NO: 30          moltype = DNA  length = 20
FEATURE                Location/Qualifiers
misc_feature           1..20
                       note = Gapdh Fwd
source                 1..20
                       mol_type = other DNA
                       organism = synthetic construct
SEQUENCE: 30
atcaacggga agcccatcac                                                     20

SEQ ID NO: 31          moltype = DNA  length = 21
FEATURE                Location/Qualifiers
misc_feature           1..21
                       note = Gapdh Rv
source                 1..21
                       mol_type = other DNA
                       organism = synthetic construct
SEQUENCE: 31
cttccacaat gccaaagttg t                                                   21

SEQ ID NO: 32          moltype = DNA  length = 23
FEATURE                Location/Qualifiers
misc_feature           1..23
                       note = Atp2a Fwd
source                 1..23
                       mol_type = other DNA
                       organism = synthetic construct
SEQUENCE: 32
gctcatggtc ctcaagatct cac                                                 23

SEQ ID NO: 33          moltype = DNA  length = 20
FEATURE                Location/Qualifiers
misc_feature           1..20
                       note = Atp2a Rv
source                 1..20
                       mol_type = other DNA
                       organism = synthetic construct
SEQUENCE: 33
gggtcagtgc ctcagctttg                                                     20

SEQ ID NO: 34          moltype = DNA  length = 21
FEATURE                Location/Qualifiers
misc_feature           1..21
                       note = Clcn1 Fwd
source                 1..21
                       mol_type = other DNA
                       organism = synthetic construct
SEQUENCE: 34
gtcctcagca agtttatgtc c                                                   21

SEQ ID NO: 35          moltype = DNA  length = 20
```

```
FEATURE                 Location/Qualifiers
misc_feature            1..20
                        note = Clcn1 Rv
source                  1..20
                        mol_type = other DNA
                        organism = synthetic construct
SEQUENCE: 35
gaatcctcgc cagtaattcc                                                   20

SEQ ID NO: 36           moltype = DNA  length = 20
FEATURE                 Location/Qualifiers
misc_feature            1..20
                        note = Nfix Fwd
source                  1..20
                        mol_type = other DNA
                        organism = synthetic construct
SEQUENCE: 36
tcgacgacag tgagatggag                                                   20

SEQ ID NO: 37           moltype = DNA  length = 20
FEATURE                 Location/Qualifiers
misc_feature            1..20
                        note = Nfix Rv
source                  1..20
                        mol_type = other DNA
                        organism = synthetic construct
SEQUENCE: 37
caaactcctt cagcgagtcc                                                   20

SEQ ID NO: 38           moltype = DNA  length = 25
FEATURE                 Location/Qualifiers
misc_feature            1..25
                        note = Mbnl1 ex5 F
source                  1..25
                        mol_type = other DNA
                        organism = synthetic construct
SEQUENCE: 38
agggagatg ctctcgggaa aagtg                                              25

SEQ ID NO: 39           moltype = DNA  length = 32
FEATURE                 Location/Qualifiers
misc_feature            1..32
                        note = Mbnl1 ex5 R
source                  1..32
                        mol_type = other DNA
                        organism = synthetic construct
SEQUENCE: 39
gttggctaga gcctgttggt attggaaaat ac                                     32

SEQ ID NO: 40           moltype = DNA  length = 28
FEATURE                 Location/Qualifiers
misc_feature            1..28
                        note = Probe Mbnl1: /56
source                  1..28
                        mol_type = other DNA
                        organism = synthetic construct
SEQUENCE: 40
tcgcaaatca gctgtgagga gattccct                                          28

SEQ ID NO: 41           moltype = DNA  length = 20
FEATURE                 Location/Qualifiers
misc_feature            1..20
                        note = Mbnl1 F
source                  1..20
                        mol_type = other DNA
                        organism = synthetic construct
SEQUENCE: 41
taccgattgc accaccaaac                                                   20

SEQ ID NO: 42           moltype = DNA  length = 21
FEATURE                 Location/Qualifiers
misc_feature            1..21
                        note = Mbnl1 R
source                  1..21
                        mol_type = other DNA
                        organism = synthetic construct
SEQUENCE: 42
gctgctttca gcaaagttgt c                                                 21
```

-continued

```
SEQ ID NO: 43            moltype = DNA  length = 24
FEATURE                  Location/Qualifiers
misc_feature             1..24
                         note = Mbnl2 probe
source                   1..24
                         mol_type = other DNA
                         organism = synthetic construct
SEQUENCE: 43
cccggcagac agcaccatga tcga                                             24

SEQ ID NO: 44            moltype = DNA  length = 19
FEATURE                  Location/Qualifiers
misc_feature             1..19
                         note = Mbnl2 F
source                   1..19
                         mol_type = other DNA
                         organism = synthetic construct
SEQUENCE: 44
gagacagact gccgctttg                                                   19

SEQ ID NO: 45            moltype = DNA  length = 21
FEATURE                  Location/Qualifiers
misc_feature             1..21
                         note = Mbnl2 R
source                   1..21
                         mol_type = other DNA
                         organism = synthetic construct
SEQUENCE: 45
ggttacggtg ttgtcgtttg t                                                21

SEQ ID NO: 46            moltype = DNA  length = 21
FEATURE                  Location/Qualifiers
misc_feature             1..21
                         note = Gapdh probe
source                   1..21
                         mol_type = other DNA
                         organism = synthetic construct
SEQUENCE: 46
cgcctggtca ccagggctgc t                                                21

SEQ ID NO: 47            moltype = DNA  length = 21
FEATURE                  Location/Qualifiers
misc_feature             1..21
                         note = Gapdh _For
source                   1..21
                         mol_type = other DNA
                         organism = synthetic construct
SEQUENCE: 47
caacggattt ggtcgtattg g                                                21

SEQ ID NO: 48            moltype = DNA  length = 25
FEATURE                  Location/Qualifiers
misc_feature             1..25
                         note = Gapdh _Rev
source                   1..25
                         mol_type = other DNA
                         organism = synthetic construct
SEQUENCE: 48
tgatggcaac aatatccact ttacc                                            25

SEQ ID NO: 49            moltype = DNA  length = 16
FEATURE                  Location/Qualifiers
misc_feature             1..16
                         note = MD23b-2 V2 3 OI with C6SSC6 and NHC6
misc_feature             1
                         note = /note="LNA modified base"
misc_feature             1
                         note = /note="nucleotide bond by a Phosphorothioate linkage"
misc_feature             2
                         note = /note="LNA modified base"
misc_feature             2
                         note = /note="nucleotide bond by a Phosphorothioate linkage"
misc_feature             3
                         note = /note="nucleotide bond by a Phosphorothioate linkage"
misc_feature             3
                         note = /note="5-Methyl-2'-O-Methyl cytidine "
misc_feature             3
                         note = /note="2 -O-Methyl-nucleotide"
misc_feature             4
```

| | | |
|---|---|---|
| misc_feature | | 4 |
| | | note = /note="5-Methyl-2'-O-Methyl cytidine " |
| misc_feature | | 4 |
| | | note = /note="2 -O-Methyl-nucleotide" |
| misc_feature | | 5 |
| | | note = /note="2'-O-MOE RNA nucleotide" |
| misc_feature | | 6 |
| | | note = /note="LNA modified base" |
| misc_feature | | 7 |
| | | note = /note="nucleotide bond by a Phosphorothioate linkage" |
| misc_feature | | 7 |
| | | note = /note="2'-O-MOE RNA nucleotide" |
| misc_feature | | 8 |
| | | note = /note="nucleotide bond by a Phosphorothioate linkage" |
| misc_feature | | 8 |
| | | note = /note="2 -O-Methyl-nucleotide" |
| misc_feature | | 9 |
| | | note = /note="LNA modified base" |
| misc_feature | | 9 |
| | | note = /note="nucleotide bond by a Phosphorothioate linkage" |
| misc_feature | | 9 |
| | | note = /note="2'-O-MOE RNA nucleotide" |
| misc_feature | | 11 |
| | | note = /note="LNA modified base" |
| misc_feature | | 11 |
| | | note = /note="2'-O-MOE RNA nucleotide" |
| misc_feature | | 12 |
| | | note = /note="LNA modified base" |
| misc_feature | | 14 |
| | | note = /note="LNA modified base" |
| misc_feature | | 14 |
| | | note = /note="nucleotide bond by a Phosphorothioate linkage" |
| misc_feature | | 14 |
| | | note = /note="2'-O-MOE RNA nucleotide" |
| misc_feature | | 15 |
| | | note = /note="LNA modified base" |
| misc_feature | | 15 |
| | | note = /note="nucleotide bond by a Phosphorothioate linkage" |
| misc_feature | | 16 |
| | | note = /note="nucleotide conjugated to (C6SSC6)(NHC6) conjugated to oleic acid" |
| source | | 1..16 |
| | | mol_type = other DNA |
| | | organism = synthetic construct |
| SEQUENCE: 49 | | |
| atccctggca atgtga | | 16 |
| | | |
| SEQ ID NO: 50 | | moltype = DNA length = 16 |
| FEATURE | | Location/Qualifiers |
| misc_feature | | 1..16 |
| | | note = MD23b-2 V2 3  OI with C6SSC6 and NHC3 |
| misc_feature | | 1 |
| | | note = /note="LNA modified base" |
| misc_feature | | 1 |
| | | note = /note="nucleotide bond by a Phosphorothioate linkage" |
| misc_feature | | 2 |
| | | note = /note="LNA modified base" |
| misc_feature | | 2 |
| | | note = /note="nucleotide bond by a Phosphorothioate linkage" |
| misc_feature | | 3 |
| | | note = /note="nucleotide bond by a Phosphorothioate linkage" |
| misc_feature | | 3 |
| | | note = /note="5-Methyl-2'-O-Methyl cytidine " |
| misc_feature | | 3 |
| | | note = /note="2 -O-Methyl-nucleotide" |
| misc_feature | | 4 |
| | | note = /note="nucleotide bond by a Phosphorothioate linkage" |
| misc_feature | | 4 |
| | | note = /note="5-Methyl-2'-O-Methyl cytidine " |
| misc_feature | | 4 |
| | | note = /note="2 -O-Methyl-nucleotide" |
| misc_feature | | 5 |
| | | note = /note="2'-O-MOE RNA nucleotide" |
| misc_feature | | 6 |
| | | note = /note="LNA modified base" |
| misc_feature | | 7 |
| | | note = /note="nucleotide bond by a Phosphorothioate linkage" |
| misc_feature | | 7 |

|  |  |
|---|---|
| | note = /note="2'-O-MOE RNA nucleotide" |
| misc_feature | 8 |
| | note = /note="nucleotide bond by a Phosphorothioate linkage" |
| misc_feature | 8 |
| | note = /note="2 -O-Methyl-nucleotide" |
| misc_feature | 9 |
| | note = /note="LNA modified base" |
| misc_feature | 9 |
| | note = /note="nucleotide bond by a Phosphorothioate linkage" |
| misc_feature | 9 |
| | note = /note="2'-O-MOE RNA nucleotide" |
| misc_feature | 11 |
| | note = /note="LNA modified base" |
| misc_feature | 11 |
| | note = /note="2'-O-MOE RNA nucleotide" |
| misc_feature | 12 |
| | note = /note="LNA modified base" |
| misc_feature | 14 |
| | note = /note="LNA modified base" |
| misc_feature | 14 |
| | note = /note="nucleotide bond by a Phosphorothioate linkage" |
| misc_feature | 14 |
| | note = /note="2'-O-MOE RNA nucleotide" |
| misc_feature | 15 |
| | note = /note="LNA modified base" |
| misc_feature | 15 |
| | note = /note="nucleotide bond by a Phosphorothioate linkage" |
| misc_feature | 16 |
| | note = /note="nucleotide conjugated to (C6SSC6)(NHC3) conjugated to oleic acid" |
| source | 1..16 |
| | mol_type = other DNA |
| | organism = synthetic construct |
| SEQUENCE: 50 | |
| atccctggca atgtga | 16 |
| SEQ ID NO: 51 | moltype = DNA  length = 16 |
| FEATURE | Location/Qualifiers |
| misc_feature | 1..16 |
| | note = MD23b-2-PS/PO 5 OI without spacer molecule |
| misc_feature | 1 |
| | note = /note="nucleotide conjugated to oleic acid" |
| misc_feature | 1 |
| | note = /note="nucleotide bond by a Phosphorothioate linkage" |
| misc_feature | 1 |
| | note = /note="LNA nucleotide" |
| misc_feature | 2 |
| | note = /note="2'-O-MOE RNA nucleotides " |
| misc_feature | 3 |
| | note = /note="5-Methyl-2'-O-Methyl cytidine" |
| misc_feature | 4 |
| | note = /note="5-Methyl-2'-O-Methyl cytidine" |
| misc_feature | 5 |
| | note = /note="5-Methyl-2'-O-Methyl cytidine" |
| misc_feature | 6 |
| | note = /note="nucleotide bond by a Phosphorothioate linkage" |
| misc_feature | 6 |
| | note = /note="LNA nucleotide" |
| misc_feature | 7 |
| | note = /note="2 -O-Methyl-nucleotide" |
| misc_feature | 8 |
| | note = /note="2 -O-Methyl-nucleotide" |
| misc_feature | 9 |
| | note = /note="nucleotide bond by a Phosphorothioate linkage" |
| misc_feature | 9 |
| | note = /note="5-Methyl-2'-O-Methyl cytidine" |
| misc_feature | 10 |
| | note = /note="LNA nucleotide" |
| misc_feature | 11 |
| | note = /note="nucleotide bond by a Phosphorothioate linkage" |
| misc_feature | 11 |
| | note = /note="2'-O-MOE RNA nucleotides " |
| misc_feature | 12 |
| | note = /note="nucleotide bond by a Phosphorothioate linkage" |
| misc_feature | 12 |
| | note = /note="LNA nucleotide" |
| misc_feature | 13 |
| | note = /note="LNA nucleotide" |
| misc_feature | 14 |

|              | note = /note="nucleotide bond by a Phosphorothioate linkage" |
| misc_feature | 14 |
|              | note = /note="2'-O-MOE RNA nucleotides " |
| misc_feature | 15 |
|              | note = /note="nucleotide bond by a Phosphorothioate linkage" |
| misc_feature | 15 |
|              | note = /note="LNA nucleotide" |
| misc_feature | 16 |
|              | note = /note="LNA nucleotide" |
| source       | 1..16 |
|              | mol_type = other DNA |
|              | organism = synthetic construct |

SEQUENCE: 51
atccctggca atgtga                                                16

| SEQ ID NO: 52 | moltype = DNA  length = 16 |
| FEATURE      | Location/Qualifiers |
| misc_feature | 1..16 |
|              | note = functional equivalent sequence of antimiR-23b-3p |
| source       | 1..16 |
|              | mol_type = other DNA |
|              | organism = synthetic construct |

SEQUENCE: 52
ytccctggca atgtga                                                16

| SEQ ID NO: 53 | moltype = DNA  length = 16 |
| FEATURE      | Location/Qualifiers |
| misc_feature | 1..16 |
|              | note = functional equivalent sequence of antimiR-23b-3p |
| source       | 1..16 |
|              | mol_type = other DNA |
|              | organism = synthetic construct |

SEQUENCE: 53
atccctygca atgtga                                                16

| SEQ ID NO: 54 | moltype = DNA  length = 16 |
| FEATURE      | Location/Qualifiers |
| misc_feature | 1..16 |
|              | note = functional equivalent sequence of antimiR-23b-3p |
| source       | 1..16 |
|              | mol_type = other DNA |
|              | organism = synthetic construct |

SEQUENCE: 54
atccctgyca atgtga                                                16

| SEQ ID NO: 55 | moltype = DNA  length = 16 |
| FEATURE      | Location/Qualifiers |
| misc_feature | 1..16 |
|              | note = functional equivalent sequence of antimiR-23b-3p |
| source       | 1..16 |
|              | mol_type = other DNA |
|              | organism = synthetic construct |

SEQUENCE: 55
atccctggcy atgtga                                                16

| SEQ ID NO: 56 | moltype = DNA  length = 16 |
| FEATURE      | Location/Qualifiers |
| misc_feature | 1..16 |
|              | note = functional equivalent sequence of antimiR-23b-3p |
| source       | 1..16 |
|              | mol_type = other DNA |
|              | organism = synthetic construct |

SEQUENCE: 56
atccctggca ytgtga                                                16

| SEQ ID NO: 57 | moltype = DNA  length = 16 |
| FEATURE      | Location/Qualifiers |
| misc_feature | 1..16 |
|              | note = functional equivalent sequence of antimiR-23b-3p |
| source       | 1..16 |
|              | mol_type = other DNA |
|              | organism = synthetic construct |

SEQUENCE: 57
atccctggca atytga                                                16

| SEQ ID NO: 58 | moltype = DNA  length = 16 |
| FEATURE      | Location/Qualifiers |
| misc_feature | 1..16 |
|              | note = functional equivalent sequence of antimiR-23b-3p |

```
source                         1..16
                               mol_type = other DNA
                               organism = synthetic construct
SEQUENCE: 58
atccctggca atgtya                                                           16

SEQ ID NO: 59                  moltype = DNA  length = 16
FEATURE                        Location/Qualifiers
misc_feature                   1..16
                               note = functional equivalent sequence of antimiR-23b-3p
source                         1..16
                               mol_type = other DNA
                               organism = synthetic construct
SEQUENCE: 59
atccctggca atgtgy                                                           16

SEQ ID NO: 60                  moltype = DNA  length = 16
FEATURE                        Location/Qualifiers
misc_feature                   1..16
                               note = functional equivalent sequence of antimiR-23b-3p
source                         1..16
                               mol_type = other DNA
                               organism = synthetic construct
SEQUENCE: 60
gtccctggca atgtga                                                           16

SEQ ID NO: 61                  moltype = DNA  length = 16
FEATURE                        Location/Qualifiers
misc_feature                   1..16
                               note = functional equivalent sequence of antimiR-23b-3p
misc_feature                   3
                               note = /note="t = uracil"
source                         1..16
                               mol_type = other DNA
                               organism = synthetic construct
SEQUENCE: 61
attcctggca atgtga                                                           16

SEQ ID NO: 62                  moltype = DNA  length = 16
FEATURE                        Location/Qualifiers
misc_feature                   1..16
                               note = functional equivalent sequence of antimiR-23b-3p
misc_feature                   4
                               note = /note="t = uracil"
source                         1..16
                               mol_type = other DNA
                               organism = synthetic construct
SEQUENCE: 62
atctctggca atgtga                                                           16

SEQ ID NO: 63                  moltype = DNA  length = 16
FEATURE                        Location/Qualifiers
misc_feature                   1..16
                               note = functional equivalent sequence of antimiR-23b-3p
misc_feature                   5
                               note = /note="t = uracil"
source                         1..16
                               mol_type = other DNA
                               organism = synthetic construct
SEQUENCE: 63
atccttggca atgtga                                                           16

SEQ ID NO: 64                  moltype = DNA  length = 16
FEATURE                        Location/Qualifiers
misc_feature                   1..16
                               note = functional equivalent sequence of antimiR-23b-3p
misc_feature                   8
                               note = /note="t = uracil"
source                         1..16
                               mol_type = other DNA
                               organism = synthetic construct
SEQUENCE: 64
atccctggta atgtga                                                           16

SEQ ID NO: 65                  moltype = DNA  length = 16
FEATURE                        Location/Qualifiers
misc_feature                   1..16
                               note = functional equivalent sequence of antimiR-23b-3p
source                         1..16
```

```
                        mol_type = other DNA
                        organism = synthetic construct
SEQUENCE: 65
atccctggcg atgtga                                                       16

SEQ ID NO: 66           moltype = DNA   length = 16
FEATURE                 Location/Qualifiers
misc_feature            1..16
                        note = functional equivalent sequence of antimiR-23b-3p
source                  1..16
                        mol_type = other DNA
                        organism = synthetic construct
SEQUENCE: 66
atccctggca gtgtga                                                       16

SEQ ID NO: 67           moltype = DNA   length = 16
FEATURE                 Location/Qualifiers
misc_feature            1..16
                        note = functional equivalent sequence of antimiR-23b-3p
source                  1..16
                        mol_type = other DNA
                        organism = synthetic construct
SEQUENCE: 67
atccctggca atgtgg                                                       16

SEQ ID NO: 68           moltype = DNA   length = 16
FEATURE                 Location/Qualifiers
misc_feature            1..16
                        note = functional equivalent sequence of antimiR-23b-3p
misc_feature            1
                        note = /note="n = hypoxanthine "
source                  1..16
                        mol_type = other DNA
                        organism = synthetic construct
SEQUENCE: 68
ntccctggca atgtga                                                       16

SEQ ID NO: 69           moltype = DNA   length = 16
FEATURE                 Location/Qualifiers
misc_feature            1..16
                        note = functional equivalent sequence of antimiR-23b-3p
misc_feature            10
                        note = /note="n = hypoxanthine "
source                  1..16
                        mol_type = other DNA
                        organism = synthetic construct
SEQUENCE: 69
atccctggcn atgtga                                                       16

SEQ ID NO: 70           moltype = DNA   length = 16
FEATURE                 Location/Qualifiers
misc_feature            1..16
                        note = functional equivalent sequence of antimiR-23b-3p
misc_feature            11
                        note = /note="n = hypoxanthine "
source                  1..16
                        mol_type = other DNA
                        organism = synthetic construct
SEQUENCE: 70
atccctggca ntgtga                                                       16

SEQ ID NO: 71           moltype = DNA   length = 16
FEATURE                 Location/Qualifiers
misc_feature            1..16
                        note = functional equivalent sequence of antimiR-23b-3p
misc_feature            16
                        note = /note="n = hypoxanthine "
source                  1..16
                        mol_type = other DNA
                        organism = synthetic construct
SEQUENCE: 71
atccctggca atgtgn                                                       16

SEQ ID NO: 72           moltype = DNA   length = 16
FEATURE                 Location/Qualifiers
misc_feature            1..16
                        note = functional equivalent sequence of antimiR-23b-3p
misc_feature            2
                        note = /note="n = hypoxanthine "
```

```
source                  1..16
                        mol_type = other DNA
                        organism = synthetic construct
SEQUENCE: 72
anccctggca atgtga                                                               16

SEQ ID NO: 73           moltype = DNA   length = 16
FEATURE                 Location/Qualifiers
misc_feature            1..16
                        note = functional equivalent sequence of antimiR-23b-3p
misc_feature            6
                        note = /note="n = hypoxanthine "
source                  1..16
                        mol_type = other DNA
                        organism = synthetic construct
SEQUENCE: 73
atcccnggca atgtga                                                               16

SEQ ID NO: 74           moltype = DNA   length = 16
FEATURE                 Location/Qualifiers
misc_feature            1..16
                        note = functional equivalent sequence of antimiR-23b-3p
misc_feature            12
                        note = /note="n = hypoxanthine "
source                  1..16
                        mol_type = other DNA
                        organism = synthetic construct
SEQUENCE: 74
atccctggca angtga                                                               16

SEQ ID NO: 75           moltype = DNA   length = 16
FEATURE                 Location/Qualifiers
misc_feature            1..16
                        note = functional equivalent sequence of antimiR-23b-3p
misc_feature            14
                        note = /note="n = hypoxanthine "
source                  1..16
                        mol_type = other DNA
                        organism = synthetic construct
SEQUENCE: 75
atccctggca atgnga                                                               16

SEQ ID NO: 76           moltype = DNA   length = 16
FEATURE                 Location/Qualifiers
misc_feature            1..16
                        note = functional equivalent sequence of antimiR-23b-3p
misc_feature            7
                        note = /note="n = hypoxanthine "
source                  1..16
                        mol_type = other DNA
                        organism = synthetic construct
SEQUENCE: 76
atccctngca atgtga                                                               16

SEQ ID NO: 77           moltype = DNA   length = 16
FEATURE                 Location/Qualifiers
misc_feature            1..16
                        note = functional equivalent sequence of antimiR-23b-3p
misc_feature            8
                        note = /note="n = hypoxanthine "
source                  1..16
                        mol_type = other DNA
                        organism = synthetic construct
SEQUENCE: 77
atccctgnca atgtga                                                               16

SEQ ID NO: 78           moltype = DNA   length = 16
FEATURE                 Location/Qualifiers
misc_feature            1..16
                        note = functional equivalent sequence of antimiR-23b-3p
misc_feature            13
                        note = /note="n = hypoxanthine "
source                  1..16
                        mol_type = other DNA
                        organism = synthetic construct
SEQUENCE: 78
atccctggca atntga                                                               16

SEQ ID NO: 79           moltype = DNA   length = 16
```

```
FEATURE                 Location/Qualifiers
misc_feature            1..16
                        note = functional equivalent sequence of antimiR-23b-3p
misc_feature            15
                        note = /note="n = hypoxanthine "
source                  1..16
                        mol_type = other DNA
                        organism = synthetic construct
SEQUENCE: 79
atccctggca atgtna                                                              16

SEQ ID NO: 80           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 80
ttygatcaag cacaa                                                               15

SEQ ID NO: 81           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 81
ttayatcaag cacaa                                                               15

SEQ ID NO: 82           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 82
ttagytcaag cacaa                                                               15

SEQ ID NO: 83           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 83
ttagatcyag cacaa                                                               15

SEQ ID NO: 84           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 84
ttagatcayg cacaa                                                               15

SEQ ID NO: 85           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 85
ttagatcaay cacaa                                                               15

SEQ ID NO: 86           moltype = DNA  length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 86
```

```
ttagatcaag cycaa                                                15

SEQ ID NO: 87           moltype = DNA   length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 87
ttagatcaag cacya                                                15

SEQ ID NO: 88           moltype = DNA   length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 88
ttagatcaag cacay                                                15

SEQ ID NO: 89           moltype = DNA   length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 89
ttggatcaag cacaa                                                15

SEQ ID NO: 90           moltype = DNA   length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 90
ttaggtcaag cacaa                                                15

SEQ ID NO: 91           moltype = DNA   length = 15
FEATURE                 Location/Qualifiers
misc_feature            1..15
                        note = /note="combined DNA/RNA molecule" /note="functional
                         equivalent sequence of antimiR-218-5p"
misc_feature            8
                        note = /note="t = uracil"
source                  1..15
                        mol_type = other DNA
                        organism = synthetic construct
SEQUENCE: 91
ttagattaag cacaa                                                15

SEQ ID NO: 92           moltype = DNA   length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 92
ttagatcgag cacaa                                                15

SEQ ID NO: 93           moltype = DNA   length = 15
FEATURE                 Location/Qualifiers
misc_feature            1..15
                        note = functional equivalent sequence of antimiR-218-5p
source                  1..15
                        mol_type = other DNA
                        organism = synthetic construct
SEQUENCE: 93
ttagatcagg cacaa                                                15

SEQ ID NO: 94           moltype = DNA   length = 15
FEATURE                 Location/Qualifiers
misc_feature            1..15
                        note = functional equivalent sequence of antimiR-218-5p
```

```
misc_feature           11
                       note = /note="t = uracil"
source                 1..15
                       mol_type = other DNA
                       organism = synthetic construct
SEQUENCE: 94
ttagatcaag tacaa                                                        15

SEQ ID NO: 95          moltype = DNA  length = 15
FEATURE                Location/Qualifiers
misc_feature           1..15
                       note = functional equivalent sequence of antimiR-218-5p
source                 1..15
                       mol_type = other DNA
                       organism = synthetic construct
SEQUENCE: 95
ttagatcaag cgcaa                                                        15

SEQ ID NO: 96          moltype = DNA  length = 15
FEATURE                Location/Qualifiers
misc_feature           1..15
                       note = /note="combined DNA/RNA molecule" /note="functional
                        equivalent sequence of antimiR-218-5p"
misc_feature           13
                       note = /note="t = uracil"
source                 1..15
                       mol_type = other DNA
                       organism = synthetic construct
SEQUENCE: 96
ttagatcaag cataa                                                        15

SEQ ID NO: 97          moltype = DNA  length = 15
FEATURE                Location/Qualifiers
misc_feature           1..15
                       note = functional equivalent sequence of antimiR-218-5p
source                 1..15
                       mol_type = other DNA
                       organism = synthetic construct
SEQUENCE: 97
ttagatcaag cacga                                                        15

SEQ ID NO: 98          moltype = DNA  length = 15
FEATURE                Location/Qualifiers
misc_feature           1..15
                       note = functional equivalent sequence of antimiR-218-5p
source                 1..15
                       mol_type = other DNA
                       organism = synthetic construct
SEQUENCE: 98
ttagatcaag cacag                                                        15

SEQ ID NO: 99          moltype = DNA  length = 15
FEATURE                Location/Qualifiers
misc_feature           1..15
                       note = functional equivalent sequence of antimiR-218-5p
misc_feature           3
                       note = /note="n = hypoxanthine "
source                 1..15
                       mol_type = other DNA
                       organism = synthetic construct
SEQUENCE: 99
ttngatcaag cacaa                                                        15

SEQ ID NO: 100         moltype = DNA  length = 15
FEATURE                Location/Qualifiers
misc_feature           1..15
                       note = functional equivalent sequence of antimiR-218-5p
misc_feature           5
                       note = /note="n = hypoxanthine "
source                 1..15
                       mol_type = other DNA
                       organism = synthetic construct
SEQUENCE: 100
ttagntcaag cacaa                                                        15

SEQ ID NO: 101         moltype = DNA  length = 15
FEATURE                Location/Qualifiers
misc_feature           1..15
                       note = functional equivalent sequence of antimiR-218-5p
```

```
                          misc_feature          8
                                                note = /note="n = hypoxanthine "
                          source                1..15
                                                mol_type = other DNA
                                                organism = synthetic construct
                          SEQUENCE: 101
                          ttagatcnag cacaa                                              15

SEQ ID NO: 102        moltype = DNA  length = 15
                          FEATURE               Location/Qualifiers
                          misc_feature          1..15
                                                note = functional equivalent sequence of antimiR-218-5p
                          misc_feature          9
                                                note = /note="n = hypoxanthine "
                          source                1..15
                                                mol_type = other DNA
                                                organism = synthetic construct
                          SEQUENCE: 102
                          ttagatcang cacaa                                              15

SEQ ID NO: 103        moltype = DNA  length = 15
                          FEATURE               Location/Qualifiers
                          misc_feature          1..15
                                                note = functional equivalent sequence of antimiR-218-5p
                          misc_feature          12
                                                note = /note="n = hypoxanthine "
                          source                1..15
                                                mol_type = other DNA
                                                organism = synthetic construct
                          SEQUENCE: 103
                          ttagatcaag cncaa                                              15

SEQ ID NO: 104        moltype = DNA  length = 15
                          FEATURE               Location/Qualifiers
                          misc_feature          1..15
                                                note = functional equivalent sequence of antimiR-218-5p
                          misc_feature          14
                                                note = /note="n = hypoxanthine "
                          source                1..15
                                                mol_type = other DNA
                                                organism = synthetic construct
                          SEQUENCE: 104
                          ttagatcaag cacna                                              15

SEQ ID NO: 105        moltype = DNA  length = 15
                          FEATURE               Location/Qualifiers
                          misc_feature          1..15
                                                note = functional equivalent sequence of antimiR-218-5p
                          misc_feature          15
                                                note = /note="n = hypoxanthine "
                          source                1..15
                                                mol_type = other DNA
                                                organism = synthetic construct
                          SEQUENCE: 105
                          ttagatcaag cacan                                              15

SEQ ID NO: 106        moltype = DNA  length = 15
                          FEATURE               Location/Qualifiers
                          misc_feature          1..15
                                                note = functional equivalent sequence of antimiR-218-5p
                          misc_feature          1
                                                note = /note="n = hypoxanthine "
                          source                1..15
                                                mol_type = other DNA
                                                organism = synthetic construct
                          SEQUENCE: 106
                          ntagatcaag cacaa                                              15

SEQ ID NO: 107        moltype = DNA  length = 15
                          FEATURE               Location/Qualifiers
                          misc_feature          1..15
                                                note = functional equivalent sequence of antimiR-218-5p
                          misc_feature          2
                                                note = /note="n = hypoxanthine "
                          source                1..15
                                                mol_type = other DNA
                                                organism = synthetic construct
                          SEQUENCE: 107
                          tnagatcaag cacaa                                              15
```

```
SEQ ID NO: 108           moltype = DNA  length = 15
FEATURE                  Location/Qualifiers
misc_feature             1..15
                         note = functional equivalent sequence of antimiR-218-5p
misc_feature             6
                         note = /note="n = hypoxanthine "
source                   1..15
                         mol_type = other DNA
                         organism = synthetic construct
SEQUENCE: 108
ttagancaag cacaa                                                          15

SEQ ID NO: 109           moltype = DNA  length = 15
FEATURE                  Location/Qualifiers
misc_feature             1..15
                         note = functional equivalent sequence of antimiR-218-5p
misc_feature             4
                         note = /note="n = hypoxanthine "
source                   1..15
                         mol_type = other DNA
                         organism = synthetic construct
SEQUENCE: 109
ttanatcaag cacaa                                                          15

SEQ ID NO: 110           moltype = DNA  length = 15
FEATURE                  Location/Qualifiers
misc_feature             1..15
                         note = functional equivalent sequence of antimiR-218-5p
misc_feature             10
                         note = /note="n = hypoxanthine "
source                   1..15
                         mol_type = other DNA
                         organism = synthetic construct
SEQUENCE: 110
ttagatcaan cacaa                                                          15

SEQ ID NO: 111           moltype = DNA  length = 16
FEATURE                  Location/Qualifiers
misc_feature             1..16
                         note = 111
misc_feature             1
                         note = /note="LNA modified base"
misc_feature             1..16
                         note = /note="nucleotide bond by a Phosphorothioate linkage"
misc_feature             4
                         note = /note="LNA modified base"
misc_feature             7
                         note = /note="LNA modified base"
misc_feature             10
                         note = /note="LNA modified base"
misc_feature             13
                         note = /note="LNA modified base"
misc_feature             16
                         note = /note="nucleotide conjugated to digoxigenina
                          NHS-ester"
source                   1..16
                         mol_type = other DNA
                         organism = synthetic construct
SEQUENCE: 111
tcacattgcc agggat                                                         16

SEQ ID NO: 112           moltype = RNA  length = 21
FEATURE                  Location/Qualifiers
modified_base            3
                         mod_base = OTHER
                         note = thymine
modified_base            6
                         mod_base = OTHER
                         note = thymine
modified_base            10
                         mod_base = OTHER
                         note = thymine
modified_base            16
                         mod_base = OTHER
                         note = thymine
modified_base            18
                         mod_base = OTHER
                         note = thymine
```

```
modified_base          21
                       mod_base = OTHER
                       note = thymine
misc_feature           1..21
                       note = 112
misc_feature           1
                       note = /note="nucleotide bond by a Phosphorothioate linkage
                       "
misc_feature           2
                       note = /note="nucleotide bond by a Phosphorothioate linkage
                       "
misc_feature           18
                       note = /note="nucleotide bond by a Phosphorothioate linkage
                       "
misc_feature           19
                       note = /note="nucleotide bond by a Phosphorothioate linkage
                       "
misc_feature           20
                       note = /note="nucleotide bond by a Phosphorothioate linkage
                       "
source                 1..21
                       mol_type = other RNA
                       organism = synthetic construct
SEQUENCE: 112
ggtaatccct ggcaatgtga t                                              21

SEQ ID NO: 113         moltype = RNA  length = 21
FEATURE                Location/Qualifiers
modified_base          3
                       mod_base = OTHER
                       note = thymine
modified_base          6
                       mod_base = OTHER
                       note = thymine
modified_base          10
                       mod_base = OTHER
                       note = thymine
modified_base          16
                       mod_base = OTHER
                       note = thymine
modified_base          18
                       mod_base = OTHER
                       note = thymine
modified_base          21
                       mod_base = OTHER
                       note = thymine
misc_feature           1..21
                       note = 113
misc_feature           1
                       note = /note="nucleotide conjugated to NHC5 conjugated to
                       oleic acid"
misc_feature           1
                       note = /note="nucleotide bond by a Phosphorothioate linkage
                       "
misc_feature           2
                       note = /note="nucleotide bond by a Phosphorothioate linkage
                       "
misc_feature           18
                       note = /note="nucleotide bond by a Phosphorothioate linkage
                       "
misc_feature           19
                       note = /note="nucleotide bond by a Phosphorothioate linkage
                       "
misc_feature           20
                       note = /note="nucleotide bond by a Phosphorothioate linkage
                       "
source                 1..21
                       mol_type = other RNA
                       organism = synthetic construct
SEQUENCE: 113
ggtaatccct ggcaatgtga t                                              21

SEQ ID NO: 114         moltype = RNA  length = 21
FEATURE                Location/Qualifiers
modified_base          3
                       mod_base = OTHER
                       note = thymine
modified_base          6
                       mod_base = OTHER
```

```
                        note = thymine
modified_base           10
                        mod_base = OTHER
                        note = thymine
modified_base           16
                        mod_base = OTHER
                        note = thymine
modified_base           18
                        mod_base = OTHER
                        note = thymine
modified_base           21
                        mod_base = OTHER
                        note = thymine
misc_feature            1..21
                        note = 114
misc_feature            1
                        note = /note="nucleotide conjugated to NHC5 conjugated to
                         linoleic acid"
misc_feature            1
                        note = /note="nucleotide bond by a Phosphorothioate linkage
                        "
misc_feature            1
                        note = /note="nucleotide bond by a Phosphorothioate linkage
                        "
misc_feature            2
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 114
ggtaatccct ggcaatgtga t                                                   21

SEQ ID NO: 115          moltype = RNA   length = 21
FEATURE                 Location/Qualifiers
modified_base           3
                        mod_base = OTHER
                        note = thymine
modified_base           6
                        mod_base = OTHER
                        note = thymine
modified_base           10
                        mod_base = OTHER
                        note = thymine
modified_base           16
                        mod_base = OTHER
                        note = thymine
modified_base           18
                        mod_base = OTHER
                        note = thymine
modified_base           21
                        mod_base = OTHER
                        note = thymine
misc_feature            1..21
                        note = 115
misc_feature            1
                        note = /note="nucleotide conjugated to Octyl conjugated to
                         Tocopherol"
```

| | | |
|---|---|---|
| misc_feature | 1 | |
| | note = /note="nucleotide bond by a Phosphorothioate linkage" | |
| misc_feature | 2 | |
| | note = /note="nucleotide bond by a Phosphorothioate linkage" | |
| misc_feature | 18 | |
| | note = /note="nucleotide bond by a Phosphorothioate linkage" | |
| misc_feature | 19 | |
| | note = /note="nucleotide bond by a Phosphorothioate linkage" | |
| misc_feature | 20 | |
| | note = /note="nucleotide bond by a Phosphorothioate linkage" | |
| source | 1..21 | |
| | mol_type = other RNA | |
| | organism = synthetic construct | |
| SEQUENCE: 115 | | |
| ggtaatccct ggcaatgtga t | | 21 |
| | | |
| SEQ ID NO: 116 | moltype = RNA length = 21 | |
| FEATURE | Location/Qualifiers | |
| modified_base | 3 | |
| | mod_base = OTHER | |
| | note = thymine | |
| modified_base | 6 | |
| | mod_base = OTHER | |
| | note = thymine | |
| modified_base | 10 | |
| | mod_base = OTHER | |
| | note = thymine | |
| modified_base | 16 | |
| | mod_base = OTHER | |
| | note = thymine | |
| modified_base | 18 | |
| | mod_base = OTHER | |
| | note = thymine | |
| modified_base | 21 | |
| | mod_base = OTHER | |
| | note = thymine | |
| misc_feature | 1..21 | |
| | note = 116 | |
| misc_feature | 1 | |
| | note = /note="nucleotide conjugated to Pro conjugated to Cholesterol" | |
| misc_feature | 1 | |
| | note = /note="nucleotide bond by a Phosphorothioate linkage" | |
| misc_feature | 2 | |
| | note = /note="nucleotide bond by a Phosphorothioate linkage" | |
| misc_feature | 18 | |
| | note = /note="nucleotide bond by a Phosphorothioate linkage" | |
| misc_feature | 19 | |
| | note = /note="nucleotide bond by a Phosphorothioate linkage" | |
| misc_feature | 20 | |
| | note = /note="nucleotide bond by a Phosphorothioate linkage" | |
| source | 1..21 | |
| | mol_type = other RNA | |
| | organism = synthetic construct | |
| SEQUENCE: 116 | | |
| ggtaatccct ggcaatgtga t | | 21 |
| | | |
| SEQ ID NO: 117 | moltype = RNA length = 21 | |
| FEATURE | Location/Qualifiers | |
| modified_base | 3 | |
| | mod_base = OTHER | |
| | note = thymine | |
| modified_base | 6 | |
| | mod_base = OTHER | |
| | note = thymine | |
| modified_base | 10 | |
| | mod_base = OTHER | |
| | note = thymine | |
| modified_base | 16 | |

```
                        mod_base = OTHER
                        note = thymine
modified_base           18
                        mod_base = OTHER
                        note = thymine
modified_base           21
                        mod_base = OTHER
                        note = thymine
misc_feature            1..21
                        note = 117
misc_feature            1
                        note = /note="nucleotide conjugated to NHC5 conjugated to
                         Palmitic Acid"
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 117
ggtaatccct ggcaatgtga t                                                    21

SEQ ID NO: 118          moltype = RNA   length = 21
FEATURE                 Location/Qualifiers
modified_base           3
                        mod_base = OTHER
                        note = thymine
modified_base           6
                        mod_base = OTHER
                        note = thymine
modified_base           10
                        mod_base = OTHER
                        note = thymine
modified_base           16
                        mod_base = OTHER
                        note = thymine
modified_base           18
                        mod_base = OTHER
                        note = thymine
modified_base           21
                        mod_base = OTHER
                        note = thymine
misc_feature            1..21
                        note = 118
misc_feature            1
                        note = /note="nucleotide conjugated to NHC5 conjugated to
                         Elaidic Acid"
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 118
ggtaatccct ggcaatgtga t                                                    21
```

```
SEQ ID NO: 119          moltype = RNA  length = 21
FEATURE                 Location/Qualifiers
modified_base           3
                        mod_base = OTHER
                        note = thymine
modified_base           6
                        mod_base = OTHER
                        note = thymine
modified_base           10
                        mod_base = OTHER
                        note = thymine
modified_base           16
                        mod_base = OTHER
                        note = thymine
modified_base           18
                        mod_base = OTHER
                        note = thymine
modified_base           21
                        mod_base = OTHER
                        note = thymine
misc_feature            1..21
                        note = 119
misc_feature            1
                        note = /note="nucleotide conjugated to NHC5 conjugated to
                        Estearic Acid"
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 119
ggtaatccct ggcaatgtga t                                                   21

SEQ ID NO: 120          moltype = RNA  length = 21
FEATURE                 Location/Qualifiers
modified_base           3
                        mod_base = OTHER
                        note = thymine
modified_base           6
                        mod_base = OTHER
                        note = thymine
modified_base           10
                        mod_base = OTHER
                        note = thymine
modified_base           16
                        mod_base = OTHER
                        note = thymine
modified_base           18
                        mod_base = OTHER
                        note = thymine
modified_base           21
                        mod_base = OTHER
                        note = thymine
misc_feature            1..21
                        note = 120
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
```

|                | |                                                                              |
|----------------|-|------------------------------------------------------------------------------|
|                | | note = /note="nucleotide bond by a Phosphorothioate linkage"                 |
| misc_feature   | 20                                                                            |
|                | | note = /note="nucleotide bond by a Phosphorothioate linkage"                 |
| misc_feature   | 21                                                                            |
|                | | note = /note="nucleotide conjugated to Teg conjugated to Cholesterol"        |
| source         | 1..21                                                                         |
|                | | mol_type = other RNA                                                         |
|                | | organism = synthetic construct                                               |
| SEQUENCE: 120  |                                                                               |
| ggtaatccct ggcaatgtga t | 21                                                                   |

| SEQ ID NO: 121 | moltype = RNA   length = 21 |
|----------------|-----------------------------|
| FEATURE        | Location/Qualifiers         |
| modified_base  | 4                           |
|                | mod_base = OTHER            |
|                | note = thymine              |
| modified_base  | 7..8                        |
|                | mod_base = OTHER            |
|                | note = thymine              |
| modified_base  | 12                          |
|                | mod_base = OTHER            |
|                | note = thymine              |
| misc_feature   | 1..21                       |
|                | note = 121                  |
| misc_feature   | 1                           |
|                | note = /note="nucleotide bond by a Phosphorothioate linkage" |
| misc_feature   | 2                           |
|                | note = /note="nucleotide bond by a Phosphorothioate linkage" |
| misc_feature   | 18                          |
|                | note = /note="nucleotide bond by a Phosphorothioate linkage" |
| misc_feature   | 19                          |
|                | note = /note="nucleotide bond by a Phosphorothioate linkage" |
| misc_feature   | 20                          |
|                | note = /note="nucleotide bond by a Phosphorothioate linkage" |
| source         | 1..21                       |
|                | mol_type = other RNA        |
|                | organism = synthetic construct |
| SEQUENCE: 121  |                             |
| acatggttag atcaagcaca a | 21                 |

| SEQ ID NO: 122 | moltype = RNA   length = 21 |
|----------------|-----------------------------|
| FEATURE        | Location/Qualifiers         |
| modified_base  | 4                           |
|                | mod_base = OTHER            |
|                | note = thymine              |
| modified_base  | 7..8                        |
|                | mod_base = OTHER            |
|                | note = thymine              |
| modified_base  | 12                          |
|                | mod_base = OTHER            |
|                | note = thymine              |
| misc_feature   | 1..21                       |
|                | note = 122                  |
| misc_feature   | 1                           |
|                | note = /note="nucleotide bond by a Phosphorothioate linkage" |
| misc_feature   | 2                           |
|                | note = /note="nucleotide bond by a Phosphorothioate linkage" |
| misc_feature   | 18                          |
|                | note = /note="nucleotide bond by a Phosphorothioate linkage" |
| misc_feature   | 19                          |
|                | note = /note="nucleotide bond by a Phosphorothioate linkage" |
| misc_feature   | 20                          |
|                | note = /note="nucleotide bond by a Phosphorothioate linkage" |
| misc_feature   | 21                          |
|                | note = /note="nucleotide conjugated to Teg conjugated to Cholesterol" |

```
                                              -continued source                  1..21
                        mol_type = other RNA
                        organism = synthetic construct
SEQUENCE: 122
acatggttag atcaagcaca a                                                   21

SEQ ID NO: 123          moltype = RNA  length = 21
FEATURE                 Location/Qualifiers
modified_base           4
                        mod_base = OTHER
                        note = thymine
modified_base           7..8
                        mod_base = OTHER
                        note = thymine
modified_base           12
                        mod_base = OTHER
                        note = thymine
misc_feature            1..21
                        note = 123
misc_feature            1
                        note = /note="nucleotide conjugated to NHC5 conjugated to
                        Oleic Acid"
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 123
acatggttag atcaagcaca a                                                   21

SEQ ID NO: 124          moltype = RNA  length = 21
FEATURE                 Location/Qualifiers
modified_base           4
                        mod_base = OTHER
                        note = thymine
modified_base           7..8
                        mod_base = OTHER
                        note = thymine
modified_base           12
                        mod_base = OTHER
                        note = thymine
misc_feature            1..21
                        note = 124
misc_feature            1
                        note = /note="nucleotide conjugated to Pro conjugated to
                        Cholesterol"
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 124
acatggttag atcaagcaca a                                                   21
```

```
SEQ ID NO: 125         moltype = RNA   length = 21
FEATURE                Location/Qualifiers
modified_base          4
                       mod_base = OTHER
                       note = thymine
modified_base          7..8
                       mod_base = OTHER
                       note = thymine
modified_base          12
                       mod_base = OTHER
                       note = thymine
misc_feature           1..21
                       note = 125
misc_feature           1
                       note = /note="nucleotide conjugated to NHC5 conjugated to
                       LinoleicAcid"
misc_feature           1
                       note = /note="nucleotide bond by a Phosphorothioate linkage
                       "
misc_feature           2
                       note = /note="nucleotide bond by a Phosphorothioate linkage
                       "
misc_feature           18
                       note = /note="nucleotide bond by a Phosphorothioate linkage
                       "
misc_feature           19
                       note = /note="nucleotide bond by a Phosphorothioate linkage
                       "
misc_feature           20
                       note = /note="nucleotide bond by a Phosphorothioate linkage
                       "
source                 1..21
                       mol_type = other RNA
                       organism = synthetic construct
SEQUENCE: 125
acatggttag atcaagcaca a                                                    21

SEQ ID NO: 126         moltype = RNA   length = 21
FEATURE                Location/Qualifiers
modified_base          4
                       mod_base = OTHER
                       note = thymine
modified_base          7..8
                       mod_base = OTHER
                       note = thymine
modified_base          12
                       mod_base = OTHER
                       note = thymine
misc_feature           1..21
                       note = 126
misc_feature           1
                       note = /note="nucleotide conjugated to NHC5 conjugated to
                       Palmitic Acid"
misc_feature           1
                       note = /note="nucleotide bond by a Phosphorothioate linkage
                       "
misc_feature           2
                       note = /note="nucleotide bond by a Phosphorothioate linkage
                       "
misc_feature           18
                       note = /note="nucleotide bond by a Phosphorothioate linkage
                       "
misc_feature           19
                       note = /note="nucleotide bond by a Phosphorothioate linkage
                       "
misc_feature           20
                       note = /note="nucleotide bond by a Phosphorothioate linkage
                       "
source                 1..21
                       mol_type = other RNA
                       organism = synthetic construct
SEQUENCE: 126
acatggttag atcaagcaca a                                                    21

SEQ ID NO: 127         moltype = RNA   length = 21
FEATURE                Location/Qualifiers
modified_base          4
                       mod_base = OTHER
```

```
                        note = thymine
modified_base           7..8
                        mod_base = OTHER
                        note = thymine
modified_base           12
                        mod_base = OTHER
                        note = thymine
misc_feature            1..21
                        note = 127
misc_feature            1
                        note = /note="nucleotide conjugated to Octyl conjugated to
                         Tocopherol"
misc_feature            1
                        note = /note="nucleotide bond by a Phosphorothioate linkage
                        "
misc_feature            2
                        note = /note="nucleotide bond by a Phosphorothioate linkage
                        "
misc_feature            18
                        note = /note="nucleotide bond by a Phosphorothioate linkage
                        "
misc_feature            19
                        note = /note="nucleotide bond by a Phosphorothioate linkage
                        "
misc_feature            20
                        note = /note="nucleotide bond by a Phosphorothioate linkage
                        "
source                  1..21
                        mol_type = other RNA
                        organism = synthetic construct
SEQUENCE: 127
acatggttag atcaagcaca a                                                     21

SEQ ID NO: 128          moltype = RNA  length = 18
FEATURE                 Location/Qualifiers
modified_base           4
                        mod_base = OTHER
                        note = thymine
modified_base           7..10
                        mod_base = OTHER
                        note = thymine
modified_base           12
                        mod_base = OTHER
                        note = thymine
modified_base           14
                        mod_base = OTHER
                        note = thymine
misc_feature            1..18
                        note = 128
misc_feature            1
                        note = /note="nucleotide conjugated to NHC6 conjugated to
                         Oleic Acid"
misc_feature            1
                        note = /note="nucleotide bond by a Phosphorothioate linkage
                        "
misc_feature            2
                        note = /note="nucleotide bond by a Phosphorothioate linkage
                        "
misc_feature            15
                        note = /note="nucleotide bond by a Phosphorothioate linkage
                        "
misc_feature            16
                        note = /note="nucleotide bond by a Phosphorothioate linkage
                        "
misc_feature            17
                        note = /note="nucleotide bond by a Phosphorothioate linkage
                        "
source                  1..18
                        mol_type = other RNA
                        organism = synthetic construct
SEQUENCE: 128
cagtactttt gtgtacaa                                                         18

SEQ ID NO: 129          moltype = DNA  length = 16
FEATURE                 Location/Qualifiers
misc_feature            1..16
                        note = 129
misc_feature            1
                        note = /note="nucleotide bond by a Phosphorothioate linkage"
```

```
misc_feature      1
                  note = /note="LNA modified base"
misc_feature      2
                  note = /note="2'-O-MOE RNA nucleotides"
misc_feature      2
                  note = /note="nucleotide bond by a Phosphorothioate linkage"
misc_feature      3
                  note = /note="nucleotide bond by a Phosphorothioate linkage
                   and 2-O-Methyl-nucleotides"
misc_feature      4
                  note = /note="nucleotide bond by a Phosphorothioate linkage
                   and 2-O-Methyl-nucleotides"
misc_feature      5
                  note = /note="nucleotide bond by a Phosphorothioate linkage
                   and 2-O-Methyl-nucleotides"
misc_feature      6
                  note = /note="nucleotide bond by a Phosphorothioate linkage"
misc_feature      6
                  note = /note="LNA modified base"
misc_feature      7
                  note = /note="nucleotide bond by a Phosphorothioate linkage
                   and 2-O-Methyl-nucleotide"
misc_feature      8
                  note = /note="nucleotide bond by a Phosphorothioate linkage
                   and 2-O-Methyl-nucleotide"
misc_feature      9
                  note = /note="nucleotide bond by a Phosphorothioate linkage
                   and 2-O-Methyl-nucleotide"
misc_feature      10
                  note = /note="nucleotide bond by a Phosphorothioate linkage"
misc_feature      10
                  note = /note="LNA modified base"
misc_feature      11
                  note = /note="2'-O-MOE RNA nucleotides"
misc_feature      11
                  note = /note="nucleotide bond by a Phosphorothioate linkage"
misc_feature      12
                  note = /note="nucleotide bond by a Phosphorothioate linkage"
misc_feature      12
                  note = /note="LNA modified base"
misc_feature      13
                  note = /note="nucleotide bond by a Phosphorothioate linkage"
misc_feature      13
                  note = /note="LNA modified base"
misc_feature      14
                  note = /note="2'-O-MOE RNA nucleotides"
misc_feature      14
                  note = /note="nucleotide bond by a Phosphorothioate linkage"
misc_feature      15
                  note = /note="nucleotide bond by a Phosphorothioate linkage"
misc_feature      15
                  note = /note="LNA modified base"
misc_feature      16
                  note = /note="LNA modified base"
source            1..16
                  mol_type = other DNA
                  organism = synthetic construct
SEQUENCE: 129
atccctggca atgtga                                                         16

SEQ ID NO: 130    moltype = DNA  length = 15
FEATURE           Location/Qualifiers
misc_feature      1..15
                  note = 130
misc_feature      1
                  note = /note="nucleotide bond by a Phosphorothioate linkage
                   and LNA modified base"
misc_feature      2
                  note = /note="nucleotide bond by a Phosphorothioate linkage
                   and 2-O-Methyl-nucleotide"
misc_feature      3
                  note = /note="nucleotide bond by a Phosphorothioate linkage
                   and 2-O-Methyl-nucleotide"
misc_feature      4
                  note = /note="nucleotide bond by a Phosphorothioate linkage
                   and LNA modified base"
misc_feature      5
                  note = /note="nucleotide bond by a Phosphorothioate linkage
                   and 2-O-Methyl-nucleotide"
```

```
misc_feature    6
                note = /note="nucleotide bond by a Phosphorothioate linkage
                and 2 -O-Methyl-nucleotide"
misc_feature    7
                note = /note="nucleotide bond by a Phosphorothioate linkage
                and LNA modified base"
misc_feature    8
                note = /note="nucleotide bond by a Phosphorothioate linkage
                and 2 -O-Methyl-nucleotide"
misc_feature    9
                note = /note="nucleotide bond by a Phosphorothioate linkage
                and 2 -O-Methyl-nucleotide"
misc_feature    10
                note = /note="nucleotide bond by a Phosphorothioate linkage
                and LNA modified base"
misc_feature    11
                note = /note="nucleotide bond by a Phosphorothioate linkage
                and 2 -O-Methyl-nucleotide"
misc_feature    12
                note = /note="nucleotide bond by a Phosphorothioate linkage
                and 2 -O-Methyl-nucleotide"
misc_feature    12
                note = /note="t= uracil"
misc_feature    13
                note = /note="nucleotide bond by a Phosphorothioate linkage
                and LNA modified base"
misc_feature    14
                note = /note="nucleotide bond by a Phosphorothioate linkage
                and 2 -O-Methyl-nucleotide"
misc_feature    14
                note = /note="nucleotide bond by a Phosphorothioate linkage
                and 2 -O-Methyl-nucleotide"
misc_feature    15
                note = /note="LNA modified base"
source          1..15
                mol_type = other DNA
                organism = synthetic construct
SEQUENCE: 130
ccctggcaat gtgat                                                           15

SEQ ID NO: 131  moltype = DNA  length = 15
FEATURE         Location/Qualifiers
misc_feature    1..15
                note = 131
misc_feature    1
                note = /note="nucleotide bond by a Phosphorothioate linkage
                and LNA modified base"
misc_feature    2
                note = /note="deoxynucleotide bond by a Phosphorothioate
                linkage "
misc_feature    3
                note = /note="deoxynucleotide bond by a Phosphorothioate
                linkage "
misc_feature    4
                note = /note="deoxynucleotide bond by a Phosphorothioate
                linkage "
misc_feature    5
                note = /note="deoxynucleotide bond by a Phosphorothioate
                linkage "
misc_feature    6
                note = /note="nucleotide bond by a Phosphorothioate linkage"
misc_feature    7
                note = /note="nucleotide bond by a Phosphorothioate linkage
                and LNA modified base"
misc_feature    8
                note = /note="deoxynucleotide bond by a Phosphorothioate
                linkage "
misc_feature    9
                note = /note="nucleotide bond by a Phosphorothioate linkage
                and LNA modifed base"
misc_feature    10
                note = /note="deoxynucleotide bond by a Phosphorothioate
                linkage "
misc_feature    11
                note = /note="deoxynucleotide bond by a Phosphorothioate
                linkage "
misc_feature    12
                note = /note="deoxynucleotide bond by a Phosphorothioate
                linkage "
```

| | | |
|---|---|---|
| misc_feature | 13 | |
| | note = /note="nucleotide bond by a Phosphorothioate linkage and LNA modified base" | |
| misc_feature | 14 | |
| | note = /note="deoxynucleotide bond by a Phosphorothioate linkage " | |
| misc_feature | 15 | |
| | note = /note="LNA modified base" | |
| source | 1..15 | |
| | mol_type = other DNA | |
| | organism = synthetic construct | |
| SEQUENCE: 131 | | |
| ccctggcaat gtgat | | 15 |
| | | |
| SEQ ID NO: 132 | moltype = DNA length = 17 | |
| FEATURE | Location/Qualifiers | |
| misc_feature | 1..17 | |
| | note = 132 | |
| misc_feature | 1 | |
| | note = /note="nucleotide bond by a Phosphorothioate linkage and LNA modified base" | |
| misc_feature | 2 | |
| | note = /note="nucleotide bond by a Phosphorothioate linkage and LNA modified" | |
| misc_feature | 3 | |
| | note = /note="nucleotide bond by a Phosphorothioate linkage and 2 -O-Methyl-nucleotide" | |
| misc_feature | 4 | |
| | note = /note="nucleotide bond by a Phosphorothioate linkage and 2 -O-Methyl-nucleotide" | |
| misc_feature | 5 | |
| | note = /note="nucleotide bond by a Phosphorothioate linkage and 2 -O-Methyl-nucleotide" | |
| misc_feature | 6 | |
| | note = /note="nucleotide bond by a Phosphorothioate linkage and LNA modified" | |
| misc_feature | 7 | |
| | note = /note="nucleotide bond by a Phosphorothioate linkage and 2 -O-Methyl-nucleotide" | |
| misc_feature | 8 | |
| | note = /note="nucleotide bond by a Phosphorothioate linkage and 2 -O-Methyl-nucleotide" | |
| misc_feature | 9 | |
| | note = /note="nucleotide bond by a Phosphorothioate linkage and " | |
| misc_feature | 10 | |
| | note = /note="nucleotide bond by a Phosphorothioate linkage and LNA modified" | |
| misc_feature | 11 | |
| | note = /note="nucleotide bond by a Phosphorothioate linkage and 2'-O-MOE RNA nucleotide" | |
| misc_feature | 12 | |
| | note = /note="nucleotide bond by a Phosphorothioate linkage and LNA modified" | |
| misc_feature | 13 | |
| | note = /note="nucleotide bond by a Phosphorothioate linkage and LNA modified base" | |
| misc_feature | 14 | |
| | note = /note="nucleotide bond by a Phosphorothioate linkage and 2 -O-Methyl-nucleotide" | |
| misc_feature | 15 | |
| | note = /note="nucleotide bond by a Phosphorothioate linkage and 2'-O-MOE RNA nucleotide" | |
| misc_feature | 16 | |
| | note = /note="nucleotide bond by a Phosphorothioate linkage and LNA modified base" | |
| misc_feature | 17 | |
| | note = /note="LNA modified base" | |
| source | 1..17 | |
| | mol_type = other DNA | |
| | organism = synthetic construct | |
| SEQUENCE: 132 | | |
| atccctggca atgtgat | | 17 |
| | | |
| SEQ ID NO: 133 | moltype = DNA length = 19 | |
| FEATURE | Location/Qualifiers | |
| misc_feature | 1..19 | |
| | note = 133 | |
| misc_feature | 1 | |

-continued

```
                       note = /note="nucleotide bond by a Phosphorothioate linkage
                        and LNA modified"
misc_feature           2
                       note = /note="deoxynucleotide bond by a Phosphorothioate
                        linkage "
misc_feature           3
                       note = /note="deoxynucleotide bond by a Phosphorothioate
                        linkage "
misc_feature           4
                       note = /note="nucleotide bond by a Phosphorothioate linkage
                        and LNA modified"
misc_feature           5
                       note = /note="deoxynucleotide bond by a Phosphorothioate
                        linkage "
misc_feature           6
                       note = /note="deoxynucleotide bond by a Phosphorothioate
                        linkage "
misc_feature           7
                       note = /note="nucleotide bond by a Phosphorothioate linkage
                        and LNA modified"
misc_feature           8
                       note = /note="deoxynucleotide bond by a Phosphorothioate
                        linkage "
misc_feature           9
                       note = /note="nucleotide bond by a Phosphorothioate linkage
                        and LNA modified"
misc_feature           10
                       note = /note="deoxynucleotide bond by a Phosphorothioate
                        linkage "
misc_feature           11
                       note = /note="deoxynucleotide bond by a Phosphorothioate
                        linkage "
misc_feature           12
                       note = /note="nucleotide bond by a Phosphorothioate linkage
                        and LNA modified"
misc_feature           13
                       note = /note="nucleotide bond by a Phosphorothioate linkage
                        and LNA modified"
misc_feature           14
                       note = /note="deoxynucleotide bond by a Phosphorothioate
                        linkage "
misc_feature           15
                       note = /note="deoxynucleotide bond by a Phosphorothioate
                        linkage "
misc_feature           16
                       note = /note="nucleotide bond by a Phosphorothioate linkage
                        and LNA modified"
misc_feature           17
                       note = /note="deoxynucleotide bond by a Phosphorothioate
                        linkage "
misc_feature           18
                       note = /note="nucleotide bond by a Phosphorothioate linkage
                        and LNA modified"
misc_feature           19
                       note = /note=" LNA modified"
source                 1..19
                       mol_type = other DNA
                       organism = synthetic construct
SEQUENCE: 133
taatccctgg caatgtgat                                                  19

SEQ ID NO: 134         moltype = DNA  length = 15
FEATURE                Location/Qualifiers
misc_feature           1..15
                       note = 134
misc_feature           1
                       note = /note="nucleotide bond by a Phosphorothioate linkage
                        and LNA modified"
misc_feature           2
                       note = /note="deoxynucleotide bond by a Phosphorothioate
                        linkage "
misc_feature           3
                       note = /note="deoxynucleotide bond by a Phosphorothioate
                        linkage "
misc_feature           4
                       note = /note="nucleotide bond by a Phosphorothioate linkage
                        and LNA modified"
misc_feature           5
                       note = /note="deoxynucleotide bond by a Phosphorothioate
```

| | |
|---|---|
| misc_feature | 6<br>note = /note="deoxynucleotide bond by a Phosphorothioate linkage " |
| misc_feature | 7<br>note = /note="nucleotide bond by a Phosphorothioate linkage and LNA modified" |
| misc_feature | 8<br>note = /note="deoxynucleotide bond by a Phosphorothioate linkage " |
| misc_feature | 9<br>note = /note="deoxynucleotide bond by a Phosphorothioate linkage " |
| misc_feature | 10<br>note = /note="nucleotide bond by a Phosphorothioate linkage and LNA modified base" |
| misc_feature | 11<br>note = /note="deoxynucleotide bond by a Phosphorothioate linkage " |
| misc_feature | 12<br>note = /note="deoxynucleotide bond by a Phosphorothioate linkage " |
| misc_feature | 13<br>note = /note="nucleotide bond by a Phosphorothioate linkage and LNA modified" |
| misc_feature | 14<br>note = /note="deoxynucleotide bond by a Phosphorothioate linkage " |
| misc_feature | 15<br>note = /note="LNA modified " |
| source | 1..15<br>mol_type = other DNA<br>organism = synthetic construct |
| SEQUENCE: 134 | |
| ccctggcaat gtgat | 15 |
| SEQ ID NO: 135<br>FEATURE | moltype = DNA length = 17<br>Location/Qualifiers |
| misc_feature | 1..17<br>note = 135 |
| misc_feature | 1<br>note = /note="nucleotide bond by a Phosphorothioate linkage and LNA modified" |
| misc_feature | 2<br>note = /note="nucleotide bond by a Phosphorothioate linkage and 2'-O-MOE RNA nucleotide" |
| misc_feature | 3<br>note = /note="deoxynucleotide bond by a Phosphorothioate linkage " |
| misc_feature | 4<br>note = /note="deoxynucleotide bond by a Phosphorothioate linkage " |
| misc_feature | 5<br>note = /note="nucleotide bond by a Phosphorothioate linkage and 2'-O-MOE RNA nucleotide" |
| misc_feature | 6<br>note = /note="deoxynucleotide bond by a Phosphorothioate linkage " |
| misc_feature | 7<br>note = /note="nucleotide bond by a Phosphorothioate linkage and 2'-O-MOE RNA nucleotide" |
| misc_feature | 8<br>note = /note="deoxynucleotide bond by a Phosphorothioate linkage " |
| misc_feature | 9<br>note = /note="deoxynucleotide bond by a Phosphorothioate linkage " |
| misc_feature | 10<br>note = /note="nucleotide bond by a Phosphorothioate linkage and LNA modified" |
| misc_feature | 11<br>note = /note="deoxynucleotide bond by a Phosphorothioate linkage " |
| misc_feature | 12<br>note = /note="nucleotide bond by a Phosphorothioate linkage and LNA modified" |
| misc_feature | 13<br>note = /note="deoxynucleotide bond by a Phosphorothioate linkage " |

```
misc_feature      14
                  note = /note="nucleotide bond by a Phosphorothioate linkage
                    and LNA modified"
misc_feature      15
                  note = /note="nucleotide bond by a Phosphorothioate linkage
                    and 2'-O-MOE RNA nucleotide"
misc_feature      16
                  note = /note="nucleotide bond by a Phosphorothioate linkage
                    and 2'-O-MOE RNA nucleotide"
misc_feature      17
                  note = /note="LNA modified"
source            1..17
                  mol_type = other DNA
                  organism = synthetic construct
SEQUENCE: 135
atccctggca atgtgat                                                       17

SEQ ID NO: 136    moltype = DNA  length = 19
FEATURE           Location/Qualifiers
misc_feature      1..19
                  note = 136
misc_feature      1
                  note = /note="nucleotide bond by a Phosphorothioate linkage
                    and 2'-O-MOE RNA nucleotide"
misc_feature      2
                  note = /note="nucleotide bond by a Phosphorothioate linkage
                    and 2'-O-MOE RNA nucleotide"
misc_feature      3
                  note = /note="nucleotide bond by a Phosphorothioate linkage"
misc_feature      4
                  note = /note="deoxynucleotide bond by a Phosphorothioate
                    linkage "
misc_feature      5
                  note = /note="nucleotide bond by a Phosphorothioate linkage
                    and 2 -O-Methyl-nucleotide"
misc_feature      6
                  note = /note="nucleotide bond by a Phosphorothioate linkage
                    and 2 -O-Methyl-nucleotide"
misc_feature      7
                  note = /note="nucleotide bond by a Phosphorothioate linkage
                    and 2 -O-Methyl-nucleotide"
misc_feature      8
                  note = /note="deoxynucleotide bond by a Phosphorothioate
                    linkage "
misc_feature      9
                  note = /note="nucleotide bond by a Phosphorothioate linkage
                    and 2 -O-Methyl-nucleotide"
misc_feature      10
                  note = /note="nucleotide bond by a Phosphorothioate linkage
                    and 2 -O-Methyl-nucleotide"
misc_feature      11
                  note = /note="deoxynucleotide bond by a Phosphorothioate
                    linkage "
misc_feature      12
                  note = /note="nucleotide bond by a Phosphorothioate linkage
                    and LNA modified"
misc_feature      13
                  note = /note="nucleotide bond by a Phosphorothioate linkage
                    and LNA modified"
misc_feature      14
                  note = /note="deoxynucleotide bond by a Phosphorothioate
                    linkage "
misc_feature      15
                  note = /note="nucleotide bond by a Phosphorothioate linkage
                    and 2 -O-Methyl-nucleotide"
misc_feature      16
                  note = /note="nucleotide bond by a Phosphorothioate linkage
                    and LNA modified"
misc_feature      17
                  note = /note="nucleotide bond by a Phosphorothioate linkage
                    and 2 -O-Methyl-nucleotide"
misc_feature      18
                  note = /note="nucleotide bond by a Phosphorothioate linkage
                    and LNA modified"
misc_feature      19
                  note = /note="2 -O-Methyl-nucleotide"
source            1..19
                  mol_type = other DNA
                  organism = synthetic construct
```

| | | |
|---|---|---|
| SEQUENCE: 136 | | |
| taatccctgg caatgtgat | | 19 |
| | | |
| SEQ ID NO: 137 | moltype = DNA  length = 15 | |
| FEATURE | Location/Qualifiers | |
| misc_feature | 1..15 | |
| | note = 137 | |
| misc_feature | 1 | |
| | note = /note="nucleotide bond by a Phosphorothioate linkage and LNA modified" | |
| misc_feature | 2 | |
| | note = /note="nucleotide bond by a Phosphorothioate linkage and 2´-O-Methyl-nucleotide" | |
| misc_feature | 3 | |
| | note = /note="t=uracil" | |
| misc_feature | 3 | |
| | note = /note="nucleotide bond by a Phosphorothioate linkage and 2´-O-Methyl-nucleotide" | |
| misc_feature | 4 | |
| | note = /note="nucleotide bond by a Phosphorothioate linkage and 2´-O-Methyl-nucleotide" | |
| misc_feature | 5 | |
| | note = /note="nucleotide bond by a Phosphorothioate linkage and 2´-O-Methyl-nucleotide" | |
| misc_feature | 6 | |
| | note = /note="nucleotide bond by a Phosphorothioate linkage and 2´-O-Methyl-nucleotide" | |
| misc_feature | 7 | |
| | note = /note="nucleotide bond by a Phosphorothioate linkage and LNA modified" | |
| misc_feature | 8 | |
| | note = /note="nucleotide bond by a Phosphorothioate linkage and 2´-O-Methyl-nucleotide" | |
| misc_feature | 9 | |
| | note = /note="nucleotide bond by a Phosphorothioate linkage and LNA modified" | |
| misc_feature | 10 | |
| | note = /note="nucleotide bond by a Phosphorothioate linkage and 2´-O-Methyl-nucleotide" | |
| misc_feature | 10 | |
| | note = /note="t = uracil" | |
| misc_feature | 11 | |
| | note = /note="nucleotide bond by a Phosphorothioate linkage and 2´-O-Methyl-nucleotide" | |
| misc_feature | 12 | |
| | note = /note="nucleotide bond by a Phosphorothioate linkage and 2´-O-Methyl-nucleotide" | |
| misc_feature | 12 | |
| | note = /note="nucleotide bond by a Phosphorothioate linkage and 2´-O-Methyl-nucleotide" | |
| misc_feature | 13 | |
| | note = /note="nucleotide bond by a Phosphorothioate linkage and LNA modified" | |
| misc_feature | 14 | |
| | note = /note="deoxynucleotide bond by a Phosphorothioate linkage " | |
| misc_feature | 15 | |
| | note = /note="LNA modified" | |
| source | 1..15 | |
| | mol_type = other DNA | |
| | organism = synthetic construct | |
| SEQUENCE: 137 | | |
| ccctggcaat gtgat | | 15 |
| | | |
| SEQ ID NO: 138 | moltype = DNA  length = 18 | |
| FEATURE | Location/Qualifiers | |
| misc_feature | 1..18 | |
| | note = 138 | |
| misc_feature | 1 | |
| | note = /note="nucleotide bond by a Phosphorothioate linkage and LNA modified" | |
| misc_feature | 2 | |
| | note = /note="nucleotide bond by a Phosphorothioate linkage and 2'-O-MOE RNA nucleotide" | |
| misc_feature | 3 | |
| | note = /note="deoxynucleotide" | |
| misc_feature | 4 | |
| | note = /note="nucleotide bond by a Phosphorothioate linkage and 2´-O-Methyl-nucleotide" | |

| | |
|---|---|
| misc_feature | 5 |
| | note = /note="nucleotide bond by a Phosphorothioate linkage" |
| misc_feature | 6 |
| | note = /note="deoxynucleotide bond by a Phosphorothioate linkage " |
| misc_feature | 7 |
| | note = /note="nucleotide bond by a Phosphorothioate linkage and 2 -O-Methyl-nucleotide" |
| misc_feature | 8 |
| | note = /note="nucleotide bond by a Phosphorothioate linkage and 2 -O-Methyl-nucleotide" |
| misc_feature | 9 |
| | note = /note="deoxynucleotide" |
| misc_feature | 10 |
| | note = /note="nucleotide bond by a Phosphorothioate linkage and 2 -O-Methyl-nucleotide" |
| misc_feature | 11 |
| | note = /note="nucleotide bond by a Phosphorothioate linkage" |
| misc_feature | 12 |
| | note = /note="nucleotide bond by a Phosphorothioate linkage and LNA modified" |
| misc_feature | 13 |
| | note = /note="deoxynucleotide" |
| misc_feature | 14 |
| | note = /note="nucleotide bond by a Phosphorothioate linkage and LNA modified" |
| misc_feature | 15 |
| | note = /note="nucleotide bond by a Phosphorothioate linkage and 2'-O-MOE RNA nucleotide" |
| misc_feature | 16 |
| | note = /note="deoxynucleotide" |
| misc_feature | 17 |
| | note = /note="nucleotide bond by a Phosphorothioate linkage and LNA modified" |
| misc_feature | 18 |
| | note = /note="LNA modified base" |
| source | 1..18 |
| | mol_type = other DNA |
| | organism = synthetic construct |

SEQUENCE: 138 taatccctgg caatgtga                                                   18

| | |
|---|---|
| SEQ ID NO: 139 | moltype = DNA  length = 15 |
| FEATURE | Location/Qualifiers |
| misc_feature | 1..15 |
| | note = 139 |
| misc_feature | 1 |
| | note = /note="nucleotide bond by a Phosphorothioate linkage and LNA modified" |
| misc_feature | 2 |
| | note = /note="nucleotide bond by a Phosphorothioate linkage and 2 -O-Methyl-nucleotides " |
| misc_feature | 3 |
| | note = /note="nucleotide bond by a Phosphorothioate linkage and 2 -O-Methyl-nucleotides " |
| misc_feature | 4 |
| | note = /note="nucleotide bond by a Phosphorothioate linkage and 2 -O-Methyl-nucleotide" |
| misc_feature | 4 |
| | note = /note="t = uracil" |
| misc_feature | 5 |
| | note = /note="nucleotide bond by a Phosphorothioate linkage and 2 -O-Methyl-nucleotides " |
| misc_feature | 6 |
| | note = /note="nucleotide bond by a Phosphorothioate linkage and 2 -O-Methyl-nucleotides " |
| misc_feature | 7 |
| | note = /note="nucleotide bond by a Phosphorothioate linkage and LNA modified" |
| misc_feature | 8 |
| | note = /note="nucleotide bond by a Phosphorothioate linkage and 2 -O-Methyl-nucleotide" |
| misc_feature | 9 |
| | note = /note="nucleotide bond by a Phosphorothioate linkage and LNA modified" |
| misc_feature | 10 |
| | note = /note="nucleotide bond by a Phosphorothioate linkage and 2 -O-Methyl-nucleotide" |
| misc_feature | 10 |

|  |  |
|---|---|
|  | note = /note="t=uracil" |
| misc_feature | 11 |
|  | note = /note="nucleotide bond by a Phosphorothioate linkage and 2 -O-Methyl-nucleotides " |
| misc_feature | 12 |
|  | note = /note="nucleotide bond by a Phosphorothioate linkage and 2 -O-Methyl-nucleotides " |
| misc_feature | 12 |
|  | note = /note="t=uracil" |
| misc_feature | 13 |
|  | note = /note="nucleotide bond by a Phosphorothioate linkage and LNA modified" |
| misc_feature | 14 |
|  | note = /note="nucleotide bond by a Phosphorothioate linkage and 2 -O-Methyl-nucleotides " |
| misc_feature | 15 |
|  | note = /note="LNA modified" |
| source | 1..15 |
|  | mol_type = other DNA |
|  | organism = synthetic construct |
| SEQUENCE: 139 |  |
| ccctggcaat gtgat | 15 |
|  |  |
| SEQ ID NO: 140 | moltype = DNA  length = 17 |
| FEATURE | Location/Qualifiers |
| misc_feature | 1..17 |
|  | note = 140 |
| misc_feature | 1 |
|  | note = /note="nucleotide bond by a Phosphorothioate linkage and LNA modified" |
| misc_feature | 2 |
|  | note = /note="nucleotide bond by a Phosphorothioate linkage and LNA modified" |
| misc_feature | 3 |
|  | note = /note="deoxynucleotide bond by a Phosphorothioate linkage " |
| misc_feature | 4 |
|  | note = /note="deoxynucleotide bond by a Phosphorothioate linkage " |
| misc_feature | 5 |
|  | note = /note="deoxynucleotide bond by a Phosphorothioate linkage " |
| misc_feature | 6 |
|  | note = /note="nucleotide bond by a Phosphorothioate linkage and LNA modified" |
| misc_feature | 7 |
|  | note = /note="deoxynucleotide bond by a Phosphorothioate linkage " |
| misc_feature | 8 |
|  | note = /note="deoxynucleotide bond by a Phosphorothioate linkage " |
| misc_feature | 9 |
|  | note = /note="deoxynucleotide bond by a Phosphorothioate linkage " |
| misc_feature | 10 |
|  | note = /note="nucleotide bond by a Phosphorothioate linkage and LNA modified" |
| misc_feature | 11 |
|  | note = /note="deoxynucleotide bond by a Phosphorothioate linkage " |
| misc_feature | 12 |
|  | note = /note="nucleotide bond by a Phosphorothioate linkage and LNA modified" |
| misc_feature | 13 |
|  | note = /note="nucleotide bond by a Phosphorothioate linkage and LNA modified" |
| misc_feature | 14 |
|  | note = /note="deoxynucleotide bond by a Phosphorothioate linkage " |
| misc_feature | 15 |
|  | note = /note="deoxynucleotide bond by a Phosphorothioate linkage " |
| misc_feature | 16 |
|  | note = /note="nucleotide bond by a Phosphorothioate linkage and LNA modified" |
| misc_feature | 17 |
|  | note = /note=" LNA modified base" |
| source | 1..17 |
|  | mol_type = other DNA |

-continued

| | | |
|---|---|---|
| SEQUENCE: 140 | organism = synthetic construct | |
| atccctggca atgtgat | | 17 |
| SEQ ID NO: 141 | moltype = DNA length = 18 | |
| FEATURE | Location/Qualifiers | |
| misc_feature | 1..18 | |
| | note = 141 | |
| misc_feature | 1 | |
| | note = /note="nucleotide bond by a Phosphorothioate linkage and LNA modified" | |
| misc_feature | 2 | |
| | note = /note="nucleotide bond by a Phosphorothioate linkage and LNA modified" | |
| misc_feature | 3 | |
| | note = /note="deoxynucleotide bond by a Phosphorothioate linkage " | |
| misc_feature | 4 | |
| | note = /note="nucleotide bond by a Phosphorothioate linkage and LNA modified" | |
| misc_feature | 5 | |
| | note = /note="deoxynucleotide bond by a Phosphorothioate linkage " | |
| misc_feature | 6 | |
| | note = /note="deoxynucleotide bond by a Phosphorothioate linkage " | |
| misc_feature | 7 | |
| | note = /note="nucleotide bond by a Phosphorothioate linkage and LNA modified" | |
| misc_feature | 8 | |
| | note = /note="deoxynucleotide bond by a Phosphorothioate linkage " | |
| misc_feature | 9 | |
| | note = /note="deoxynucleotide bond by a Phosphorothioate linkage " | |
| misc_feature | 10 | |
| | note = /note="deoxynucleotide bond by a Phosphorothioate linkage " | |
| misc_feature | 11 | |
| | note = /note="nucleotide bond by a Phosphorothioate linkage and LNA modified" | |
| misc_feature | 12 | |
| | note = /note="nucleotide bond by a Phosphorothioate linkage and 2 -O-Methyl-nucleotide" | |
| misc_feature | 13 | |
| | note = /note="nucleotide bond by a Phosphorothioate linkage and LNA modified" | |
| misc_feature | 14 | |
| | note = /note="deoxynucleotide bond by a Phosphorothioate linkage " | |
| misc_feature | 15 | |
| | note = /note="nucleotide bond by a Phosphorothioate linkage and 2 -O-Methyl-nucleotide" | |
| misc_feature | 16 | |
| | note = /note="nucleotide bond by a Phosphorothioate linkage and 2 -O-Methyl-nucleotide" | |
| misc_feature | 17 | |
| | note = /note="nucleotide bond by a Phosphorothioate linkage and 2 -O-Methyl-nucleotide" | |
| misc_feature | 18 | |
| | note = /note=" LNA modified base" | |
| source | 1..18 | |
| | mol_type = other DNA | |
| | organism = synthetic construct | |
| SEQUENCE: 141 | | |
| aatccctggc aatgtgat | | 18 |
| SEQ ID NO: 142 | moltype = DNA length = 18 | |
| FEATURE | Location/Qualifiers | |
| misc_feature | 1..18 | |
| | note = 142 | |
| misc_feature | 1 | |
| | note = /note="nucleotide bond by a Phosphorothioate linkage and LNA modified" | |
| misc_feature | 2 | |
| | note = /note="nucleotide bond by a Phosphorothioate linkage and LNA modified" | |
| misc_feature | 3 | |
| | note = /note="deoxynucleotide bond by a Phosphorothioate | |

| | |
|---|---|
| | linkage " |
| misc_feature | 4 |
| | note = /note="nucleotide bond by a Phosphorothioate linkage and LNA modified" |
| misc_feature | 5 |
| | note = /note="deoxynucleotide bond by a Phosphorothioate linkage " |
| misc_feature | 6 |
| | note = /note="deoxynucleotide bond by a Phosphorothioate linkage " |
| misc_feature | 7 |
| | note = /note="nucleotide bond by a Phosphorothioate linkage and LNA modified" |
| misc_feature | 8 |
| | note = /note="deoxynucleotide bond by a Phosphorothioate linkage " |
| misc_feature | 9 |
| | note = /note="deoxynucleotide bond by a Phosphorothioate linkage " |
| misc_feature | 10 |
| | note = /note="deoxynucleotide bond by a Phosphorothioate linkage " |
| misc_feature | 11 |
| | note = /note="nucleotide bond by a Phosphorothioate linkage and LNA modified" |
| misc_feature | 12 |
| | note = /note="nucleotide bond by a Phosphorothioate linkage and LNA modified" |
| misc_feature | 13 |
| | note = /note="deoxynucleotide bond by a Phosphorothioate linkage " |
| misc_feature | 14 |
| | note = /note="nucleotide bond by a Phosphorothioate linkage and LNA modified" |
| misc_feature | 15 |
| | note = /note="deoxynucleotide bond by a Phosphorothioate linkage " |
| misc_feature | 16 |
| | note = /note="deoxynucleotide bond by a Phosphorothioate linkage " |
| misc_feature | 17 |
| | note = /note="nucleotide bond by a Phosphorothioate linkage and LNA modified" |
| misc_feature | 18 |
| | note = /note=" LNA modified base" |
| source | 1..18 |
| | mol_type = other DNA |
| | organism = synthetic construct |
| SEQUENCE: 142 | |
| aatccctggc aatgtgat | 18 |
| | |
| SEQ ID NO: 143 | moltype = DNA  length = 17 |
| FEATURE | Location/Qualifiers |
| misc_feature | 1..17 |
| | note = 143 |
| misc_feature | 1 |
| | note = /note="nucleotide bond by a Phosphorothioate linkage and LNA modified" |
| misc_feature | 2 |
| | note = /note="nucleotide bond by a Phosphorothioate linkage and LNA modified" |
| misc_feature | 3 |
| | note = /note="deoxynucleotide bond by a Phosphorothioate linkage " |
| misc_feature | 4 |
| | note = /note="deoxynucleotide bond by a Phosphorothioate linkage " |
| misc_feature | 5 |
| | note = /note="deoxynucleotide bond by a Phosphorothioate linkage " |
| misc_feature | 6 |
| | note = /note="nucleotide bond by a Phosphorothioate linkage and LNA modified" |
| misc_feature | 7 |
| | note = /note="deoxynucleotide bond by a Phosphorothioate linkage " |
| misc_feature | 8 |
| | note = /note="deoxynucleotide bond by a Phosphorothioate linkage " |

```
misc_feature       9
                   note = /note="deoxynucleotide bond by a Phosphorothioate
                    linkage "
misc_feature       10
                   note = /note="deoxynucleotide bond by a Phosphorothioate
                    linkage "
misc_feature       11
                   note = /note="nucleotide bond by a Phosphorothioate linkage
                    and LNA modified"
misc_feature       12
                   note = /note="nucleotide bond by a Phosphorothioate linkage
                    and LNA modified"
misc_feature       13
                   note = /note="deoxynucleotide bond by a Phosphorothioate
                    linkage "
misc_feature       14
                   note = /note="nucleotide bond by a Phosphorothioate linkage
                    and LNA modified"
misc_feature       15
                   note = /note="deoxynucleotide bond by a Phosphorothioate
                    linkage "
misc_feature       16
                   note = /note="nucleotide bond by a Phosphorothioate linkage
                    and LNA modified"
misc_feature       17
                   note = /note="LNA modified base"
source             1..17
                   mol_type = other DNA
                   organism = synthetic construct
SEQUENCE: 143
atccctggca atgtgat                                                        17

SEQ ID NO: 144     moltype = DNA   length = 18
FEATURE            Location/Qualifiers
misc_feature       1..18
                   note = 144
misc_feature       1
                   note = /note="nucleotide bond by a Phosphorothioate linkage
                    and LNA modified"
misc_feature       2
                   note = /note="nucleotide bond by a Phosphorothioate linkage
                    and 2'-O-MOE RNA nucleotide"
misc_feature       3
                   note = /note="deoxynucleotide bond by a Phosphorothioate
                    linkage "
misc_feature       4
                   note = /note="nucleotide bond by a Phosphorothioate linkage
                    and 2 -O-Methyl-nucleotide"
misc_feature       5
                   note = /note="nucleotide bond by a Phosphorothioate linkage
                    and 2 -O-Methyl-nucleotide"
misc_feature       6
                   note = /note="deoxynucleotide bond by a Phosphorothioate
                    linkage "
misc_feature       7
                   note = /note="nucleotide bond by a Phosphorothioate linkage
                    and 2 -O-Methyl-nucleotide"
misc_feature       8
                   note = /note="nucleotide bond by a Phosphorothioate linkage
                    nucleotide bond by a Phosphorothioate linkage and 2
                    -O-Methyl-nucleotide"
misc_feature       9
                   note = /note="deoxynucleotide bond by a Phosphorothioate
                    linkage "
misc_feature       10
                   note = /note="nucleotide bond by a Phosphorothioate linkage
                    and 2 -O-Methyl-nucleotide"
misc_feature       11
                   note = /note="nucleotide bond by a Phosphorothioate linkage
                    and 2 -O-Methyl-nucleotide"
misc_feature       12
                   note = /note="nucleotide bond by a Phosphorothioate linkage
                    and 2'-O-MOE RNA nucleotide"
misc_feature       13
                   note = /note="deoxynucleotide bond by a Phosphorothioate
                    linkage "
misc_feature       14
                   note = /note="nucleotide bond by a Phosphorothioate linkage
                    and 2'-O-MOE RNA nucleotide"
```

| | |
|---|---|
| misc_feature | 15<br>note = /note="nucleotide bond by a Phosphorothioate linkage and LNA modified" |
| misc_feature | 16<br>note = /note="deoxynucleotide bond by a Phosphorothioate linkage " |
| misc_feature | 17<br>note = /note="nucleotide bond by a Phosphorothioate linkage and LNA modified" |
| misc_feature | 18<br>note = /note="LNA modified base" |
| source | 1..18<br>mol_type = other DNA<br>organism = synthetic construct |

SEQUENCE: 144
taatccctgg caatgtga                                                    18

| | |
|---|---|
| SEQ ID NO: 145<br>FEATURE | moltype = DNA  length = 21<br>Location/Qualifiers |
| misc_feature | 1..21<br>note = 145 |
| misc_feature | 1<br>note = /note="nucleotide bond by a Phosphorothioate linkage and LNA modified" |
| misc_feature | 2<br>note = /note="nucleotide bond by a Phosphorothioate linkage and 2'-O-MOE RNA nucleotide" |
| misc_feature | 3<br>note = /note="t=uracil" |
| misc_feature | 3<br>note = /note="nucleotide bond by a Phosphorothioate linkage and 2'-O-MOE RNA nucleotide" |
| misc_feature | 4<br>note = /note="nucleotide bond by a Phosphorothioate linkage and 2 -O-Methyl-nucleotide" |
| misc_feature | 5<br>note = /note="nucleotide bond by a Phosphorothioate linkage and 2 -O-Methyl-nucleotide" |
| misc_feature | 6<br>note = /note="nucleotide bond by a Phosphorothioate linkage and 2'-O-MOE RNA nucleotide" |
| misc_feature | 6<br>note = /note="t=uracil" |
| misc_feature | 7<br>note = /note="nucleotide bond by a Phosphorothioate linkage and LNA modified" |
| misc_feature | 8<br>note = /note="nucleotide bond by a Phosphorothioate linkage nucleotide bond by a Phosphorothioate linkage and 2 -O-Methyl-nucleotide" |
| misc_feature | 9<br>note = /note="nucleotide bond by a Phosphorothioate linkage and 2'-O-MOE RNA nucleotide" |
| misc_feature | 10<br>note = /note="nucleotide bond by a Phosphorothioate linkage and 2 -O-Methyl-nucleotide" |
| misc_feature | 10<br>note = /note="t=uracil" |
| misc_feature | 11<br>note = /note="nucleotide bond by a Phosphorothioate linkage and 2 -O-Methyl-nucleotide" |
| misc_feature | 12<br>note = /note="nucleotide bond by a Phosphorothioate linkage and 2'-O-MOE RNA nucleotide" |
| misc_feature | 13<br>note = /note="nucleotide bond by a Phosphorothioate linkage and LNA modified" |
| misc_feature | 14<br>note = /note="nucleotide bond by a Phosphorothioate linkage and 2'-O-MOE RNA nucleotide" |
| misc_feature | 15<br>note = /note="nucleotide bond by a Phosphorothioate linkage and LNA modified" |
| misc_feature | 16<br>note = /note="nucleotide bond by a Phosphorothioate linkage and 2'-O-MOE RNA nucleotide" |
| misc_feature | 16<br>note = /note="t=uracil" |
| misc_feature | 17 |

|  |  |
|---|---|
|  | note = /note="nucleotide bond by a Phosphorothioate linkage and 2'-O-MOE RNA nucleotide" |
| misc_feature | 18 |
|  | note = /note="nucleotide bond by a Phosphorothioate linkage and 2'-O-MOE RNA nucleotide" |
| misc_feature | 18 |
|  | note = /note="t=uracil" |
| misc_feature | 19 |
|  | note = /note="nucleotide bond by a Phosphorothioate linkage and LNA modified" |
| misc_feature | 20 |
|  | note = /note="nucleotide bond by a Phosphorothioate linkage and 2'-O-MOE RNA nucleotide" |
| misc_feature | 21 |
|  | note = /note="LNA modified base" |
| source | 1..21 |
|  | mol_type = other DNA |
|  | organism = synthetic construct |
| SEQUENCE: 145 | |
| ggtaatccct ggcaatgtga t | 21 |

| | |
|---|---|
| SEQ ID NO: 146 | moltype = DNA  length = 15 |
| FEATURE | Location/Qualifiers |
| misc_feature | 1..15 |
|  | note = 146 |
| misc_feature | 1 |
|  | note = /note="nucleotide bond by a Phosphorothioate linkage" |
| misc_feature | 2 |
|  | note = /note="deoxynucleotide bond by a Phosphorothioate linkage" |
| misc_feature | 3 |
|  | note = /note="deoxynucleotide bond by a Phosphorothioate linkage" |
| misc_feature | 4 |
|  | note = /note="nucleotide bond by a Phosphorothioate linkage" |
| misc_feature | 5 |
|  | note = /note="deoxynucleotide bond by a Phosphorothioate linkage " |
| misc_feature | 6 |
|  | note = /note="deoxynucleotide bond by a Phosphorothioate linkage " |
| misc_feature | 7 |
|  | note = /note="nucleotide bond by a Phosphorothioate linkage " |
| misc_feature | 8 |
|  | note = /note="deoxynucleotide bond by a Phosphorothioate linkage " |
| misc_feature | 9 |
|  | note = /note="deoxynucleotide bond by a Phosphorothioate linkage " |
| misc_feature | 10 |
|  | note = /note="nucleotide bond by a Phosphorothioate linkage and 2 -O-Methyl-nucleotide" |
| misc_feature | 11 |
|  | note = /note="deoxynucleotide bond by a Phosphorothioate linkage" |
| misc_feature | 12 |
|  | note = /note="nucleotide bond by a Phosphorothioate linkage " |
| misc_feature | 13 |
|  | note = /note="deoxynucleotide bond by a Phosphorothioate linkage " |
| misc_feature | 14 |
|  | note = /note="deoxynucleotide bond by a Phosphorothioate linkage" |
| misc_feature | 15 |
|  | note = /note="nucleotide bond by a Phosphorothioate linkage " |
| source | 1..15 |
|  | mol_type = other DNA |
|  | organism = synthetic construct |
| SEQUENCE: 146 | |
| ttagatcaag cacaa | 15 |

| | |
|---|---|
| SEQ ID NO: 147 | moltype = DNA  length = 15 |
| FEATURE | Location/Qualifiers |
| misc_feature | 1..15 |
|  | note = 147 |
| misc_feature | 1 |

| | | |
|---|---|---|
| | | note = /note="nucleotide bond by a Phosphorothioate linkage and LNA modified" |
| misc_feature | 2 | |
| | | note = /note="nucleotide bond by a Phosphorothioate linkage and LNA modified" |
| misc_feature | 3 | |
| | | note = /note="nucleotide bond by a Phosphorothioate linkage and 2'-Fluoro RNA nucleotide" |
| misc_feature | 4 | |
| | | note = /note="nucleotide bond by a Phosphorothioate linkage and 2'-Fluoro RNA nucleotide" |
| misc_feature | 5 | |
| | | note = /note="nucleotide bond by a Phosphorothioate linkage and 2'-Fluoro RNA nucleotide" |
| misc_feature | 6 | |
| | | note = /note="nucleotide bond by a Phosphorothioate linkage and 2'-Fluoro RNA nucleotide" |
| misc_feature | 7 | |
| | | note = /note="nucleotide bond by a Phosphorothioate linkage and 2'-Fluoro RNA nucleotide" |
| misc_feature | 8 | |
| | | note = /note="nucleotide bond by a Phosphorothioate linkage and 2'-Fluoro RNA nucleotide" |
| misc_feature | 9 | |
| | | note = /note="nucleotide bond by a Phosphorothioate linkage and 2'-Fluoro RNA nucleotide" |
| misc_feature | 10 | |
| | | note = /note="nucleotide bond by a Phosphorothioate linkage and 2'-Fluoro RNA nucleotide" |
| misc_feature | 11 | |
| | | note = /note="nucleotide bond by a Phosphorothioate linkage and 2'-Fluoro RNA nucleotide" |
| misc_feature | 12 | |
| | | note = /note="nucleotide bond by a Phosphorothioate linkage and 2'-Fluoro RNA nucleotide" |
| misc_feature | 13 | |
| | | note = /note="nucleotide bond by a Phosphorothioate linkage and 2'-Fluoro RNA nucleotide" |
| misc_feature | 14 | |
| | | note = /note="nucleotide bond by a Phosphorothioate linkagenucleotide bond by a Phosphorothioate linkage and LNA modified" |
| misc_feature | 15 | |
| | | note = /note="nucleotide bond by a Phosphorothioate linkage and LNA modified" |
| source | 1..15 | |
| | | mol_type = other DNA |
| | | organism = synthetic construct |
| SEQUENCE: 147 | | |
| ttagatcaag cacaa | | 15 |
| | | |
| SEQ ID NO: 148 | moltype = DNA length = 18 | |
| FEATURE | Location/Qualifiers | |
| misc_feature | 1..18 | |
| | | note = 148 |
| misc_feature | 1 | |
| | | note = /note="nucleotide bond by a Phosphorothioate linkage and LNA modified" |
| misc_feature | 2 | |
| | | note = /note="nnucleotide bond by a Phosphorothioate linkage and LNA modified" |
| misc_feature | 3 | |
| | | note = /note="deoxynucleotide bond by a Phosphorothioate linkage" |
| misc_feature | 4 | |
| | | note = /note="nucleotide bond by a Phosphorothioate linkage and 2'-Fluoro RNA nucleotide" |
| misc_feature | 5 | |
| | | note = /note="deoxynucleotide bond by a Phosphorothioate linkage" |
| misc_feature | 6 | |
| | | note = /note="deoxynucleotide bond by a Phosphorothioate linkage " |
| misc_feature | 7 | |
| | | note = /note="nucleotide bond by a Phosphorothioate linkage and LNA modified" |
| misc_feature | 8 | |
| | | note = /note="deoxynucleotide bond by a Phosphorothioate linkage" |

```
misc_feature          9
                      note = /note="deoxynucleotide bond by a Phosphorothioate
                      linkage"
misc_feature          10
                      note = /note="deoxynucleotide bond by a Phosphorothioate
                      linkage"
misc_feature          11
                      note = /note="nnucleotide bond by a Phosphorothioate
                      linkage and LNA modified"
misc_feature          12
                      note = /note="nucleotide bond by a Phosphorothioate linkage
                      and 2'-O-MOE RNA nucleotide"
misc_feature          13
                      note = /note="nucleotide bond by a Phosphorothioate linkage
                      and LNA modified"
misc_feature          14
                      note = /note="nucleotide bond by a Phosphorothioate linkage
                      and LNA modified"
misc_feature          15
                      note = /note="deoxynucleotide bond by a Phosphorothioate
                      linkage"
misc_feature          16
                      note = /note="nucleotide bond by a Phosphorothioate linkage
                      and 2'-O-MOE RNA nucleotide"
misc_feature          17
                      note = /note="nucleotide bond by a Phosphorothioate linkage
                      and 2'-O-MOE RNA nucleotide"
misc_feature          18
                      note = /note="nucleotide bond by a Phosphorothioate linkage
                      and LNA modified"
source                1..18
                      mol_type = other DNA
                      organism = synthetic construct
SEQUENCE: 148
tggttagatc aagcacaa                                                    18

SEQ ID NO: 149        moltype = DNA  length = 17
FEATURE               Location/Qualifiers
misc_feature          1..17
                      note = 149
misc_feature          1
                      note = /note="nucleotide bond by a Phosphorothioate linkage
                      and LNA modified"
misc_feature          2
                      note = /note="nucleotide bond by a Phosphorothioate linkage
                      and LNA modified"
misc_feature          3
                      note = /note="deoxynucleotide bond by a Phosphorothioate
                      linkage"
misc_feature          4
                      note = /note="deoxynucleotide bond by a Phosphorothioate
                      linkage "
misc_feature          5
                      note = /note="deoxynucleotide bond by a Phosphorothioate
                      linkage"
misc_feature          6
                      note = /note="nucleotide bond by a Phosphorothioate linkage
                      and LNA modified"
misc_feature          7
                      note = /note="deoxynucleotide bond by a Phosphorothioate
                      linkage "
misc_feature          8
                      note = /note="deoxynucleotide bond by a Phosphorothioate
                      linkage"
misc_feature          9
                      note = /note="deoxynucleotide bond by a Phosphorothioate
                      linkage"
misc_feature          10
                      note = /note="nucleotide bond by a Phosphorothioate linkage
                      and LNA modified"
misc_feature          11
                      note = /note="deoxynucleotide bond by a Phosphorothioate
                      linkage "
misc_feature          12
                      note = /note="nucleotide bond by a Phosphorothioate linkage
                      and LNA modified"
misc_feature          13
                      note = /note="nucleotide bond by a Phosphorothioate linkage
                      and LNA modified"
```

| | |
|---|---|
| misc_feature | 14<br>note = /note="deoxynucleotide bond by a Phosphorothioate linkage " |
| misc_feature | 15<br>note = /note="deoxynucleotide bond by a Phosphorothioate linkage" |
| misc_feature | 16<br>note = /note="nucleotide bond by a Phosphorothioate linkage and LNA modified" |
| misc_feature | 17<br>note = /note="nucleotide bond by a Phosphorothioate linkage and LNA modified" |
| source | 1..17<br>mol_type = other DNA<br>organism = synthetic construct |
| SEQUENCE: 149<br>ggttagatca agcacaa | 17 |
| SEQ ID NO: 150<br>FEATURE | moltype = DNA  length = 18<br>Location/Qualifiers |
| misc_feature | 1..18<br>note = 150 |
| misc_feature | 1<br>note = /note="nucleotide bond by a Phosphorothioate linkage and LNA modified" |
| misc_feature | 2<br>note = /note="nucleotide bond by a Phosphorothioate linkage and 2'-O-MOE RNA nucleotide" |
| misc_feature | 3<br>note = /note="deoxynucleotide bond by a Phosphorothioate linkage" |
| misc_feature | 4<br>note = /note="nucleotide bond by a Phosphorothioate linkage and 2 -O-Methyl-nucleotides " |
| misc_feature | 5<br>note = /note="nucleotide bond by a Phosphorothioate linkage and 2 -O-Methyl-nucleotides " |
| misc_feature | 6<br>note = /note="deoxynucleotide bond by a Phosphorothioate linkage" |
| misc_feature | 7<br>note = /note="nucleotide bond by a Phosphorothioate linkage and 2 -O-Methyl-nucleotides " |
| misc_feature | 8<br>note = /note="nucleotide bond by a Phosphorothioate linkage and 2 -O-Methyl-nucleotides " |
| misc_feature | 9<br>note = /note="deoxynucleotide bond by a Phosphorothioate linkage" |
| misc_feature | 10<br>note = /note="nucleotide bond by a Phosphorothioate linkage and 2 -O-Methyl-nucleotides " |
| misc_feature | 11<br>note = /note="nucleotide bond by a Phosphorothioate linkage and 2 -O-Methyl-nucleotides " |
| misc_feature | 12<br>note = /note="nucleotide bond by a Phosphorothioate linkage and 2'-O-MOE RNA nucleotide" |
| misc_feature | 13<br>note = /note="deoxynucleotide bond by a Phosphorothioate linkage" |
| misc_feature | 14<br>note = /note="nucleotide bond by a Phosphorothioate linkage and 2'-O-MOE RNA nucleotide" |
| misc_feature | 15<br>note = /note="nucleotide bond by a Phosphorothioate linkage and LNA modified" |
| misc_feature | 16<br>note = /note="deoxynucleotide bond by a Phosphorothioate linkage" |
| misc_feature | 17<br>note = /note="nucleotide bond by a Phosphorothioate linkage and LNA modified" |
| misc_feature | 18<br>note = /note="nucleotide bond by a Phosphorothioate linkage and LNA modified" |
| source | 1..18<br>mol_type = other DNA<br>organism = synthetic construct |

```
SEQUENCE: 150
atggttagat caagcaca                                                    18

SEQ ID NO: 151          moltype = DNA  length = 19
FEATURE                 Location/Qualifiers
misc_feature            1..19
                        note = 151
misc_feature            1
                        note = /note="nucleotide bond by a Phosphorothioate linkage
                          and LNA modified"
misc_feature            2
                        note = /note="deoxynucleotide bond by a Phosphorothioate
                          linkage "
misc_feature            3
                        note = /note="deoxynucleotide bond by a Phosphorothioate
                          linkage"
misc_feature            4
                        note = /note="nucleotide bond by a Phosphorothioate linkage
                          and LNA modified"
misc_feature            5
                        note = /note="deoxynucleotide bond by a Phosphorothioate
                          linkage"
misc_feature            6
                        note = /note="deoxynucleotide bond by a Phosphorothioate
                          linkage"
misc_feature            7
                        note = /note="nucleotide bond by a Phosphorothioate linkage
                          and LNA modified"
misc_feature            8
                        note = /note="deoxynucleotide bond by a Phosphorothioate
                          linkage"
misc_feature            9
                        note = /note="nucleotide bond by a Phosphorothioate linkage
                          and LNA modified"
misc_feature            10
                        note = /note="deoxynucleotide bond by a Phosphorothioate
                          linkage"
misc_feature            11
                        note = /note="deoxynucleotide bond by a Phosphorothioate
                          linkage"
misc_feature            12
                        note = /note="nucleotide bond by a Phosphorothioate linkage
                          and LNA modified"
misc_feature            13
                        note = /note="nucleotide bond by a Phosphorothioate linkage
                          and LNA modified"
misc_feature            14
                        note = /note="deoxynucleotide bond by a Phosphorothioate
                          linkage"
misc_feature            15
                        note = /note="deoxynucleotide bond by a Phosphorothioate
                          linkage"
misc_feature            16
                        note = /note="nucleotide bond by a Phosphorothioate linkage
                          and LNA modified"
misc_feature            17
                        note = /note="deoxynucleotide bond by a Phosphorothioate
                          linkage"
misc_feature            18
                        note = /note="nucleotide bond by a Phosphorothioate linkage
                          and LNA modified"
misc_feature            19
                        note = /note="nucleotide bond by a Phosphorothioate linkage
                          and LNA modified"
source                  1..19
                        mol_type = other DNA
                        organism = synthetic construct
SEQUENCE: 151
atggttagat caagcacaa                                                   19

SEQ ID NO: 152          moltype = DNA  length = 21
FEATURE                 Location/Qualifiers
misc_feature            1..21
                        note = 152
misc_feature            1
                        note = /note="nucleotide bond by a Phosphorothioate linkage
                          and 2'-O-MOE RNA nucleotide"
misc_feature            2
                        note = /note="nucleotide bond by a Phosphorothioate linkage
```

| | | |
|---|---|---|
| misc_feature | 3 | |
| | note = /note="nucleotide bond by a Phosphorothioate linkage and 2'-Fluoro RNA nucleotide" | |
| misc_feature | 4 | |
| | note = /note="nucleotide bond by a Phosphorothioate linkage and 2'-Fluoro RNA nucleotide" | |
| misc_feature | 5 | |
| | note = /note="nucleotide bond by a Phosphorothioate linkage and 2'-Fluoro RNA nucleotide" | |
| misc_feature | 6 | |
| | note = /note="deoxynucleotide bond by a Phosphorothioate linkage" | |
| misc_feature | 7 | |
| | note = /note="nucleotide bond by a Phosphorothioate linkage and 2'-Fluoro RNA nucleotide" | |
| misc_feature | 8 | |
| | note = /note="nucleotide bond by a Phosphorothioate linkage and 2'-Fluoro RNA nucleotide" | |
| misc_feature | 9 | |
| | note = /note="nucleotide bond by a Phosphorothioate linkage and 2'-Fluoro RNA nucleotide" | |
| misc_feature | 10 | |
| | note = /note="nucleotide bond by a Phosphorothioate linkage and 2'-Fluoro RNA nucleotide" | |
| misc_feature | 11 | |
| | note = /note="nucleotide bond by a Phosphorothioate linkage and 2'-Fluoro RNA nucleotide" | |
| misc_feature | 12 | |
| | note = /note="nucleotide bond by a Phosphorothioate linkage and 2'-Fluoro RNA nucleotide" | |
| misc_feature | 13 | |
| | note = /note="nucleotide bond by a Phosphorothioate linkage and 2'-Fluoro RNA nucleotide" | |
| misc_feature | 14 | |
| | note = /note="nucleotide bond by a Phosphorothioate linkage and 2'-Fluoro RNA nucleotide" | |
| misc_feature | 15 | |
| | note = /note="nucleotide bond by a Phosphorothioate linkage and 2'-Fluoro RNA nucleotide" | |
| misc_feature | 16 | |
| | note = /note="nucleotide bond by a Phosphorothioate linkage and 2'-Fluoro RNA nucleotide" | |
| misc_feature | 17 | |
| | note = /note="nucleotide bond by a Phosphorothioate linkage and 2'-Fluoro RNA nucleotide" | |
| misc_feature | 18 | |
| | note = /note="nucleotide bond by a Phosphorothioate linkage and 2'-Fluoro RNA nucleotide" | |
| misc_feature | 19 | |
| | note = /note="nucleotide bond by a Phosphorothioate linkage and 2'-Fluoro RNA nucleotide" | |
| misc_feature | 20 | |
| | note = /note="nucleotide bond by a Phosphorothioate linkage and 2'-O-MOE RNA nucleotide" | |
| misc_feature | 21 | |
| | note = /note="nucleotide bond by a Phosphorothioate linkage and 2'-O-MOE RNA nucleotide" | |
| source | 1..21 | |
| | mol_type = other DNA | |
| | organism = synthetic construct | |
| SEQUENCE: 152 | | |
| acatggttag atcaagccca a | | 21 |
| | | |
| SEQ ID NO: 153 | moltype = DNA  length = 17 | |
| FEATURE | Location/Qualifiers | |
| misc_feature | 1..17 | |
| | note = 153 | |
| misc_feature | 1 | |
| | note = /note="nucleotide bond by a Phosphorothioate linkage and LNA modified" | |
| misc_feature | 2 | |
| | note = /note="nucleotide bond by a Phosphorothioate linkage and LNA modified" | |
| misc_feature | 3 | |
| | note = /note="deoxynucleotide bond by a Phosphorothioate linkage " | |
| misc_feature | 4 | |
| | note = /note="deoxynucleotide bond by a Phosphorothioate | |

| | | |
|---|---|---|
| | | linkage " |
| misc_feature | 5 | |
| | | note = /note="deoxynucleotide bond by a Phosphorothioate linkage " |
| misc_feature | 6 | |
| | | note = /note="nucleotide bond by a Phosphorothioate linkage and LNA modified" |
| misc_feature | 7 | |
| | | note = /note="deoxynucleotide bond by a Phosphorothioate linkage " |
| misc_feature | 8 | |
| | | note = /note="deoxynucleotide bond by a Phosphorothioate linkage " |
| misc_feature | 9 | |
| | | note = /note="deoxynucleotide bond by a Phosphorothioate linkage " |
| misc_feature | 10 | |
| | | note = /note="deoxynucleotide bond by a Phosphorothioate linkage " |
| misc_feature | 11 | |
| | | note = /note="nucleotide bond by a Phosphorothioate linkage and LNA modified" |
| misc_feature | 12 | |
| | | note = /note="nucleotide bond by a Phosphorothioate linkage and LNA modified" |
| misc_feature | 13 | |
| | | note = /note="deoxynucleotide bond by a Phosphorothioate linkage " |
| misc_feature | 14 | |
| | | note = /note="nucleotide bond by a Phosphorothioate linkage and LNA modified" |
| misc_feature | 15 | |
| | | note = /note="deoxynucleotide bond by a Phosphorothioate linkage " |
| misc_feature | 16 | |
| | | note = /note="nucleotide bond by a Phosphorothioate linkage and LNA modified" |
| misc_feature | 17 | |
| | | note = /note="nucleotide bond by a Phosphorothioate linkage and LNA modified" |
| source | 1..17 | |
| | | mol_type = other DNA |
| | | organism = synthetic construct |
| SEQUENCE: 153 | | |
| ggttagatca agcacaa | | 17 |
| | | |
| SEQ ID NO: 154 | moltype = DNA length = 16 | |
| FEATURE | Location/Qualifiers | |
| misc_feature | 1..16 | |
| | | note = 154 |
| misc_feature | 1 | |
| | | note = /note="nucleotide bond by a Phosphorothioate linkage and LNA modified" |
| misc_feature | 2 | |
| | | note = /note="nucleotide bond by a Phosphorothioate linkage and 2'-O-MOE RNA nucleotide" |
| misc_feature | 3 | |
| | | note = /note="deoxynucleotide bond by a Phosphorothioate linkage " |
| misc_feature | 4 | |
| | | note = /note="deoxynucleotide bond by a Phosphorothioate linkage " |
| misc_feature | 5 | |
| | | note = /note="nucleotide bond by a Phosphorothioate linkage and LNA modified" |
| misc_feature | 6 | |
| | | note = /note="deoxynucleotide bond by a Phosphorothioate linkage" |
| misc_feature | 7 | |
| | | note = /note=" nucleotide bond by a Phosphorothioate linkage and 2'-O-MOE RNA nucleotide" |
| misc_feature | 8 | |
| | | note = /note="nucleotide bond by a Phosphorothioate linkage and 2'-O-MOE RNA nucleotide" |
| misc_feature | 9 | |
| | | note = /note="deoxynucleotide bond by a Phosphorothioate linkage " |
| misc_feature | 10 | |
| | | note = /note="nucleotide bond by a Phosphorothioate linkage |

|  |  |
|---|---|
|  | and LNA modified" |
| misc_feature | 11 |
|  | note = /note="nucleotide bond by a Phosphorothioate linkage and LNA modified" |
| misc_feature | 12 |
|  | note = /note="deoxynucleotide bond by a Phosphorothioate linkage " |
| misc_feature | 13 |
|  | note = /note="nucleotide bond by a Phosphorothioate linkage and LNA modified" |
| misc_feature | 14 |
|  | note = /note="deoxynucleotide bond by a Phosphorothioate linkage " |
| misc_feature | 15 |
|  | note = /note="nucleotide bond by a Phosphorothioate linkage and LNA modified" |
| misc_feature | 16 |
|  | note = /note="nucleotide bond by a Phosphorothioate linkage and LNA modified" |
| source | 1..16 |
|  | mol_type = other DNA |
|  | organism = synthetic construct |
| SEQUENCE: 154 | |
| ggttagatca agcaca | 16 |
| | |
| SEQ ID NO: 155 | moltype = DNA  length = 19 |
| FEATURE | Location/Qualifiers |
| misc_feature | 1..19 |
|  | note = 155 |
| misc_feature | 1 |
|  | note = /note="nucleotide bond by a Phosphorothioate linkage and LNA modified" |
| misc_feature | 2 |
|  | note = /note="nucleotide bond by a Phosphorothioate linkage and 2'-O-MOE RNA nucleotide" |
| misc_feature | 3 |
|  | note = /note="nucleotide bond by a Phosphorothioate linkage and 2 -O-Methyl-nucleotide" |
| misc_feature | 4 |
|  | note = /note="nucleotide bond by a Phosphorothioate linkage and 2 -O-Methyl-nucleotide" |
| misc_feature | 5 |
|  | note = /note="nucleotide bond by a Phosphorothioate linkage and 2 -O-Methyl-nucleotide" |
| misc_feature | 6 |
|  | note = /note="nucleotide bond by a Phosphorothioate linkage and 2 -O-Methyl-nucleotide" |
| misc_feature | 7 |
|  | note = /note="nucleotide bond by a Phosphorothioate linkage and 2 -O-Methyl-nucleotide" |
| misc_feature | 8 |
|  | note = /note="nucleotide bond by a Phosphorothioate linkage and 2 -O-Methyl-nucleotide" |
| misc_feature | 9 |
|  | note = /note="nucleotide bond by a Phosphorothioate linkage and 2 -O-Methyl-nucleotide" |
| misc_feature | 10 |
|  | note = /note="nucleotide bond by a Phosphorothioate linkage and 2 -O-Methyl-nucleotide" |
| misc_feature | 11 |
|  | note = /note="DEOXYnucleotide bond by a Phosphorothioate linkage " |
| misc_feature | 12 |
|  | note = /note="nucleotide bond by a Phosphorothioate linkage and 2'-O-MOE RNA nucleotide" |
| misc_feature | 13 |
|  | note = /note="nucleotide bond by a Phosphorothioate linkage and LNA modified" |
| misc_feature | 14 |
|  | note = /note="nucleotide bond by a Phosphorothioate linkage and LNA modified" |
| misc_feature | 15 |
|  | note = /note="nucleotide bond by a Phosphorothioate linkage and 2'-O-MOE RNA nucleotide" |
| misc_feature | 16 |
|  | note = /note="nucleotide bond by a Phosphorothioate linkage and LNA modified" |
| misc_feature | 17 |
|  | note = /note="nucleotide bond by a Phosphorothioate linkage |

```
                        and LNA modified"
misc_feature            18
                        note = /note="nucleotide bond by a Phosphorothioate linkage
                         and 2'-O-MOE RNA nucleotide"
misc_feature            19
                        note = /note="nucleotide bond by a Phosphorothioate linkage
                         and LNA modified"
source                  1..19
                        mol_type = other DNA
                        organism = synthetic construct
SEQUENCE: 155
atggttagat caagcacaa                                                          19

SEQ ID NO: 156          moltype = DNA  length = 17
FEATURE                 Location/Qualifiers
misc_feature            1..17
                        note = 156
misc_feature            1
                        note = /note="nucleotide bond by a Phosphorothioate linkage
                         and LNA modified"
misc_feature            2
                        note = /note="nucleotide bond by a Phosphorothioate linkage
                         and 2'-O-MOE RNA nucleotide"
misc_feature            3
                        note = /note="deoxynucleotide bond by a Phosphorothioate
                         linkage "
misc_feature            4
                        note = /note="nucleotide bond by a Phosphorothioate linkage
                         and 2 -O-Methyl-nucleotide"
misc_feature            5
                        note = /note="nucleotide bond by a Phosphorothioate linkage
                         and 2 -O-Methyl-nucleotide"
misc_feature            6
                        note = /note="deoxynucleotide bond by a Phosphorothioate
                         linkage "
misc_feature            7
                        note = /note="nucleotide bond by a Phosphorothioate linkage
                         and 2 -O-Methyl-nucleotide"
misc_feature            8
                        note = /note="deoxynucleotide bond by a Phosphorothioate
                         linkage"
misc_feature            9
                        note = /note="nucleotide bond by a Phosphorothioate linkage
                         and 2 -O-Methyl-nucleotide"
misc_feature            10
                        note = /note="nucleotide bond by a Phosphorothioate linkage
                         and 2 -O-Methyl-nucleotide"
misc_feature            11
                        note = /note="nucleotide bond by a Phosphorothioate linkage
                         and LNA modified"
misc_feature            12
                        note = /note="deoxynucleotide bond by a Phosphorothioate
                         linkage"
misc_feature            13
                        note = /note="nucleotide bond by a Phosphorothioate linkage
                         and LNA modified"
misc_feature            14
                        note = /note="nucleotide bond by a Phosphorothioate linkage
                         and 2'-O-MOE RNA nucleotide "
misc_feature            15
                        note = /note="deoxynucleotide bond by a Phosphorothioate
                         linkage"
misc_feature            16
                        note = /note="nucleotide bond by a Phosphorothioate linkage
                         and LNA modified"
misc_feature            17
                        note = /note="nucleotide bond by a Phosphorothioate linkage
                         and LNA modified"
source                  1..17
                        mol_type = other DNA
                        organism = synthetic construct
SEQUENCE: 156
atggttaatc aagcaca                                                            17

SEQ ID NO: 157          moltype = DNA  length = 16
FEATURE                 Location/Qualifiers
misc_feature            1..16
                        note = 157
misc_feature            1
```

|              |                                                                                                   |
|--------------|---------------------------------------------------------------------------------------------------|
|              | note = /note="nucleotide bond by a Phosphorothioate linkage and LNA modified"                     |
| misc_feature | 2                                                                                                 |
|              | note = /note="deoxynucleotide bond by a Phosphorothioate linkage"                                 |
| misc_feature | 3                                                                                                 |
|              | note = /note="deoxynucleotide bond by a Phosphorothioate linkage "                                |
| misc_feature | 4                                                                                                 |
|              | note = /note="deoxynucleotide bond by a Phosphorothioate linkage"                                 |
| misc_feature | 5                                                                                                 |
|              | note = /note="nucleotide bond by a Phosphorothioate linkage and LNA modified"                     |
| misc_feature | 6                                                                                                 |
|              | note = /note="deoxynucleotide bond by a Phosphorothioate linkage"                                 |
| misc_feature | 7                                                                                                 |
|              | note = /note="deoxynucleotide bond by a Phosphorothioate linkage"                                 |
| misc_feature | 8                                                                                                 |
|              | note = /note="deoxynucleotide bond by a Phosphorothioate linkage"                                 |
| misc_feature | 9                                                                                                 |
|              | note = /note="deoxynucleotide bond by a Phosphorothioate linkage"                                 |
| misc_feature | 10                                                                                                |
|              | note = /note="deoxynucleotide bond by a Phosphorothioate linkage"                                 |
| misc_feature | 11                                                                                                |
|              | note = /note="nucleotide bond by a Phosphorothioate linkage and LNA modified"                     |
| misc_feature | 12                                                                                                |
|              | note = /note="nucleotide bond by a Phosphorothioate linkage and LNA modified"                     |
| misc_feature | 13                                                                                                |
|              | note = /note="deoxynucleotide bond by a Phosphorothioate linkage"                                 |
| misc_feature | 14                                                                                                |
|              | note = /note="deoxynucleotide bond by a Phosphorothioate linkage"                                 |
| misc_feature | 15                                                                                                |
|              | note = /note="nucleotide bond by a Phosphorothioate linkage and LNA modified"                     |
| misc_feature | 16                                                                                                |
|              | note = /note="nucleotide bond by a Phosphorothioate linkage and LNA modified"                     |
| source       | 1..16                                                                                             |
|              | mol_type = other DNA                                                                              |
|              | organism = synthetic construct                                                                    |
| SEQUENCE: 157 |                                                                                                  |
| gttagatcaa gcacaa |                                                                               16              |
| SEQ ID NO: 158 | moltype = DNA  length = 16                                                                      |
| FEATURE      | Location/Qualifiers                                                                               |
| misc_feature | 1..16                                                                                             |
|              | note = 158                                                                                        |
| misc_feature | 1                                                                                                 |
|              | note = /note="nucleotide bond by a Phosphorothioate linkage"                                      |
| misc_feature | 1                                                                                                 |
|              | note = /note="LNA modified base"                                                                  |
| misc_feature | 1                                                                                                 |
|              | note = /note="nucleotide conjugated to NHC6 conjugated to Oleic Acid"                             |
| misc_feature | 2                                                                                                 |
|              | note = /note="2'-O-MOE RNA nucleotides"                                                           |
| misc_feature | 2                                                                                                 |
|              | note = /note="nucleotide bond by a Phosphorothioate linkage"                                      |
| misc_feature | 3                                                                                                 |
|              | note = /note="nucleotide bond by a Phosphorothioate linkage and 2 -O-Methyl-nucleotides "         |
| misc_feature | 4                                                                                                 |
|              | note = /note="nucleotide bond by a Phosphorothioate linkage and 2 -O-Methyl-nucleotides "         |
| misc_feature | 5                                                                                                 |
|              | note = /note="nucleotide bond by a Phosphorothioate linkage and 2 -O-Methyl-nucleotides "         |
| misc_feature | 6                                                                                                 |
|              | note = /note="nucleotide bond by a Phosphorothioate linkage"                                      |

```
misc_feature        6
                    note = /note="LNA modified base"
misc_feature        7
                    note = /note="nucleotide bond by a Phosphorothioate linkage
                     and 2 -O-Methyl-nucleotide"
misc_feature        8
                    note = /note="nucleotide bond by a Phosphorothioate linkage
                     and 2 -O-Methyl-nucleotide"
misc_feature        9
                    note = /note="nucleotide bond by a Phosphorothioate linkage
                     and 2 -O-Methyl-nucleotide"
misc_feature        10
                    note = /note="nucleotide bond by a Phosphorothioate linkage"
misc_feature        10
                    note = /note="LNA modified base"
misc_feature        11
                    note = /note="2'-O-MOE RNA nucleotides"
misc_feature        11
                    note = /note="nucleotide bond by a Phosphorothioate linkage"
misc_feature        12
                    note = /note="nucleotide bond by a Phosphorothioate linkage"
misc_feature        12
                    note = /note="LNA modified base"
misc_feature        13
                    note = /note="nucleotide bond by a Phosphorothioate linkage"
misc_feature        13
                    note = /note="LNA modified base"
misc_feature        14
                    note = /note="2'-O-MOE RNA nucleotides"
misc_feature        14
                    note = /note="nucleotide bond by a Phosphorothioate linkage"
misc_feature        15
                    note = /note="nucleotide bond by a Phosphorothioate linkage"
misc_feature        15
                    note = /note="LNA modified base"
misc_feature        16
                    note = /note="LNA modified base"
source              1..16
                    mol_type = other DNA
                    organism = synthetic construct
SEQUENCE: 158
atccctggca atgtga                                                          16

SEQ ID NO: 159      moltype = DNA  length = 16
FEATURE             Location/Qualifiers
misc_feature        1..16
                    note = 159
misc_feature        1
                    note = /note="LNA modified base"
misc_feature        1
                    note = /note="nucleotide bond by a Phosphorothioate linkage"
misc_feature        2
                    note = /note="LNA modified base"
misc_feature        2
                    note = /note="nucleotide bond by a Phosphorothioate linkage"
misc_feature        3
                    note = /note="nucleotide bond by a Phosphorothioate linkage"
misc_feature        3
                    note = /note="5-Methyl-2'-O-Methyl cytidine "
misc_feature        3
                    note = /note="2 -O-Methyl-nucleotide"
misc_feature        4
                    note = /note="nucleotide bond by a Phosphorothioate linkage"
misc_feature        4
                    note = /note="5-Methyl-2'-O-Methyl cytidine "
misc_feature        4
                    note = /note="2 -O-Methyl-nucleotide"
misc_feature        5
                    note = /note="2'-O-MOE RNA nucleotide"
misc_feature        6
                    note = /note="LNA modified base"
misc_feature        7
                    note = /note="nucleotide bond by a Phosphorothioate linkage"
misc_feature        7
                    note = /note="2'-O-MOE RNA nucleotide"
misc_feature        8
                    note = /note="nucleotide bond by a Phosphorothioate linkage"
misc_feature        8
                    note = /note="2 -O-Methyl-nucleotide"
```

| | |
|---|---|
| misc_feature | 9<br>note = /note="LNA modified base" |
| misc_feature | 9<br>note = /note="nucleotide bond by a Phosphorothioate linkage" |
| misc_feature | 9<br>note = /note="2'-O-MOE RNA nucleotide" |
| misc_feature | 11<br>note = /note="LNA modified base" |
| misc_feature | 11<br>note = /note="2'-O-MOE RNA nucleotide" |
| misc_feature | 12<br>note = /note="LNA modified base" |
| misc_feature | 14<br>note = /note="LNA modified base" |
| misc_feature | 14<br>note = /note="nucleotide bond by a Phosphorothioate linkage" |
| misc_feature | 14<br>note = /note="2'-O-MOE RNA nucleotide" |
| misc_feature | 15<br>note = /note="LNA modified base" |
| misc_feature | 15<br>note = /note="nucleotide bond by a Phosphorothioate linkage" |
| misc_feature | 16<br>note = /note="nucleotide conjugated to threoninol<br> conjugated to oleic acid" |
| source | 1..16<br>mol_type = other DNA<br>organism = synthetic construct |
| SEQUENCE: 159 | |
| atccctggca atgtga | 16 |
| SEQ ID NO: 160<br>FEATURE | moltype = DNA  length = 16<br>Location/Qualifiers |
| misc_feature | 1..16<br>note = 160 |
| misc_feature | 1<br>note = /note="LNA modified base" |
| misc_feature | 1<br>note = /note="nucleotide bond by a Phosphorothioate linkage" |
| misc_feature | 2<br>note = /note="LNA modified base" |
| misc_feature | 2<br>note = /note="nucleotide bond by a Phosphorothioate linkage" |
| misc_feature | 3<br>note = /note="nucleotide bond by a Phosphorothioate linkage" |
| misc_feature | 3<br>note = /note="5-Methyl-2'-O-Methyl cytidine " |
| misc_feature | 4<br>note = /note="nucleotide bond by a Phosphorothioate linkage" |
| misc_feature | 4<br>note = /note="5-Methyl-2'-O-Methyl cytidine " |
| misc_feature | 5<br>note = /note="2'-O-MOE RNA nucleotide" |
| misc_feature | 6<br>note = /note="LNA modified base" |
| misc_feature | 7<br>note = /note="nucleotide bond by a Phosphorothioate linkage" |
| misc_feature | 7<br>note = /note="2'-O-MOE RNA nucleotide" |
| misc_feature | 8<br>note = /note="nucleotide bond by a Phosphorothioate linkage" |
| misc_feature | 8<br>note = /note="2 -O-Methyl-nucleotide" |
| misc_feature | 9<br>note = /note="nucleotide bond by a Phosphorothioate linkage" |
| misc_feature | 9<br>note = /note="2'-O-MOE RNA nucleotide" |
| misc_feature | 10<br>note = /note="LNA modified base" |
| misc_feature | 11<br>note = /note="2'-O-MOE RNA nucleotide" |
| misc_feature | 12<br>note = /note="LNA modified base" |
| misc_feature | 13<br>note = /note="LNA modified base" |
| misc_feature | 14<br>note = /note="nucleotide bond by a Phosphorothioate linkage" |
| misc_feature | 14<br>note = /note="2'-O-MOE RNA nucleotide" |

```
misc_feature       15
                   note = /note="LNA modified base"
misc_feature       15
                   note = /note="nucleotide bond by a Phosphorothioate linkage"
misc_feature       16
                   note = /note="nucleotide conjugated to NH2C6"
misc_feature       16
                   note = /note="LNA modified base"
source             1..16
                   mol_type = other DNA
                   organism = synthetic construct
SEQUENCE: 160
atccctggca atgtga                                                       16
```

OLIGONUCLEOTIDES CONJUGATED TO OLEIC ACID AND USES THEREOF

REFERENCE TO AN ELECTRONIC SEQUENCE LISTING

The contents of the electronic sequence listing (920235_401_SEQ_LISTING.xml; Size: 824,499 bytes; and Date of Creation: Mar. 7, 2024) is herein incorporated by reference in its entirety.

TECHNICAL FIELD OF THE INVENTION

The present invention relates to the field of medicine. More specifically, the invention relates to oligonucleotide antagonists of endogenous microRNAs, particularly hsa-miR-218-5p and hsa-miR-23b-3p, that are conjugated to oleic acid, and their uses.

BACKGROUND OF THE INVENTION

Myotonic dystrophy type 1 (DM1) is a rare genetic disease with no current effective treatment. DM1 is associated with a substantial disease burden resulting in impairment across many different patient systems and tissues. Muscle weakness and fatigue constitute the two most common disease manifestations, reported by 93% and 90% of patients, respectively, followed by muscle locking (73%). Other phenotypes include cardiac dysfunctions, cataracts, insulin resistance, and cognitive impairment. DM1 disease is based on CTG repeat expansions occurring in the DM1 protein kinase (DMPK) gene, which are transcribed into pathogenic mRNAs. It is currently well established that CUG expansions bind with high affinity to the Muscleblind-like (MBNL1, 2, and 3) family of proteins, thereby inhibiting their normal function, but other alterations may contribute to MBNL1 and MBNL2 depletion. In skeletal muscle and brain, MBNL1 and MBNL2, respectively, are preferentially expressed, whereas MBNL3 is expressed primarily during embryonic development and adult tissue regeneration.

MBNL1 and MBNL2 proteins control alternative splicing and polyadenylation of several transcripts, specifically by causing a shift from foetal to adult patterns, and act antagonistically to CUGBP Elav-like family member 1 (CELF) proteins in splice regulation, which are found upregulated and mislocated in DM1. Further, it has been shown that there is genetic redundancy between MBNL1 and 2 genes, as the deletion of only one resulted in the upregulation of the other and occupancy of its binding sites in target RNAs (see Lee 2013. Compound loss of muscleblind-like function in myotonic dystrophy. EMBO Mol Med 5:1887-900.) The depletion of MBNL1 protein function has been shown to be a critical factor in the course of the disease. Indeed, MBNL1 loss of function accounts for more than 80% of mis-splicing events and nearly 70% of expression defects. MBNL genes and/or MBNL protein upregulation in DM1 mice and patient-derived fibroblasts is well tolerated and rescues several symptoms, such as myotonia and mis-splicing events, as well as the reduction of foci formation, opening the path for the development of therapeutic approaches aimed at increasing the expression of these genes. MBNL1 and MBNL2 depletion also impinge on several other gene expression processes, for example impairing trafficking of membrane-associated mRNAs or miRNA biogenesis.

MicroRNAs (also referred herein as "miRNA" or "miRs") are a class of small non-coding RNAs that play important roles in regulating gene expression, particularly in gene silencing. In human cells, the expression of hsa-miR-23b-3p and hsa-miR-218-5p has been shown to regulate MBNL1 and MBNL2 transcripts directly by luciferase reporter assay (Cerro-Herreros et al. 2018 Nat. Commun. 9, 2482). Silencing of hsa-miR-23b-3p and hsa-miR-218-5p increases Muscleblind-like protein expression and alleviates myotonic dystrophy phenotypes in mammalian models. On the other hand, antimiRs are a class of oligonucleotides that prevents other molecules, such as microRNAs, from binding to a target site on an RNA, particularly in messenger RNA (mRNA) molecules. The use of regular antimiRs as therapeutic molecules has limitations in their development as drug candidates, including a short life span due to degradation in the cellular environment, poor cellular intake from extracellular media, and limited therapeutic window expressed as the ratio of the concentrations at which a compound reaches median toxicity and efficacy (TC50/EC50) so that the higher the ratio, the better. Thus, methods aimed at increasing antimiRs stability, potency, tissue-specific uptake, and therapeutic window, among other pharmacological parameters, need to be further developed in order to exploit the full potential of antimiRs in inhibiting their target hsa-miR-218-5p and hsa-miR-23b-3p.

On the one hand, albumin is one of the most abundant proteins in plasma and provides the transport of fatty acids, drugs, ions and other metabolites. Conjugation of the oligonucleotides with fatty acids may increase the albumin binding affinity of the oligonucleotides, enhancing their ability to cross the endothelial barrier and improving their functional uptake into muscles, thereby increasing the oligonucleotide potency in vivo. However, the wide variety of saturated and unsaturated fatty acids that differ in their structure may, in turn, influence protein binding or activity of fatty acid conjugates, leaving unclear what the optimal fatty acid for enhancing oligonucleotide potency is.

On the other hand, other chemical modifications can be included in the oligonucleotides to increase their pharmacological parameters. Among said modifications, phosphorothioate (PS) linkages continue to show promising results as first-generation antisense oligos, although they present important limitations that are still hampering the development of fully modified (full PS) therapeutic oligonucleotides. Said limitations include the toxicity of PS-oligos reported in some studies in mice, rats, monkeys, and humans. In mice and rats, these side effects include thrombocytopenia, the elevation of liver transaminases, hyperplasia of reticuloendothelial cells in various organs, and renal tubular changes (UM Sarmiento, et al. In vivo toxicological effects of rel A antisense phosphorothioates in CD-1 mice. Antisense Res Dev. 1994 Summer; 4(2):99-107. doi: 10.1089/ard.1994.4.99. PMID: 7950306; S Agrawal et al. Mixed-backbone oligonucleotides as second generation antisense oligonucleotides: In vitro and in vivo studies. Proceedings of the National Academy of Sciences March 1997, 94 (6) 2620-2625; DOI: 10.1073/pnas.94.6.2620). In monkeys, the side effects observed are activation of complement (Agrawal, Sudhir, et al. "Novel enzymatic and immunological responses to oligonucleotides." Toxicology letters 82 (1995): 431-434.) and prolongation of activated partial thromboplastin time (aPTT). Because similar side effects have been observed after administration of dextran sulfate, the inference is that these side effects are caused by the polyanionic nature of PS-oligos and are not nucleotide-sequence-specific. Thus, oligonucleotides with reduced toxicity but increased stability need to be developed.

The present invention overcomes these limitations by providing improved antimiRs conjugated to oleic acid.

BRIEF DESCRIPTION OF THE INVENTION

Figure 1:
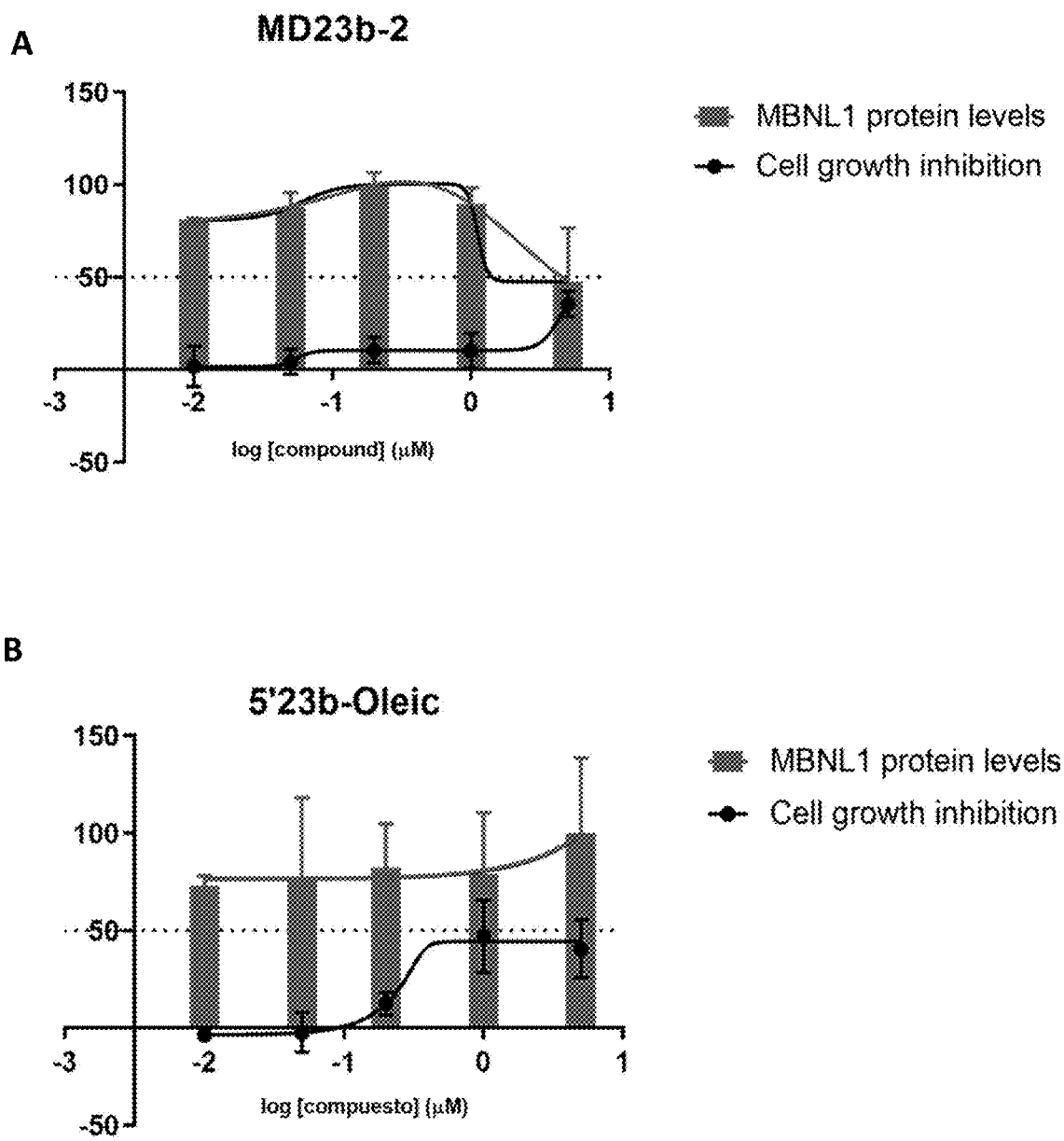
FIG. 1. Evaluation of toxicity and efficacy on DM1 cells. Representation of toxicity (percentage of cell growth inhibition, black) and efficacy (percentage of MBNL1 expression increase, compared to mock-transfected cells, grey) on DM1 myotubes after lipofection with (A) MD23b-2, (B) 5'-23b-Oleic, (C) non-conjugated-23b or (D) 218-D/LNA2 at 5 different concentrations (for MD23b-2, 5'-23b-Oleic and non-conjugated-23b: 10 nM, 50 nM, 200 nM, 1 μM and 5 μM; and for 218-D/LNA2: 0.08 nM, 0.4 nM, 2 nM, 10 nM and 50 nM). The dotted line indicates TC50 and EC50 levels. Each concentration was tested in triplicate. Error bars=standard error of the mean (SEM). The Graphpad's equation "Bell-shaped dose response" has been used to fit the dose-response curves.
Figure 1:
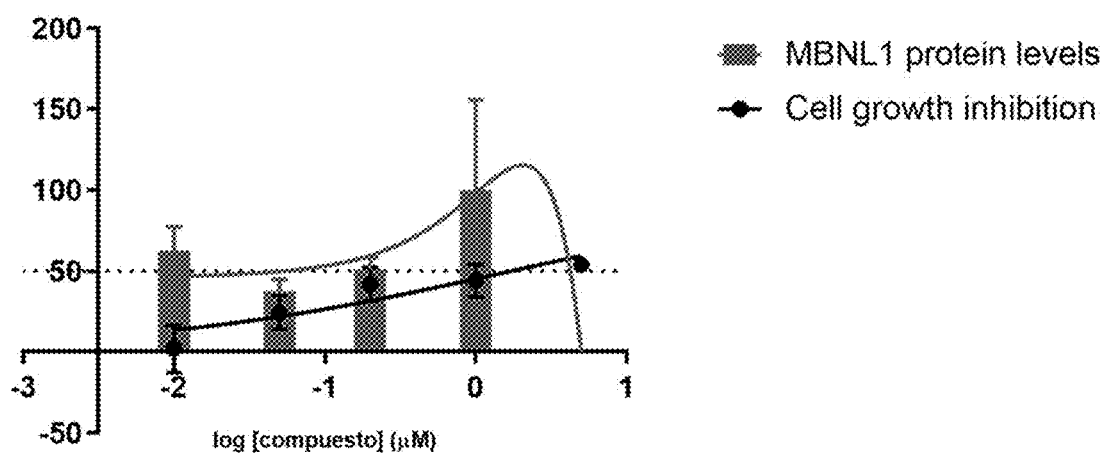
Figure 1:
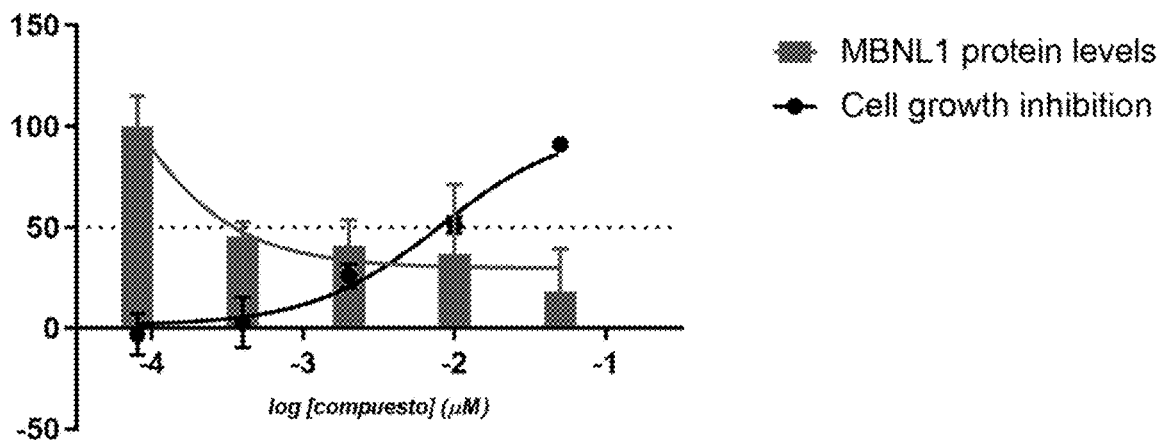

In one aspect, the present invention relates to an oligonucleotide molecule, or a mixture of two or more of said molecules, wherein said oligonucleotide molecule comprises between 10 to 30 nucleotides in length, wherein said oligonucleotide molecule comprises at least two nucleotides chemically linked by a phosphorothioate linkage, and wherein said oligonucleotide molecule is conjugated at its 3' and/or 5' ends to at least one oleic acid molecule. Preferably, wherein the molecule is an antagonist of a microRNA, more preferably wherein the microRNA is the human hsa-miR-23b-3p or the human hsa-miR-218-5p.

In an embodiment, the oligonucleotide molecule according to the first aspect comprises between 15 to 30 nucleotides in length, comprises at least two nucleotides linked by a phosphodiester linkage, wherein the number of nucleotides that are chemically linked by a phosphorothioate linkage is greater than the number of nucleotides that are chemically linked by a phosphodiester linkage.

In an embodiment, the oligonucleotide molecule according to the first aspect comprises between 15 to 30 nucleotides in length, and wherein said oligonucleotide molecule also comprises a fragment composed of a succession of at least 15 consecutive nitrogen bases of nucleotides that are identical in at least 80% to the sequence of a region present in SEQ ID NO: 1 (antimiR-218-5p) or 2 (antimiR-23b-3p), or SEQ ID NO: 52-110.

In an embodiment, the oligonucleotide molecule according to the first aspect comprises between 15 to 30 nucleotides in length, and wherein said oligonucleotide molecule also comprises a fragment composed of a succession of at least 15 consecutive nitrogen bases of nucleotides that are identical to the sequence of a region present in SEQ ID NO: 1 (antimiR-218-5p) or 2 (antimiR-23b-3p).

In an embodiment, the oligonucleotide molecule according to the first aspect comprises at least one chemical modification, wherein the chemical modification is selected from the group of:
  i) 2'-O-methyl (2'OMe),
  ii) 2'-O-Methoxyethyl (2' MOE), and/or
  iii) an extra bridge connecting the 2' oxygen and 4' carbon (LNA).

In an embodiment, the oligonucleotide molecule according to the first aspect comprises between 15 to 30 nucleotides in length, and wherein said oligonucleotide molecule also comprises a fragment composed of a succession of at least 15 consecutive nitrogen bases of nucleotide that are identical in at least 80% to the sequence of a region present in SEQ ID NOs: 3, 4, 5, 22, 23, 24, 49, 50 or 51 (antagonists of hsa-miR-23b) or SEQ ID NOs: 7, 8, 9, 14, 25, 26, 27, or 28 (antagonists of hsa-miR-218-5p).

In an embodiment, the oligonucleotide molecule according to the first aspect comprises between 15 to 30 nucleotides in length, wherein the nucleotide sequence of said oligonucleotide consists of SEQ ID NOs: 3, 4, 5, 22, 23, 24, 49, 50 or 51 (antagonists of hsa-miR-23b) or SEQ ID NOs: 7, 8, 9, 14, 25, 26, 27, or 28 (antagonists of hsa-miR-218-5p).

In another aspect, the present invention relates to composition, preferably a pharmaceutical composition, comprising at least an oligonucleotide molecule as defined in the first aspect or any of its embodiments, or a mixture of two or more of them, optionally further comprising a carrier and/or one or more pharmaceutically acceptable excipients.

In another aspect, the present invention relates to composition as defined in the second aspect or any of its embodiment, for use in therapy.

In another aspect, the present invention relates to composition as defined in the second aspect or any of its embodiment, for use in targeting muscular cells in a subject in need thereof.

In another aspect, the present invention relates to composition as defined in the second aspect or any of its embodiment, for use in the prevention or treatment of muscular diseases or in the prevention or treatment of RNAopathies.

Preferably, the disease is myotonic dystrophy, more preferably myotonic dystrophy is of type 1.

In another aspect is provided an oligonucleotide molecule consisting of SEQ ID NOs: 22, 23, or 25, wherein the spacer molecule defined in said SEQ ID NOs: 22, 23 and 25 is selected from the group consisting of NHC3, NHC5, NHC6, and threoninol. For example, in some aspects the oligonucleotide molecule consists of SEQ ID NO: 3, SEQ ID NO: 4 or SEQ ID NO: 7.

In another aspect, a pharmaceutical composition is provided, comprising an oligonucleotide molecule consisting of SEQ ID NOs: 22, 23, or 25, wherein the spacer molecule defined in said SEQ ID NOs: 22, 23 and 25 is selected from the group consisting of NHC3, NHC5, NHC6, and threoninol, and a pharmaceutically acceptable carrier or excipient, or a combination thereof. In some aspects, the pharmaceutical composition comprises an oligonucleotide molecule consisting of SEQ ID NO: 3, SEQ ID NO: 4 or SEQ ID NO: 7.

In still different aspects is provided a method for treatment of RNAopathies, comprising administering a pharmaceutical composition comprising an oligonucleotide molecule consisting of SEQ ID NOs: 22, 23, or 25, wherein the spacer molecule defined in said SEQ ID NOs: 22, 23 and 25 is selected from the group consisting of NHC3, NHC5, NHC6, and threoninol, and a pharmaceutically acceptable carrier or excipient, or a combination thereof, to a subject in need thereof. In some aspects, the pharmaceutical composition used in such methods comprises an oligonucleotide molecule consisting of SEQ ID NO: 3, SEQ ID NO: 4 or SEQ ID NO: 7.

In another aspect is provided a method for treatment of muscular diseases or nervous system diseases, or both, comprising administering a pharmaceutical composition comprising an oligonucleotide molecule consisting of SEQ ID NOs: 22, 23, or 25, wherein the spacer molecule defined in said SEQ ID NOs: 22, 23 and 25 is selected from the group consisting of NHC3, NHC5, NHC6, and threoninol, and a pharmaceutically acceptable carrier or excipient, or a combination thereof, to a subject in need thereof. In some aspects, the disease is myotonic dystrophy, such as type 1 myotonic dystrophy. In some aspects of any of the foregoing methods, the pharmaceutical composition comprises an oligonucleotide molecule consisting of SEQ ID NO: 3, SEQ ID NO: 4 or SEQ ID NO: 7.

DESCRIPTION OF THE INVENTION

General Definitions

It must be noted that, as used herein, the singular forms "a", "an", and "the", include plural references unless the context clearly indicates otherwise. Further, unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the present invention.

The term "about" when referring to a given amount or quantity indicates that a number can vary between +20% around its indicated value. Preferably "about" means±10% around its value, more preferably "about" means±10, 8, 6, 5, 4, 3, 2% around its value, or even "about" means±1% around its value, in that order of preference.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein, the term "comprising" can be substituted with the term "containing" or "including" or sometimes when used herein with the term "having". Any of the aforementioned terms (comprising, containing, including, having), whenever used herein in the context of an aspect or embodiment of the present invention may be substituted with the term "consisting of", though less preferred.

When used herein, "consisting of" excludes any element, step, or ingredient not specified in the claim element. When used herein, "consisting essentially of" does not exclude materials or steps that do not materially affect the basic and novel characteristics of the claim.

As used herein, names referring to murine genes are typed italicized with an uppercase letter followed by all lowercase letters. Murine protein designations follow the same rules as murine gene symbols, but are not italicized. When referring to human genes or proteins, uppercase letters are always used, being italicized in the case of the gene. Nevertheless, a skilled person will be able to infer the precise nature of the biomolecule (protein, gene, transcript) and species from the technical context of the description.

By "oligonucleotide," as referred herein is meant any short segment of DNA, RNA, or DNA/RNA, including both natural and synthetic nucleotides. As used in this invention, the term "oligonucleotide molecules" includes both oligonucleotides as such, as well as the "oligonucleotide analogues". "Oligonucleotide analogues" are the molecules derived therefrom that incorporate some chemical modification in at least one of the nucleotide units that form them, either in the phosphate group, the pentose or one of the nitrogenous bases; the modifications consisting in the addition of non-nucleotide groups at the 5' and/or 3' ends are also included as well as phosphorodiamidate morpholino oligomers, peptide nucleic acids (PNAs; mimics of DNA in which the deoxyribose phosphate backbone is replaced by a pseudo-peptide polymer to which the nucleobases are linked), and the like. By extension, for the purposes of this invention and as used herein, the terms "oligonucleotide molecule" and "oligonucleotide analogue" or "oligonucleotide analogue molecule" also include sponges of microRNAs or microRNA sponges, as it can be considered that the main constituent of the same are tandem repeats of oligonucleotides, characterized in that each of these oligonucleotides are in themselves or contain a binding site of a microRNA of interest. For the sake of clarity, it is mentioned that the oligonucleotide sequences disclosed herein and numbered as "SEQ ID NO", comprise a nucleobase sequence together with chemical modifications and/or fatty acid conjugation, if any. For example, SEQ ID NO 3 refers to the nucleobase sequence "ATCCCTGGCAATGTGA", together with the LNA, phosphorothioate linkages, and 5-Methyl-2'-O-Methyl cytidine, modifications, among others. Thus, this sequence is represented herein as SEQ ID NO 3: AbsTbs(5Mc)s(5Mc)sCmTbGmsgsCms-AbAm-TbGbTmsGbsAb(NHC6)(OleicAcid).

By "antagonist oligonucleotide" is referred herein as an oligonucleotide that is able to block or inhibit the natural function of a molecule, in this case, a microRNA. Thus, the antagonist oligonucleotides of the present invention are inhibitor molecules that avoid the activation, stability or function of the antimiR to which they bind. In the context of the present invention, "antagonist" is synonymous of "inhibitor" and can thus be used interchangeably. For example, an "antagonist oligonucleotide of hsa-miR-23b-3p" refers to an oligonucleotide molecule that inhibits the function of the hsa-miR-23b-3p.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the same nucleobase or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (BLAST in the resources of the National Center for Biotechnology Information, CLUSTAL in the resources of the European Bioinformatics Institute, GAP, BESTFIT, FASTA, and TFASTA in the Wisconsin Genetics Software Package, Genetics Computer Group (GCG), 575 Science Dr., Madison, Wis.), or by inspection. It should be noted that the "percentage of identity" as used herein is decided in the context of a local alignment, i.e., it is based on the alignment of regions of local similarity between nucleobase sequences, contrary to a global alignment, which aims to align two sequences across their entire span. Thus, in the context of the present invention, percentage identity is calculated preferably only based on the local alignment comparison algorithm.

Often, especially in the case of antimiRs, chemical modifications are incorporated to the corresponding nucleotide units, which mainly affect the ribose moiety and/or phosphate, modifications that are difficult to depict in the usual representations of nucleotide sequences, in which the nucleotide present in a given position is identified by the abbreviation of the nitrogenous base that is part of it. Therefore, in the present invention, there are compared molecules of microRNA antagonists that refer to the percentage of identity between the sequences of the nitrogenous bases or nucleobases of the nucleotide or nucleotide analogue units present in these units, as this is what indicates whether two molecules or sequence fragments are designed from the same original basic nucleotide sequence, independently of the different chemical modifications that may have been included in the nucleotides in each case.

As used in this specification, it is understood that two chains of nucleotide molecules are 100% complementary when the nucleotide or nucleotide analogue sequence of one of them, read in the 5'-3' sense, is the sequence of nucleotides or nucleotide analogues that present the nitrogenous bases which pair with the nitrogenous bases of nucleotides or nucleotide analogues of the other sequence, read in the 3'-5' sense. That is to say, the sequence 5'-UAGC-3' would be complementary to the sequences 3'-AUCG-5' and 3'-ATCG-5', which would be, respectively, sequences 5'-GCUA-3' and 5'-GCTA-3' read in the 5'-3' sense. In an embodiment, it is preferred that the antagonist molecule comprises in its sequence a fragment that is identical to the complementary sequence to that of the seed region of the microRNA to be antagonized, at least with regard to the complementarity of the nitrogenous bases.

As used herein, "antimiRs" refer to oligonucleotides, preferably oligoribonucleotides, that are complementary to a microRNA, preferably a mature microRNA, that is their target and they bind to with great affinity inhibiting it. Therefore, antimiRs refer to oligonucleotides, usually chemically modified with respect to the corresponding oligomer composed only of nucleotide units, and that are complementary and thus inhibitors of a target microRNA. In the particular case of the present invention, the antimiRs described herein are preferably at least partially complementary to human microRNAs hsa-miR-23b-3p or hsa-miR-218-5p.

As used herein, "microRNA sponges" are usually designed so that they inhibit microRNAs with a complementary heptameric or octameric fragment (seed region), such that a single sponge construct can be used to block a whole family of microRNAs sharing the same motif, although they may also contain the entire target sequence for a specific microRNA or only a miRNA-specific region, devoid of the seed region, to make it specific.

The expressions "pharmaceutically acceptable" or "pharmacologically acceptable" refer to molecular entities and compositions that do not produce any adverse, allergic or other reactions when administered to an animal or human being. As used herein, "pharmaceutically acceptable vehicle" includes solvents, buffers, solutions, dispersion media, coatings, antibacterial and antifungal agents, isotonic and absorption retarding agents, fatty acids such as oleic acid, and similar acceptable agents for use in formulation pharmaceuticals, such as pharmaceutical products suitable for administration to human beings.

"Preventing", "to prevent", or "prevention", include without limitation, decreasing, reducing or ameliorating the risk of a symptom, disorder, condition, or disease, and protecting an animal from a symptom, disorder, condition, or disease. A prevention may be applied or administered prophylactically.

"Treating", "to treat", or "treatment", include without limitation, restraining, slowing, stopping, reducing, ameliorating, or reversing the progression or severity of an existing symptom, clinical sign, disorder, condition, or disease. A treatment may be applied or administered therapeutically.

By "TC50" or "half-maximal inhibitory concentration" is referred herein as the concentration of an inhibitor administered to test organism or test cell lines that produces toxic effects in 50 percent of a population of exposed organisms or cell lines in a given time period.

By "EC50" or "half-maximal effective concentration" is referred herein as the concentration of an antagonist or inhibitor required to obtain a response halfway between the baseline and maximum in a given time period. That is, EC50 is the concentration required to obtain a 50% of the effect caused by the treatment.

By "Emax" is referred herein as the maximum response achievable from an applied or dosed agent, in this case, an antagonist molecule. Emax is measured as the maximum fold change of the target protein, e.g. MBNL1 protein, obtained after transfection with a specific antimiR-23b-3p or antimiR-218-5p compared to the mock (transfected with vehicle or non-transfected).

The "Tindex" or "therapeutic index/ratio" is a quantitative measurement of the relative safety of a drug. In the present invention, the Tindex is defined as the ratio between the amount of a therapeutic agent that causes 50% toxicity (TC50) and the amount that causes 50% of the therapeutic effect (EC50), multiplied by the maximum response achievable:

$$Tindex=(TC50/EC50)*Emax$$

The term "3' end", as used herein, designates the end of a nucleotide strand that has the hydroxyl group of the third carbon in the sugar-ring at its terminus. The term "5' end", as used herein, designates the end of a nucleotide strand that has the fifth carbon in the sugar-ring at its terminus.

DETAILED DESCRIPTION

As stated above, improved oligonucleotides comprising chemical modifications resulting in less toxicity but increased therapeutic effect need to be developed. Thus, two main objectives were covered by the present invention. On the one hand, it was an objective of the present invention to evaluate what is the best fatty acid to be conjugated to the oligonucleotide, and to design oligonucleotides that have the maximum allowed amount of PS linkages that provide the beneficial effect to the molecule but without being too toxic for administration in vivo. On the other hand, the present invention also provides specific microRNA inhibitors, particularly oligonucleotide molecules or analogues thereof, aimed at correcting the insufficient function of MBNL (Muscleblind-like) proteins, partially originating from overexpression of hsa-miR-23b-3p and hsa-miR-218-5p in patients with myotonic dystrophy (DM), preferably myotonic dystrophy 1 (DM1).

First, the inventors tested in vitro the effects of conjugating previously published antagomiR-23b and antagomiR-218 oligonucleotides (Cerro-Herreros et al. 2018 Nat. Commun. 9, 2482) with different hydrophobic moieties, (including lipids and fatty acids) (Table 1) in terms of toxicity, efficacy (levels of MBNL1 protein) and therapeutic index (Tindex). The antagomiR sequences used in this study contained all 2'OME modified nucleotides and a mix of phosphorothioate (PS) linkages and phosphodiester (PO) linkages. Surprisingly, it was found that, for both the antagomiR-23b and antagomiR-218 oligonucleotides, the conjugation with oleic acid produced the most important improvement of the Tindex.

Figure 11:
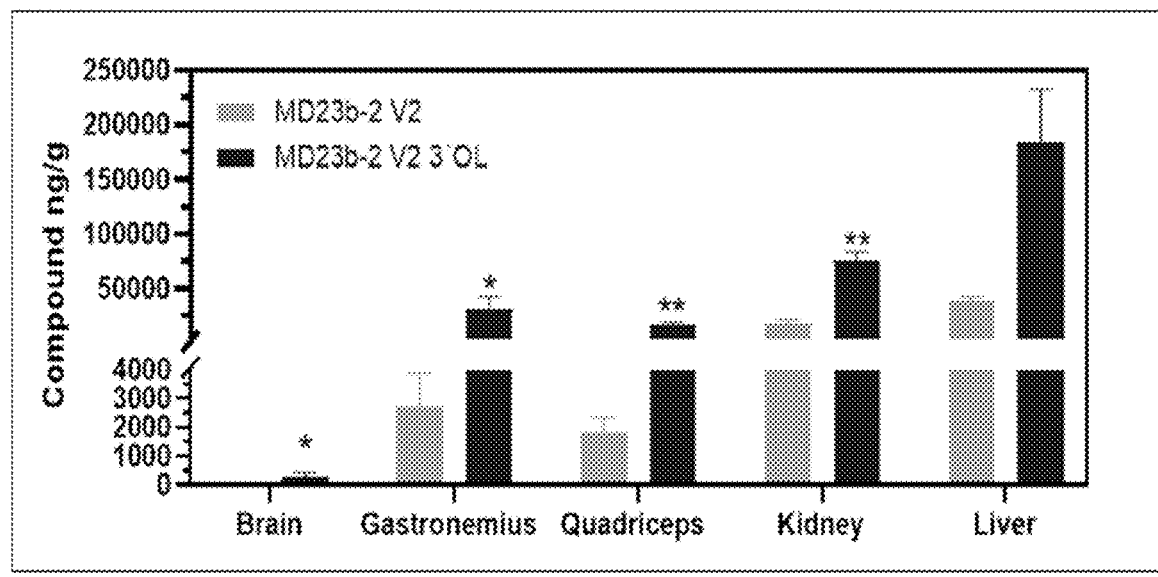
FIG. 11. Determination of MD23b-2 V2 3'Ol and MD23b-2 V2 (ng/g) in the brain, gastrocnemius, quadriceps, kidney, and liver by ELISA. Statistical comparisons between MD23b-2 V2 3'Ol and MD23b-2 V2 for the specified tissues were performed using Student's t-test. Statistical significance was set to $p<0.05$ ( $p<0.01$, * $p<0.001$). Error bars=SEM.
Figure 12:
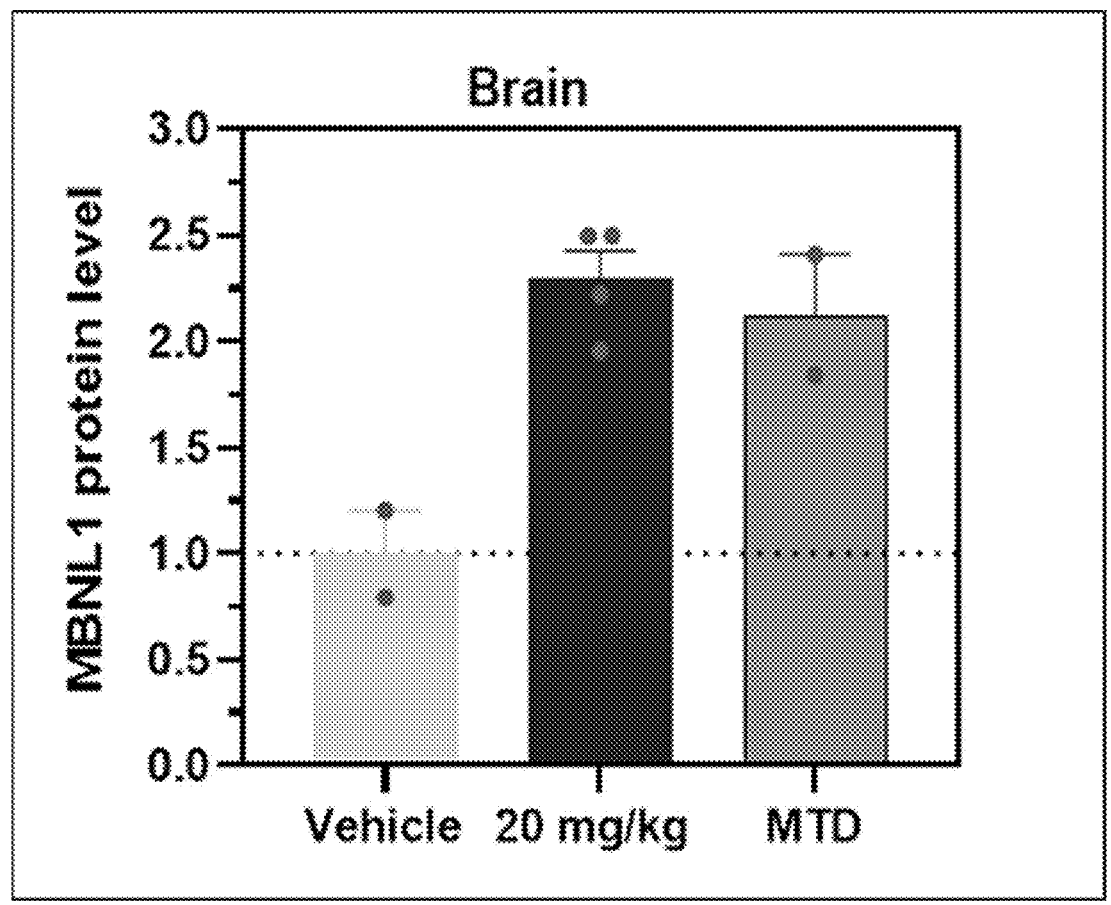
FIG. 12: MBNL1 relative levels. Phase I and Phase II. Quantification of MBNL1 levels by Western Blot in protein extracts from brain of the NHP. Comparison of MBNL1 protein levels in brain NHP from the phase I, two weeks after the last administration and phase II, three weeks after the last administration. In the western blots, GAPDH levels were used as internal standard and the data was normalized to the MBNL1 protein levels in PBS-treated NHP (group 2), which were given the value of 1. Data is mean±SEM.

Next, inventors tested the ability of oleic acid to act as a carrier, and the experiment shown in FIG. 11 and Example 9 demonstrated that oleic acid is an excellent carrier or vehicle to deliver oligonucleotides to tissues such as muscle and central nervous system (CNS). Further, FIGS. 12-13 and Example 10 demonstrate that the vehiculization of the oligonucleotide molecule by the oleic acid does not only occur in an animal model with DM1 phenotype, but also in healthy animals (in this case, monkeys). These results open the path for therapeutic uses of oleic acid as a carrier when conjugated to oligonucleotide molecules, especially in the context of diseases affecting muscle and/or CNS, which were two of the main tissued where the oleic acid enhanced the delivery of the oligonucleotide.

DM1 is a neuromuscular disease that affects muscle tissue, but also central nervous system. Hence, the inventors screened for the antimiR sequence with the best Tindex in DM1 cells among a pool of antimiRs with lengths ranging between 15 and 22 nucleotides, including nucleotides carrying different chemical modifications such as LNA, 2'OME and 2'MOE. The best performing antagonist of human hsa-miR-23b-3p in this study was MD23b-2, and the oligo with the best Tindex for an antagonist of human hsa-miR-218-5p was 218-D/LNA2 (see Tables, 2 and 3, FIG. 1). Modified versions of each of these two molecules were combined with oleic acid, and the resulting molecules were tested in a murine model of DM1 ($HSA^{LR}$ mice) and in DM1 cells (only for a modified version of MD23-b2). The results of these tests revealed that the conjugation of oleic acid to an oligonucleotide that comprises a mixture of PS/PO increases the therapeutic effect of said oligonucleotide (see Table 4, Table 5 and Table 6). Overall, the results obtained in the present study led the authors to conclude that the best fatty acid to be conjugated to the oligonucleotide molecule to improve the levels of MBNL1 in DM1 cells and a mouse model of the disease is oleic acid, and that this conjugation improves the therapeutic index of the oligonucleotide when a mixture of PS/PO linkages is present in the molecule.

In view of these results, in a first aspect, the present invention relates to an oligonucleotide and/or oligonucleotide analogue molecule, or a mixture of two or more of said molecules, wherein the oligonucleotide and/or oligonucleotide analogue molecule is conjugated to at least one oleic acid molecule at the 3' and/or 5' ends of said oligonucleotide and/or oligonucleotide analogue molecule. Preferably, the oligonucleotide and/or oligonucleotide analogue is an antagonist of a microRNA. Preferably, the oligonucleotide and/or oligonucleotide analogue is an antagonist of the microRNA selected from the group consisting of human hsa-miR-23b-3p or the human hsa-miR-218-5p.

The microRNAs hsa-miR-23b-3p and hsa-miR-218-5p are repressors of the expression of MBNL genes, among other gene transcripts, and thus it is their repressive capacity that will be diminished by the presence of its antagonists. In the context of the present invention, inhibitors, silencers or blockers are compounds that are capable of producing a decrease in the endogenous activity of said hsa-miR-23b-3p and hsa-miR-218-5p, and thus these three terms have been included under the denomination of "antagonist". While, strictly speaking, the term "silencing" could be interpreted as the absolute annulment of such activity, since the difference between such annulment or a non-absolute decrease in repressive activity may depend on the concentration of the compound used, it will be sufficient for a compound to result in a decrease in the repressive activity of a microRNA to be considered an inhibitor, silencer, blocker or, in short, an antagonist thereof. In addition, taking into account the knowledge about the possibility of inhibiting microRNA function by targeting the mature microRNA, the precursor microRNA (pre-microRNA or pre-miRNA) or the primary microRNA (pri-microRNA or pri-miRNA), a compound could be considered a microRNA inhibitor, silencer, blocker or antagonist according to the present invention if it targets the mature microRNA, but also if it targets the precursor microRNA or the primary microRNA transcript, provided that it is capable of producing a decrease in the endogenous activity of said microRNA. Therefore, as used herein, the four terms (inhibitors, silencers, blockers or antagonists) are used as synonyms in this specification.

With regard to the nucleotide sequence of the antagonists of the present invention, it is important to note that there should be sufficient complementarity with the endogenous molecules to which they must bind. Said endogenous molecule is preferably a microRNA molecule, more preferably the hsa-miR-23b-3p or hsa-miR-218-5p molecules. Human hsa-miR-218-5p and hsa-miR-23b-3p differ in the sequence of nucleotides which must be taken into account for the design of the sequence of antagonists and their microRNA binding site.

The "microRNA binding site" is the nucleotide sequence comprised in the antagonist that is complementary or partially complementary to at least a portion of its target microRNA. Preferably, the microRNA binding sites of the antagonists defined herein are complementary or partially complementary to at least a portion of hsa-miR-23b-3p or hsa-miR-218-5p. The sequence of the binding site can be a perfect match, meaning that it has perfect complementarity to the microRNA. Alternatively, the sequence can be partially complementary, meaning that one or more mismatches may occur when the microRNA is base-paired to the binding site of the antagonist. Importantly, if the antagonist is partially complementary to the target microRNAs (preferably hsa-miR-23b-3p or hsa-miR-218-5p) its binding site preferably contains perfect or near-perfect complementarity (90%, 91%92%, 93%, 94%, 95%, 96%, 97%, 98%, 99% or preferably 100% complementary) to the seed region of the target microRNAs (preferably hsa-miR-23b-3p or hsa-miR-218-5p). The "seed region" of a microRNA normally comprises or consists of nucleotide 2 to nucleotide 7 from the 5' end of the microRNA.

Thus, in the design of the antimiRs of the present invention, the sequence of the mature versions of the target microRNAs and their seed region can be considered. We show below the sequences of their mature versions, wherein the seed region of each of them is represented in bold, and their access code (Mimat) in the miRbase database (www.mirbase.org):

Hsa (*Homo sapiens*)-miR-218-5p (MIMAT0000275): 5'-UUGUGCUUGAUCUAACCAUGU-3' (SEQ ID NO: 10); Seed region: UGUGCU (SEQ ID NO: 12) hsa-miR-23b-3p (MIMAT0000418): 5'-AUCACAUUGCCAGGGAUUACCAC-3' (SEQ ID NO: 11); Seed region: UCACAU (SEQ ID NO: 13)

In an embodiment, the oligonucleotide and/or oligonucleotide analogues molecules are inhibitors, blockers or antagonists of the types known as antimiRs and microRNA sponges. Preferably, the oligonucleotide and/or analogue thereof, according to the first aspect or any of its embodiments, is an antimiR, more preferably an antimiR of hsa-miR-218-5p or hsa-miR-23b-3p.

In an embodiment, the oligonucleotide and/or analogue thereof is at least 10, 11, 12, 13, 14, 15, 16, 17, 18, 19, 20, 21, 22, 23, 24, 25 nucleotides in length. In an embodiment, the oligonucleotide and/or analogue thereof is between 10-50 nucleotides in length, more preferably between 10-30 or 15-25 nucleotides in length. Preferably, the oligonucleotide molecule and/or analogue thereof is an antimiR whose sequence comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 60%, 70%, 80%, 85%, 90%, 91%, 92%, 93%, 94%, 95%, 96%, 97%, 98%, 99% or 99.5%, or 100% to the complementary sequence of a region present in SEQ ID NOs: 10 (hsa-miR-218-5p) or 11 (hsa-miR-23b-3p). More preferably, the sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the complementary sequence of SEQ ID NOs: 10 (hsa-miR-218-5p) or 11 (hsa-miR-23b-3p).

In an embodiment, the antagonist is an antimiR and its sequence comprises a fragment composed of a succession of at least 5-8 nucleotide or nucleotide analogue units wherein the sequence of the nitrogenous bases of said nucleotide or nucleotide analogue units is identical in at least 90%, 91%, 92%, 93%, 94%, 95%, 96%, 97%, 98%, 99% or 100% to the complementary sequence of the seed region of the hsa-miR-23b-3p as set forth in SEQ ID NO: 13. Preferably, said antimiR comprises a fragment composed of a succession of at least 5-8 nucleotide or nucleotide analogue units that are 100% complementary to the seed region as set forth in SEQ ID NO: 13. In an embodiment, the antagonist is an antimiR whose sequence comprises a first fragment and a second fragment, wherein the first fragment is composed of a succession of at least 5-8 nucleotide or nucleotide analogue units wherein the sequence of the nitrogenous bases of said first fragment is identical in at least 90%, 91%, 92%, 93%, 94%, 95%, 96%, 97%, 98%, 99% or 100% to the complementary sequence of the seed region of the hsa-miR-23b-3p as set forth in SEQ ID NO: 13, and wherein the second fragment is adjacent to the first fragment (i.e., it is located upstream and/or downstream of the first fragment) and it is composed of a succession of at least 7, 8, 9, 10, 11, 12, 13, 14, 15, or 16 consecutive nitrogen bases of nucleotide or nucleotide analogue units that are identical in at least 60%, 70%, 80%, 85%, 90%, 91%, 92%, 93%, 94%, 95%, 96%, 97%, 98%, 99% or 99.5%, or 100% to the complementary sequence of a region present in SEQ ID NOs: 11. By "adjacent" is referred herein as immediately next to the first fragment, i.e., without any nucleotide in between the first and the second fragments. In some alternative embodiments, the second fragment is located 6, 7, 8, 9, 10, or 11 nucleotides upstream and/or downstream of the first fragment. More preferably, the second fragment is located 1, 2, 3, 4, or 5 nucleotides upstream and/or downstream of the first fragment.

In an embodiment, the antagonist is an antimiR and its sequence comprises a fragment composed of a succession of at least 5-8 nucleotide or nucleotide analogue units wherein the sequence of the nitrogenous bases of said nucleotide or nucleotide analogue units is identical in at least 90%, 91%, 92%, 93%, 94%, 95%, 96%, 97%, 98%, 99% or 100% to the complementary sequence of the seed region of the hsa-miR-218-5p as set forth in SEQ ID NO: 12. Preferably, said antimiR comprises a fragment composed of a succession of at least 5-8 nucleotide or nucleotide analogue units that are 100% complementary to the seed region as set forth in SEQ ID NO: 12. In an embodiment, the antagonist is an antimiR whose sequence comprises a first fragment and a second fragment, wherein the first fragment is composed of a succession of at least 5-8 nucleotide or nucleotide analogue units wherein the sequence of the nitrogenous bases of said first fragment is identical in at least 90%, 91%, 92%, 93%, 94%, 95%, 96%, 97%, 98%, 99% or 100% to the complementary sequence of the seed region of the hsa-miR-218-5p as set forth in SEQ ID NO: 12, and wherein the second fragment is adjacent to the first fragment (i.e., it is located upstream and/or downstream of the first fragment) and it is composed of a succession of at least 7, 8, 9, 10, 11, 12, 13, 14, 15, or 16 consecutive nitrogen bases of nucleotide or nucleotide analogue units that are identical in at least 60%, 70%, 80%, 85%, 90%, 91%, 92%, 93%, 94%, 95%, 96%, 97%, 98%, 99% or 99.5%, or 100% to the complementary sequence of a region present in SEQ ID NOs: 10. By "adjacent" is referred herein as immediately followed to the first fragment, i.e., without any nucleotide in between the first and the second fragments. In some alternative embodiments, the second fragment is located 6, 7, 8, 9, 10, or 11 nucleotides upstream and/or downstream of the first fragment. More preferably, the second fragment is located 1, 2, 3, 4, or 5 nucleotides upstream and/or downstream of the first fragment.

Also comprised within the concept of oligonucleotide and/or oligonucleotide analogue molecules useful for the purpose of the present invention and comprised within its scope are those microRNA inhibitors, blockers or antagonists that act on pri-microRNAs or pre-microRNAs, usually altering microRNAs biogenesis and having a negative effect on microRNAs activity, mainly due to a decrease of the available active microRNA. In animal cells, immature pri-miRNAs are processed into pre-miRNAs by the Microprocessor complex in the nucleus, and are then transported into the cytoplasm to undergo further processing into mature miRNAs. It thus must be understood that targeting the pri-microRNA and/or the pre-microRNA of hsa-miR-23b-3p or hsa-miR-218-5p and altering their biogenesis so that the levels of said microRNAs are decreased should also result in a decrease of their activity. Therefore, for the purpose of the present invention, an antagonist of hsa-miR-23b-3p or an antagonist of hsa-miR-218-5p must be understood to comprise not only those molecules capable of acting the mature forms, but also those molecules capable of acting on the pri-microRNA or the pre-microRNA and decreasing the levels of the mature forms of hsa-miR-23b-3p or hsa-miR-218-5p. In order to design them, it must be taken into account that:

The primary microRNA (pri-microRNA) of hsa-miR-23b-3p is the transcripts of gene AOPEP (ENSG00000148120; chr9:97488983-97849441).

The microRNA precursor (pre-microRNA) of hsa-miR-23b-3p corresponds to genomic positions hg19 chr9: 97847490-97847586 [+] and to the sequence: CUCAG-GUGCUCUGGCUGCUUGGGUUCCUGGCAUGCU GAUUUGUGACUUAAG AUUAAAAUCA-CAUUGCCAGGGAUUACCACGCAACCACGAC-CUUGGC (SEQ ID NO: 19). As this sequence is longer than hsa-miR-23b-3p, it is possible to design an antagonist specific to the pre-microRNA.

hsa-miR-218-5p has two genomic positions encoding for it and two precursor pre-microRNAs, Pre-hsa-mir-218-1 (chr4:20529898-20530007): GUGAUAAU-GUAGCGAGAUUUUCUGUUGUGCUUGAUC-UAACCAUGUGGUUGCG AGGUAUGAGUAAAACAUGGUUCCGU-CAAGCACCAUGGAACGUCACGCAGCUU UCUACA (SEQ ID NO: 20), and Pre-mir-218-2 (chr5: 1681951 SI-168195260): GACCAGU-CGCUGCGGGGCUUUCCUUUGUGCUUGAUC-UAACCAUGUGGUGGAA CGAUGGAAACGGAACAUGGUUCUGU- CAAGCACCGCGGAAAGCACCGUGCUCU CCUGCA (SEQ ID NO: 21). Both precursors could be used for the design of antagonists.

Pre-hsa-mir-218-1 derives from intramolecular hairpin structures located inside the transcripts of gene SLIT2 (ENSG00000145147: chr4:20254883-20621284) while hsa-miR-218-5p-2 derives from the gene SLIT3 (ENSG00000184347, chr5:168088745-168728133 for hsa-miR-218-5p-2), which can be regarded, respectively, as their pri-miRNAs. No other mature microRNAs are part of the same cluster. Then, in the case of hsa-miR-218-5p, both the pre-miRNAs or the pri-miRNAs could be envisaged as targets of antagonists to reduce the mature miRNA and increase MBNL protein levels.

As shown in the examples below, particularly in Table 1 and Table 4, the authors of the present invention developed and optimized several antimiRs against hsa-miR-23b-3p and hsa-miR-218-5p, whose Tindex was greatly improved with the addition of oleic acid. Among them, the specific sequence of the antimiRs comprising the SEQ ID NOs: 1 (antagonist of the human hsa-miR-218-5p) and SEQ ID NO: 2 (antagonist of the human hsa-miR-23b-3p) are specially mentioned due to their optimal characteristic and efficiency in DM1 cells, as shown in the Example section.

Further, functional equivalents of SEQ ID NO: 1 or 2 are also contemplated herein, where specific changes in particular nucleobases would not significantly destabilize the molecule and thus, its therapeutic effect would be maintained. Said functional equivalent sequences are set forth in SEQ ID NO: 52-79 (functional equivalents of the antimiR-23b-3p of SEQ ID NO: 2), and SEQ ID NO: 80-110 (functional equivalents of the antimiR-218-5p of SEQ ID NO: 1). By "functional equivalents" is referred herein to other oligonucleotides that differ in their nucleobase sequence from that of SEQ ID NO: 1 or 2, but which perform the same function and provide the same utility or technical effect as SEQ ID NO: 1 or 2.

Thus, in an embodiment, the oligonucleotide molecule and/or analogue thereof is an antagonist of the human hsa-miR-218-5p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 1 (TTAGATCAAGCACAA) or SEQ ID NO: 80-110. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 1 or SEQ ID NO: 80-110.

In a further embodiment, the oligonucleotide molecule and/or analogue thereof is an antagonist of the human hsa-miR-23b-3p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 2 (ATCCCTGGCAATGTGA) or SEQ ID NO: 52-79.

Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 2 or SEQ ID NO: 52-79.

It is noted that, in the oligonucleotide molecule and/or analogue thereof according to the present invention, each uracil and thymine base within the full length of the oligonucleotide molecule and/or analogue, preferably each uracil and thymine base in the seed region, can be optionally replaced, respectively, by a thymine or uracil base. This applies for all the "T" nucleobases comprised in all the oligonucleotides disclosed herein, except for SEQ ID NO: 52-110, where at certain positions, a "U" instead of "T" is preferred. In said certain positions, a U, rather than a T, is thus included.

Likewise, each guanosine base within the full length of the oligonucleotide molecule and/or analogue, preferably each guanosine in the seed region, can be optionally replaced, respectively, by a hypoxanthine base. This applies for all the oligonucleotides disclosed herein.

Figure 4:
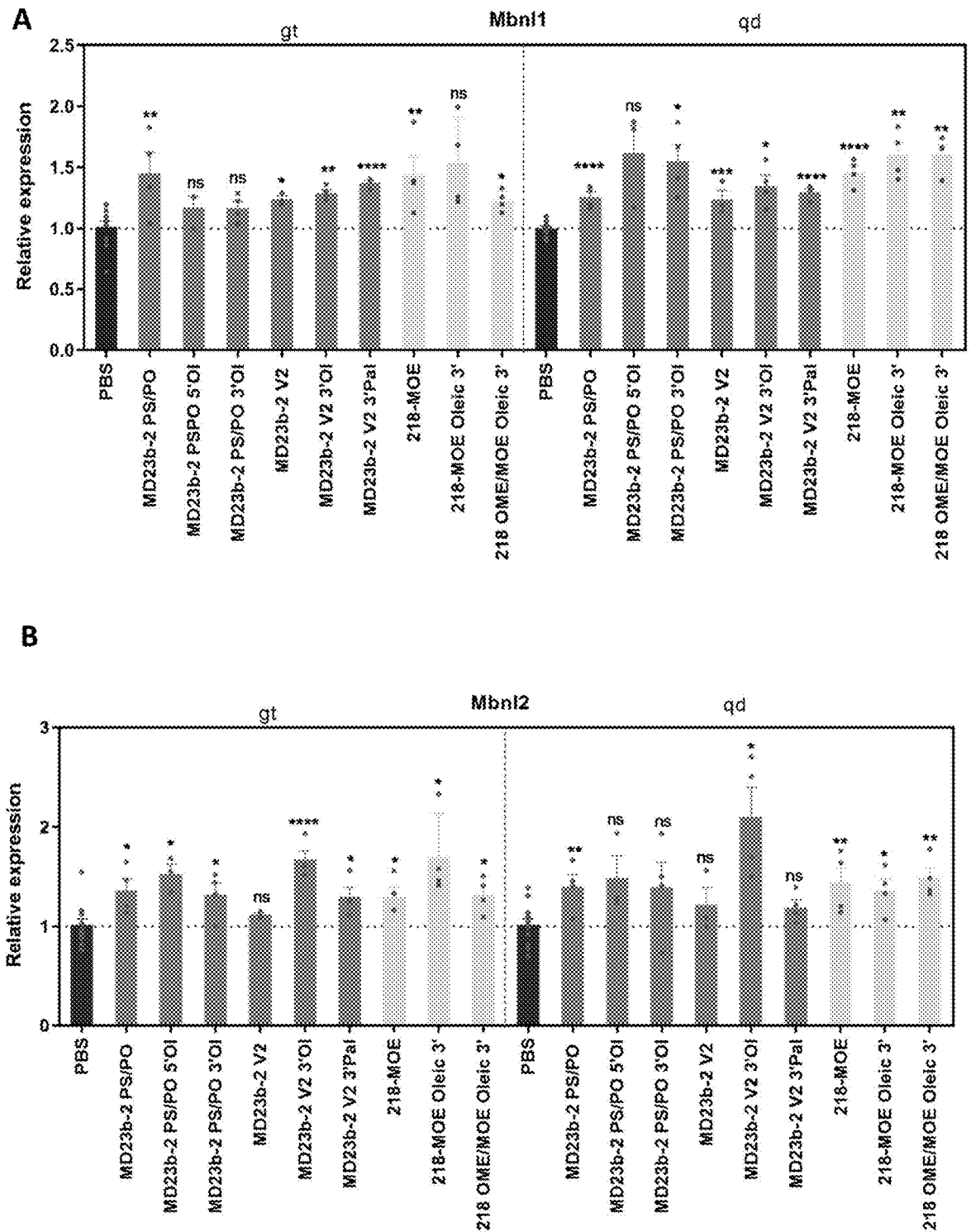
FIG. 4. Expression of Mbnl1 and Mbnl2 on skeletal muscles of treated $HSA^{LR}$ mice. (A) Mbnl1 and (B) Mbnl2 transcript levels were quantified by qRT-PCR relative to Gapdh endogenous control on gastrocnemius (gt) and quadriceps (qd) muscles; (C) Mbnl1 protein levels relative to endogenous tubulin control using quantitative dot blot. $HSA^{LR}$ mice received an IV injection in the tail vein with PBS or the different antimiRs, all at the same concentration (3 mg/Kg). Gastrocnemius and quadriceps muscles were dissected 5 days after the injection and the tissues were processed for RNA and protein analysis. Statistical comparisons were all performed against PBS-treated $HSA^{LR}$ values with a Student's t-test. p values: ns=not significant, *$p<0.05$,  $p<0.01$, * $p<0.001$, **** $p<0.0001$. Data points represent individual mouse values. Error bars=standard error of the mean (SEM).
Figure 4:
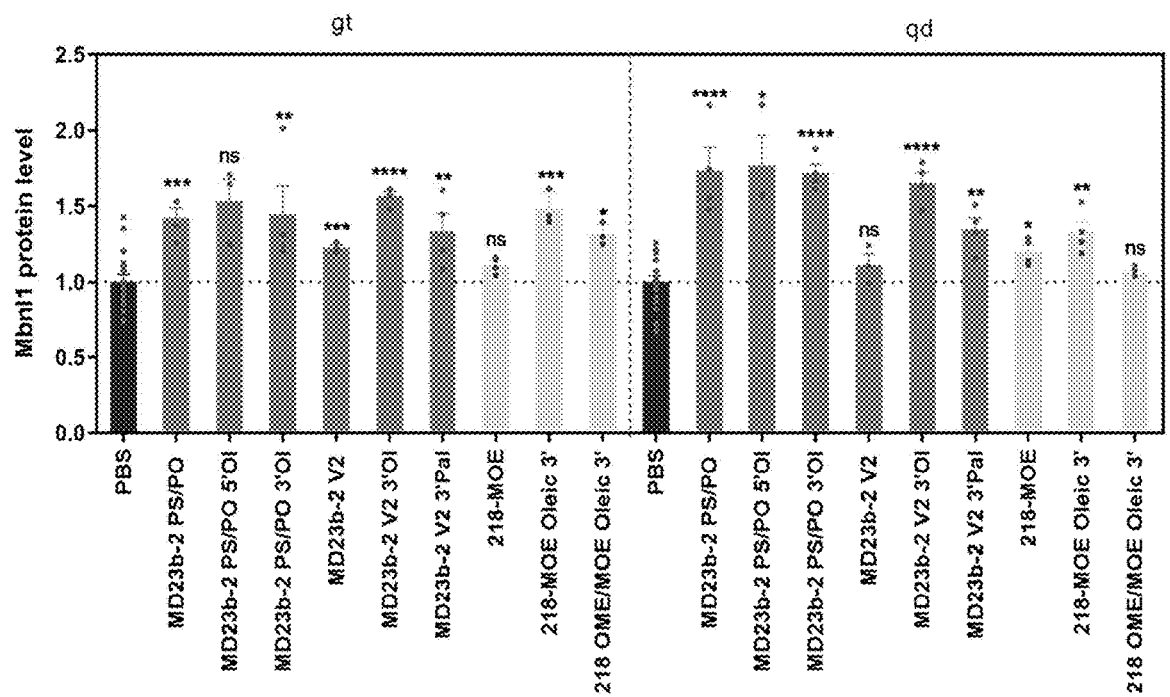

In an embodiment, the oligonucleotide and/or oligonucleotide analogue that is an antagonist human hsa-miR-23b-3p or the human hsa-miR-218-5p is capable of increasing the endogenous levels of MBNL proteins, preferably MBNL1 and/or MBNL2 proteins. Preferably, the oligonucleotide and/or oligonucleotide analogue is identical in at least 60%, 70%, 80%, 85%, 90%, 91%, 92%, 93%, 94%, 95%, 96%, 97%, 98%, 99% or 99.5%, or 100% to the sequence of a region present in SEQ ID NO: 1 (antimiR-218-5p) or 2 (antimiR-23b-3p), or SEQ ID NO: 52-110, and is capable of increasing the endogenous levels of MBNL proteins, preferably MBNL1 and/or MBNL2 proteins. Preferably, the increase in the endogenous levels of MBNL proteins is a statistically significant increase in comparison to untreated cells or untreated tissues, wherein preferably the statistical comparison is performed using a Student's t-test, see e.g., FIG. 4. Most preferably, the increase, preferably statistically significant increase, in the endogenous levels of MBNL proteins is of at least 1.2-, 1.3-, 1.4-, or 1.5-fold change in treated cells of muscular tissues (more preferably quadriceps and gastrocnemius) with respect to untreated cells of muscular tissues. Preferably, the increase in endogenous levels of MBNL proteins in treated cells or tissues is of at least 15%, 20%, 30%, 40%, 50% or more when compared to untreated cells or tissues. By "untreated cell or tissue" is referred herein to one or more cells or tissues, including whole animals such as mice, that are healthy or present a DM1 phenotype, and that have not been treated with the oligonucleotide and/or oligonucleotide analogue of the first aspect or any of its embodiments. Preferably, the untreated cell is a muscular cells and the untreated tissue is muscular tissue.

The antimiRs of the present invention, including those as defined in SEQ ID NO: 1 or 2, can be further optimized in order to improve their in vivo stability and efficacy. To do so, several modifications in their chemical architecture have been described (for a review, see Mckenzie et al., Recent progress in non-native nucleic acid modifications. Chem. Soc. Rev., 2021, 50, 5126-5164). These modifications can be made in the pentose (in the preferred embodiment in which the oligonucleotide is an oligoribonucleotide, the modification would be in the ribose), in the internucleotide linkage, or in the nucleobase, or in a combination thereof. When the oligonucleotides or oligoribonucleotides of the present invention are chemically modified, they are considered in the context of the present invention as oligonucleotide analogues or oligoribonucleotide analogues, respectively. In an embodiment, the antimiR is an oligonucleotide analogue and it comprises at least six, seven, eight, nine, ten, eleven, twelve, thirteen, fourteen, fifteen or sixteen chemical modifications along the whole molecule. In an embodiment, the antimiR is an oligoribonucleotide analogue that comprises all its nucleotides chemically modified.

Modifications in the internucleotide linkage: It is considered included in the possible modifications that give rise to the oligonucleotides analogues of the present invention the modifications that give rise to phosphorothioate linkages, which are modifications that affect phosphate groups that are part of the "skeleton" of the polynucleotide chain, giving rise to the introduction of a sulphur atom in substitution of an oxygen atom of the phosphate group that is not acting as a bridge between nucleotides; these modifications cause the linkages between nucleotides to be resistant to degradation by nucleases, in addition to other desirable pharmacological properties, so they are commonly inserted between the last 3-5 nucleotides at the 5' or 3' ends of oligonucleotides to inhibit degradation by exonucleases, increasing their stability.

In a preferred embodiment, at least one, two, three, four, five, six, seven, eight, nine, ten, eleven, twelve, thirteen, fourteen, fifteen, or more than fifteen of the nucleotides comprised in the oligonucleotide or oligonucleotide analogue molecule according to the first aspect or any of its embodiments are chemically linked by a phosphorothioate linkage. Preferably, the oligonucleotide and/or oligonucleotide analogue according to the first aspect or any of its embodiments comprises between 10 to 30 nucleotides in length and comprises at least two nucleotides chemically linked by a phosphorothioate linkage, wherein said oligonucleotide and/or oligonucleotide analogue is conjugated at its 3' and/or 5' ends to at least one oleic acid molecule. In an even more preferred embodiment, the oligonucleotide or oligonucleotide analogue molecule comprises a mixture of PS and phosphodiester (PO) linkages, wherein at least two nucleotides of said molecule are chemically linked by a phosphorothioate linkage and at least two nucleotides of said molecule are linked by a phosphodiester linkage. In a further preferred embodiment, the number of nucleotides that are chemically linked by a phosphorothioate (PS) linkage is greater than the number of nucleotides that are chemically linked by a phosphodiester linkage. In an embodiment, the oligonucleotide molecule and/or analogue thereof is between 13-17 nucleotides long, and comprises at least 7, 8, 9, or 10 nucleotides that are chemically linked by a phosphorothioate (PS) linkage. In an embodiment, the ratio of PS:PO in the oligonucleotide molecule and/or analogue thereof is 1.2:1, 1.5:1, 1.7:1, 2:1, 2.2: 1, 2.5:1, 2.7:1, 3:1. Preferably, the ratio PS:PS in the oligonucleotide molecule and/or analogue thereof is between 1.2:1 and 2.7:1, more preferably 1.5:1 or 2.5:1. By "ratio PS:PO" is referred herein as the number of PS linkages per PO linkage. For instance, when an oligonucleotide molecule consists of 15 nucleotides and has 10 PS linkages and 4 POs linkages (see, e.g., SEQ ID NO: 7), it is said that said molecule has a ratio PS:PO of 2.5:1. In an embodiment, more than 50%, 55%, preferably 60%, 70% or 75% of the linkages between the nucleotides are PS linkages.

In an embodiment, all the nucleotides comprised in the oligonucleotide or oligonucleotide analogue molecule are chemically linked by a phosphorothioate linkage. As stated above, preferably, the oligonucleotide or oligonucleotide analogue molecule is an antagonist of a microRNA (i.e., an antimiR).

Modifications in the pentose, preferably in the ribose: The most widely used sugar modifications are those that are located in the OH group at the 2' position. Among them, the most important ones in the context of the present invention are 2'fluoro (2'F: introduction of a fluorine atom at the ribose 2' position), 2'-O-methoxyethyl (MOE), or 2'O-methyl (OMe) modifications. Thus, in an embodiment, the oligonucleotide or oligonucleotide analogue molecule, preferably the antimiR, according to the present invention is chemically modified to comprise at least one pentose with one of the following modifications: 2'fluoro (2'F: introduction of a fluorine atom at the ribose 2' position), 2'-O-methoxyethyl (MOE), and/or 2'O-methyl (OMe). In an embodiment, all the nucleotides in the oligonucleotide molecule are 2'OME modified nucleotides.

Another modification that can be performed in the oligonucleotide or oligonucleotide analogue molecule, preferably the antimiR, of the present invention is the formation of Bicyclic 2'-4' modifications. There are a variety of ribose derivatives that lock the carbohydrate ring into the 3'-endo conformation by the formation of bicyclic structures with a bridge between the 2' oxygen and the 4' position. In an embodiment, the formation of a bridge between the 2' oxygen and the 4' carbon locks the ribose in the 3' endo conformation, leading to a modification called locked nucleic acids, or LNA. The introduction of LNAs modifications highly increases the stability of the antimiR-target miRNA hybrids making them significantly more thermodynamically stable and resistant to degradation, which especially happens when said modifications are placed at the ends of the molecule. In an embodiment, the first nucleotide starting from the 3' region comprises an LNA modification. In another embodiment, each of the two first oligonucleotides starting from the 5' region comprises an LNA modification. More modifications of bicyclic nucleotides include bridged nucleic acids, ethyl-bridged (ENAs), constrained ethyl (cEt) nucleic acids, bicyclic (bicyclo-DNA) and tricyclic (Tricyclo-DNA)s structures and Conformationally Restricted Nucleotides (CRN) with a varying affinity for target sequences.

More modifications include the so-called PMOs (nucleic acids where ribose has been substituted by a morpholino group). By "morpholino" is understood as bases attached to a backbone of methylenemorpholine rings linked through phosphorodiamidate groups. Another backbone modifications are the so-called PNAs ("Peptide Nucleic Acid': peptide nucleic acid in which the ribose-phosphate group is replaced by an amino acid moiety so that the skeleton of the nucleotide analogue is a structure of repeat units of N-(2-aminoethyl)-glycine linked by peptide linkages).

In an embodiment, an oligonucleotide or oligonucleotide analogue molecule, preferably the antimiR, according to the present invention, is chemically modified to comprise at least one pentose of the nucleotides forming the antimiR comprises morpholino nucleic acids (PMOs) or peptide nucleic acids (PNAs).

Modifications in the nucleobase: Because of its frequent use, also included among the chemical modifications that give rise to the oligonucleotides, preferably oligoribonucleotide analogues of the invention, preferably the antimiR, is the 5 methylation of the nitrogenous base cytosine (C), which decreases the detection of the oligonucleotide analogue by the immune system. Thus, in an embodiment, at least one, two, three, four, five, or more than five of the nucleotides comprised in the oligonucleotide and/or oligonucleotide analogue molecule, preferably the antimiR, according to the first aspect or any of its embodiments comprises a methylated cytosine. In a preferred embodiment, all the cytosines in the oligonucleotide or oligonucleotide analogue molecule, preferably the antimiR, according to the first aspect or any of its embodiments, are methylated.

Another possible modification is 2,6 diaminopurine that is able to form base pairs with thymidine or uridine with an extra H-bond (3 H-bonds instead of 2 present in the natural A:T base pairs). Thus, in an embodiment, at least one, two, three, four, five, or more than five of the nucleotides comprised in the oligonucleotide and/or oligonucleotide analogue molecule according to the first aspect or any of its embodiments comprises a 2,6 diaminopurine.

As can be deduced from the definition of "oligonucleotide molecules" and that of "oligonucleotide analogues", also included within the definition of oligonucleotide analogues are hybrid molecules, in which some units present modifications and others do not, as well as hybrids between analogues of nucleic acids and peptides or, even, hybrid molecules in which some of the nucleotide units are nucleotides (or analogues thereof) and others are deoxynucleotides (nucleotides in which the sugar is deoxyribose), as well as analogues of the latter, i.e. RNA-DNA hybrids and analogues thereof. Other chemical modifications are possible and known, which are also comprised within the possible modifications that give rise to oligonucleotide analogues.

With regard to the possible chemical modifications included in the oligonucleotide and/or oligonucleotide analogue molecule, the term will be applied especially in the case of one or more of the usual modifications known to those skilled in the art of molecular biology, in terms of basic research and, in particular, in the search for therapeutic applications of these molecules. Information on such modifications can be found in the general common knowledge. Modifications of the Oligonucleotide and/or Oligonucleotide Analogue Molecule with Other Non-Nucleotide Molecules.

As stated above, the first aspect of the present invention provides an oligonucleotide and/or oligonucleotide analogue molecule that is preferably an antimiR, more preferably an antagonist of the human hsa-miR-23b-3p or of the human hsa-miR-218-5p, or a mixture of two or more of said molecules, wherein the oligonucleotide and/or oligonucleotide analogue molecule is conjugated to at least one oleic acid molecule at the 3' and/or 5' ends of said oligonucleotide and/or oligonucleotide analogue molecule. Thus, all the oligonucleotides included in the present invention are conjugated to at least one oleic acid molecule at their 3' and/or 5'.

Figure 8:
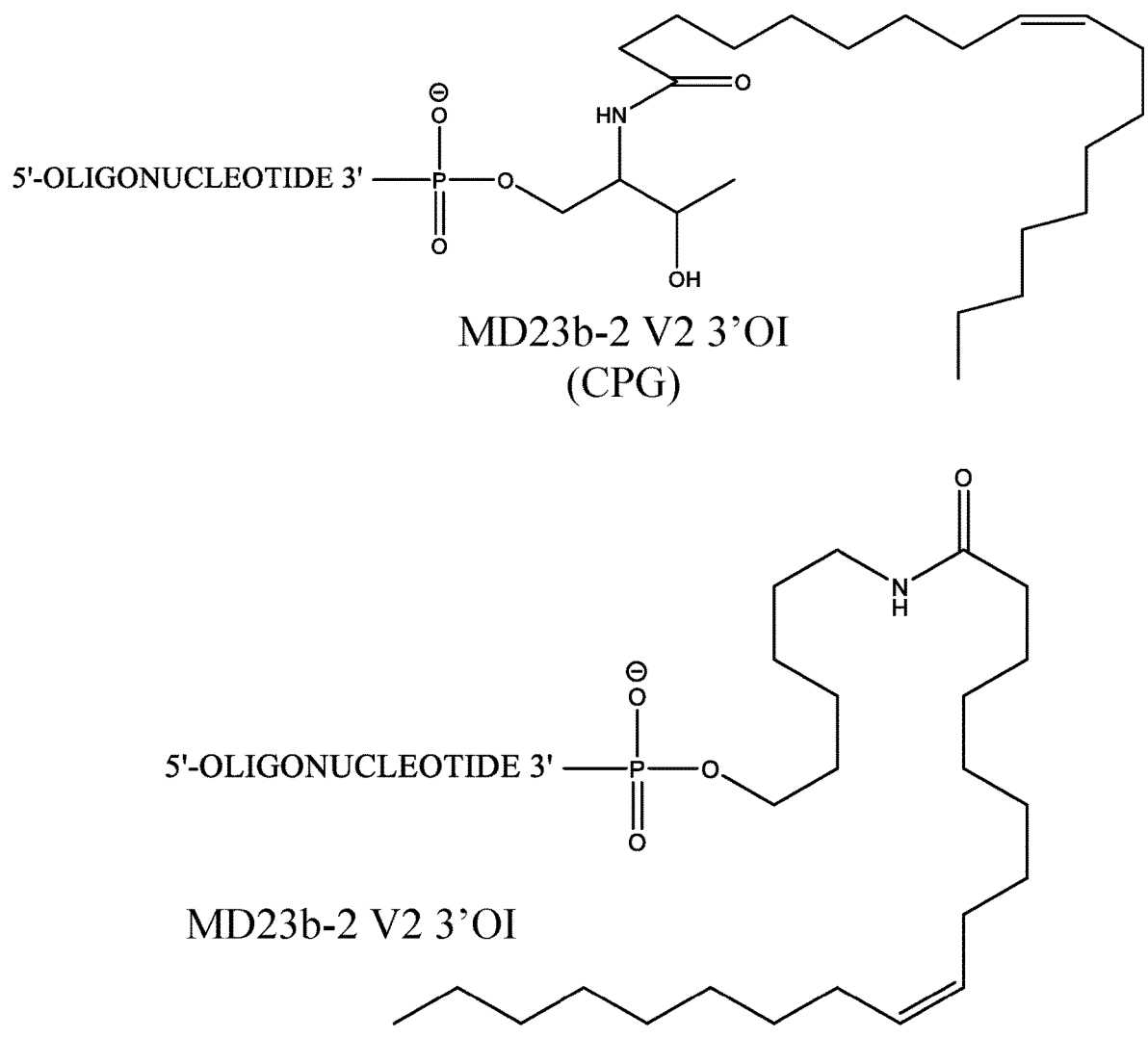
FIG. 8. Chemical structure of different linkers used to connect MD23b-2 V2 oligo and Oleic acid. The draw of the entire resulting molecule, except for the oligonucleotide component, was generated with the ChemDraw software.
Figure 8:
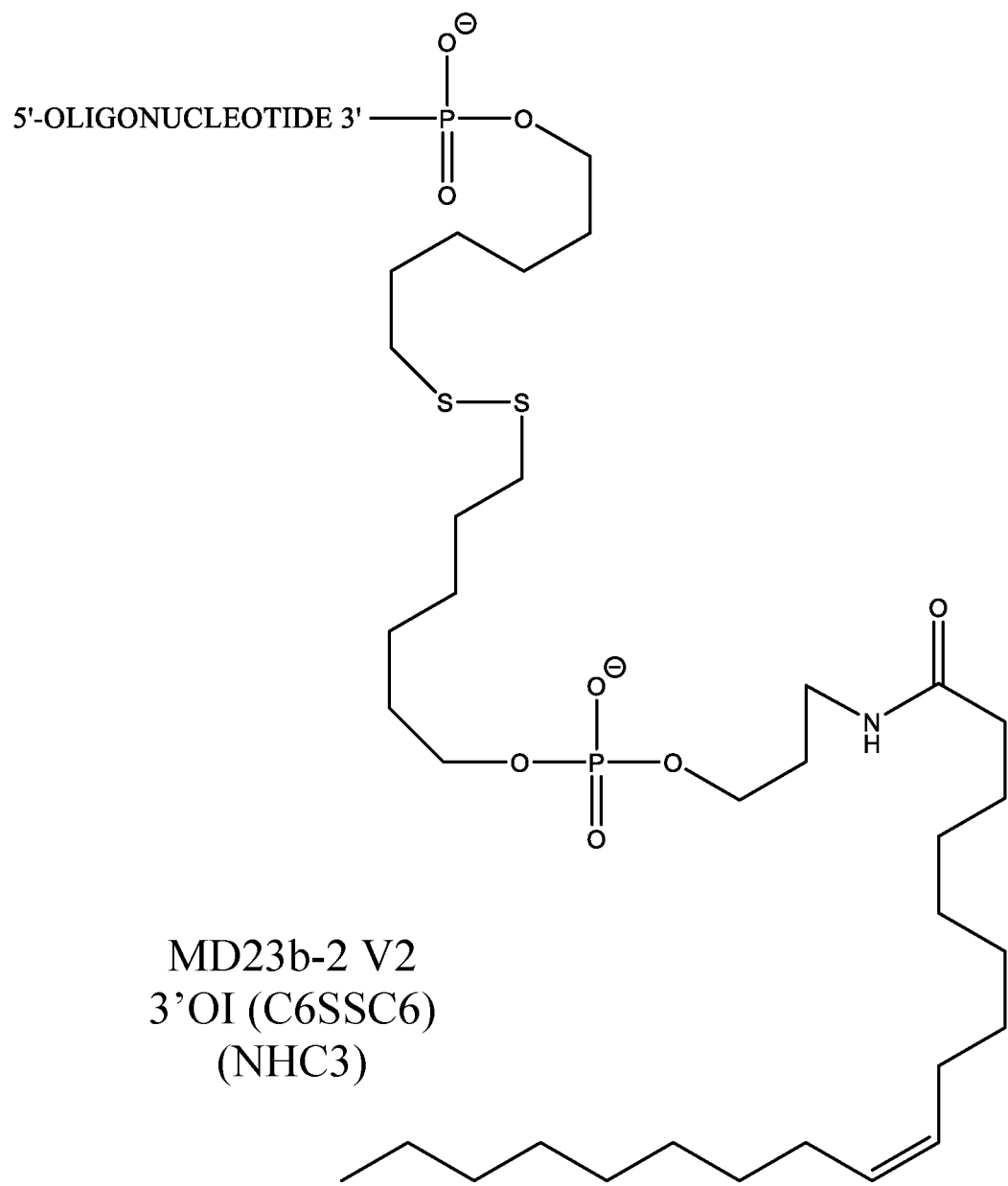

In some embodiments, other non-nucleotide molecules, such as organic compounds, can also be conjugated at the 3' and/or 5' end of the oligonucleotide and/or oligonucleotide analogue molecule. Said conjugation can be a direct conjugation or by means of a spacer molecule. By "spacer molecule" is referred herein to any molecule or molecules that connect, on the one hand, the oligonucleotide or oligonucleotide analogue and, on the other hand, the non-nucleotide molecule, preferably the oleic acid. The spacer molecule or molecules can be coupled at the 3' or 5' end of the oligonucleotide or oligonucleotide analogue. Preferably, the spacer molecule is covalently bound to said oligonucleotide. Preferably, the spacer molecule(s) are bound on one end via a bond between a terminal carbon on the spacer to an oxygen group in the 3'terminal phosphate of the oligonucleotide and on the other end by a bond between the terminal nitrogen group on the linker which forms an amide bond with the carboxy group of oleic acid, e.g. as depicted in FIG. 8.

In a preferred embodiment, the spacer molecule is selected from the group consisting of 3-aminopropyl (NHC3), 5-aminopentyl (NHC5), 6-aminohexyl (NHC6), threoninol or a derivative thereof. In other embodiments, the spacer molecule or molecules may comprise a Thiol-Modifier C6 S-S (C6SSC6). In a further embodiment, the spacer may comprise a Thiol-Modifier C6 S-S (C6SSC6) directly bound to the oligonucleotide, and followed by a 3-aminopropyl (NHC3), 6-aminohexyl (NHC6), threoninol or a derivative thereof (see FIG. 8).

In some embodiments, the oligonucleotide may be provided as a prodrug and may comprise a spacer molecule comprising or consisting of a self-immolative group. By "self-immolative" group is referred herein to a molecule that will spontaneous and irreversibly disassembly from the molecule to which it is conjugated, in this case the oligonucleotide. In an embodiment, the self-immolative group is a disulfide linkage that will be reduced inside the cells by naturally occurring thiols such as glutathione, resulting in the release of the oligonucleotide.

The spacer may be an aliphatic linear or branched hydrocarbon chain, cyclohexyl phenyl and other aromatic spacers, as well as polar spacers based on one or several units of ethylene glycol, glycerol, amino acid, peptide, or carbohydrates. In some cases, the oleyl derivative can be covalently linked to the amino groups by an amide linkage or directly to the nucleobases with an amine linkage as well as to the phosphate linkage as oleyl phosphate.

Preferably, the oleic acid is conjugated to the oligonucleotide at its 3' end. More preferably, the oleic acid is conjugated by means of a spacer molecule, preferably NHC6, threoninol or NHC3, as shown in FIG. 8. Please note that the addition of the spacer molecule as a connector between the oligonucleotide and the oleic acid is not mandatory, see, e.g., SEQ ID NO: 51 wherein the oleic acid is conjugated at the 5' end of the oligonucleotide and/or oligonucleotide analogue molecule by means of direct conjugation.

Preferably, all the oligonucleotides molecules disclosed in the present invention are conjugated to at least one oleic acid molecule at their 3' and/or 5' ends, wherein the oligonucleotides molecules further comprise at least two nucleotides chemically linked by a phosphorothioate linkage. Preferably, the oligonucleotides molecules further comprise at least two nucleotides chemically linked by a phosphorothioate linkage and at least two nucleotides of said molecule are linked by a phosphodiester linkage. More preferably, the number of nucleotides that are chemically linked by a phosphorothioate (PS) linkage is greater than the number of nucleotides that are chemically linked by a phosphodiester (PO) linkage.

Different means known in the art can be used to prepare the oligonucleotides of the present invention. In particular, the oligonucleotides may be synthesized by solid-phase or liquid-phase methods. The oligonucleotide functionalized with the spacer molecule as well as the oleyl-oligonucleotide conjugate may be prepared using solid-phase oligonucleotide synthesis protocols. In this methodology, a solid support such as controlled pore glass (CPG) is functionalized with the first nucleotide in the 3'-end of the oligonucleotide sequence and the oligonucleotide is usually synthesized in the 3' to 5' direction. The introduction of a spacer molecule at the 5' position is performed by using a phosphoramidite derivative of the spacer molecule that will introduce the spacer molecule through a phosphate linkage to the 5'-position of the oligonucleotide. The introduction of the spacer molecule at the 3' position requires the preparation of a solid support functionalized with a linker molecule, which is a molecule used to bind the nucleotide to the support. Examples of linker molecules are labile compounds such as phthalimido or succinyl linkers. Of note, while the spacer is conjugated to the oligonucleotide molecule and remains conjugated thereto, the linker is a temporary conjugation that aims the immobilization of the oligonucleotide when it is being synthesized using solid-phase methods.

In the case of liquid-phase preparation method, instead of the type of linker defined for the solid-phase method, a protecting group may be used, such as benzoyl or acetyl.

Among all the oligonucleotides disclosed in the context of the present invention, the following embodiments, including the modifications and combination of modifications, are considered preferred:

In an embodiment, the oligonucleotide and/or oligonucleotide analogue molecule according to the first aspect or any of its embodiments comprises between 10 to 30 nucleotides in length and is an antimiR-type oligonucleotide analogue, wherein at least two nucleotides of said molecule are chemically linked by a phosphorothioate linkage and at least two nucleotides of said molecule are linked by a phosphodiester linkage, preferably wherein the number of nucleotides that are chemically linked by a phosphorothioate linkage is greater than the number of nucleotides that are chemically linked by a phosphodiester linkage, and wherein:
 a. the sequence of the nitrogenous bases of the monomeric units of nucleotides or nucleotide analogues is at least 85%, 90%, 93%, 95%, 98%, or 100% complementary to the endogenous molecules to which they must bind (preferably, a microRNA molecule, more preferably the hsa-miR-23b-3p of SEQ ID NO: 11 or hsa-miR-218-5p of SEQ ID NO: 10), and
 b. it is conjugated at the 5'-end and/or at the 3'-end with at least one oleic acid molecule, preferably by means of a spacer molecule.

In an embodiment, the oligonucleotide and/or oligonucleotide analogue molecule according to the first aspect or any of its embodiments comprises between 10 to 30 nucleotides in length and is an antimiR-type oligonucleotide analogue, wherein at least two nucleotides of said molecule are chemically linked by a phosphorothioate linkage and at least two nucleotides of said molecule are linked by a phosphodiester linkage, preferably wherein the number of nucleotides that are chemically linked by a phosphorothioate linkage is greater than the number of nucleotides that are chemically linked by a phosphodiester linkage, and wherein:
 a. the sequence of the oligonucleotide comprises a first fragment and a second fragment, wherein the first fragment is composed of a succession of at least 5-8 nucleotide or nucleotide analogue units that is identical in at least 90%, 91%, 92%, 93%, 94%, 95%, 96%, 97%, 98%, 99% or 100% to the complementary sequence of the seed region of the hsa-miR-23b-3p as set forth in SEQ ID NO: 13, and wherein the second fragment is adjacent to the first fragment (i.e., it is located upstream and/or downstream of the first fragment) and it is composed of a succession of at least 7, 8, 9, 10, 11, 12, 13, 14, 15, or 16 consecutive nitrogen bases of nucleotide or nucleotide analogue units that are identical in at least 60%, 70%, 80%, 85%, 90%, 91%, 92%, 93%, 94%, 95%, 96%, 97%, 98%, 99% or 99.5%, or 100% to the complementary sequence of a region present in SEQ ID NOs: 11, and
 b. it is conjugated at the 5'-end and/or at the 3'-end with at least one oleic acid molecule, preferably by means of a spacer molecule.

In an embodiment, the oligonucleotide and/or oligonucleotide analogue molecule according to the first aspect or any of its embodiments comprises between 10 to 30 nucleotides in length and is an antimiR-type oligonucleotide analogue, wherein at least two nucleotides of said molecule are chemically linked by a phosphorothioate linkage and at least two nucleotides of said molecule are linked by a phosphodiester linkage, preferably wherein the number of nucleotides that are chemically linked by a phosphorothioate linkage is greater than the number of nucleotides that are chemically linked by a phosphodiester linkage, and wherein:
 a. the sequence of the oligonucleotide comprises a first fragment and a second fragment, wherein the first fragment is composed of a succession of at least 5-8 nucleotide or nucleotide analogue units that is identical in at least 90%, 91%, 92%, 93%, 94%, 95%, 96%, 97%, 98%, 99% or 100% to the complementary sequence of the seed region of the hsa-miR-218-5p as set forth in SEQ ID NO: 12, and wherein the second fragment is adjacent to the first fragment (i.e., it is located upstream and/or downstream of the first fragment) and it is composed of a succession of at least 7, 8, 9, 10, 11, 12, 13, 14, 15, or 16 consecutive nitrogen bases of nucleotide or nucleotide analogue units that are identical in at least 60%, 70%, 80%, 85%, 90%, 91%, 92%, 93%, 94%, 95%, 96%, 97%, 98%, 99% or 99.5%, or 100% to the complementary sequence of a region present in SEQ ID NO: 10, and
 b. it is conjugated at the 5'-end and/or at the 3'-end with at least one oleic acid molecule, preferably by means of a spacer molecule.

In an embodiment, the oligonucleotide and/or oligonucleotide analogue molecule according to the first aspect or any of its embodiments comprises between 10 to 30 nucleotides in length, wherein:
 a. at least two nucleotides of said molecule are chemically linked by a phosphorothioate linkage and at least two nucleotides of said molecule are linked by a phosphodiester linkage, preferably wherein the number of nucleotides that are chemically linked by a phosphorothioate linkage is greater than the number of nucleotides that are chemically linked by a phosphodiester linkage,
 b. its sequence comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 1 or 2 or SEQ ID NO: 52-110, and
 c. it is conjugated at the 5'-end and/or at the 3'-end with at least one oleic acid molecule, preferably by means of a spacer molecule.

In an embodiment, the oligonucleotide and/or oligonucleotide analogue molecule according to the first aspect or any of its embodiments comprises between 10 to 30 nucleotides in length and is an antimiR-type oligonucleotide analogue wherein at least two nucleotides of said molecule are chemically linked by a phosphorothioate linkage and at least two nucleotides of said molecule are linked by a phosphodiester linkage, preferably wherein the number of nucleotides that are chemically linked by a phosphorothioate linkage is greater than the number of nucleotides that are chemically linked by a phosphodiester linkage, and wherein:
 a. at least one of the monomeric units is a nucleotide analogue that presents one or more chemical modifications in the pentose moiety, preferably in the ribose, in the internucleotide linkage, in the nitrogenous base, or in all of them, b. the sequence of the nitrogenous bases of the monomeric units of nucleotides or nucleotide analogues is at least 85%, 90%, 93%, 95%, 98%, or 100% identical to the sequence of nitrogenous bases of the monomeric units of nucleotides of the oligonucleotide SEQ ID NO: 1 or of the oligonucleotide SEQ ID NO: 2, or of their functional equivalents SEQ ID NO: 52-110, and that, c. it is conjugated at the 5'-end and/or at the 3'-end with at least one oleic acid molecule, preferably by means of a spacer molecule.

In a preferred embodiment, at least one, two, three, four, five, six, seven, eight, nine, ten, eleven, twelve, thirteen, fourteen, fifteen, or more than fifteen of the nucleotides comprised in the oligonucleotide or oligonucleotide analogue molecule according to the first aspect or any of its embodiments comprise at least one modification selected from the group comprising or consisting of: locked nucleic acids, 2'-methoxy, 2'-O-methoxyethyl-, 2'fluoro, BNA, PMO, PNA, CRN, 2,6 diaminopurine, methylated cytosine and/or any combination thereof.

In a preferred embodiment, the oligonucleotide and/or oligonucleotide analogue molecule comprises between 10 to 30 nucleotides in length and is an antagonist of the human hsa-miR-23b-3p or hsa-miR-218-5p comprises at least two nucleotides that are chemically linked by a phosphorothioate linkage and at least two nucleotides that are chemically linked by a phosphodiester linkage, wherein preferably the number of nucleotides that are chemically linked by a phosphorothioate linkage is greater than the number of nucleotides that are chemically linked by a phosphodiester linkage, and wherein said oligonucleotide is conjugated to at least one oleic acid molecule, wherein said one oleic acid molecule is conjugated at the 3' and/or 5' ends of said oligonucleotide and/or analogue thereof. Preferably, said oligonucleotide and/or oligonucleotide analogue that is conjugated to at least one molecule of oleic acid at its 3' and/or 5' ends and that comprises more PS linkages than PO linkages comprises, consists, or consists essentially of a fragment composed of a succession of at least 15 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% of the sequence to a region present in SEQ ID NO: 1 (antimiR-218-5p) or SEQ ID NO: 2 (antimiR-23b-3p), or any of their functional equivalents of SEQ ID NO: 52-110.

In a preferred embodiment, at least three, four, five, six, seven, eight, or more than eight of the nucleotides comprised in the oligonucleotide and/or oligonucleotide analogue molecule are chemically modified, wherein said chemical modification is selected from the group of i) 2'-O-methyl (2'OMe), ii) 2'-O-Methoxyethyl (2' MOE), and/or iii) an extra bridge connecting the 2' oxygen and 4' carbon (LNA), and/or any combination thereof. In a further embodiment, the nucleotides comprised in oligonucleotide analogue molecule are chemically modified so as to include an extra bridge connecting the 2' oxygen and 4' carbon (LNA) of at least the nucleotides located at the 3' and 5' ends of the oligonucleotide. More preferably, the LNA modification is introduced in at least the last 4th, 3rd, preferably 2nd, or last nucleotide(s) located at the 3' and 5' ends of the oligonucleotide. Also, preferably, at least one of the nucleotides comprised in the oligonucleotide and/or oligonucleotide analogue molecule is 2,6 diaminopurine and/or at least a methylated cytosine.

In a further embodiment, the oligonucleotide molecule and/or analogue thereof is an antagonist of the human hsa-miR-23b-3p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 3 or SEQ ID NO: 22 (MD23b-2 V2 3' Ol), wherein said oligonucleotide molecule and/or analogue thereof comprises at least an oleic acid conjugated at the 3' end. Preferably, the full-length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full-length sequence of the nitrogenous bases of the oligonucleotide in SEQ ID NO: 3 or SEQ ID NO: 22 (MD23b-2 V2 3'Ol), wherein said oligonucleotide molecule and/or analogue thereof comprises at least an oleic acid conjugated at the 3' end. In an embodiment, the oligonucleotide consists of SEQ ID NO: 3 or SEQ ID NO: 22.

In a further embodiment, the oligonucleotide molecule and/or analogue thereof is an antagonist of the human hsa-miR-23b-3p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 4 or SEQ ID NO: 23 (MD23b-2 PS/PO 3'Ol), wherein said oligonucleotide molecule and/or analogue thereof comprises at least an oleic acid conjugated at the 3' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 4 or SEQ ID NO: 23 (MD23b-2 PS/PO 3'Ol), wherein said oligonucleotide molecule and/or analogue thereof comprises at least an oleic acid conjugated at the 3' end. In an embodiment, the oligonucleotide consists of SEQ ID NO: 4 or SEQ ID NO: 23.

In a further embodiment, the oligonucleotide molecule and/or analogue thereof is an antagonist of the human hsa-miR-23b-3p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 5 or SEQ ID NO: 24 or SEQ ID NO: 51 (MD23b-2 PS/PO 5' Ol), wherein said oligonucleotide molecule and/or analogue thereof comprises at least an oleic acid conjugated at the 5' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 5 or SEQ ID NO: 24 or SEQ ID NO: 51 (MD23b-2 PS/PO 5' Ol), wherein said oligonucleotide molecule and/or analogue thereof comprises at least an oleic acid conjugated at its 5' end. In an embodiment, the oligonucleotide consists of SEQ ID NO: 5 or SEQ ID NO: 24 or SEQ ID NO: 51.

In a further embodiment, the oligonucleotide molecule and/or analogue thereof is an antagonist of the human hsa-miR-23b-3p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 49 or SEQ ID NO: 50 (MD23b-2 V2 3' Ol with C6SSC6), wherein said oligonucleotide molecule and/or analogue thereof comprises at least an oleic acid conjugated at the 3' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 49 or SEQ ID NO: 50 (MD23b-2 V2 3' Ol with C6SSC6), wherein said oligonucleotide molecule and/or analogue thereof comprises at least an oleic acid conjugated at its 5' end. In an embodiment, the oligonucleotide consists of SEQ ID NO: 49 or SEQ ID NO: 50 (MD23b-2 V2 3' Ol with C6SSC6).

In a further embodiment, the oligonucleotide molecule and/or analogue thereof is an antagonist of the human hsa-miR-218-5p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 7 or SEQ ID NO: 25 (hsa-miR-218-5p MOE Oleic 3'), wherein said oligonucleotide molecule and/or analogue thereof comprises at least an oleic acid conjugated at the 3' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 7 or SEQ ID NO: 25 (hsa-miR-218-5p MOE Oleic 3'), wherein said oligonucleotide molecule and/or analogue thereof comprises at least an oleic acid conjugated at the 3' end. In an embodiment, the oligonucleotide consists of SEQ ID NO: 7 or SEQ ID NO: 25.

In a further embodiment, the oligonucleotide molecule and/or analogue thereof is an antagonist of the human hsa-miR-218-5p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 8 or SEQ ID NO: 26 (hsa-miR-218-5p MOE DD Oleic 3'), wherein said oligonucleotide molecule and/or analogue thereof comprises at least an oleic acid conjugated at the 3' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 8 or SEQ ID NO: 26 (hsa-miR-218-5p MOE DD Oleic 3'), wherein said oligonucleotide molecule and/or analogue thereof comprises at least an oleic acid conjugated at the 3' end. In an embodiment, the oligonucleotide consists of SEQ ID NO: 8 or SEQ ID NO: 26.

In a further embodiment, the oligonucleotide molecule and/or analogue thereof is an antagonist of the human hsa-miR-218-5p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 9 or SEQ ID NO: 27 (hsa-miR-218-5p OME/MOE Oleic 3'), wherein said oligonucleotide molecule and/or analogue thereof comprises at least an oleic acid conjugated at the 3' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 9 or SEQ ID NO: 27 (hsa-miR-218-5p OME/MOE Oleic 3'), wherein said oligonucleotide molecule and/or analogue thereof comprises at least an oleic acid conjugated at the 3' end. In an embodiment, the oligonucleotide consists of SEQ ID NO: 9 or SEQ ID NO: 27.

In a further embodiment, the oligonucleotide molecule and/or analogue thereof is an antagonist of the human hsa-miR-218-5p and it comprises, consists, or consists essentially of a fragment composed of a succession of at least 7, 8, 9, 10, 11, 12, 13, 14, 15, or 16 consecutive nitrogen bases of nucleotide or nucleotide analogue units that are identical in at least 50%, 60%, 70%, 80%, 85%, 90%, 91%, 92%, 93%, 94%, 95%, 96%, 97%, 98%, 99% or 100% to the sequence of a region present in SEQ ID NO: 14 or SEQ ID NO: 28 (hsa-miR-218-5p OME/MOE Oleic 3'2), wherein said oligonucleotide molecule and/or analogue thereof comprises at least an oleic acid conjugated at the 3' end. Preferably, the full length sequence of the nitrogen bases of the nucleotide or nucleotide analogue units comprised in the oligonucleotide molecule and/or analogue thereof is identical in at least 60%, 70%, 80%, 85%, 90%, 91%, 92%, 93%, 94%, 95%, 96%, 97%, 98%, 99% or 99.5%, or 100% to the full length sequence of the nitrogenous bases of the oligonucleotide in SEQ ID NO: 14 or SEQ ID NO: 28 (hsa-miR-218-5p OME/MOE Oleic 3'2), wherein said oligonucleotide molecule and/or analogue thereof comprises at least an oleic acid conjugated at the 3' end. In an embodiment, the oligonucleotide consists of SEQ ID NO: 14 or SEQ ID NO: 28.

Preferably, the oligonucleotide molecule and/or analogue thereof of the first aspect comprises, or consists of SEQ ID NOS SEQ ID NOs: 3, 4, 5, 22, 23, 24, 49, 50 or 51 (antagonists of hsa-miR-23b) or SEQ ID NOs: 7, 8, 9, 14, 25, 26, 27, or 28 (antagonists of hsa-miR-218-5p), or a sequence that has 85%, 86%, 87%, 88%, 89%, 90%, 91%, 92%, 93%, 94%, 95%, 96%, 97%, 98%, 99% or 100% sequence identity to SEQ ID NOs: 3, 4, 5, 22, 23, 24, 49, 50, 51, 7, 8, 9, 14, 25, 26, 27, or 28.

Preferably, the oligonucleotide and/or oligonucleotide analogue is identical in at least 80%, 85%, 90%, 91%, 92%, 93%, 94%, 95%, 96%, 97%, 98%, 99% or 99.5%, or 100% to any of SEQ ID NOs: 3, 4, 5, 22, 23, 24, 49, 50, 51, 7, 8, 9, 14, 25, 26, 27, or 28, preferably to SEQ ID NOs: 3, 4, 7, 22, 23 or 25, and is capable of increasing, preferably statistically increasing, the endogenous levels of MBNL proteins, preferably MBNL1 and/or MBNL2 proteins in comparison to untreated cells or tissue. Most preferably, the oligonucleotide molecule and/or analogue thereof of the first aspect consists of SEQ ID NOs: 3, 4, 5, 22, 23, 24, 49, 50, 51, 7, 8, 9, 14, 25, 26, 27, or 28. It is noted that, in the context of the present invention, when a oligonucleotide molecule and/or analogue thereof is said to specifically consists of a specific SEQ ID NO, it is understood that said oligonucleotide molecule and/or analogue thereof also consists of the chemical modifications, spacer molecule, and oleic acid conjugation as set forth in said SEQ ID NO. For instance, when an oligonucleotide molecule and/or analogue thereof consists of SEQ ID NO: 3, 4, or 7, it is interpreted that said oligonucleotide molecule and/or analogue thereof consists of the nucleotide sequence defined in SEQ ID NOs 3, 4, or 7, and the chemical modifications, spacer, and oleic acid conjugation defined in said SEQ ID NOs: 3, 4 or 7. The detailed description of the chemical modifications included in each SEQ ID NOs is included in section "Sequence Listing".

Additionally, also comprised within the present invention are compounds such as oligonucleotide molecules and/or analogues thereof in the form of a prodrug, i.e., in a form or nature that is not fully active but that will be converted or metabolized within the body upon administration to give rise to the fully pharmacologically active oligonucleotides molecules and/or analogues thereof described herein.

The cellular expression of the microRNA to be inhibited should also be considered. According to miRGator v3.0 (miRGator v3.0: a microRNA portal for deep sequencing, expression profiling and mRNA targeting. Sooyoung Cho et al., Nucleic Acids Research, Volume 41, Issue D1, 1 Jan. 2013, Pages D252-D257, https://doi.org/10.1093/nar/gks1168), hsa-miR-218-5p is expressed in: adipose tissue, brain, central nervous system, kidney, heart, liver and biliary system, lung, pharynx, nasopharynx, nose, placenta, spleen, stem cells, testicle, uterus and joints. hsa-miR-23b-3p, on the other hand, is expressed in: the central nervous system, gastrointestinal tract, adipose tissue, breast, bladder, heart, keratinocytes, kidney, liver and biliary system, lung, lymphoid cells, nose, pharynx, placenta, prostate, skin, spleen, stem cells, testicle, thyroid gland and uterus. Thus, a possible embodiment of the invention considered is an oligonucleotide and/or oligonucleotide analogue molecule that is preferably an antimiR, more preferably an antagonist of hsa-miR-218-5p or hsa-miR-23b-3p, or a mixture of two or more of said molecules, and that the target miRNA is expressed at least in one or more organs selected from the group of the brain, cerebellum, hippocampus or other organs of the central nervous system, skeletal muscle, heart, adipose tissue, kidney, liver and biliary system, lung, pharynx, nasopharynx, nose, placenta, spleen, testicle, uterus, gastrointestinal tract, breast, bladder, prostate, skin, keratinocytes and lymphoid cells or in one or more cells of a primary culture from one of those organs or of an established cell line derived from one of those organs (including induced pluripotent stem cells, known by the acronym IPSCs) or stem cells from one of these organs. The choice of the specific microRNA to be antagonized, in particular, the choice specifically between the human hsa-miR-218-5p or the human hsa-miR-23b-3pp, will also determine the range of tissues where the antagonistic effect can be exerted.

In a second aspect, the present invention relates to a composition, preferably a pharmaceutical composition, comprising at least an oligonucleotide as defined in the first aspect or any of its embodiments, or a mixture of two or more of them, optionally further comprising a carrier and/or one or more pharmaceutically acceptable excipients. Preferably, the composition comprises an antimiR as defined in the first aspect or any of its embodiments, more preferably an antagonist of the human hsa-miR-218-5p or the human hsa-miR-23b-3p. In an embodiment, the compositions that comprise one of these anti-microRNAs or their mixtures, as well as any other anti-microRNA directed against the human hsa-miR-218-5p or the human hsa-miR-23b-3p or mixtures thereof, or in general any oligonucleotide and/or oligonucleotide analogue molecule that is an inhibitor of one of these microRNAs or of another microRNA that down-regulates the expression of the human gene MBNL1 and/or MBNL2, including compositions which also comprise a pharmaceutically acceptable carrier and/or excipient.

In one possible embodiment, the pharmaceutical composition comprises an effective dose of an inhibitor or antagonist, preferably an antimiR, more preferably an antagonist of the human hsa-miR-218-5p or of the human hsa-miR-23b-3pp or a mixture thereof, as defined in the first aspect or any of its embodiments. Preferably, the inhibitor/antagonist of the human hsa-miR-218-5p present in the composition is the antimiR type inhibitor used in the examples of this invention represented by SEQ ID NO: 1 or its functional equivalents of SEQ ID NO: 80-110; and the inhibitor/antagonist of the human hsa-miR-23b-3p present in the composition is the antimiR type inhibitor represented by SEQ ID NO: 2 or its functional equivalents of SEQ ID NO: 52-79, where the inhibitor is conjugated at its 3' and/or 5' ends to at least one oleic acid molecule. More preferably, the inhibitor(s)/antagonist(s) comprised in the composition will be present at a concentration that allows the administration of a therapeutically effective dose.

An "effective dose" or "therapeutically effective dose" is a sufficient amount to achieve a beneficial or desired clinical outcome. An effective dose of an inhibitor/antagonist of a microRNA, according to previous results obtained with molecules directed against other microRNAs, can be from about 0.5 mg/kg to about 100 mg/kg, preferably from about 1.5 mg/kg to 100 mg/kg in mice or from about 0.75 mg/kg to 50 mg/kg in rats. However, the precise determination of what would be considered an effective dose in humans can be based on individual factors for each patient, including size, age, and the nature of the inhibitor or antagonist (for example, if it is an expression construct, an antimiR or oligonucleotide analogue, etc). Nonetheless, the dosages can be easily determined by ordinary experts skilled in the art based on this description and the knowledge of the art.

For its clinical application, the compositions according to the uses of this invention, will then be considered pharmaceutical compositions of this invention, and they can be prepared in an appropriate form for the desired application. It may be necessary or convenient to administer multiple doses to the subject during a particular treatment period, administering doses daily, weekly, monthly, every two months, every three months or every six months. In certain embodiments, the subject receives an initial dose at the beginning, which is larger than one or more subsequent doses or maintenance doses. In certain embodiments, the subject receives dosis periodically or chronically, especially in the case of treatment of chronic diseases, such as DM1.

Colloidal dispersion systems, such as macromolecule complexes, nanocapsules, micro-spheres, pearls and lipid-based systems that include oil-in-water emulsions, micelles, mixed micelles, other oligonucleotide-based delivery vehicles, and liposomes, can be used as administration vehicles of the inhibitors/antagonists of this invention, with which the pharmaceutical composition of the invention is formed. Another possibility is to prepare the pharmaceutical compositions of the invention using appropriate salts and buffers to make the administration vehicles stable and to assist in the capture by the target cells. The compositions of this invention can be aqueous compositions that comprise an effective amount of the administration vehicle and which comprise either the oligonucleotide molecules of the invention, independently or forming liposomes or other complexes, or expression vectors thereof, dissolved or dispersed in a pharmaceutically acceptable carrier or aqueous medium.

Additional active ingredients may also be incorporated into the compositions, provided that they do not inactivate the molecules of this invention or their expression vectors.

The solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary storage and use conditions, these preparations generally contain a preservative to prevent the growth of microorganisms. The oligonucleotides can also be prepared in a solution of phosphate-buffered saline and sodium chloride. For example, the oligonucleotides can be prepared in phosphate-buffered saline at a pH of between 6.5 and 8, preferably at a pH of about 6.8-7 and sodium chloride at a concentration of about 150 mM.

The compositions of this invention can usually be formulated in a neutral or salt form. Pharmaceutically acceptable salts include, for example, acid addition salts (formed with free amino groups of the protein) derived from inorganic acids (e.g., hydrochloric or phosphoric acids), or organic acids (e.g. acetic, oxalic, tartaric, mandelic acids), and the like. Salts formed with free carboxyl groups of the protein can also be derived from inorganic bases (for example, sodium, potassium, ammonium, calcium, or ferric hydroxides) or organic bases (e.g. isopropylamine, trimethylamine, histidine, procaine, and the like).

In a third aspect, the present invention provides an oligonucleotide as defined in the first aspect or any of its embodiment, or a composition, preferably a pharmaceutical composition, as defined in the second aspect or any of its embodiments for use in therapy. Preferably, the oleic acid conjugated to the oligonucleotide molecule and/or analogue thereof acts as a vehicle to deliver said oligonucleotide molecule and/or analogue thereof to relevant tissues, such as muscle and/or CNS. Thus, the oligonucleotide molecule or analogue thereof according to the first aspect and conjugated at its 3' and/or 5' ends to at least one oleic acid molecule may be for use in a method of treatment by therapy in a human subject in need thereof, wherein said oligonucleotide molecule and/or analogue thereof is an active ingredient of said treatment by therapy, and wherein said oleic acid molecule is used as a pharmaceutically acceptable vehicle or carrier of said oligonucleotide molecule and/or analogue thereof. The term "active ingredient" is used in the present invention to refer the substance which is pharmaceutically active and responsible of the therapeutic effect. In the case of antagonists of antimiRs, the active ingredient is the molecule, preferably the oligonucleotide molecule, that targets the endogenous miR. Most preferably, the term "active ingredient" is used herein to refer to the oligonucleotide molecule and/or analogue thereof defined in the first aspect of the present invention.

In a fourth aspect, the present invention provides an oligonucleotide as defined in the first aspect or any of its embodiment, or a composition, preferably a pharmaceutical composition, as defined in the second aspect or any of its embodiments for use in the prevention or treatment of muscular and/or nervous system diseases, preferably muscular diseases involving weakness and wasting away of muscle tissue, particularly involving loss of muscular strength, increasing disability, and deformity, and/or preferably nervous system diseases that involve structural and/or functional changes in the brain and/or other tissues of the CNS. Preferably, muscular diseases are muscular dystrophy diseases. Preferably, the muscular dystrophy diseases are selected from the group consisting of Becker muscular dystrophy, congenital muscular dystrophy, Duchenne muscular dystrophy, Distal muscular dystrophy, Emery-Dreifuss muscular dystrophy, Facioscapulohumeral muscular dystrophy, Limb-Girdle muscular dystrophy, Myotonic dystrophy, and Oculopharyngeal muscular dystrophy. Preferably, the muscular disease is myotonic dystrophy, preferably of type 1 and/or 2. Preferably, the use according to the fourth aspect includes the use of the at least one oleic acid molecule as a vehicle when conjugated to an oligonucleotide molecule and/or analogue thereof to deliver said oligonucleotide molecule and/or analogue thereof to the relevant tissue, such as muscle and/or to CNS.

In an alternative fourth aspect, the present invention provides an oligonucleotide as defined in the first aspect or any of its embodiment, or a composition, preferably a pharmaceutical composition, as defined in the second aspect or any of its embodiments for use in the prevention or treatment of diseases characterized by insufficient amount or function of MBNL genes and/or proteins in a subject in need thereof. Preferably, said use includes the use of the at least one oleic acid molecule as a vehicle when conjugated to an oligonucleotide molecule and/or analogue thereof to deliver said oligonucleotide molecule and/or analogue thereof to the relevant tissue, such as muscle and/or to CNS. By "insufficient amount or function of MBNL genes and/or proteins" is referred herein to statistically significant lower amounts or function of MBNL genes and/or proteins in comparison to a healthy subject. In a further alternative fourth aspect, the present invention provides an oligonucleotide as defined in the first aspect or any of its embodiment, or a composition, preferably a pharmaceutical composition, as defined in the second aspect or any of its embodiments for use in targeting muscular and/or CNS cells in a subject in need thereof, preferably muscular cells in a subject suffering from DM or DM1. By "targeting muscular and/or CNS cells" is referred herein as increasing the insufficient amounts of MBNL proteins and/or genes in said cells. CNS cells include preferably neurons, but also glial cells (astrocytes, oligodendrocytes, ependymal cells, and microglia), choroid plexus cells, cells related to blood vessels and coverings. Muscular cells include smooth, preferably skeletal, and cardiac cells. Preferably, the increase is a statistically significant increase, preferably in comparison to a control cell or an untreated cell.

In a further alternative fourth aspect, the present invention provides an oligonucleotide as defined in the first aspect or any of its embodiment, or a composition, preferably a pharmaceutical composition, as defined in the second aspect or any of its embodiments for use in the prevention or treatment of diseases characterized by the expression of toxic RNAs (also called RNAopathies or RNA-mediated/RNA-dominant diseases). Preferably, said use includes the use of the at least one oleic acid molecule as a vehicle when conjugated to an oligonucleotide molecule and/or analogue thereof to deliver said oligonucleotide molecule and/or analogue thereof to the relevant tissue, such as muscle and/or to CNS. Said diseases are usually characterized by the expansion of unstable microsatellite repeats caused by unusual mutation mechanisms, wherein the expression of the expansions of a repetitive element create a sink for RNA-binding proteins by increasing the mass of target RNA per nucleus and also by increasing the avidity of RNA-protein interaction due to a high local concentration of binding sites in each mutant transcript, among other mechanisms. Preferably, the RNAopathies or RNA-mediated/RNA-dominant diseases are neuromuscular or neurodegenerative diseases, more preferably selected from the group consisting of DM type 1 (ORPHA:273) or type 2 (ORPHA: 606); Fragile X-Associated Tremor/Ataxia Syndrome (ORPHA:93256; FXTAS); C9ORF72 Amyotrophic Lateral Sclerosis and/or Frontotemporal Dementia(ORPHA: 275872; ALS/FTD); Spinocerebellar Ataxias (SCAs) or benign adult familial myoclonic epilepsy (BAFME).

In a further alternative fourth aspect, the present invention provides an oligonucleotide as defined in the first aspect or any of its embodiment, or a composition, preferably a pharmaceutical composition, as defined in the second aspect or any of its embodiments for use in the prevention or treatment of diseases characterized by an excess in the amount or function of miR-23b-3p and/or miR-218-5p. By "excessive amount or function of miR-23b-3p and/or miR-218-5p" is referred herein to statistically significant higher amounts or function of miR-23b-3p and/or miR-218-5p in comparison to those in a healthy subject. Preferably, the disease characterized by an excess in the amount or function of miR-23b-3p and/or miR-218-5p is myotonic dystrophy, preferably of type 1 and/or 2. Preferably, said use includes the use of the at least one oleic acid molecule as a vehicle when conjugated to an oligonucleotide molecule and/or analogue thereof to deliver said oligonucleotide molecule and/or analogue thereof to the relevant tissue, such as muscle and/or to CNS.

Preferably, the oligonucleotide or oligonucleotide analogue molecule as defined in the first aspect or any of its embodiments, alone or comprised in the pharmaceutical composition, for use according to the third or fourth aspects is an inhibitor of the human hsa-miR-218-5p or of the human hsa-miR-23b-3p with SEQ ID NO: 1 or 2, respectively, or a sequence with at least 50%, 60%, 70%, 80%, 85%, 90%, 91%, 92%, 93%, 94%, 95%, 96%, 97%, 98%, 99% or 100% sequence identity with SEQ ID NO: 1 or 2. Preferably, the oligonucleotide or oligonucleotide analogue molecule as defined in the first aspect or any of its embodiments, alone or comprised in the pharmaceutical composition, for use according to the third or fourth aspects is an inhibitor of the human hsa-miR-218-5p or of the human hsa-miR-23b-3p with SEQ ID NO: 80-110 or 52-79, respectively, or a sequence with at least 50%, 60%, 70%, 80%, 85%, 90%, 91%, 92%, 93%, 94%, 95%, 96%, 97%, 98%, 99% or 100% sequence identity with SEQ ID NO: 80-110 or 52-79.

More preferably, the oligonucleotide or oligonucleotide analogue molecule as defined in the first aspect or any of its embodiments for use according to the third or fourth aspects is an antagonist comprising or consisting of SEQ ID NO: 3, 4, or 5 (antimiRs against hsa-miR-23b-3p) or SEQ ID NO: 7, 8, 9 or 14 (antimiRs against hsa-miR-218-5p), or a sequence with at least 50%, 60%, 70%, 80%, 85%, 90%, 91%, 92%, 93%, 94%, 95%, 96%, 97%, 98%, 99% or 100% sequence identity with SEQ ID NO: 3, 4, or 5 (antimiRs against hsa-miR-23b-3p) or with SEQ ID NO: 7, 8, 9 or 14 (antimiRs against hsa-miR-218-5p). More preferably, the oligonucleotide or oligonucleotide analogue molecule as defined in the first aspect or any of its embodiments for use according to the third or fourth aspects is an antagonist comprising or consisting of SEQ ID NO: 22, 23, 24, 49, 50 or 51 (antimiRs against hsa-miR-23b-3p) or SEQ ID NO: 25, 26, 27 or 28 (antimiRs against hsa-miR-218-5p), or a sequence with at least 50%, 60%, 70%, 80%, 85%, 90%, 91%, 92%, 93%, 94%, 95%, 96%, 97%, 98%, 99% or 100% sequence identity with SEQ ID NO: 3, 4, or 5 (antimiRs against hsa-miR-23b-3p) or with SEQ ID NO: 7, 8, 9 or 14 (antimiRs against hsa-miR-218-5p). As mentioned above in the first aspect, the oligonucleotides or analogues thereof for use according to the third and fourth aspects also comprise at least one oleic acid molecule conjugated at their 3' and/or 5' ends.

In an embodiment of the fourth aspect, the treatment is a palliative treatment of one or more symptoms of myotonic dystrophy type 1 and/or type 2, or a palliative treatment of one or more of the muscular disorders that are part of the symptoms of myotonic dystrophy type 1 and/or type 2. In a preferred embodiment of the fourth aspect, the treatment is for chronic myotonic dystrophy type 1 and/or type 2. In a preferred embodiment, the treatment is a therapeutic treatment. Preferably, said use includes the use of the at least one oleic acid molecule as a vehicle when conjugated to an oligonucleotide molecule and/or analogue thereof to deliver said oligonucleotide molecule and/or analogue thereof to the relevant tissue, such as muscle and/or to CNS.

In an embodiment of the third and fourth aspects, the subject in need thereof is a mammal, preferably a human being, more preferably a human suffering from DM, preferably DM1.

The administration of the antagonist through a possible expression vector thereof allows to direct the expression to a tissue or group of specific tissues according to the tropism of the base vector itself and/or by choosing control elements that give rise to the expression of the coding sequence linked to them only in specific tissues. In addition, some specific dosage forms may favour greater access to one or other organs. Thus, also a possible embodiment, combinable with any other, of the third and fourth aspects of the present invention more directly referring to the therapeutic application thereof, could be defined as: use of one of the oligonucleotide and/or oligonucleotide analogue molecules of the invention, a mixture of two or more of them, or a composition comprising at least one of said molecules, for the manufacture of a medicinal product for the treatment of myotonic dystrophy type 1 by inhibition or antagonism of the action of a human hsa-miR-218-5p or hsa-miR-23b-3p in at least one or more organs selected from the group of the brain, cerebellum, hippocampus, or other central nervous system organs, skeletal muscle, heart, adipose tissue, kidney, liver and biliary system, lung, pharynx, nasopharynx, nose, placenta, spleen, testicle, uterus, gastrointestinal tract, breast, bladder, prostate, skin, keratinocytes and lymphoid cells or stem cells from one or more of these organs. Other organs that can also be targeted by the oligonucleotides of the present invention are selected from the group of the brain, cerebellum, hippocampus or another organ of the central nervous system, skeletal muscle, heart, adipose tissue, kidney, liver and biliary system, lung, pharynx, nasopharynx, nose, placenta, spleen, testicle and uterus, gastrointestinal tract, breast, bladder, prostate, skin, keratinocytes and lymphoid cells or stem cells from one or more of these organs, or combinations thereof, as desired or appropriate.

Given the stability of the antimiRs, direct administration to mammals, preferably human beings, can be considered, for example via subcutaneous or systemic routes, preferably intravenously or intrathecal, for example dissolved or suspended in a pharmaceutically acceptable carrier, such as water or an aqueous solution such as saline or phosphate buffer, or intraarticular delivery. The composition in which they are administered may contain pharmaceutically acceptable excipients.

The active compositions of this invention can be administered by any of the common routes, provided that the target tissue is available through that route. This includes oral, nasal, intrathecal, or buccal routes and, preferably, the administration may be via an intradermal, transdermal, subcutaneous, intramuscular, intraperitoneal, or intravenous route. As previously commented, it is common for compositions comprising antimiRs to be formulated for intravenous or subcutaneous administration. However, since oleic acid enhances the delivery of the oligonucleotide molecule and/or analogue thereof to muscle and/or CNS cells when the administration is intravenous (see Examples 9 and 10), it is a preferred embodiment that the administration is intravenous, intraarterial or subcutaneous. Further, it is also preferably that said intravenous, intraarterial or subcutaneous administration is a chronic administration, which means that it is carried out periodically (uring the entire life of the patient in need thereof.

After formulation, the solutions are preferably administered in a form that is compatible with the dosage formulation and in such a quantity that it is therapeutically effective. Formulations can be easily administered in a variety of dosage forms such as injectable solutions, drug release capsules, and the like.

A further aspect provides a method of treating DM, preferably DM1, in a subject in need thereof, the method comprising administering the oligonucleotides or pharmaceutical compositions of the present invention to a patient in need thereof. In some embodiments, the oligonucleotides will be present at a concentration that allows the administration of a therapeutically effective dose. Preferably, said method of treatment includes the use of the at least one oleic acid molecule as a vehicle when conjugated to an oligonucleotide molecule and/or analogue thereof to deliver said oligonucleotide molecule and/or analogue thereof to the relevant tissue, such as muscle and/or to CNS.

As explained above, the Examples provide evidence on how the oleic acid is capable of increasing the delivery to target issues such as muscle and brain. This lead to the conclusion that oleic acid is capable of not only reducing the toxicity when a higher amount of PS with respect to PO is included in the molecule, but also oleic acid is an efficient vehicle to transport the oligonucleotide molecule and/or analogue thereof to target tissues, such as muscle and/or CNS. In view of this, a fifth aspect of the present invention relates to the use of at least one oleic acid molecule as a pharmaceutically acceptable vehicle or carrier when said oleic acid is conjugated to a oligonucleotide molecule and/or analogue thereof, preferably conjugated to the 3' or the 5' of said oligonucleotide molecule and/or analogue. Importantly, the use of at least one oleic acid molecule as a pharmaceutically acceptable vehicle or carrier refers to a use in which the oleic acid molecule is responsible of the transport, delivery, carriage, of the oligonucleotide molecule and/or analogue thereof to which it is conjugated, to a specific target tissue, preferably muscle and/or CNS tissue. In this context, "vehicle" and "carrier" are considered synonymous and thus are used interchangeably.

The skilled person in the art knows how to test whether oleic acid is acting as a vehicle for the oligonucleotide molecule and/or analogue thereof to which it is conjugated to. For example, a way of evaluating whether the at least one oleic acid is being used a vehicle is by measuring the amount of the oligonucleotide molecule and/or analogue thereof that arrives at a target tissue (preferably CNS and/or muscle tissue) after intravenous, intraarterial or subcutaneous administration, and comparing said amount to the amount present in said tissue when the oligonucleotide molecule and/or analogue thereof is administrated not conjugated to the at least one oleic acid.

Preferably, the oligonucleotide molecule and/or analogue thereof to which the oleic acid is conjugated is the oligonucleotide molecule and/or analogue thereof defined in the first aspect of the present invention, or any of its embodiments. Hence, a preferred embodiment of the fifth aspect refers to the use of at least one oleic acid molecule as a pharmaceutically acceptable vehicle or carrier when said oleic acid conjugated to the 3' end or the 5' end of the oligonucleotide molecule and/or analogue thereof defined in the first aspect, preferably wherein said oligonucleotide molecule and/or analogue thereof is the active ingredient of a method of treatment by therapy as defined in the third or fourth aspects of the present invention or any of their embodiments. It is noted that the conjugation between the oligonucleotide molecule and/or analogue thereof may be a direct conjugation or a conjugation throughout a spacer molecule, as described in under the first aspect of the present invention. Preferably, the oleic acid used as a vehicle is conjugated to the oligonucleotide molecule and/or analogue thereof via a spacer molecule selected from the group consisting of of NHC3, NHC5, NHC6, threoninol, and a derivative thereof.

In an embodiment of the fifth aspect, only one oleic acid molecule is conjugated to the 5' end or 3' end of the oligonucleotide molecule and/or analogue thereof of the first aspect or any of its embodiments, so that the single oleic acid molecule acts as a vehicle of said oligonucleotide molecule and/or analogue thereof. In an embodiment of the fifth aspect, only one oleic acid molecule is conjugated to the oligonucleotide molecule and/or analogue thereof of the first aspect or any of its embodiments, so that the single oleic acid molecule acts as a vehicle of said oligonucleotide molecule and/or analogue thereof, and the oligonucleotide molecule o and/or analogue thereof defined in the first aspect acts as an active ingredient in a method of treatment by therapy as defined in the third or fourth aspects.

In a preferred embodiment, the at least one oleic acid molecule conjugated to the oligonucleotide molecule and/or analogue thereof as defined in the first aspect of the present invention, or any of its embodiments, is capable of transporting said oligonucleotide molecule and/or analogue thereof to tissues of interest, such as muscle and/or CNS, with more efficiency that when the oligonucleotide molecule and/or analogue thereof is not conjugated to oleic acid, as shown in Example 9 or 10. Hence, the oleic acid molecule is used as an active ingredient delivery vehicle, wherein the active ingredient component is the oligonucleotide molecule and/or analogue thereof as defined in the first aspect or any of its embodiments.

In an embodiment, the at least one oleic acid molecule is used as a pharmaceutically acceptable vehicle or carrier when conjugated to the 3' end or the 5' end of the oligonucleotide molecule and/or analogue of the first aspect or any of its embodiments, wherein the oligonucleotide molecule and/or analogue thereof comprises a mixture of phosphorothioate and phosphodiester linkages chemically linking the nucleotides, preferably wherein the number of nucleotides that are chemically linked by a phosphorothioate linkage is greater than the number of nucleotides that are chemically linked by a phosphodiester linkage.

In an embodiment, the at least one oleic acid molecule is used as a pharmaceutically acceptable vehicle or carrier when conjugated to the 3' end or the 5' end of the oligonucleotide molecule and/or analogue of the first aspect or any of its embodiments, wherein said oligonucleotide molecule and/or analogue thereof is an antagonist of a microRNA, preferably an antagonist of the human hsa-miR-23b-3p or the human hsa-miR-218-5p.

In an embodiment, the at least one oleic acid molecule is used as a pharmaceutically acceptable vehicle or carrier when conjugated to the 3' end or the 5' end of the oligonucleotide molecule and/or analogue of the first aspect or any of its embodiments, wherein the oleic acid used as a vehicle delivers said oligonucleotide molecule and/or analogue thereof to muscular and/or CNS cells in a subject in need thereof when said oligonucleotide molecule and/or analogue thereof is administrated via intravenous, intraarterial or subcutaneous route.

In an embodiment, at least one oleic acid molecule is used as a pharmaceutically acceptable vehicle or carrier when conjugated to the 3' end or the 5' end of the oligonucleotide molecule and/or analogue thereof as defined in the first aspect or any of its embodiments, wherein said oligonucleotide molecule and/or analogue thereof is the active ingredient of a method of treatment by therapy that comprises the prevention or treatment of muscular diseases, nervous system diseases, and/or RNAopathies.

In an embodiment, the at least one oleic acid molecule is used as a pharmaceutically acceptable vehicle or carrier when conjugated to the 3' end or the 5' end of the oligonucleotide molecule or analogue thereof as defined in the first aspect or any of its embodiments, wherein said oligonucleotide molecule and/or analogue thereof is the active ingredient of a method of treatment by therapy that comprises the prevention or treatment of myotonic dystrophy, preferably myotonic dystrophy is of type 1.

In a fifth aspect, the invention also provides a conjugate, wherein the conjugate consists of at least one oleic acid conjugated to the 3' end or 5' end of the oligonucleotide molecule or analogue thereof as defined in the first aspect or any of its embodiments, wherein said oligonucleotide molecule or analogue thereof is used as an active ingredient in a method of treatment by therapy as defined in the third or fourth aspects or any of their embodiments, and wherein the at least one oleic acid is used as a pharmaceutically acceptable vehicle for delivering said oligonucleotide molecule or analogue thereof to the target tissues, such as CNS and/or muscle tissue.

The following clauses are also included in the present invention:

1. An oligonucleotide molecule, or a mixture of two or more of said molecules, wherein said oligonucleotide molecule comprises between 10 to 30 nucleotides in length, wherein said oligonucleotide molecule comprises at least two nucleotides chemically linked by a phosphorothioate linkage, and wherein said oligonucleotide molecule is conjugated at its 3' and/or 5' ends to at least one oleic acid molecule.

2. The oligonucleotide molecule of clause 1, wherein the molecule is an antagonist of a microRNA.

3. The oligonucleotide molecule of clause 2, wherein the microRNA is the human hsa-miR-23b-3p or the human hsa-miR-218-5p.

4. The oligonucleotide molecule according to any of clauses 1 to 3, wherein said oligonucleotide molecule comprises between 15 to 30 nucleotides in length, wherein at least two nucleotides of said molecule are linked by a phosphodiester linkage and wherein the number of nucleotides that are chemically linked by a phosphorothioate linkage is greater than the number of nucleotides that are chemically linked by a phosphodiester linkage.

5. The oligonucleotide molecule according to of any of clauses 1 to 4, wherein said oligonucleotide molecule comprises between 15 to 30 nucleotides in length, and wherein said oligonucleotide molecule comprises a fragment composed of a succession of at least 15 consecutive nitrogen bases of nucleotides that are identical in at least 80% to the sequence of a region present in SEQ ID NO: 1 (antimiR-218-5p) or 2 (antimiR-23b-3p), or SEQ ID NO: 52-110.

6. The oligonucleotide molecule according to any of clauses 1 to 5, wherein said oligonucleotide molecule comprises between 15 to 30 nucleotides in length, and wherein said oligonucleotide molecule comprises a fragment composed of a succession of at least 15 consecutive nitrogen bases of nucleotides that are identical to the sequence of a region present in SEQ ID NO: 1 (antimiR-218-5p) or 2 (antimiR-23b-3p).

7. The oligonucleotide molecule according to any of clauses 1 to 6, comprising at least one chemical modification, wherein the chemical modification is selected from the group of:
   i) 2'-O-methyl (2'OMe),
   ii) 2'-O-Methoxyethyl (2' MOE), and/or
   iii) an extra bridge connecting the 2' oxygen and 4' carbon (LNA).

8. The oligonucleotide molecule according to any of clauses 1 to 7, wherein said oligonucleotide molecule comprises between 15 to 30 nucleotides in length, and wherein said oligonucleotide molecule comprises a fragment composed of a succession of at least 15 consecutive nitrogen bases of nucleotide that are identical in at least 80% to the sequence of a region present in SEQ ID NOs: 3, 4, 5, 22, 23, 24, 49, 50 or 51 (antagonists of hsa-miR-23b) or SEQ ID NOs: 7, 8, 9, 14, 25, 26, 27, or 28 (antagonists of hsa-miR-218-5p).

9. The oligonucleotide molecule according to any of clauses 1 to 8, wherein said oligonucleotide molecule comprises between 15 to 30 nucleotides in length, and wherein the nucleotide sequence of said oligonucleotide consists of SEQ ID NOs: 3, 4, 5, 22, 23, 24, 49, 50 or 51 (antagonists of hsa-miR-23b) or SEQ ID NOs: 7, 8, 9, 14, 25, 26, 27, or 28 (antagonists of hsa-miR-218-5p).

10. A composition, preferably a pharmaceutical composition, comprising at least an oligonucleotide molecule as defined in any of clauses 1 to 9, or a mixture of two or more of them, optionally further comprising a carrier and/or one or more pharmaceutically acceptable excipients.

11. A composition, preferably a pharmaceutical composition, comprising at least an oligonucleotide molecule as defined in any of clauses 1 to 9, or a mixture of two or more of them, optionally further comprising a carrier and/or one or more pharmaceutically acceptable excipients, for use in therapy.

12. A composition, preferably a pharmaceutical composition, comprising at least an oligonucleotide as defined in any of clauses 1 to 9, or a mixture of two or more of them, optionally further comprising a carrier and/or one or more pharmaceutically acceptable excipients, for use in targeting muscular cells in a subject in need thereof.

13. A composition, preferably a pharmaceutical composition, comprising at least an oligonucleotide as defined in any of clauses 1 to 9, or a mixture of two or more of them, optionally further comprising a carrier and/or one or more pharmaceutically acceptable excipients, for use in the prevention or treatment of muscular diseases or in the prevention or treatment of RNAopathies.

14. The composition, preferably a pharmaceutical composition, for use according to clause 13, wherein the disease is myotonic dystrophy.

15. The composition, preferably a pharmaceutical composition, for use according to clause 14, wherein the myotonic dystrophy is of type 1.

Sequence Listing (5' to 3' Direction)

As mentioned above, the SEQ ID NOs listed below and as referred throughout the application comprise a nucleobase sequence and, for those of the oligonucleotides that depart from their natural chemistry, also their chemical modifications and/or fatty acid conjugation. The following nomenclature has been used throughout the entire specification to define the chemical modifications included in the SEQ ID NOs disclosed herein:

LNA nucleotides are indicated by the combinations of a capital letter and a small letter: Ab, Gb, Tb, Cb, Phosphorothioate linkages are indicated by small "s" letters, 2'-O-MOE RNA nucleotides are indicated by a combination of a capital letter and a small letter: Am, Cm, Gm, Tm, 2'-O-Methyl-nucleotides are represented by the small letters: a, g, c, u, 2'-Fluoro RNA nucleotides are indicated by a combination of a capital letter and a small letter: Af, Cf, Gf, Tf, 2'-O-Methyl-2,6-diaminopurine modification is indicated with the expression (dap), deoxynucleotides are indicated by the combination of small letter and capital letter: dA, dC, dG, dT, 2'-OMe-5-methyluridine or 2'-OMe-ribothymidine is represented by small "t" letter, 5-Methyl-2'-O-Methyl cytidine are represented by the expression (5Mc), the expression (OleicAcid) means that the oligonucleotide is conjugated to Oleic Acid, the expression (PalmiticAcid) means that the oligonucleotide is conjugated to Palmitic Acid, the (spacer molecule) is preferably selected from the group consisting of NHC3, NHC5, NHC6, threoninol, or a derivative thereof. Preferably, the spacer molecule is NHC6 or NHC3, "Y" is used for any pyrimidine (C or U/T)

"I" is used for hypoxanthine because hypoxanthine is the nucleobase of inosine.

```
SEQ ID NO 1: Antagonist of the human hsa-miR-218-5p:
TTAGATCAAGCACAA

SEQ ID NO 2: Antagonist of the human hsa-miR-23b-3p:
ATCCCTGGCAATGTGA

SEQ ID NO 3: MD23b-2 V2 3'Ol:
AbsTbs(5Mc)s(5Mc)sCmTbGmsgsCmsAbAmTbGbTmsGbsAb(NHC6)(OleicAcid)

SEQ ID NO 4: MD23b-2-PS/PO 3'Ol:
AbsTms(5Mc)s(5Mc)(5Mc)Tbgsgs(5Mc)sAbAmTbGbsTmsGbsAb(NHC6)(OleicAcid)

SEQ ID NO 5: MD23b-2-PS/PO 5'Ol:
(OleicAcid)(NHC6)AbsTms(5Mc)s(5Mc)(5Mc)Tbgsgs(5Mc)sAbAmTbGbsTmsGbsAb SEQ ID NO: 6: MD23b-2-PS/PO:
AbsTms(5Mc)s(5Mc)(5Mc)Tbgsgs(5Mc)sAbAmTbGbsTmsGbsAb SEQ ID NO 7: 218 MOE Oleic 3':
Tbs TbsAmsGbsAmsTmsCbAmsAmGbCmAbsCmsAbsAb(NHC6)(OleicAcid)

SEQ ID NO: 8: 218 MOE DD Oleic 3':
TbsTbsAmsGbsAmsTmsCbAmsAmsGbCmAbsCms(dap)s(dap)(NHC6)(OleicAcid)

SEQ ID NO: 9: 218 OME/MOE oleic 3':
TbsTmsasGbsastsCbAmsAmGbCmAbsCmsAmsAb(NHC6)(OleicAcid)

SEQ ID NO: 10: hsa-miR-218-5p:
UUGUGCUUGAUCUAACCAUGU

SEQ ID NO: 11: hsa-miR-23b-3p:
AUCACAUUGCCAGGGAUUACCAC

SEQ ID NO: 12: seed region of hsa-miR-218-5p:
UGUGCU

SEQ ID NO: 13: seed region of hsa-miR-23b-3p:
UCACAU
```

-continued

SEQ ID NO: 14: 218 OME/MOE oleic 3'2:
TbsTbsasGbsastsCbAmsAmGbCmAbsCmsAmsAb(NHC6)(OleicAcid)

SEQ ID NO: 15: 218 MOE:
Tbs TbsAmsGbsAmsTmsCbAmsAmGbCmAbsCmsAbsAb

SEQ ID NO: 16 MD23b-2 V2 3'Pal:
AbsTbs(5Mc)s(5Mc)sCmTbGmsgsCmsAbAmTbGbTmsGbsAb(NHC6)(PalmiticAcid)

SEQ ID NO: 17: MD23b-2 V2:
AbsTbs(5Mc)s(5Mc)sCmTbGmsgsCmsAbAmTbGbTmsGbsAb

SEQ ID NO: 18: MD23 MOE:
AbsTbsCmsCmCmsTmsGmGmsCmAmAmsTbGmsTmGbsAb

SEQ ID NO: 19: The microRNA precursor (pre-microRNA) of hsa-miR-23b-3p:
CUCAGGUGCUCUGGCUGCUUGGGUUCCUGGCAUGCUGAUUUGUGACUUAAGAUUAA
AAUCACAUUGCCAGGGAUUACCACGCAACCACGACCUUGGC SEQ ID NO: 20: Pre-hsa-miR-218-5p-1 (chr4:20529898-20530007):
GUGAUAAUGUAGCGAGAUUUUCUGUUGUGCUUGAUCUAACCAUGUGGUUGCGAGGU
AUGAGUAAAACAUGGUUCCGUCAAGCACCAUGGAACGUCACGCAGCUUUCUACA SEQ ID NO: 21: Pre-miR-218-2 (chr5:1681951 SI-168195260):
GACCAGUCGCUGCGGGGCUUUCCUUUGUGCUUGAUCUAACCAUGUGGUGGAACGAU
GGAAACGGAACAUGGUUCUGUCAAGCACCGCGGAAAGCACCGUGCUCUCCUGCA SEQ ID NO 22: MD23b-2 V2 3'Ol without specific spacer molecule: AbsTbs(5Mc)s(5Mc)sCmTbGmsgsCmsAbAmTbGbTmsGbsAb(Spacer molecule)(OleicAcid), wherein the spacer molecule is preferably selected from the group consisting of NHC3, NHC5, NHC6, threoninol, or a derivative thereof.

SEQ ID NO 23: MD23b-2-PS/PO 3'Ol without specific spacer molecule: AbsTms(5Mc)s(5Mc)(5Mc) Tbgsgs(5Mc)sAbAmTbGbsTmsGbsAb(Spacer molecule)(OleicAcid), wherein the spacer molecule is preferably selected from the group consisting of NHC3, NHC5, NHC6, threoninol, or a derivative thereof.

SEQ ID NO 24: MD23b-2-PS/PO 5'Ol without specific spacer molecule: (OleicAcid)(Spacer molecule)AbsTms(5Mc)s(5Mc)(5Mc) Tbgsgs(5Mc)sAbAmTbGbsTmsGbsAb, wherein the spacer molecule is preferably selected from the group consisting of NHC3, NHC5, NHC6, threoninol, or a derivative thereof.

SEQ ID NO 25: 218 MOE Oleic 3' without specific spacer molecule: TbsTbsAmsGbsAmsTmsCbAmsAmGbCmAbsCmsAbsAb(Spacer molecule)(OleicAcid), wherein the spacer molecule is preferably selected from the group consisting of NHC3, NHC5, NHC6, threoninol, or a derivative thereof.

SEQ ID NO: 26: 218 MOE DD Oleic 3' without specific spacer molecule: TbsTbsAmsGbsAmsTmsCbAmsAmsGbCmAbsCms(dap)s(dap)(Spacer molecule)(OleicAcid), wherein the spacer molecule is preferably selected from the group consisting of NHC3, NHC5, NHC6, threoninol, or a derivative thereof.

SEQ ID NO: 27: 218 OME/MOE oleic 3' without specific spacer molecule: TbsTmsasGbsastsCbAmsAmGbCmAbsCmsAmsAb(Spacer molecule)(OleicAcid), wherein the spacer molecule is preferably selected from the group consisting of NHC3, NHC5, NHC6, threoninol, or a derivative thereof.

SEQ ID NO: 28: 218 OME/MOE oleic 3'2 without specific spacer molecule: TbsTbsasGbsastsCbAmsAmGbCmAbsCmsAmsAb(Spacer molecule)(OleicAcid), wherein the spacer molecule is preferably selected from the group consisting of NHC3, NHC5, NHC6, threoninol, or a derivative thereof.

SEQ ID NO: 29: MD23b-2 V2 3'Pal without specific spacer molecule: AbsTbs(5Mc)s(5Mc)sCmTbGmsgsCmsAbAmTbGbTmsGbsAb(Spacer molecule)(PalmiticAcid), wherein the spacer molecule is preferably selected from the group consisting of NHC3, NHC5, NHC6, threoninol, or a derivative thereof.

SEQ ID NO 49: MD23b-2 V2 3'Ol with C6SSC6 and NHC6   AbsTbs(5Mc)s(5Mc)sCmTbGmsgsCmsAbAmTbGbTmsGbsAb(C6SSC6)(NHC6)(OleicAcid)

SEQ ID NO: 50: MD23b-2 V2 3' Ol with C6SSC6 and NHC3   AbsTbs(5Mc)s(5Mc)sCmTbGmsgsCmsAbAmTbGbTmsGbsAb(C6SSC6)(NHC3)(OleicAcid)

SEQ ID NO 51: MD23b-2-PS/PO 5'Ol without spacer molecule: (OleicAcid)AbsTms(5Mc)s(5Mc)(5Mc) Tbgsgs(5Mc)sAbAmTbGbsTmsGbsAb.

SEQ ID NO 52: functional equivalent sequence of antimiR-23b-3p:
YTCCCTGGCAATGTGA SEQ ID NO 53: functional equivalent sequence of antimiR-23b-3p:
ATCCCTYGCAATGTGA SEQ ID NO 54: functional equivalent sequence of antimiR-23b-3p:
ATCCCTGYCAATGTGA SEQ ID NO 55: functional equivalent sequence of antimiR-23b-3p:
ATCCCTGGCYATGTGA SEQ ID NO 56: functional equivalent sequence of antimiR-23b-3p:
ATCCCTGGCAYTGTGA -continued SEQ ID NO 57: functional equivalent sequence of antimiR-23b-3p:
ATCCCTGGCAATYTGA SEQ ID NO 58: functional equivalent sequence of antimiR-23b-3p:
ATCCCTGGCAATGTYA SEQ ID NO 59: functional equivalent sequence of antimiR-23b-3p:
ATCCCTGGCAATGTGY SEQ ID NO 60: functional equivalent sequence of antimiR-23b-3p:
GTCCCTGGCAATGTGA SEQ ID NO 61: functional equivalent sequence of antimiR-23b-3p:
ATUCCTGGCAATGTGA SEQ ID NO 62: functional equivalent sequence of antimiR-23b-3p:
ATCUCTGGCAATGTGA SEQ ID NO 63 functional equivalent sequence of antimiR-23b-3p:
ATCCUTGGCAATGTGA SEQ ID NO 64: functional equivalent sequence of antimiR-23b-3p:
ATCCCTGGUAATGTGA SEQ ID NO 65: functional equivalent sequence of antimiR-23b-3p:
ATCCCTGGCGATGTGA SEQ ID NO 66: functional equivalent sequence of antimiR-23b-3p:
ATCCCTGGCAGTGTGA SEQ ID NO 67: functional equivalent sequence of antimiR-23b-3p:
ATCCCTGGCAATGTGG SEQ ID NO 68: functional equivalent sequence of antimiR-23b-3p:
ITCCCTGGCAATGTGA SEQ ID NO 69: functional equivalent sequence of antimiR-23b-3p:
ATCCCTGGCIATGTGA SEQ ID NO 70: functional equivalent sequence of antimiR-23b-3p:
ATCCCTGGCAITGTGA SEQ ID NO 71: functional equivalent sequence of antimiR-23b-3p:
ATCCCTGGCAATGTGI SEQ ID NO 72: functional equivalent sequence of antimiR-23b-3p:
AICCCTGGCAATGTGA SEQ ID NO 73: functional equivalent sequence of antimiR-23b-3p:
ATCCCIGGCAATGTGA SEQ ID NO 74: functional equivalent sequence of antimiR-23b-3p:
ATCCCTGGCAAIGTGA SEQ ID NO 75: functional equivalent sequence of antimiR-23b-3p:
ATCCCTGGCAATGIGA SEQ ID NO 76: functional equivalent sequence of antimiR-23b-3p:
ATCCCTIGCAATGTGA SEQ ID NO 77: functional equivalent sequence of antimiR-23b-3p:
ATCCCTGICAATGTGA SEQ ID NO 78: functional equivalent sequence of antimiR-23b-3p:
ATCCCTGGCAATITGA SEQ ID NO 79: functional equivalent sequence of antimiR-23b-3p:
ATCCCTGGCAATGTIA SEQ ID NO 80: functional equivalent sequence of antimiR-218-5p:
TTYGATCAAGCACAA SEQ ID NO 81: functional equivalent sequence of antimiR-218-5p:
TTAYATCAAGCACAA SEQ ID NO 82: functional equivalent sequence of antimiR-218-5p:
TTAGYTCAAGCACAA SEQ ID NO 83: functional equivalent sequence of antimiR-218-5p:
TTAGATCYAGCACAA -continued SEQ ID NO 84: functional equivalent sequence of antimiR-218-5p:
TTAGATCAYGCACAA SEQ ID NO 85: functional equivalent sequence of antimiR-218-5p:
TTAGATCAAYCACAA SEQ ID NO 86: functional equivalent sequence of antimiR-218-5p:
TTAGATCAAGCYCAA SEQ ID NO 87: functional equivalent sequence of antimiR-218-5p:
TTAGATCAAGCACYA SEQ ID NO 88: functional equivalent sequence of antimiR-218-5p:
TTAGATCAAGCACAY SEQ ID NO 89: functional equivalent sequence of antimiR-218-5p:
TTGGATCAAGCACAA SEQ ID NO 90: functional equivalent sequence of antimiR-218-5p:
TTAGGTCAAGCACAA SEQ ID NO 91: functional equivalent sequence of antimiR-218-5p:
TTAGATUAAGCACAA SEQ ID NO 92: functional equivalent sequence of antimiR-218-5p:
TTAGATCGAGCACAA SEQ ID NO 93: functional equivalent sequence of antimiR-218-5p:
TTAGATCAGGCACAA SEQ ID NO 94: functional equivalent sequence of antimiR-218-5p:
TTAGATCAAGUACAA SEQ ID NO 95: functional equivalent sequence of antimiR-218-5p:
TTAGATCAAGCGCAA SEQ ID NO 96: functional equivalent sequence of antimiR-218-5p:
TTAGATCAAGCAUAA SEQ ID NO 97: functional equivalent sequence of antimiR-218-5p:
TTAGATCAAGCACGA SEQ ID NO 98: functional equivalent sequence of antimiR-218-5p:
TTAGATCAAGCACAG SEQ ID NO 99: functional equivalent sequence of antimiR-218-5p:
TTIGATCAAGCACAA SEQ ID NO 100: functional equivalent sequence of antimiR-218-5p:
TTAGITCAAGCACAA SEQ ID NO 101: functional equivalent sequence of antimiR-218-5p:
TTAGATCIAGCACAA SEQ ID NO 102: functional equivalent sequence of antimiR-218-5p:
TTAGATCAIGCACAA SEQ ID NO 103: functional equivalent sequence of antimiR-218-5p:
TTAGATCAAGCICAA SEQ ID NO 104: functional equivalent sequence of antimiR-218-5p:
TTAGATCAAGCACIA SEQ ID NO 105: functional equivalent sequence of antimiR-218-5p:
TTAGATCAAGCACAI SEQ ID NO 106: functional equivalent sequence of antimiR-218-5p:
ITAGATCAAGCACAA SEQ ID NO 107: functional equivalent sequence of antimiR-218-5p:
TIAGATCAAGCACAA SEQ ID NO 108: functional equivalent sequence of antimiR-218-5p:
TTAGAICAAGCACAA SEQ ID NO 109: functional equivalent sequence of antimiR-218-5p:
TTAIATCAAGCACAA -continued SEQ ID NO 110: functional equivalent sequence of antimiR-218-5p:
TTAGATCAAICACAA SEQ ID NO 111:
TbsCsAsCbsAsTsTbsGsCsCbsAsGsGbsGsAsTb-Digoxigenin NHS ester The following examples merely illustrate the present invention.

EXAMPLES

Materials and Methods

Cell Culture Experimentation

Immortalized MyoD-inducible (doxycycline) DM1 and control fibroblasts (Arandel L., et al. (2017). "*Immortalized human myotonic dystrophy muscle cell lines to assess therapeutic compounds.*" Dis Model Mech 10(4): 487-497.) were grown in DMEM with 4.5 g/L glucose, 1% P/S, and 10% FBS (Sigma, Saint Louis, Misuri). Fibroblast transdifferentiation into myotubes was according to (Cerro-Herreros et al. (2018). "*miR-23b and miR-218 silencing increase Muscleblind-like expression and alleviate myotonic dystrophy phenotypes in mammalian models*". Nat. Commun. 9, 2482). Transdifferentiation was induced at day 0, and test compounds were added to the cell culture medium at different concentrations (for MD23b-2, MD23b-8, MD23b-4, MD23b-13, MD23b-7, MD23b-14, MD-23b-1, 23-LNA4, MD23b-10, MD23b-3, AntimiR-23b, MD23b-6, MD23b-12, MD23b-9, MD23b-5, MD23b-11, 23-LNA6, non-conjugated-23b, 5'-23b-Oleic, 5'-23b-Linoleic, 5'-23b-MeToc, 5'-23b-MeChol, 5'-23b-MePal, 5'-23b-Elaidic, 5'-23b-Estearic, OL-MD23b-2, MD23b-2-PS/PO, MD23b-2-PS/PO 5'Ol, non-conjugated-218, Ax-218, 5'-218-Oleic, 5'-218-MeChol, 5'-218-Linoleic, 5'-218-MePal, 5'-218-MeToc, Sc-Oleic, MD218-12, MD218-6, MD218-11, non-conjugated-218, MD218-13, MD218-5, MD218-4, MD218-15, MD218-10, MD218-3: 10 nM, 50 nM, 200 nM, 1 UM and 5 µM; for 23-LNA8, AX-23b, MD23b-2 V2 3'Ol, MD23b-2 V2 3'Ol (C6SSC6) (NHC6), MD23b-2 V2 3'Ol (C6SSC6) (NHC3), and MD23b-2 V2 3'Ol (threoninol): 2 nM, 10 nM, 50 nM, 200 nM and 1 µM; 23-D/LNA1, 23-D/LNA2 and 218-2F/LNA1: 0.4 nM, 2 nM, 10 nM, 50 nM and 200 nM); and for 218-D/LNA2, 218-2F/MOE: 0.08 nM, 0.4 nM, 2 nM, 10 nM and 50 nM) by lipofection with X-tremeGENE™ HP (Roche, Basel, Switzerland) and were replaced with fresh differentiation medium 4 h afterward. Cells were collected on day 4 in the differentiation medium and processed for protein extraction.

Cell Proliferation Assay

Cells seeded at $10^5$ cells/ml in 96-well plates were transfected 24 h later with antimiRs, as previously explained; after 96 h, cell proliferation was measured using the CellTiter 96® Aqueous Non-Radioactive Cell Proliferation Assay (Promega, Madison, Wisconsin). The TC50 was calculated using non-linear least-squares regression, and absorbance levels were determined using an Infinite M200 PRO plate reader (Tecan, Männedorf, Switzerland).

Quantitative Dot Blot (QDB) Assay

For the activity assay, cells were seeded in 6-well plates at a density of $8 \times 10^4$ cells per well and transfected 24 h later with antimiRs, as previously explained. For total protein extraction, human muscle cells were sonicated while mouse muscles (gastrocnemius and quadriceps) were homogenized in Pierce® RIPA buffer (Thermo Scientific, Waltham, Massachusetts) supplemented with protease and phosphatase inhibitor cocktails (Roche Applied Science, Penzberg, Germany). Quantification of total protein was performed with a Pierce® BCA protein assay kit (Thermo Scientific, Waltham, Massachusetts) using bovine serum albumin as standard. For the immunodetection assay, 1 µg/well of cell samples and 2 µg/well of mice samples were denatured (100° C. for 5 min) and loaded in QDB plates (Quanticision Diagnostics Inc, Research Triangle Park, North Carolina). Each cell sample was loaded in quadruplicate on two different plates; one was used to detect MBNL1 and the other for GAPDH, which was used here as an endogenous control. In the case of mouse samples, each sample was loaded in quadruplicate on three different plates, one for detection of MBNL1, one for Tubulin, which was used as endogenous control, and the other for anti-mouse IgG secondary antibody as a negative control to subtract background. For the QDB protocol, the protein is prepared at 2 µg/well. Each sample is loaded in quadruplicate on two different plates, one is used for the detection of MBNL1 and the other for GAPDH, which is used here as an endogenous control. For the preparation of the sample mix (enough for 10 samples, to account for pipetting errors) put the protein extract at the indicated concentration, add 10.4 µl of loading buffer 4X and finally complete to 50 µl of ddH2O. Once the sample is prepared, boil it for 5 min in water and after protein denaturation, leave it on ice. To load the samples, place the QDB plates (Quanticision Diagnostics, Inc) upside down. On each membrane circle, put 5 µl of the protein mix previously prepared. The loaded QDB plates are allowed to dry at room temperature for 30 minutes in a well-ventilated space to dry the membrane completely. After the dry, dip the QDB plate in the transfer buffer (0.039 M Glycine, 0.048 M Tris, 0.37% SDS, 20% methyl alcohol) and gently shake the plate for 1 min. The plate was rinsed with TBST (137 mM NaCl, 2.7 mM KCl, 20 mM Tris, pH7.4, plus 0.1% Tween-20) for 3 times, and blotted with blocking buffer (5% non-fat milk in TBST) in one container. The plate was incubated with primary mouse anti-MBNL1 (1:1000, ab77017, Abcam) or mouse anti-GAPDH (1:500, clone G-9, Santa Cruz) overnight at 4° C. into a 96 well plate. The plate was washed three times with TBST and incubated again with the secondary antibody anti-mouse-POD (1:200, Sigma-Aldrich) for 2 hours before the plate was washed again for three times with TBST. The plate was inserted into a 96 well plate loaded with 100 µL/well ECL substrate (Pierce) solution for 1 minute before it was inserted into a white 96 well plate for chemiluminescence signal quantification using a Tecan Infiniti 200 pro microplate reader with the option "plate with cover" chosen in the user interface.

Plates were incubated at 4° C. overnight with primary mouse anti-MBNL1 (1:200, MB1a(4A8), (DSHB, Iowa City, Iowa) and rabbit anti-α-tubulin (1:1000, PA5-16891, Thermo Fisher) antibodies. The primary antibodies were detected using goat horseradish peroxidase (HRP)-conjugated anti-Mouse-IgG and anti-Rabbit-IgG secondary antibodies (1:3500, (Sigma-Aldrich, Saint Louis, Missouri), respectively. Immunoreaction was detected using Pierce™ ECL Western reagent (Thermo Scientific, Waltham, Massachusetts), and luminescence was acquired using an Infinite M200 PRO plate reader (Tecan, Männedorf, Switzerland).

RNA Extraction, Reverse Transcription PCR (RT-PCR) and Real-Time Quantitative Reverse Transcription PCR (qRT-PCR)

Total RNA from murine gastrocnemius and quadriceps muscle was isolated using the miRNeasy Mini Kit (Qiagen, Hilden, Germany) according to the manufacturer's instructions. One microgram of RNA was digested with DNase I (Invitrogen, Carlsbad, California) and reverse-transcribed with SuperScript II (Invitrogen, Carlsbad, California) using random hexanucleotides. For subsequent PCR reactions, 20 ng of cDNA was used with GoTaq polymerase (Promega, Madison, Wisconsin). Specific primers were used to analyze the alternative splicing of Atp2a1, Nfix, Mbnl1 and Clcn1 in mouse samples (both muscles). Gapdh levels established the endogenous reference levels using 0.2 ng of cDNA. PCR products were separated on a 2% agarose gel and quantified using ImageJ software (NIH, Bethesda, Maryland). Percentage splice recovery index (PSR) was defined as value $\%_{SI}$ minus $\overline{X} \%_{DSI}$, divided by $\overline{X} \%_{DSI}$ minus $\overline{X} \%_{HSI}$ (SI: splicing inclusion of each sample; DSI: disease splicing inclusion; HSI: healthy splicing inclusion; in all cases splicing refers to the inclusion of the indicated alternative exon). This ratio was calculated for ATP2A1, NFIX, MBNL1 and CLCN1. The primer sequences and exons analyzed are available in (Cerro-Herreros et al. 2018 2018 Jun. 26; 9(1):2482. doi: 10.1038/s41467-018-04892-4.) and are reproduced below:

```
SEQ ID NO: 30: Gapdh Fwd:
ATCAACGGGAAGCCCATCAC

SEQ ID NO: 31: Gapdh Rv:
CTTCCACAATGCCAAAGTTGT

SEQ ID NO: 32: Atp2a Fwd:
GCTCATGGTCCTCAAGATCTCAC

SEQ ID NO: 33: Atp2a Rv:
GGGTCAGTGCCTCAGCTTTG

SEQ ID NO: 34: Clcn1 Fwd:
GTCCTCAGCAAGTTTATGTCC

SEQ ID NO: 35: Clcn1 Rv:
GAATCCTCGCCAGTAATTCC

SEQ ID NO: 36: Nfix Fwd:
TCGACGACAGTGAGATGGAG

SEQ ID NO: 37: Nfix Rv:
CAAACTCCTTCAGCGAGTCC

SEQ ID NO: 38: Mbn/1 ex5 F:
AGGGGAGATGCTCTCGGGAAAAGTG

SEQ ID NO: 39: Mbnl1 ex5 R:
GTTGGCTAGAGCCTGTTGGTATTGGAAAATAC
```

We used 1 ng of mouse tissue cDNA as a template for multiplex qRT-PCR using the QuantiFast Probe PCR Kit reagent. Commercial TaqMan probes (Qiagen, Hilden, Germany) were used for mouse (MBNL1 and MBNL2; FAM-labeled probes) and reference (GAPDH; MAX-labeled probe) genes. Results were normalized to Gapdh endogenous gene expression. The primers used are the following:

```
SEQ ID NO: 40: Probe Mbnl1:
/56-FAM/TCGCAAATCAGCTGTGAGGAGATTCCCT/3IAbRQSp/

SEQ ID NO: 41: Mbnl1 F:
TACCGATTGCACCACCAAAC

SEQ ID NO: 42: Mbnl1 R:
GCTGCTTTCAGCAAAGTTGTC

SEQ ID NO: 43: Mbnl2 probe:
/56-FAM/CCCGGCAGACAGCACCATGATCGA/3IAbRQSp/

SEQ ID NO: 44: Mbnl2 F:
GAGACAGACTGCCGCTTTG

SEQ ID NO: 45: Mbnl2 R:
GGTTACGGTGTTGTCGTTTGT

SEQ ID NO: 46: Gapdh probe:
/5MAXN/-CGCCTGGTCACCAGGGCTGCT-/3BHQ_1/

SEQ ID NO: 47: Gapdh_For:
CAACGGATTTGGTCGTATTGG

SEQ ID NO: 48: Gapdh_Rev:
TGATGGCAACAATATCCACTTTACC
```

MiRNA expression in muscle tissues was quantified using specific miRCURY™-locked nucleic acid microRNA PCR primers (Qiagen, Hilden, Germany) according to the manufacturer's instructions. Relative gene expression was normalized to U1 (YP00203909) and U6 (YP00203907) snRNAs.

Expression levels were measured using a QuantStudio 5 Real-Time PCR System (Applied Biosystems, Foster City, California). Expression relative to the endogenous gene and control group was calculated using the $2^{-\Delta\Delta Ct}$ method. Pairs of samples were compared using two-tailed t-tests ($\alpha=0.05$), applying Welch's correction when necessary. The statistical differences were estimated by the Student's t-tests ($p<0.05$) on normalized data.

Animal Experimentation and Oligonucleotides Administration

Mouse handling and experimental procedures followed the European law regarding laboratory animal care and experimentation (2003/65/C.E.) and were approved by Conselleria de Agricultura, Generalitat Valenciana. Homozygous transgenic HSA$^{LR}$ (line 20 b) mice (Mankodi et al. 2000 Science: 289(5485): 1769-73. doi: 10.1126/science.289.5485.1769) were provided by Prof. C. Thornton (University of Rochester Medical Center, Rochester, NY, USA). Experimental groups were FVB as normal control and HSA$^{LR}$ treated with PBS as a negative control, in addition to HSA$^{LR}$ mice treated with all experimental oligonucleotides. The sample size was four mice per treatment group, twelve mice for PBS, and eighteen mice for the FVB group. All the groups were injected intravenously (tail vein) with 150 μl of 1×PBS (vehicle) or the specific oligonucleotides (see FIG. 2-5) with a single dose of 3 mg/kg. Four days after injection, the mice were sacrificed, and the tissues of interest were frozen in liquid nitrogen for the molecular assays.

Electromyography Studies

Electromyography was performed before the treatment and at the time of sacrifice under general anaesthesia, as previously described (Kanadia et al. 2006 Proc Natl Acad Sci USA. 2006 Aug. 1; 103(31):11748-53. doi: 10.1073/pnas.0604970103). The determination was performed blindly to eliminate bias. Five needle insertions were performed in each quadriceps muscle of both hind limbs, and myotonic discharges were graded on a five-point scale: 0, no myotonia; 1, occasional myotonic discharge in ≤50% of the needle insertions; 2, myotonic discharge in >50% of the insertions; 3, Myotonic discharge in nearly all of the insertions; and 4, myotonic discharge in all insertions.

Forelimb Grip Strength Test

The forelimb grip strength was measured with a Grip Strength Meter (BIO-GS3; Bioseb, Pinellas Park, Florida). The peak pull force (measured in grams) was recorded on a digital force transducer when the mouse grasped the bar. The gauge of the force transducer was reset to 0 g after each measurement. Tension was recorded by the gauge at the time the mouse released its forepaws from the bar. We performed three consecutive measurements at 30 s intervals. The bodyweight measurement was performed in parallel. The final value is obtained by dividing the average value of the grip force by the bodyweight of each mouse. The bodyweight measurement was performed in parallel, and the experiment was performed with animals identified by a code to eliminate experimental bias.

Radar Charts

The values obtained are represented as the recovery index (RI), and it measures how close the different parameter values obtained with treated $HSA^{LR}$ mice are from those of FVB controls. This RI is obtained for the different parameters (Mbnl1 protein, Mbnl1/2 expression level, Splicing recovery, Mbnl1 ex5 inclusion recovery, and functional recovery) of each mouse after treatment according to this formula: value % MT minus X % MNT, divided by X % MH minus X % MNT (where MT is the value of each mice treated (PBS or oligonucleotide), MNT is $HSA^{LR}$ mice treated with PBS (PBS), and MH is healthy mice value (FVB)). These values range from 0 to 1, where 0 are untreated mice ($HSA^{LR}$-PBS) and 1 are healthy mice (FVB).

Mbnl1 protein refers to the average of the values obtained by Quantitative dot blot of both muscles (quadriceps and gastrocnemius) of each treatment group.

Mbnl1/2 expression level refers to the average of the mRNA values of genes Mbnl1 and Mbnl2 obtained by real-time PCR in both muscles (quadriceps and gastrocnemius) and of each group of treatment applying the previous formula.

Splicing recovery refers to the average percentage of inclusion for Nfix exon 7, Atp2a1 exon 22 and Clcn1 exon 7a of both muscles of each group treatment.

Mbnl1 ex5 inclusion recovery refers to the percentage of inclusion for Mbnl1 exon 5 of both muscles of each group treatment.

Functional recovery refers to the average of the values obtained by force/weight of each mouse after treatment and the grade of myotonic discharges of each group treatment. The Forelimb grip strength test was used to obtain the force and the electromyography was used to obtain the grade of myotonic discharges.

Example 1

We have previously shown that inhibiting miR-23b-3p or miR-218-5p could be therapeutic in Myotonic Dystrophy (Cerro-Herreros et al. 2018 Nat. Commun. 26; 9(1):2482. doi: 10.1038/s41467-018-04892-4.) by using commercially available antimiRs with antagomiR structure against miR-23b-3p (Ax-23b) or miR-218-5p (Ax-218). Transfection of human DM1 cells with these antagomiRs and their injection in a mouse model of the disease produced a downregulation of the target miRNA expression and concomitant upregulation of MBNL1, which was their direct target. The antagomiRs used were long (22 nt), contained almost the entire complementary sequence to the miRNA, and were all composed of 2'OME nucleotides. They carried phosphorothioate linkages between the nucleotides in the 3' and 5' ends to improve stability of the nucleotidic part of the molecule and were bound to cholesterol in 3' as a carrier to enhance the pharmacokinetic behavior and cellular internalization. Looking for the most effective and safe carrier, we combined the polynucleotidic part of Ax-23b (sequence name: non-conjugated-23b in table 1) with different lipidic carriers either in 3' or 5' end of the molecule, including; the sterols cholesterol and tocopherol; and the fatty acids palmitoyl acid, stearic acid, elaidic acid, linoleic acid and oleic acid (List of molecules in Table 1). We performed a screen on human DM1 cells (Arandel L., et al. (2017). Dis Model Mech 10(4): 487-497.). "*Immortalized human myotonic dystrophy muscle cell lines to assess therapeutic compounds.*" Dis Model Mech 10(4): 487-497.) transfected with these conjugated antagomiRs, looking for their effects on toxicity (cell viability study), and MBNL1 protein levels.

Each of these molecules was transfected into DM1 human myotubes in a range of 5 different concentrations and the percentage of cell viability and the levels of MBNL1 protein were quantified. We ranked the antimiRs according to their therapeutic index (TI), defined as:

$$TI=(TC50/EC50)*Emax$$

Where:

TC50 is the concentration of compound that reduces the cell viability to 50% of the mock EC50 is the concentration of compound that produces 50% of Emax Emax is the maximum fold change of MBNL1 protein obtained after transfection with a specific antimiR compared to the mock (transfected with the vehicle).

From these experiments, we concluded that:

The conjugation with oleic acid (cis-monounsaturated fatty acid with 18 carbon atoms) was the one producing the highest Tindex (see table 1). The curves of toxicity and efficacy (levels of MBNL1 protein) of the molecules named "non-conjugated-23b" and "5'-23b-Oleic" are shown in FIGS. 1 C and B for a direct comparison. Importantly, the low Tindex of the scramble oligo conjugated to oleic acid ("Sc-Oleic) shows that oleic acid itself has no impact on the Tindex Linoleic acid (cis-polyunsaturated fatty acid with 18 carbon atoms) was the second most effective carrier. Surprisingly, the Tindex results obtained with elaidic acid (a trans isomer of oleic acid), palmitic acid (a saturated non-esterified fatty acid with 16 carbon atoms), and stearic acid (saturated fatty acid having a carbon chain with 18 carbon atoms) were significantly lower. Therefore, our data show that cis-unsaturated fatty acids are better carriers for antimiRs in our DM1 cells.

Cholesterol was the only of the carriers that we tested conjugated in two different positions; 3' and 5'. According to our data, it seemed that the conjugation in 3' worked more efficiently than in 5'. The use of cholesterol derivatives as the tocopherol did not improve the Tindex.

We carried out the same experiments conjugating the nucleotidic part of Ax-218 (sequence name: non-conjugated-218 in table 1) with different lipidic carriers (Table 1). Oleic acid was confirmed as the best carrier among all the fatty acids tested and cholesterol worked better in 3' than 5'. However, it is noted that cholesterol has been associated with toxicity in the liver in mice, even though the hepatic changes may become reversible after a recovery period (see Cholesterol Registration Dossier ECHA, Apr. 4, 2017, available on https://echa.europa.eu/es/registration-dossier/-/registered-dossier/11031/7/6/1 #). However, as the therapeutic posology for the oligonucleotide is intended to be a chronic treatment, cholesterol as a linker may increase the risk of toxicity in the liver. On the contrary, oleic acid has a good safety profile and has been used as a food additive with beneficial effects in humans (see FDA Response Letter to the Health Claim Petition Concerning Oleic Acid, Nov. 19, 2018 available at https://www.fda.gov/food/cfsan-constituent-updates/fda-completes-review-qualified-health-claim-petition-oleic-acid-and-risk-coronary-heart-disease).

Once we had found an appropriate carrier, our next step was to optimize the sequence and chemical modifications contained in the antimiR molecule that would be conjugated to the carrier. Therefore, we also performed the same in vitro screening, looking for the most effective sequence and chemical modifications that improve the Tindex of non-conjugated (unconjugated) antimiRs in DM1 cells. We generated a group of different single-stranded molecules (lengths ranging between 16 and 22 nucleotides) that were complementary to different parts of human miR-23b-3p or miR-218-5p. The molecules included in this screening carried different chemical modifications, including LNA, 2'OME and 2'MOE oligonucleotide, and all the linkages between nucleotides were phosphorothioate (PS) (list of molecules tested in Tables 2 and 3).

The molecule with a better Tindex score against miR-23b-3p was MD23b-2, and in the case of the antimiR molecules designed to inhibit miR-218-5p, the best scoring molecule was 218-D/LNA2 (see Tables 2 and 3). Importantly, MD23b-2 showed significantly higher effects on MBNL1 levels (Emax), and Tindex, than 218-D/LNA2. The curves of toxicity and efficacy (levels of MBNL1 protein) of these molecules are shown in FIGS. 1A and D.

Next, we tested the effects of conjugation of oleic acid on the best scoring antimiR sequence MD23b-2 (Table 4). Surprisingly, the conjugated molecule (Ol-MD23b-2) exhibited a reduced Tindex compared to the MD23b-2. On the other hand, we have observed that oleic acid conjugation to oligonucleotides that had a mix of PS/PO increased their Tindex (Table 4). This data confirms that the effects of oleic acid in the Tindex are surprisingly remarkable in mixed PS/PO oligonucleotides.

TABLE 1

| NAME | SEQUENCE | TC50 (µM) | EC50 (µM) | Emax (maximum fold change) | Tindex |
|---|---|---|---|---|---|
| non-conjugated-23b | gsgsuaauccuggcaaugusgsasu | 1.704 | 0.22 | 1.100 | 8.5 |
| 5'-23b-Oleic | (OleicAcid)(NHC5)gsgsuaauccuggcaaugusgsasu | 4.040 | 0.010 | 2.726 | 1101.4 |
| 5'-23b-Linoleic | (LinoleicAcid)(NHC5)gsgsuaauccuggcaaugusgsasu | 40.630 | 0.186 | 1.835 | 400.077 |
| 5'-23b-Me Toc | (Tocopherol)(Octyl)gsgsuaauccuggcaaugusgsasu | 3.460 | 0.100 | 2.211 | 76.617 |
| 5'-23b-MeChol | (Cholesterol)(Pro)gsgsuaauccuggcaaugusgsasu | 1.027 | 1.136 | 13.654 | 12.3 |
| 5'-23b-MePal | (PalmiticAcid)(NHC5)gsgsuaauccuggcaaugusgsasu | 2.156 | 0.460 | 1.497 | 7.0 |
| 5'-23b-Elaidic | (ElaidicAcid)(NHC5)gsgsuaauccuggcaaugusgsasu | 0.700 | 1.148 | 1.840 | 0.7 |
| 5'-23b-Estearic | (EstearicAcid)(NHC5)gsgsuaauccuggcaaugusgsasu | 0.432 | 1.178 | 1.304 | 0.8 |
| Ax-23b | gsgsuaauccuggcaaugusgsasus(Teg)(Cholesterol) | 1.301 | 0.007 | 1.674 | 302.0 |
| non-conjugated-218 | ascsaugguuagaucaagcascsasa | 0.953 | 0.06 | 2.525 | 40.1054 |
| Ax-218 | ascsaugguuagaucaagcascsasa(Teg)(Cholesterol) | 2.704 | 0.025 | 3.133 | 334.178 |
| 5'-218-Oleic | (OleicAcid)(NHC5)ascsaugguuagaucaagcascsasa | 14.230 | 0.137 | 1.613 | 167.61 |
| 5'-218-MeChol | (Cholesterol)(Pro)ascsaugguuagaucaagcascsasa | 1.143 | 0.075 | 8.264 | 125.094 |
| 5'-218-Linoleic | (LinoleicAcid)(NHC5)ascsaugguuagaucaagcascsasa | 1.533 | 0.045 | 2.272 | 77.374 |
| 5-218-MePal | (PalmiticAcid)(NHC5)ascsaugguuagaucaagcascsasa | 3.508 | 0.244 | 3.8567 | 55.373 |
| 5'-218-MeToc | (Tocopherol)(Octyl)ascsaugguuagaucaagcascsasa | 2.56 | 0.210 | 2.453 | 29.846 |
| Sc-Oleic | (OleicAcid)(NHC6)csasguacuuuuguguascsasa | 7.69 | — | 1.2 | — |

TABLE 2

| Name | SEQUENCE | TC50 (µM) | EC50 (µM) | Emax (maximum fold change) | Tindex |
|---|---|---|---|---|---|
| MD23b-2 | AbsTmscscscsTbsgsgscsAbsAmsTbsGbsTmsGbsAb | 14.000 | 0.010 | 3.173 | 4442.2 |
| 23-LNA8 | CbscscsTosgsgsCbsasasTbsgsusGbsasTb | 0.471 | 0.002 | 2.916 | 686.3 |
| 23-D/LNA1 | CbsdCsdCsdTsdGsdGsCbsdAsAbsdTsdGsdTsGbsdAsTb | 0.098 | 0.001 | 1.654 | 201.7 |
| MD23b-8 | AbsTbscscscsTbsgsgscsAbsAmsTbsgbstsGmsAbsTb | 1.510 | 0.030 | 1.762 | 88.3 |
| MD23b-13 | TbsdAsdAsTbsdCsdCsCbsdTsGbsdGsdCsAbsAbsdTsdGsTbsdGsAbsTb | 2.271 | 0.068 | 2.246 | 75.3 |
| 23-D/LNA2 | CbsdCsdCsTbsdGsdGsCbsdAsdAsTbsdGsdTsGbsdAsTb | 0.598 | 0.020 | 1.636 | 50.1 |
| MD23b-7 | AbsTmsdCsdCsCmsdTsGmsdGsdCsAbsdAsTbsdGsTbsGmsAmsTb | 0.263 | 0.019 | 2.342 | 32.4 |
| MD23b-14 | TmsAmsasdTscscscsdTsgsgsdCsAbsAbsdTsgsTbsgsAbst | 1.604 | 0.235 | 3.563 | 24.3 |
| 23-LNA4 | CbscscsusgsgsCbsasAbsusgsusGbsasTb | 0.122 | 0.010 | 1.465 | 17.9 |
| MD23b-10 | TbsAmsdAtsCsdCscstsdGgsCsAbsdATbsGmsdTGbsAb | 0.128 | 0.021 | 2.497 | 15.5 |
| AntimiR-23b | CbscscsusgsgsCbsasAbsusgsusGbsasTb | 0.116 | 0.043 | 4.193 | 11.4 |
| MD23b-6 | AbsTbsdCsdCsdCsTbsdGsdGsdCsAbsdAsTbsGbsdTsdGsAbsTb | 0.117 | 0.026 | 2.191 | 9.9 |
| MD236-12 | AbsAbsdTsCbsdCsdCsTbsdGsdGsdCsAbsasTbsGbstsgsasTb | 0.481 | 0.154 | 2.701 | 8.5 |
| MD23b-9 | AbsAbsdTsCbsdCsdCsTbsdGsdGsdCsAbsAbsdTsGbsdTsdGsAbsTb | 0.370 | 0.357 | 4.078 | 4.2 |
| MD23b-5 | AbsTbsdCsdCsdCsTbsdGsdGsdCsdAsAbsTbsdGsTbsdGsAbsTb | 0.175 | 0.112 | 1.208 | 1.9 |
| MD23b-11 | TbsAmsdAstscsdCscstsdGsgscsAmsdAsTmsGbsdTsGbsAb | 0.110 | 0.102 | 1.473 | 1.6 |
| 23-LNA6 | GbsgsusasasusCbscscsusgsgsCbsasAbsusgsusGbsasTb | 0.078 | 0.255 | 2.153 | 0.7 |

TABLE 3

| Name | SEQUENCE | TC50 (µM) | EC50 (µM) | Emax (maximum fold change) | Tindex |
|---|---|---|---|---|---|
| 218-D/LNA2 | TbsdTsdAsGbsbdAsdTsCbsdAsdAsGbsdCsAbsdCsdAsAbs | 0.008 | 0.0008 | 2.536 | 250.319 |
| 218-2F/LNA1 | TbsTbsAfsGfsAfsTfsCfsAfsAfsGfsCfsAfsCfsAbsAbs | 0.149 | 0.002 | 2.049 | 139.270 |
| MD218-12 | TbsGbsdGsTbsdTsdAsGbsdAsdTsdCsAbsAmsGbsCbsdAsCmsAmsAbs | 0.282 | 0.010 | 2.977 | 83.832 |
| MD218-6 | GbsGbsdTsdTsdAsGbsdAsdTsdCsAbsdAsGbsCbsdAsdCsAbsAbs | 0.300 | 0.010 | 1.893 | 56.695 |
| MD218-11 | AbsTmsdGsgstsdTsasgsdAstscsAmsdAsGmsCbsdAsCbsAbs | 0.193 | 0.010 | 2.378 | 45.777 |
| MD218-13 | AbsdTsdGsGbsdTsTsAbsdGsAbsdTsdCsAbsAbsdGsdCsAbsdCsAbsAbs | 0.124 | 0.010 | 3.151 | 39.009 |
| 218-2F/MOE | AmsCmsAfsTfsGfsGfsTfsTfsAfsGfsAfsTfsCfsAfsAfsGfsCfsCfsCfsAmsAms | 0.012 | 0.0004 | 1.399 | 38.334 |
| MD218-5 | GbsGbsdTsdTsdAsGbsdAsdTsdCsdAsAbsGbsdCsAbsdCsAbsAbs | 0.350 | 0.024 | 2.117 | 30.264 |
| MD218-4 | GbsGmsdTsdTsAbsdGsAmsTmsdCsAbsAbsdGsCbsdAsCbsAbs | 0.299 | 0.024 | 2.380 | 29.850 |
| MD218-15 | AbsTmsgsgststsasgsastsdCsAmsAbsGbsCmsAbsCbsAmsAbs | 0.318 | 0.016 | 1.498 | 28.949 |
| MD218-10 | AbsTmsdGsgstsdTsagdAstscsAbsdAsGbsCmsdAsCbsAbs | 0.546 | 0.051 | 1.893 | 20.295 |
| MD218-3 | GbsdTsdTsdAsGbsdAsdTsdCsAbsAbsdGsCbsdAsdCsAbsAbs | 0.461 | 0.038 | 1.649 | 20.182 |

TABLE 4

| NAME | SEQUENCE | TC50 (μM) | EC50 (μM) | Emax (maximum fold change) | Tindex |
|---|---|---|---|---|---|
| MD23b-2 | AbsTmscscscsTbsgsgscsAbsAmsTbsGbsTmsGbsAb | 14.000 | 0.010 | 3.173 | 4442.2 |
| OL-MD23b-2 | (OleicAcid)(NHC6) AbsTmscscscsTbsgsgscsAbsAmsTbsGbsTmsGbsAb | 9.257 | 0.020 | 2.053 | 950.2 |
| MD23b-2-PS/PO | AbsTms(5Mc)s(5Mc)(5Mc)Tbgsgs(5Mc)sAbAmTbGbsTmsGbsAb | 1.635 | 0.047 | 1.913 | 66.5 |
| MD23b-2-PS/PO 5'Ol | (OleicAcid)(NHC6)AbsTms(5Mc)s(5Mc)(5Mc)Tbgsgs(5Mc)sAbAmTbGbsTmsGbsAb | 2.920 | 0.010 | 2.202 | 643.0 |

Example 2

Next, we took the best performing oligo against miR-23b-3p (MD23b-2), and against miR-218-5p (218-D/LNA2) in vitro, and applied several modifications to these molecules to improve their ADMET (Absorption, Distribution, Metabolism, Excretion and Toxicity) properties, in order to assess their in vivo therapeutic potential in the mouse model of DM1 ($HSA^{LR}$). The rationale behind the modifications introduced was the following:

(1) Methylation of Cytosines is a well-known method of inhibiting immune system activation by in vivo treatment with antisense oligos (Joseph J. Senn, et al. Non-CpG-Containing Antisense 2'-Methoxyethyl Oligonucleotides Activate a Proinflammatory Response Independent of Toll-Like Receptor 9 or Myeloid Differentiation Factor 88. Journal of Pharmacology and Experimental Therapeutics Sep. 1, 2005, 314 (3) 972-979; DOI: https://doi.org/10.1124/jpet.105.084004).

(2) Chemically modified nucleotides of LNA and 2'MOE-modified type are known to be more stable than standard RNA, DNA or 2'OME modified oligos (W. Brad Wan and Punit P. Seth. 2016. The Medicinal Chemistry of Therapeutic Oligonucleotides).

(3) In all the molecules tested in vitro, phosphodiester (PO) linkages between nucleotides have been substituted by phosphorothioate (PS) linkages in order to increase their stability and efficacy. Fully modified PS oligos are widely used in in vitro studies. However, some toxicity in vivo associated with an excess of PS linkages in a single molecule has been previously reported (e.g., Smith and Zain. 2019. Therapeutic oligonucleotides: State of the Art. Annual Review of Pharmacology and Toxicology, and Hu et al. 2020. Therapeutic siRNA: state of the art. Signal transduction and targeted therapy), and mixed oligos PS/PO have proven to be more stable in vivo (Zhang, et al. In vivo stability, disposition and metabolism of a "hybrid" oligonucleotide phosphorothioate in rats. Biochemical Pharmacology. Volume 50, Issue 4, 1995, Pages 545-556, ISSN 0006-2952, https://doi.org/10.1016/0006-2952(95)00159-W. Therefore, in order to design antisense oligos that could be tested in in vivo models, we decided to reduce the amount of PS linkages in subsequent in vivo studies.

Taking into account these 3 criteria, we generated 4 antisense oligos:
MD23b-2 PS/PO, which conserves the same chemical modifications found in MD23b-2 but with lower PS content and all cytosines methylated.
MD23b-2 V2, with the same sequence as MD23b-2 but with some OME modifications in 2' substituted by MOE, lower PS content, and all cytosines methylated.
218 MOE, with the sequence of 218-D/LNA2, all-natural DNA nucleotides substituted by 2'MOE, all cytosines methylated, and lower PS content.
218 OME/MOE, with the sequence of 218-D/LNA2, all-natural DNA nucleotides substituted by 2'MOE or 2'MOE, all cytosines methylated, and lower PS content.

These molecules were used non-conjugated (with the exception of 218 OME/MOE) and conjugated with oleic acid in order to assess their therapeutic potential in $HSA^{LR}$ mice (model of DM1, see Mankodi, A., et al. (2000). "Myotonic dystrophy in transgenic mice expressing an expanded CUG repeat." Science 289(5485): 1769-1773.). Specifically; MD23b-2 PS/PO was used non-conjugated, conjugated with oleic acid in 3'(MD23b 2 PS/PO 3'Ol) and conjugated with oleic acid in 5'(MD23b-2 PS/PO 5'Ol) in order to assess the effect of the conjugation site with the oleic acid on the therapeutic effect. MD23b-2 V2 was used non-conjugated, conjugated to Oleic acid in 3' (MD23b-2 V2 3'Ol), and conjugated with palmitic acid in 3 (MD23b-2 V2 3'Palm) to confirm whether the conjugation with oleic acid produced stronger effects of the antimiRs than the conjugation with palmitic acid, also in vivo. The two antimiRs against miR-218-5p, were both conjugated with oleic acid in 3'.

Figure 2:
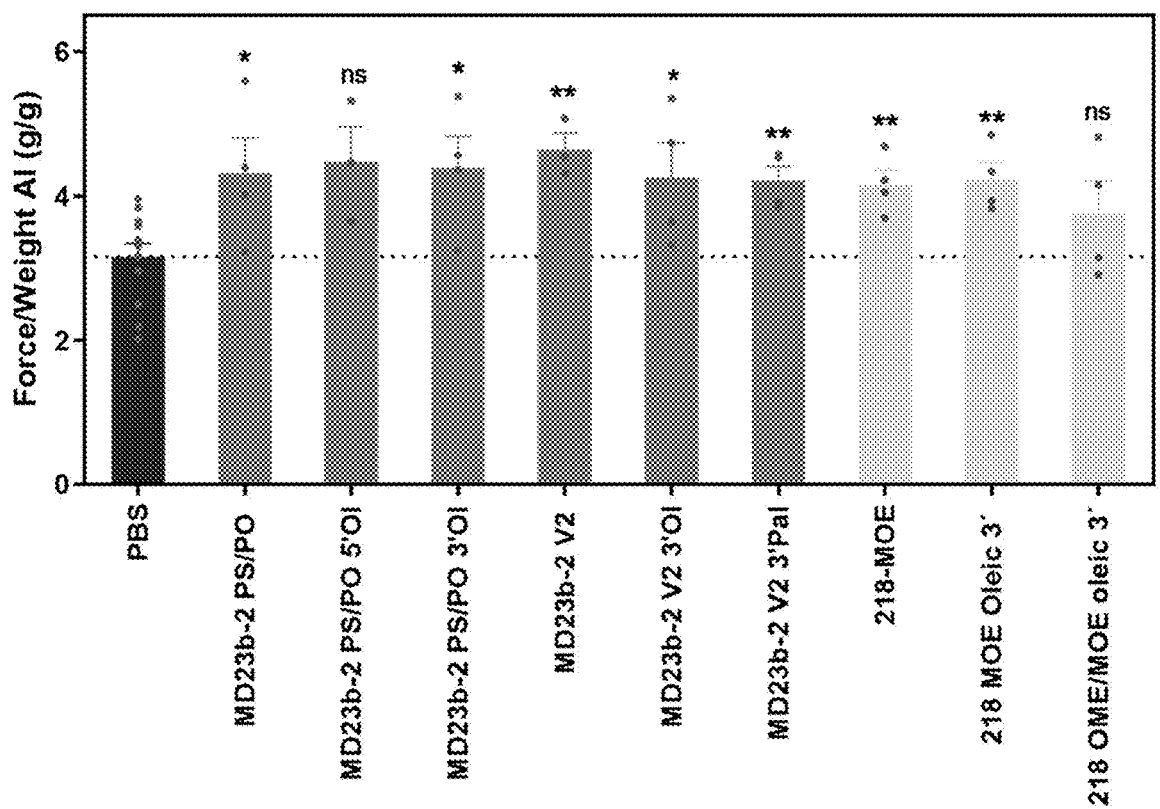
FIG. 2. Functional efficacy assays in $HSA^{LR}$ mice 5 days after injection of the indicated treatments. (A) Force/Weight and (B) Myotonia grade were analyzed 5 days after a single injection (AI) of different antimiRs at 3 mg/Kg. The data in A were analyzed by unpaired Student's t-test compared to $HSA^{LR}$ mice treated with PBS (PBS). p values: ns=not significant, *$p<0.05$,  $p<0.01$, * $p<0.001$. Data points represent individual mouse values. Error bars=standard error of the mean (SEM).
Figure 2:
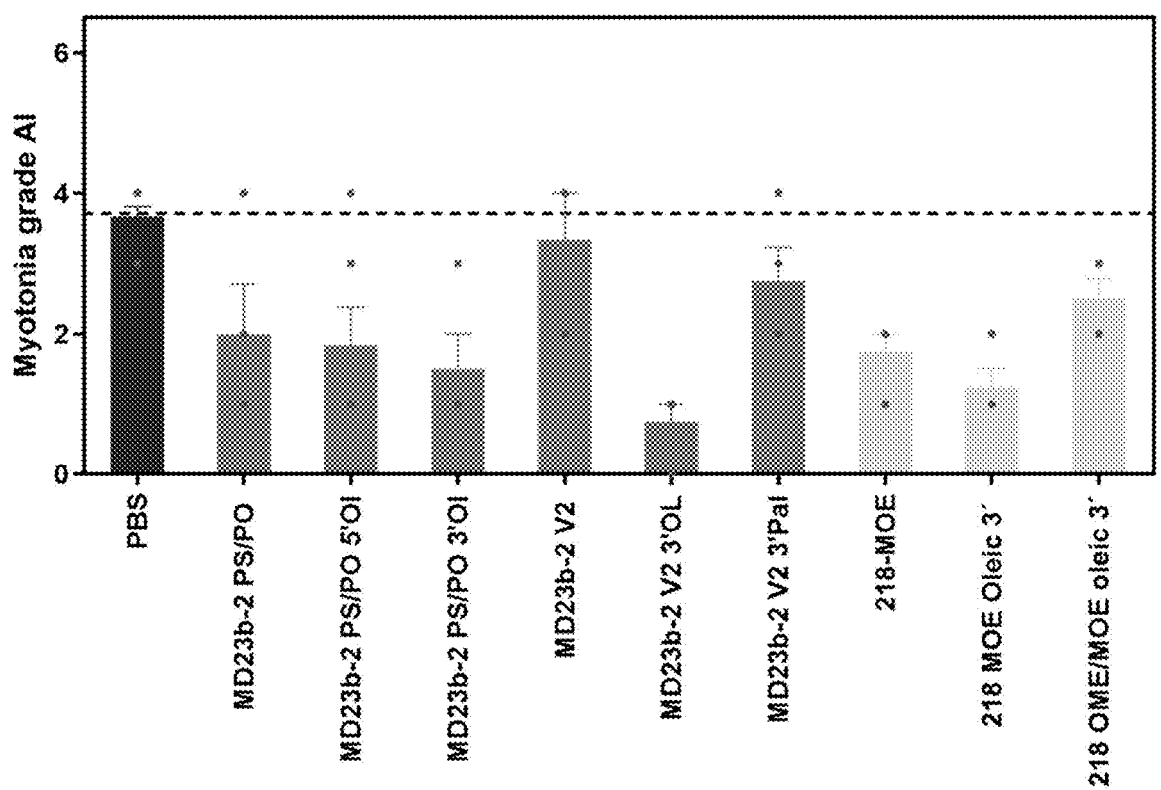
Figure 3:
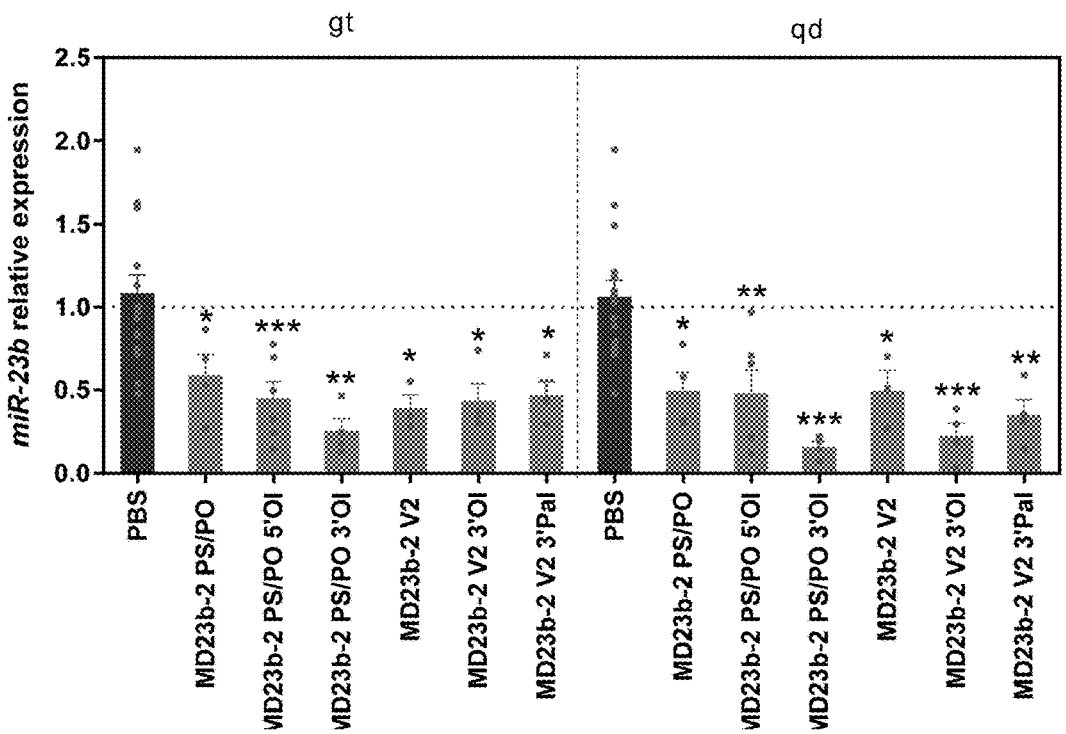
FIG. 3. miRNA levels on muscle tissues. (A) miR-23b-3p and (B) miR-218-5p expression levels relative to U1 and U6 snRNA endogenous controls were quantified by qRT-PCR on gastrocnemius (gt) and quadriceps (qd) muscles. $HSA^{LR}$ mice received an IV injection in the tail vein with either PBS or the different antimiRs, all at the same concentration (3 mg/Kg). Mice were sacrificed 5 days after the injection and the muscles were dissected and processed for RNA extraction. Statistical comparisons were all performed against PBS-treated $HSA^{LR}$ values with a Student's t-test. p values: ns=not significant, *$p<0.05$,  $p<0.01$, * $p<0.001$, **** $p<0.0001$. Data points represent individual mouse values. Error bars=standard error of the mean (SEM).
Figure 3:
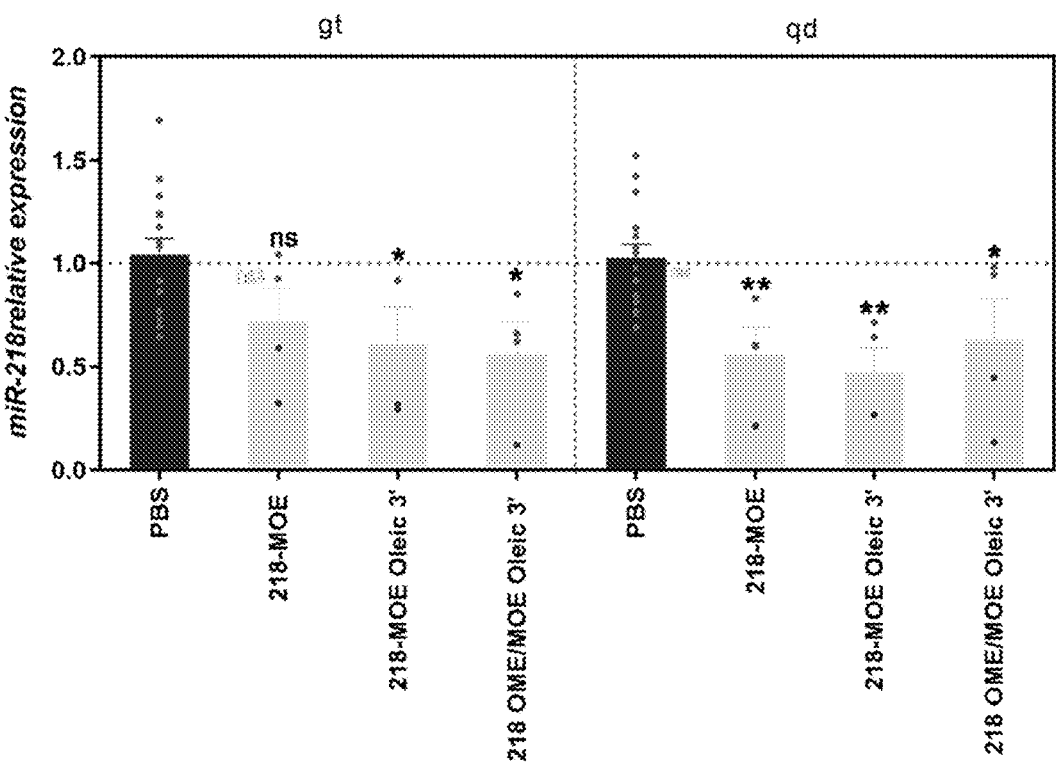

All these molecules were injected intravenously at a concentration of 3 mg/Kg in the tail vein of 3-5 months old $HSA^{LR}$ mice. The strength and myotonia of these mice were evaluated just before the injection and also before their sacrifice 5 days after the single injection. FIG. 2 shows the results of the grip strength normalized to weight (A) and the myotonia (B) levels measured just before the sacrifice of the mice. In all the mice treated with antimiRs, the strength was improved in comparison to the PBS-injected mice, but this difference was statistically significant only for some of the antimiRs. Similarly, myotonia was reduced in the antimiR-treated mice. The most important reductions in myotonia were achieved by the molecules MD23b-2 V2 3'Ol and 218 MOE Oleic 3'. For both molecules, the oleic acid conjugated molecules produced stronger rescue than the non-conjugated versions, and it produces stronger effects when conjugated at 3'.

Example 3

At the moment of sacrifice, we dissected the quadriceps and gastrocnemius muscles of the hind limbs of the mice and processed them for protein and RNA extraction. qPCR after retrotranscription of extracted RNA, with specific probes to detect the levels of miR-23b-3p (FIG. 3A) or miR-218-5p (FIG. 3B) showed that all antimiRs reduced the levels of its corresponding miRNA efficiently. Importantly, non-conjugated versions of the antimiRs tended to be less efficient than the conjugated ones. In the case of the antimiRs against miR-218-5p, 218 MOE was the least effective one.

Example 4 qRT-PCR was used to quantify the levels of expression of Mbnl1 (FIG. 4A) and Mbnl2 (FIG. 4B) transcripts in quadriceps and gastrocnemius, and the total protein extracted from these muscles was processed for protein Mbnl1 detection by quantitative dot blot analysis (FIG. 4C). Although small differences were detected between antimiR-23b-3p and antimiR-218-5p regarding the level of Mbnl1 transcripts, miR-23b-3b antimiRs had a stronger effect on Mbnl protein. Importantly, we observed no difference between placing the oleic acid carrier either in 3' or 5' in the molecule MD23b-2 PS/PO, and in the case of the molecules MD23b-2 V2, the non-conjugated version was clearly less efficient than the conjugated versions with oleic or palmitoyl acids, and the oleic acid had a stronger effect, particularly on Mbnl2 transcript and Mbnl1 protein levels.

Example 5

Figure 5:
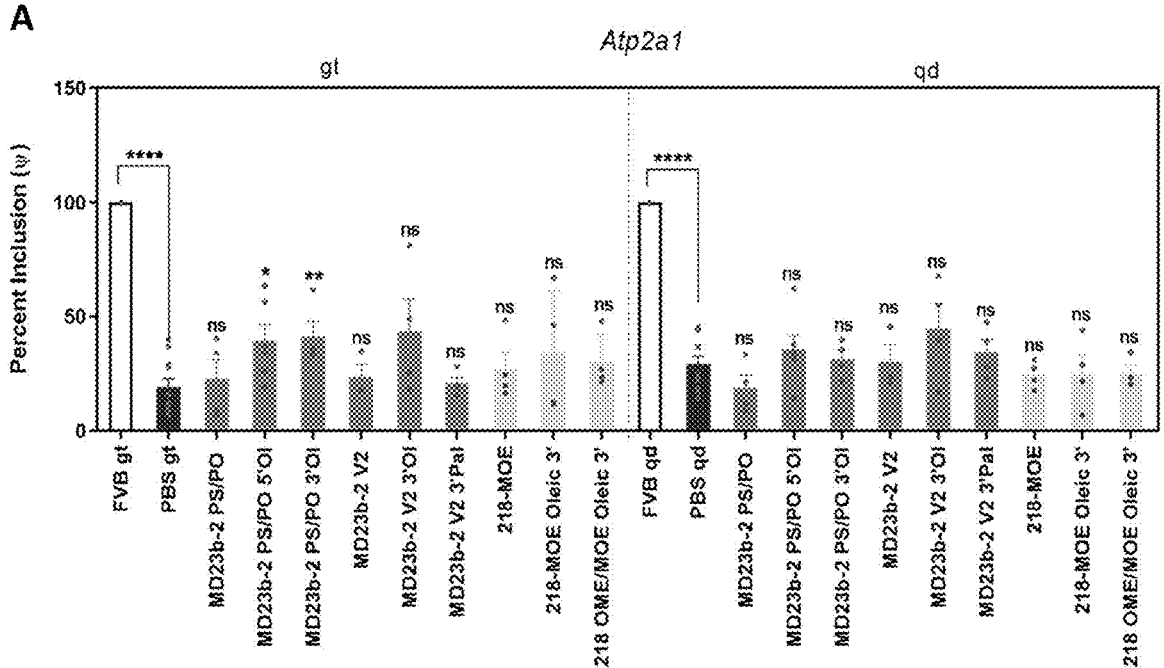
FIG. 5. AntimiRs improved Mbnl-dependent missplicing of transcripts. $HSA^{LR}$ mice received an IV injection in the tail vein with PBS or the different antimiRs, all at the same concentration (3 mg/Kg). Gastrocnemius and quadriceps muscles were dissected 5 days after the injection and the tissues were processed for RNA extraction. (A) RT-PCR semiquantitative analyses of the splicing of (A) Atp2a1 exon 22, (B) Nfix exon 7, (C) Mbnl1 exon 5, and (D) Clcn1 exon 7a in gastrocnemius (gt) and quadriceps (qd) muscles. Exon inclusion levels of healthy control mice (FVB) are also included for comparison. Statistical comparisons were all performed against PBS-treated $HSA^{LR}$ values with a Student's t-test. p values: ns=not significant, *$p<0.05$,  $p<0.01$, * $p<0.001$, **** $p<0.0001$. Data points represent individual mouse values. Error bars=standard error of the mean (SEM).
Figure 5:
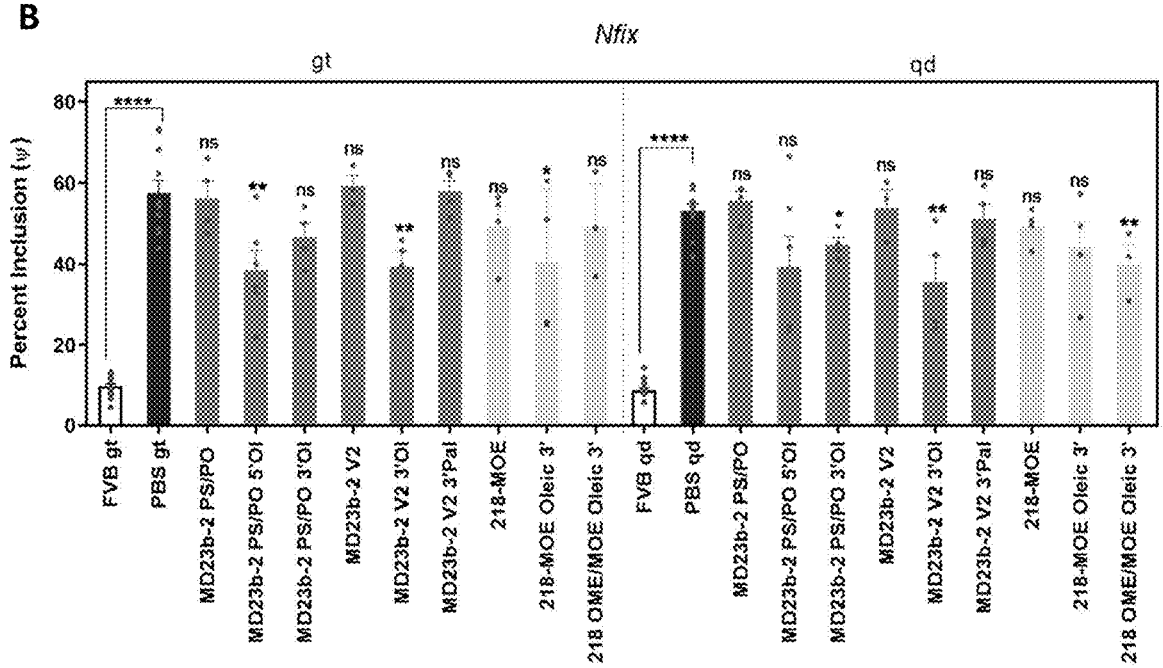
Figure 5:
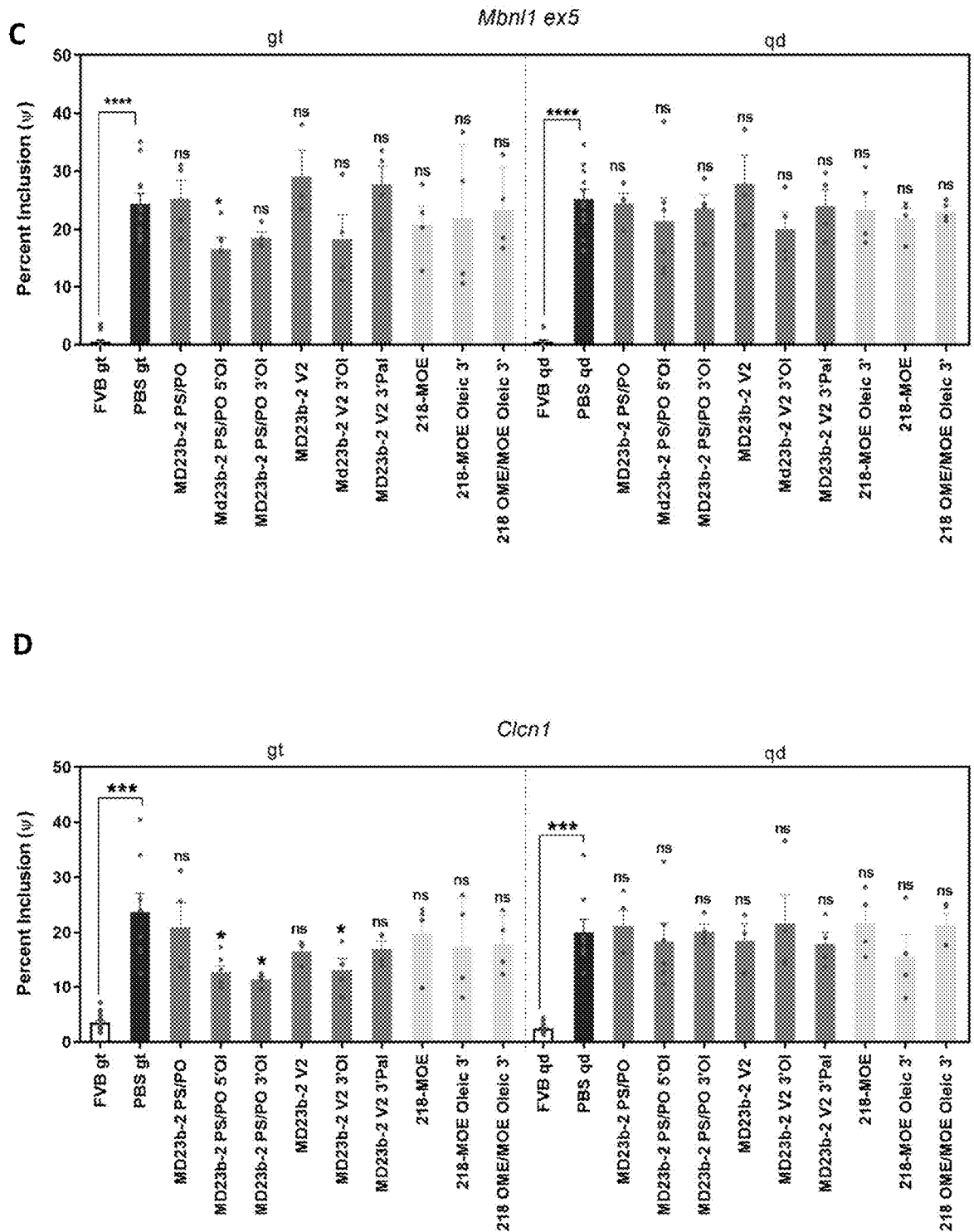
Figure 6:
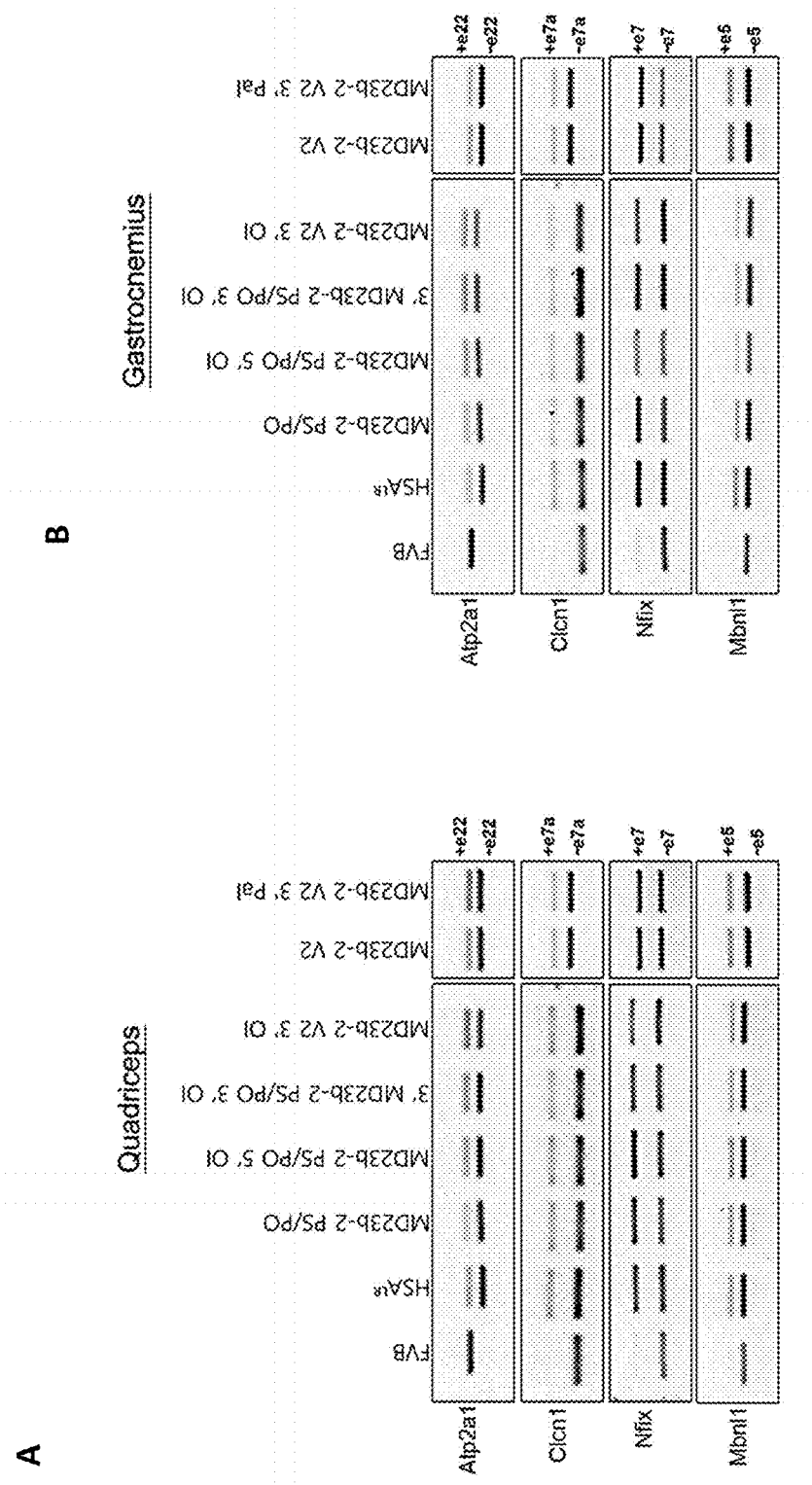
FIG. 6. Representative agarose gels used for the quantifications summarized in FIG. 5 of Atp2a1, Clcn1, Nfix, and Mbnl1 transcripts in gastrocnemius and quadriceps muscles. Effect of treatment with the indicated oligonucleotides against miR-23b-3p (A,B) and miR-218-5p (C,D). Splicing patterns of wild-type mice (FVB) and PBS-treated $HSA^{LR}$ mice are also shown for comparison.
Figure 6:
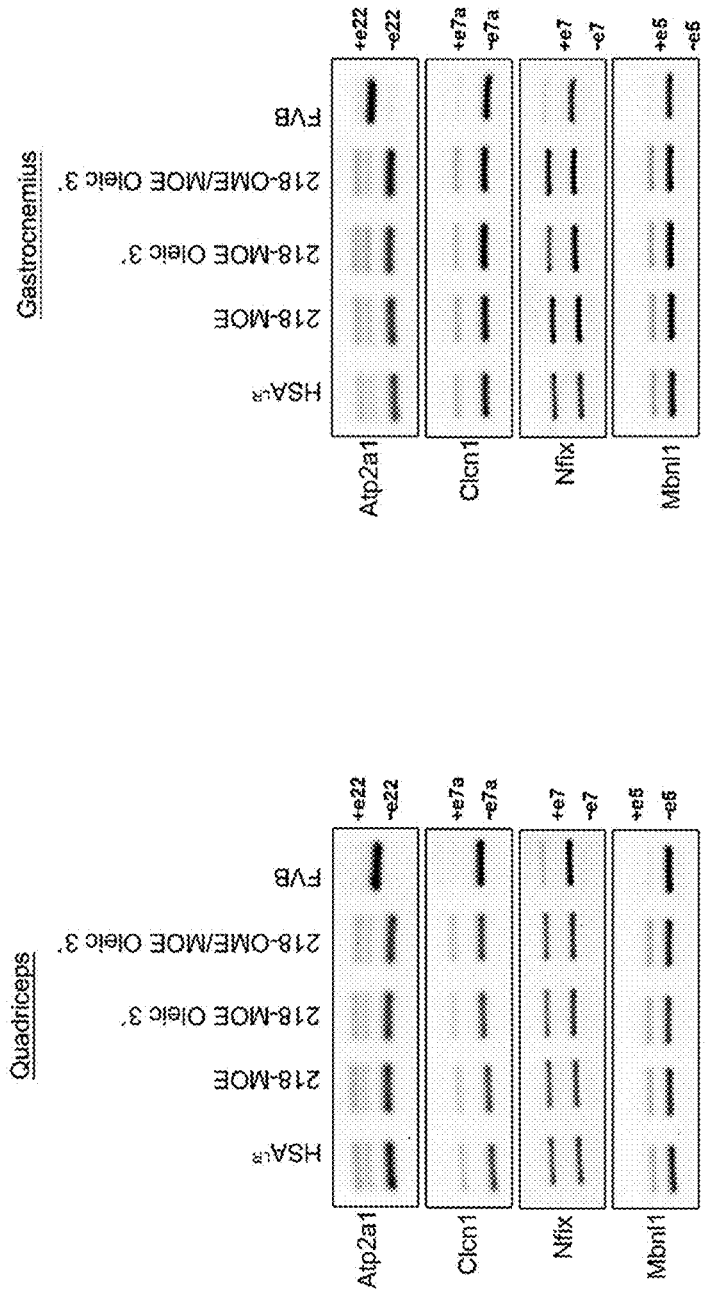

Total RNA was also used to analyse the missplicing of transcripts regulated by Mbnl1 protein, such as Atp2a1 exon 22, Nfix exon 7, Mbnl1 exon 5, and Chloride channel (Clcn1) exon 7a (FIGS. 5 and 6).

Nfix, Clcn1, Atp2a1 and Mbnl1 transcripts showed abnormally increased inclusion of exon 7, 7a, 22, and 5, respectively, in $HSA^{LR}$ mice, but they recovered between 30%-50% of normal values in muscles after being treated with 3 mg/kg with MD23-b V2 3'Ol and other similar molecules.

Example 6

To analyze all the DM1-related functional and molecular phenotypes that we have measured in the model mice, we generated spider graphs (FIG. 7) calculating a recovery index for each individual mouse (RIm) for the different parameters (Mbnl1 protein, Mbnl1/2 expression level, Splicing recovery, Mbnl1 ex5 inclusion recovery, and functional recovery) of each mouse after treatment according to this formula:

$$RIm = \frac{\text{Value}_{MT}/\overline{X}_{MNT}}{\overline{X}_{MH}/\overline{X}_{MNT}}$$

where $\text{Value}_{MT}$ is the individual value of each treated (PBS or oligonucleotide injected) mouse, $\overline{X}_{MNT}$ is the mean value of the non-treated disease mice (PBS injected), and $\overline{X}_{MH}$ is the mean value of the healthy mice group (FVB). Next individual RI values (RIm) were averaged to generate the global RI values represented in FIG. 7.

These values range from 0 to 1, where 0 are untreated mice ($HSA^{LR}$-PBS) and 1 are healthy mice (FVB). Mbnl1 protein refers to the average of the values obtained by Quantitative dot blot of both muscles (quadriceps and gastrocnemius) of each group treatment. Mbnl1/2 expression level refers to the average of the values obtained by real-time PCR of both muscles (quadriceps and gastrocnemius) and genes (Mbnl1 and Mbnl2) of each group treatment applying the previous formula. Splicing recovery refers to the average percentage of inclusion for Nfix exon 7, Atp2a1 exon 22 and Clcn1 exon 7a of both muscles of each group treatment. Mbnl1 ex5 inclusion recovery refers to the percentage of inclusion for Mbnl1 exon 5 of both muscles of each group treatment. Functional recovery refers to the average of the values obtained by force/weight of each mouse after treatment and the grade of myotonic discharges of each treatment group.

Figure 7:
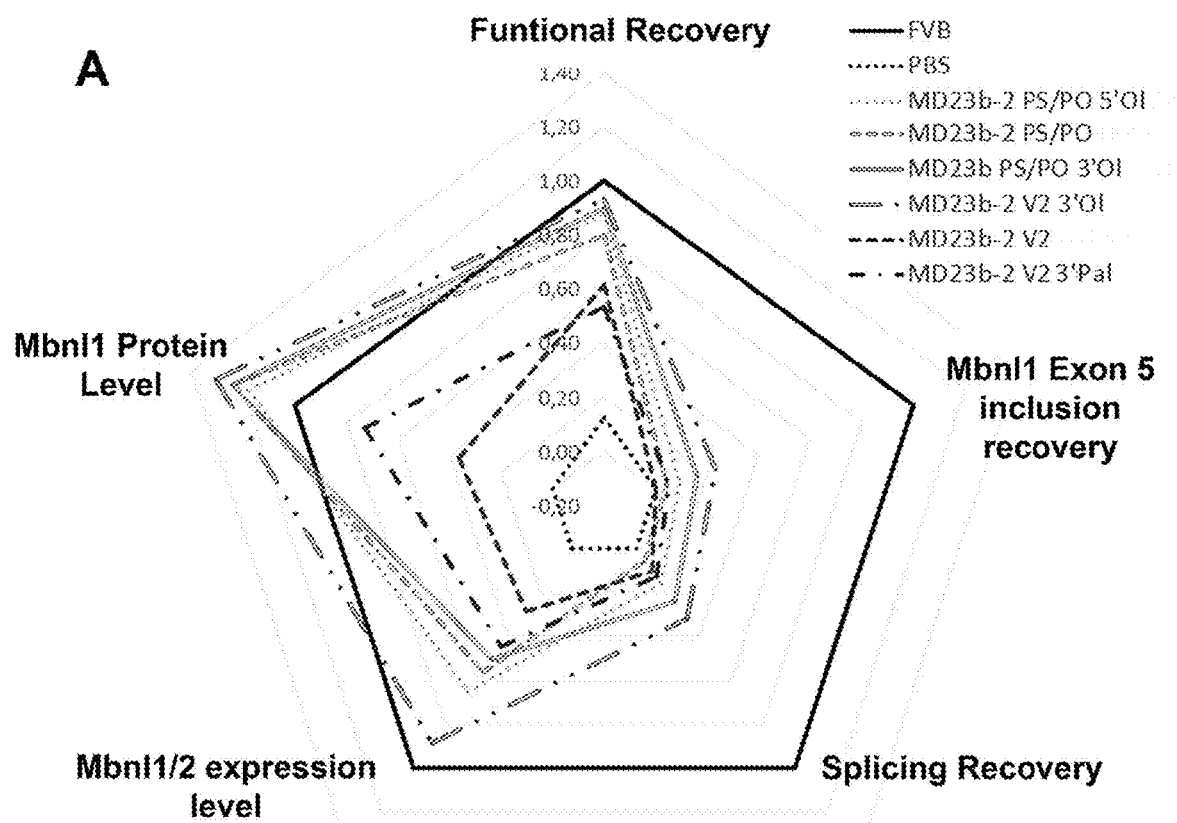
FIG. 7. Spider graphs showing the effect of the indicated treatments on several DM1-related molecular or functional phenotypes in $HSA^{LR}$ mice. The values represented are the recovery index (RI), and they measure how close the different values of treated $HSA^{LR}$ mice are compared to FVB controls' parameters, represented as 1 (solid black line). Panel (A) summarizes RI for antimiRs against miR-23b-3p, while (B) focuses on RI for antimiRs against miR-218-5p. For more representation details, see "Radar charts" in the Materials and Methods section.
Figure 7:
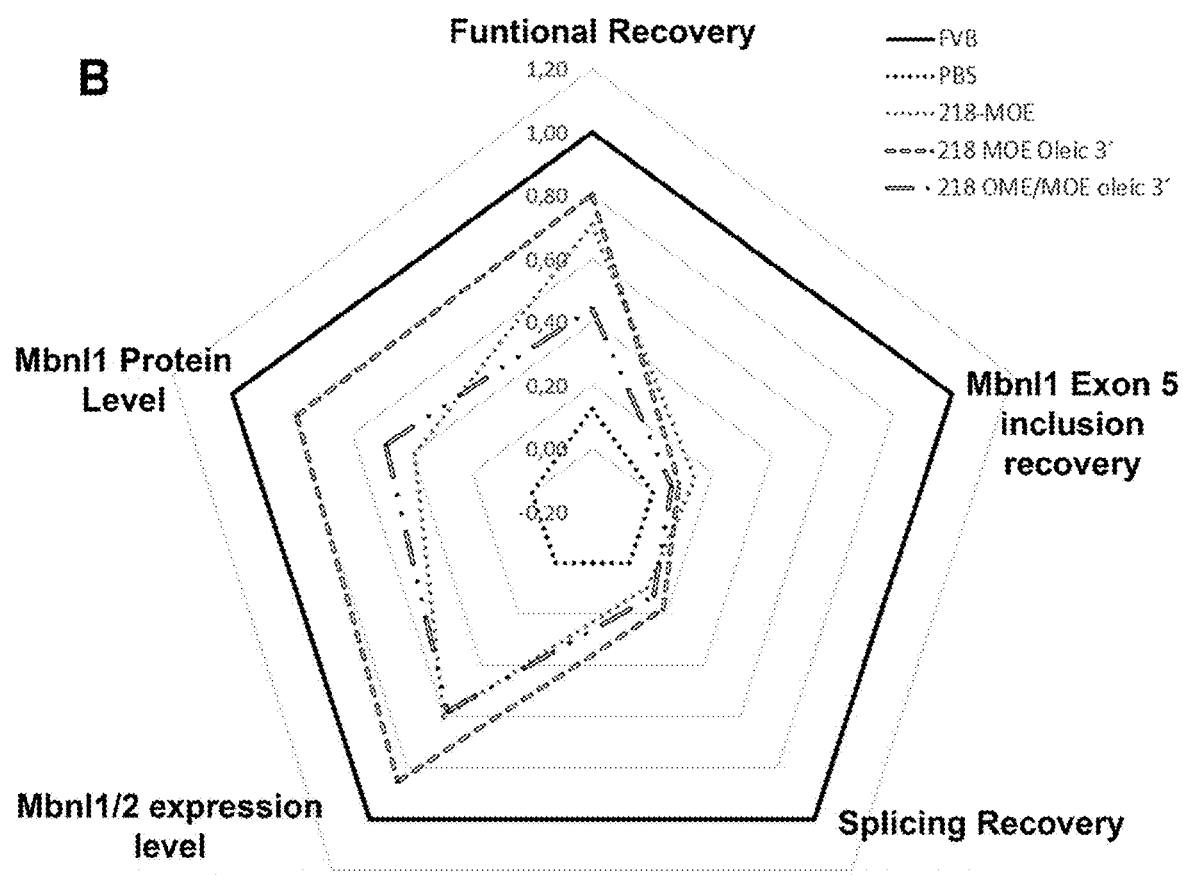

The representation of these graphs in FIG. 7 and Tables 5 and 6 shows that MD23b-2 V2 3'Ol was the antimiR molecule that produced the strongest rescue of all the phenotypes studied. Of note, the difference in efficacy when this same antimiR sequence was non-conjugated or conjugated with palmitic acid supports our surprising results in the in vitro studies and confirms a clear stronger therapeutic effect for the molecule when conjugated with the oleic acid. The second-best performing molecule was MD23b-2 PS/PO 3'Ol, which was slightly better than MD23b-2 PS/PO 5'Ol. These data also support the results obtained in vitro with the conjugation of cholesterol, confirming that the conjugation of the carrier in 3' is beneficial. As observed in vitro, the antimiRs against miR-218-5p produced lower phenotype rescue. The data supports a stronger therapeutic effect of the inhibition of miR-23b-3p (FIG. 7B and Table 5) compared to the inhibition of miR-218-5p (FIG. 7B and Table 6). In the case of the molecule 218 MOE (FIG. 7B), also the conjugation with the oleic acid improves its activity in vivo. Thus, it confirms that the effects of oleic acid conjugation on the therapeutic effects in vivo are not limited to a specific nitrogenous base sequence but are of more general application.

TABLE 5

| Treatment | FVB | PBS | MD23b-2 PS/PO 5'Ol | MD23b-2 PS/PO | MD23b PS/PO 3'Ol | MD23b-2 V2 3'Ol | MD23b-2 V2 | MD23b-2 V2 3'Pal |
|---|---|---|---|---|---|---|---|---|
| Functional recovery | 1.00 | 0.00 | 0.88 | 0.80 | 0.90 | 0.93 | 0.62 | 0.53 |
| Mbnl1 exon 5 inclusion recovery | 1.00 | 0.00 | 0.09 | 0.04 | 0.16 | 0.23 | 0.00 | 0.05 |
| Splicing recovery | 1.00 | 0.00 | 0.16 | 0.05 | 0.24 | 0.32 | 0.10 | 0.13 |
| Mbnl1/2 expression level | 1.00 | 0.00 | 0.65 | 0.56 | 0.51 | 0.88 | 0.29 | 0.45 |
| Mbnl1 Protein level | 1.00 | 0.00 | 1.18 | 1.24 | 1.24 | 1.31 | 0.36 | 0.73 |

TABLE 6

| Treatment | FVB | PBS | 218-D/LNA2 | 218-MOE | 218-MOE Oleic 3' | 218-OME/MOE Oleic 3' |
|---|---|---|---|---|---|---|
| Functional recovery | 1.00 | 0.00 | 0.67 | 0.71 | 0.80 | 0.44 |
| Mbnl1 exon 5 inclusion recovery | 1.00 | 0.00 | 0.43 | 0.14 | 0.09 | 0.07 |
| Splicing recovery | 1.00 | 0.00 | 0.41 | 0.10 | 0.18 | 0.13 |
| Mbnl1/2 expression level | 1.00 | 0.00 | 0.52 | 0.61 | 0.85 | 0.58 |
| Mbnl1 Protein level | 1.00 | 0.00 | 2.16 | 0.39 | 0.79 | 0.49 |

Example 7

Figure 9:
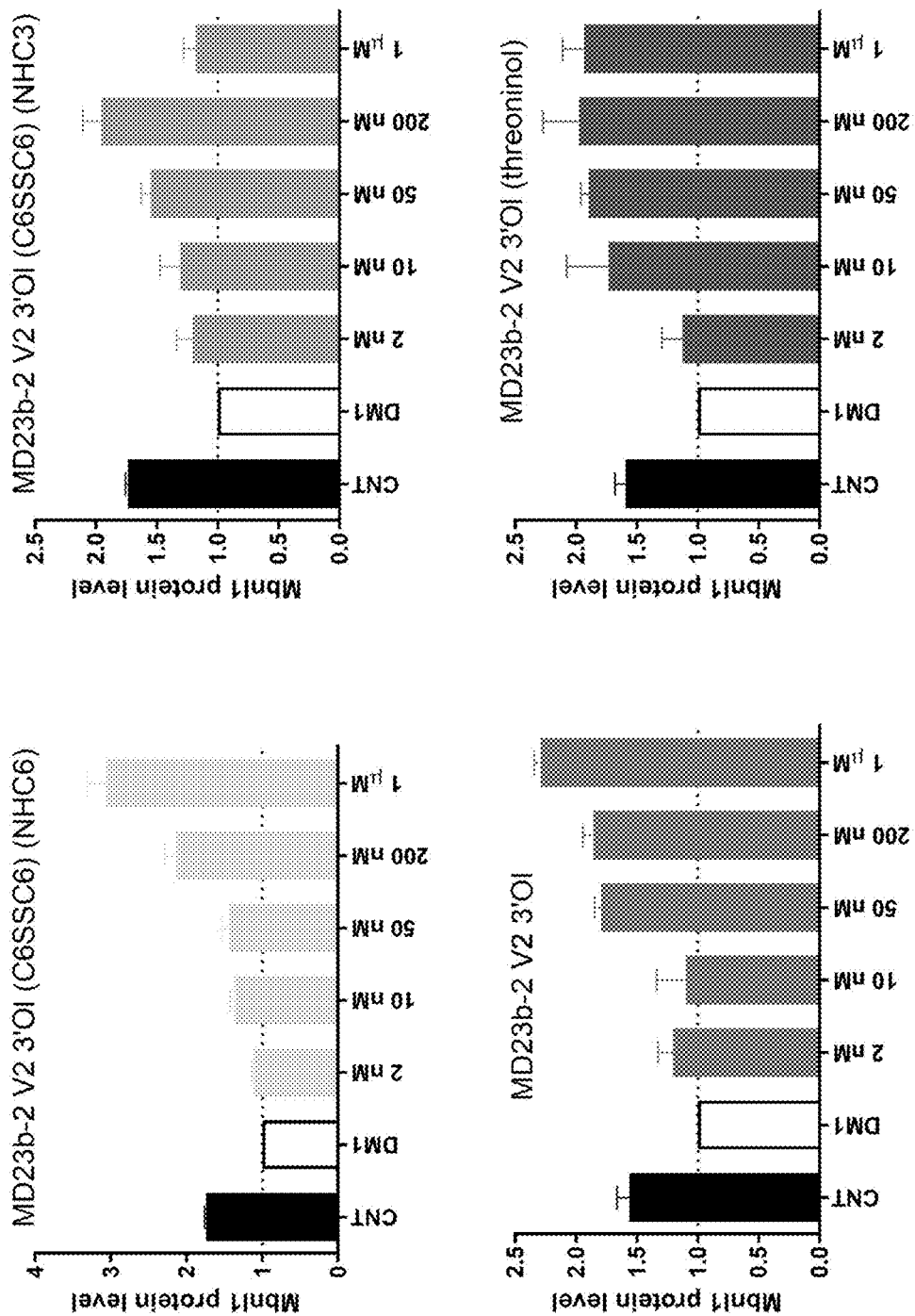
FIG. 9. Quantification of MBNL1 protein in DM1 cells treated with the indicated concentrations of oligo MD23b-2 V2 conjugated to the oleic acid in 3' using the different linkers drawn in FIG. 8. Protein levels were quantified by Quantitative dot blot analysis (QDB) and normalized to endogenous GAPDH. The resulting protein levels from DM1 cells treated with transfection reagent only (DM1) were given the value of 1, and the rest of the data were normalized accordingly. Statistical comparisons shown were all performed against DM1 cells treated with transfection reagent via Student's t-test. p values: ns=not significant, *$p<0.05$,  $p<0.01$, and * $p<0.001$. Error bars=standard error of the mean (SEM).
Figure 10A:
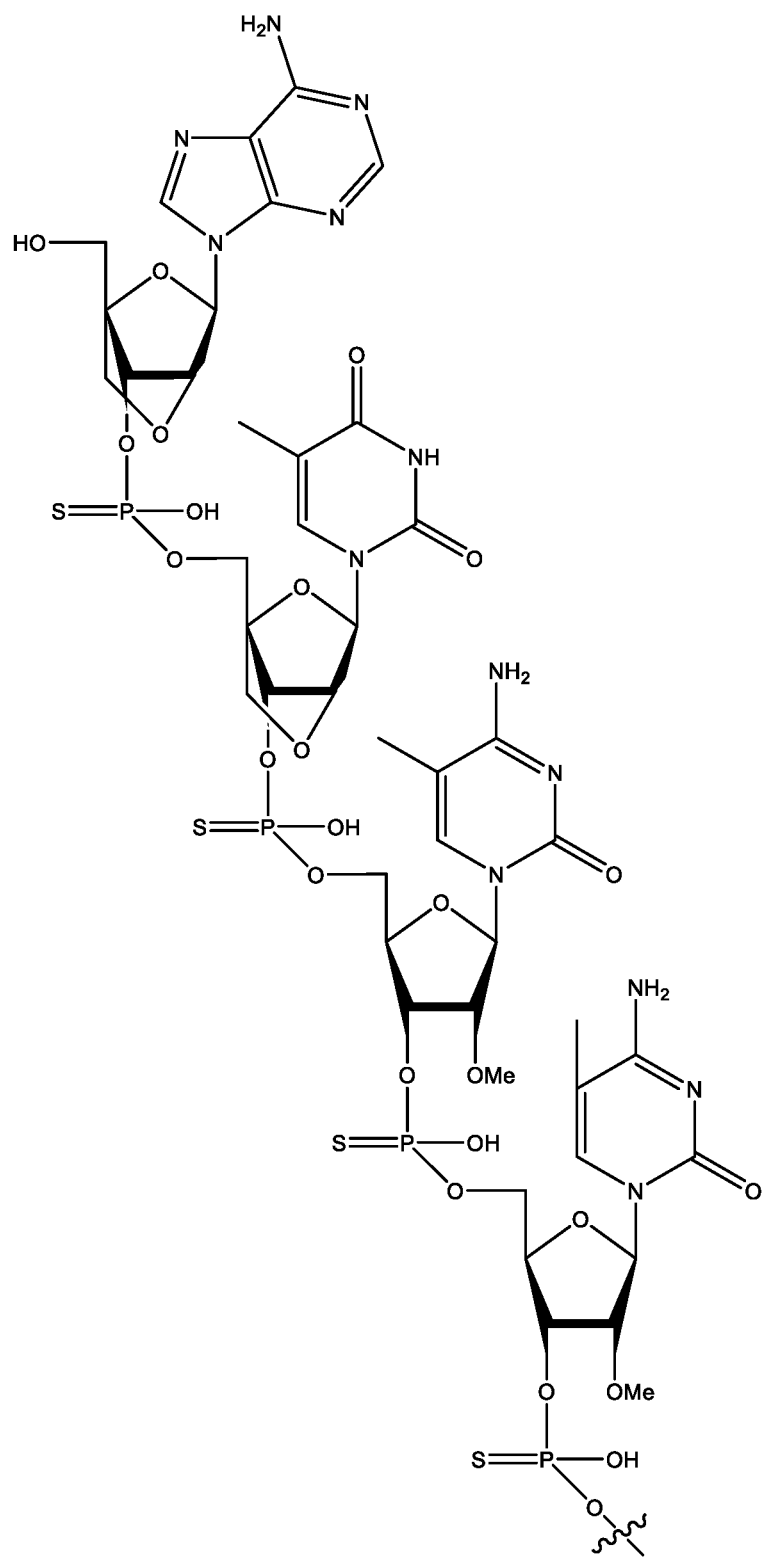
FIG. 10. A) Chemical structure of MD23b-2 V2 3'Ol oligo. The draw of the complete molecule was generated with the ChemDraw software. B) Chemical structure of MD23b-2-PS/PO 3'Ol oligo. The draw of the complete molecule was generated with the ChemDraw software C) Chemical structure of 218 MOE Oleic 3' oligo. The draw of the complete molecule was generated with the ChemDraw software.
Figure 10A:
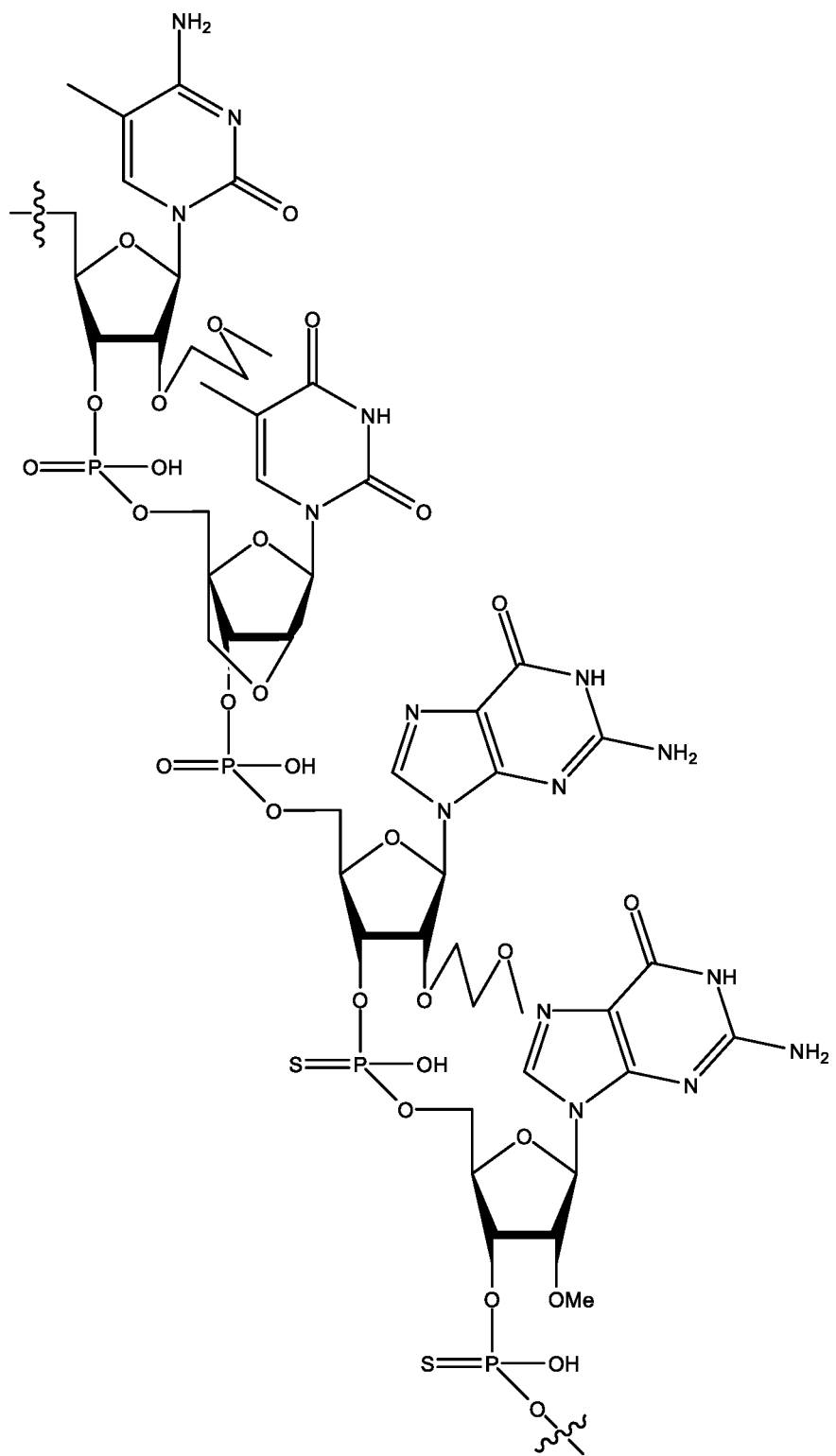
Figure 10A:
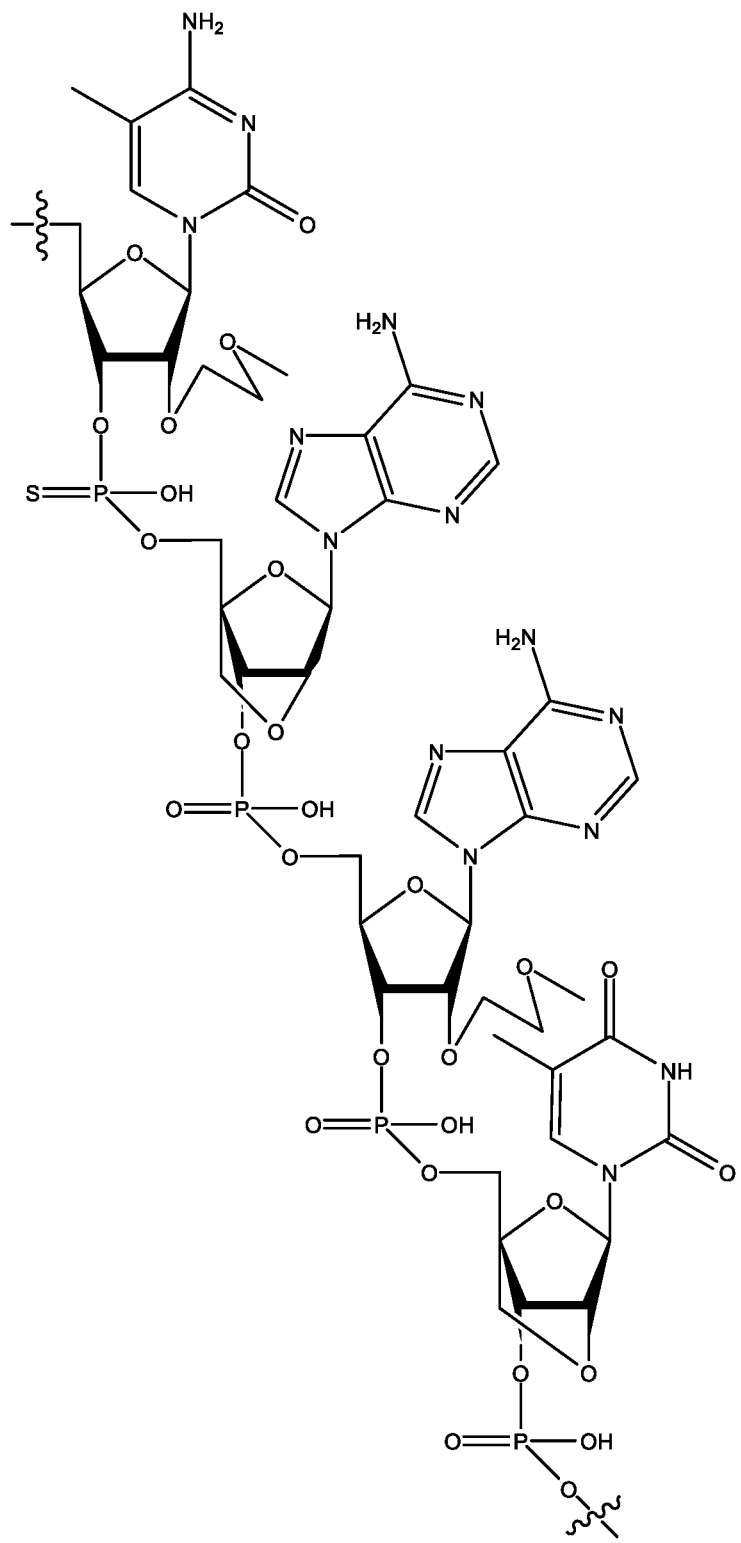
Figure 10A:
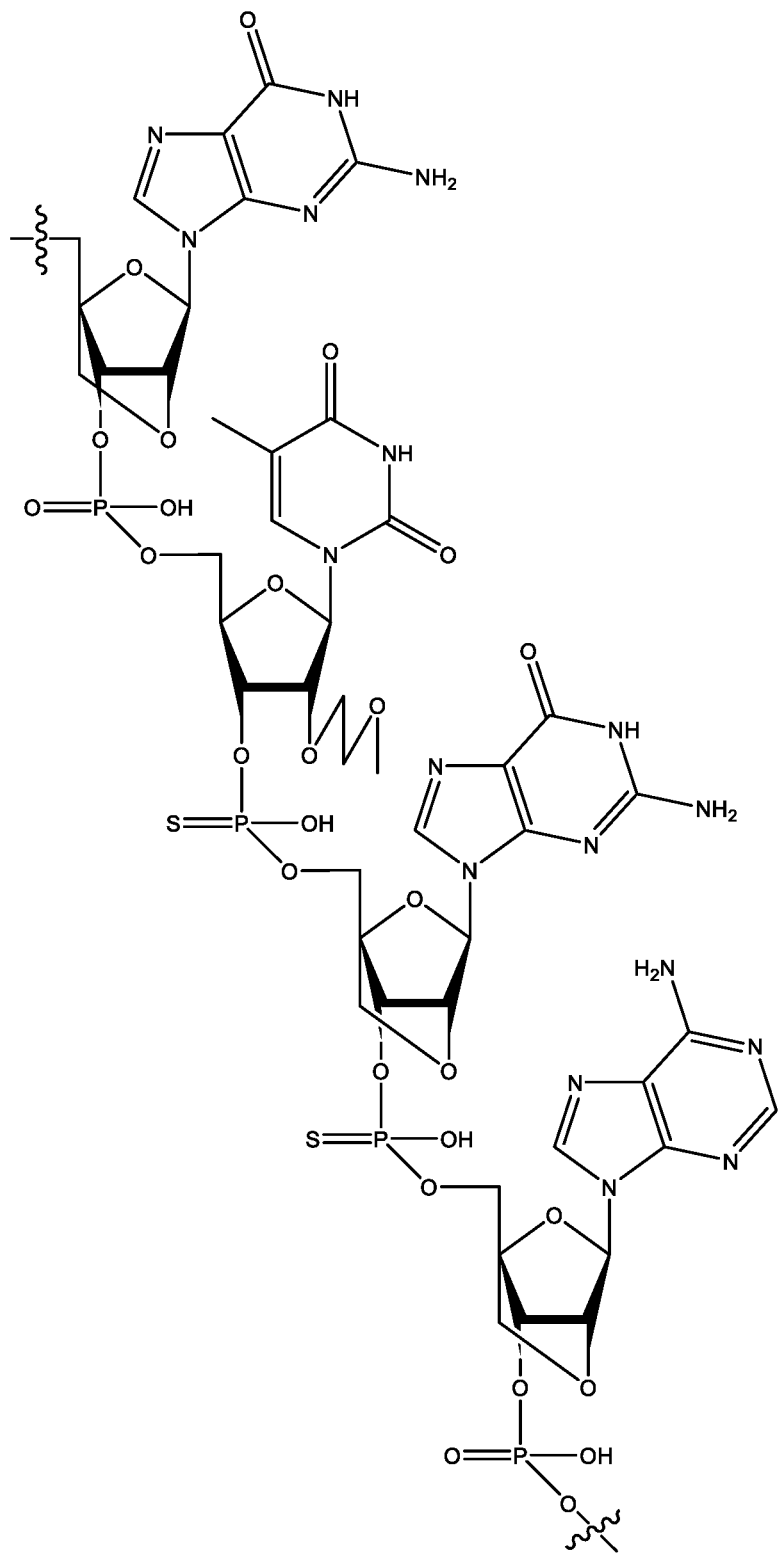
Figure 10A:
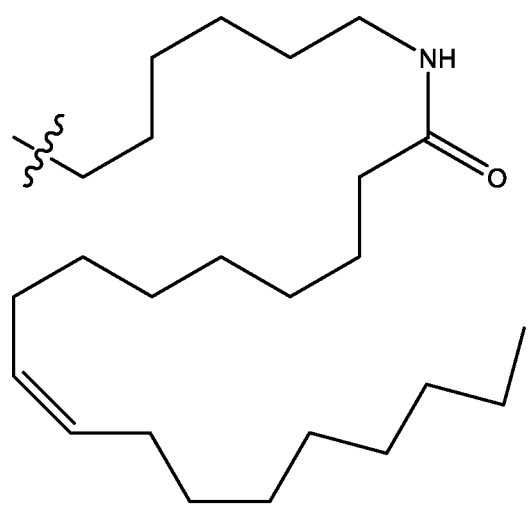
Figure 10B:
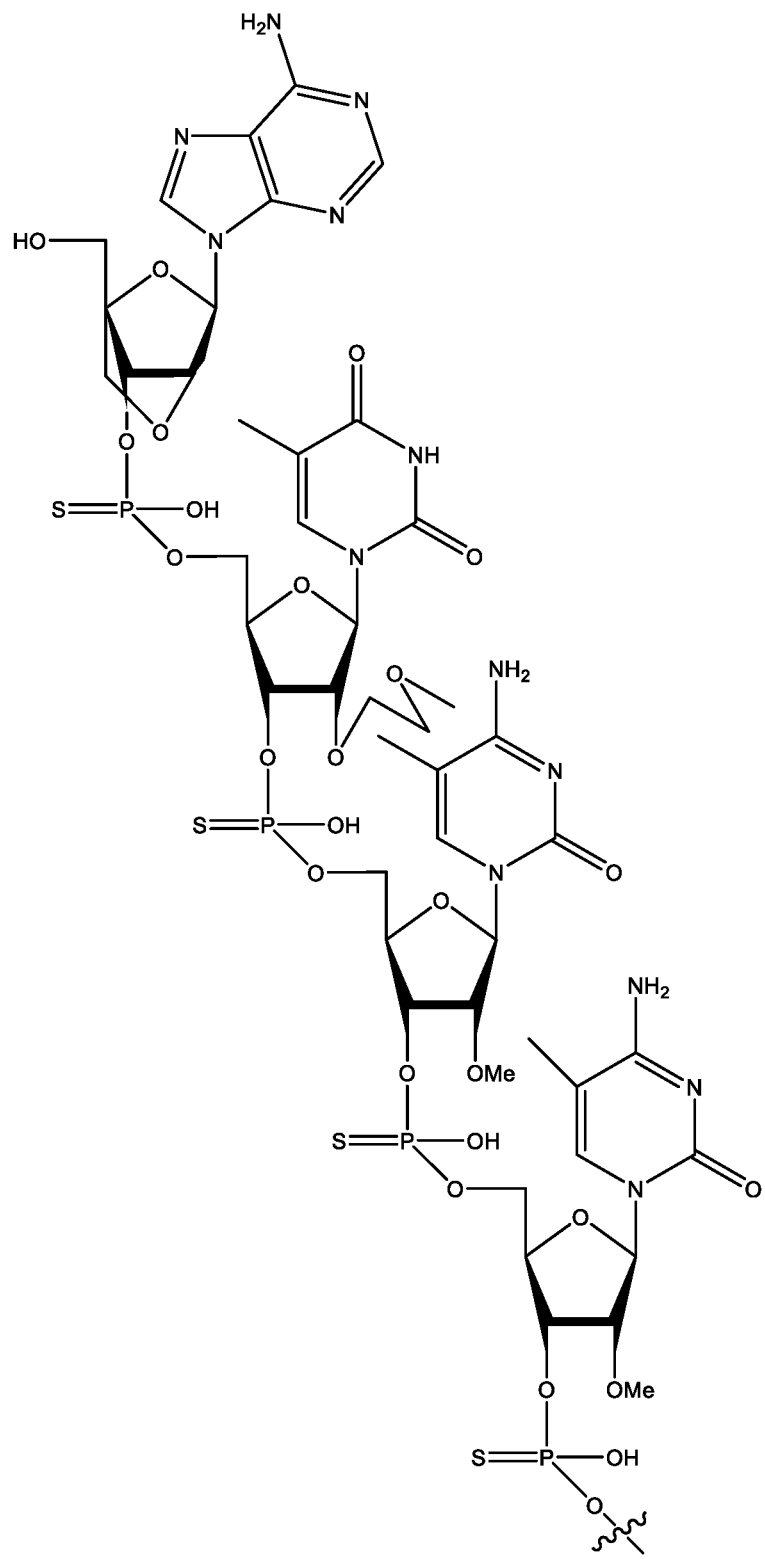
Figure 10B:
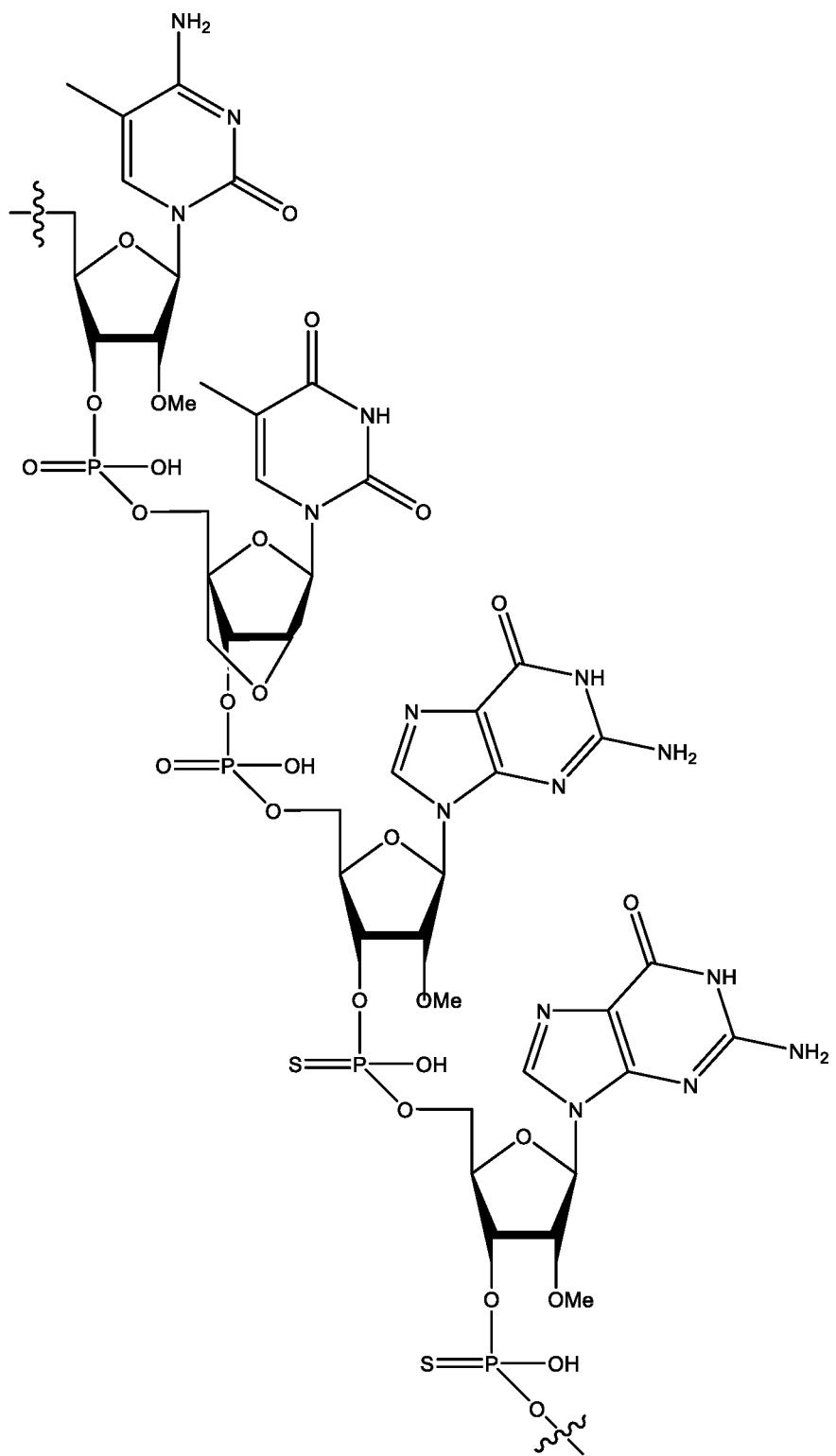
Figure 10B:
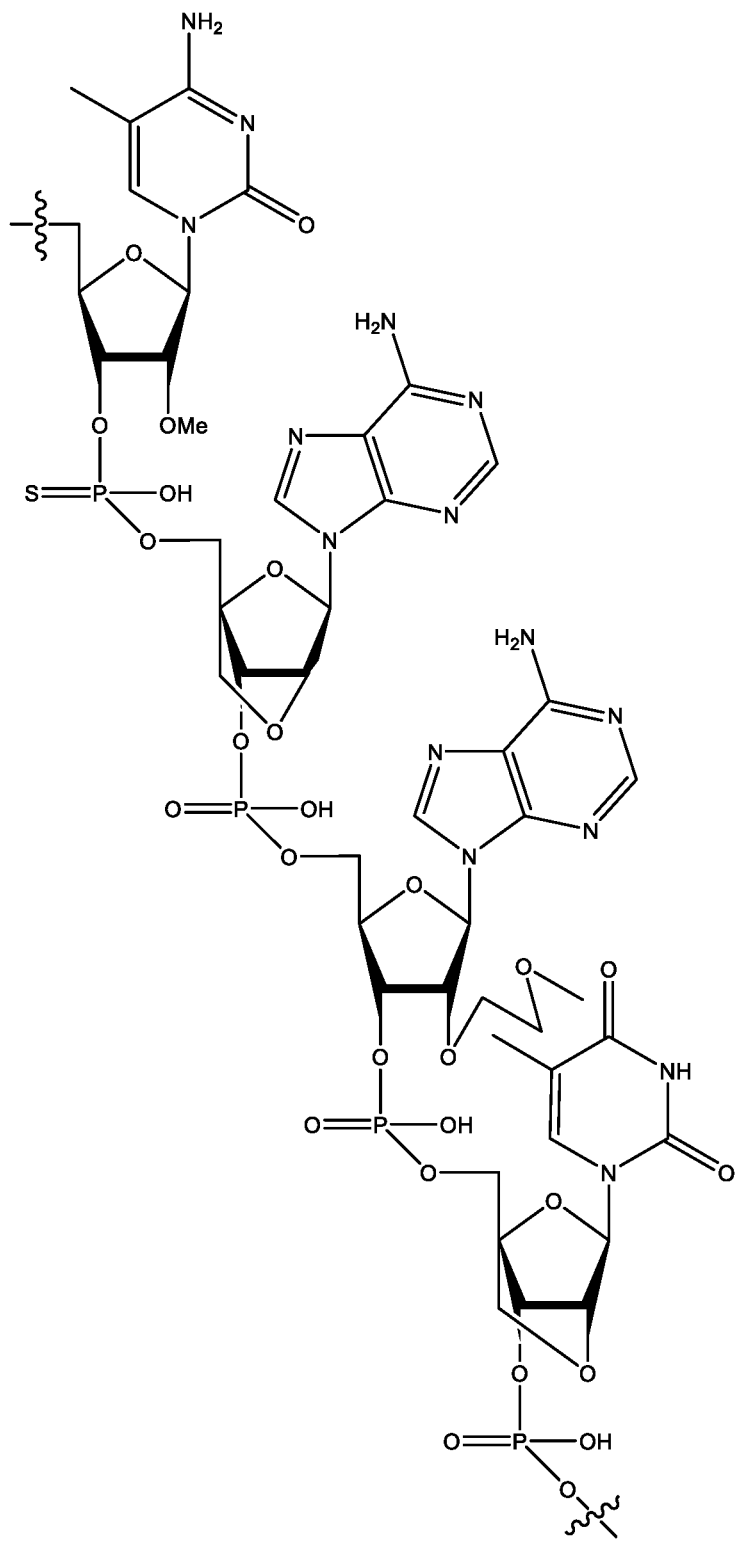
Figure 10B:
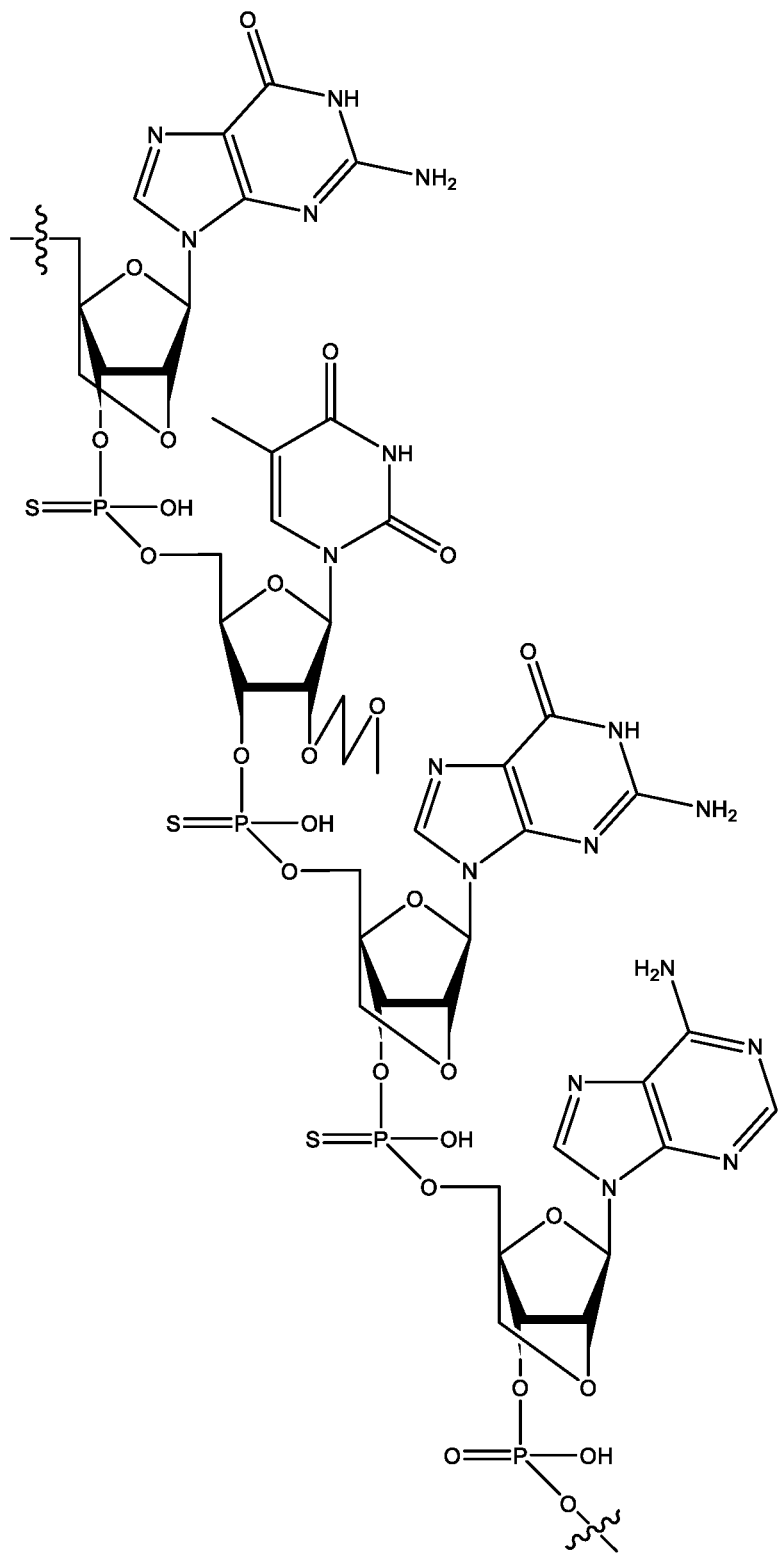
Figure 10B:
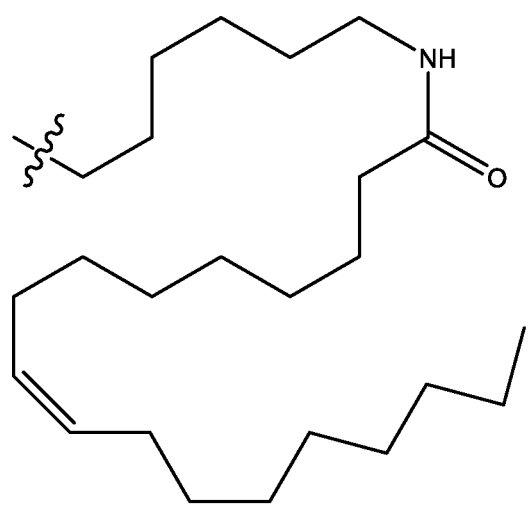
Figure 10C:
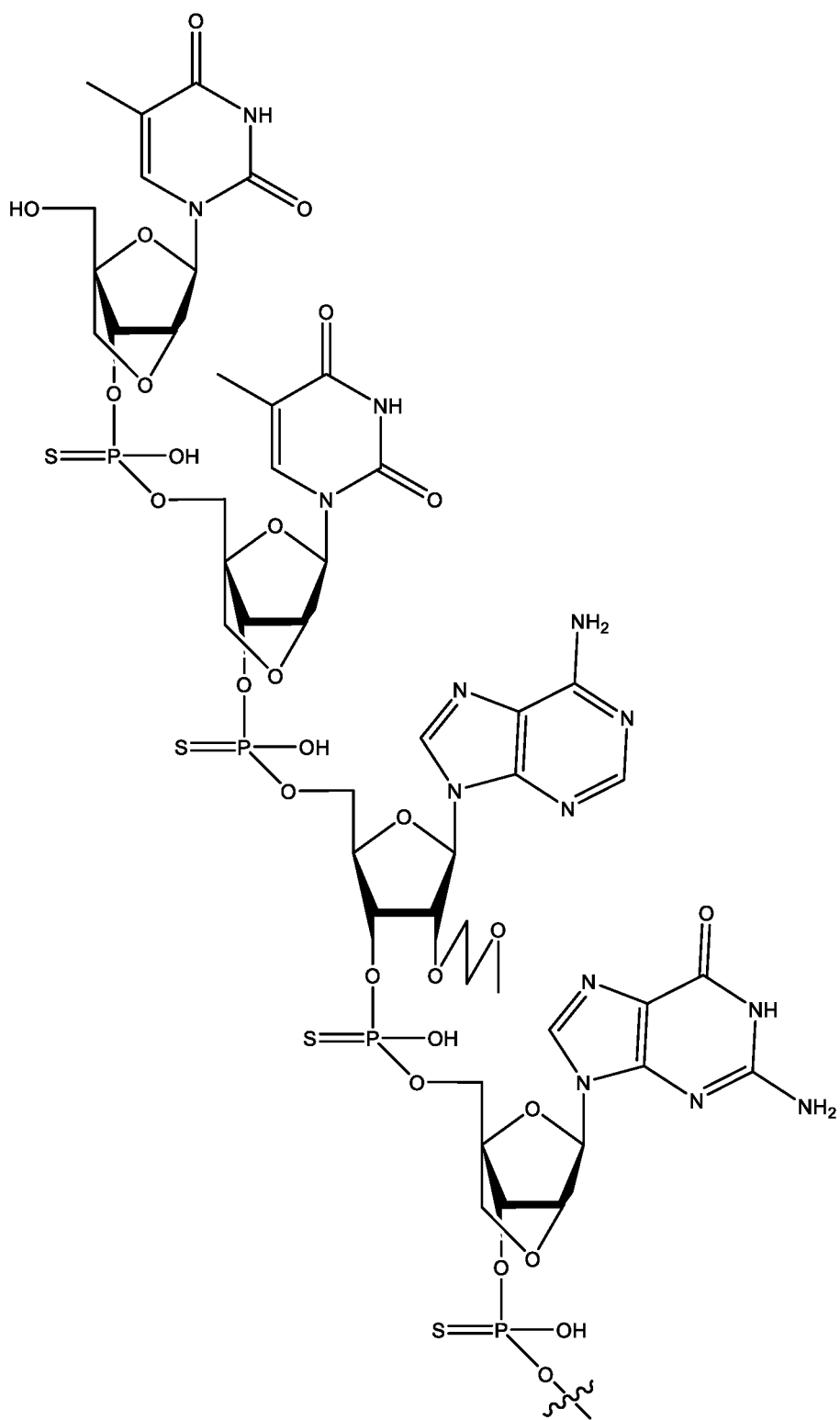
Figure 10C:
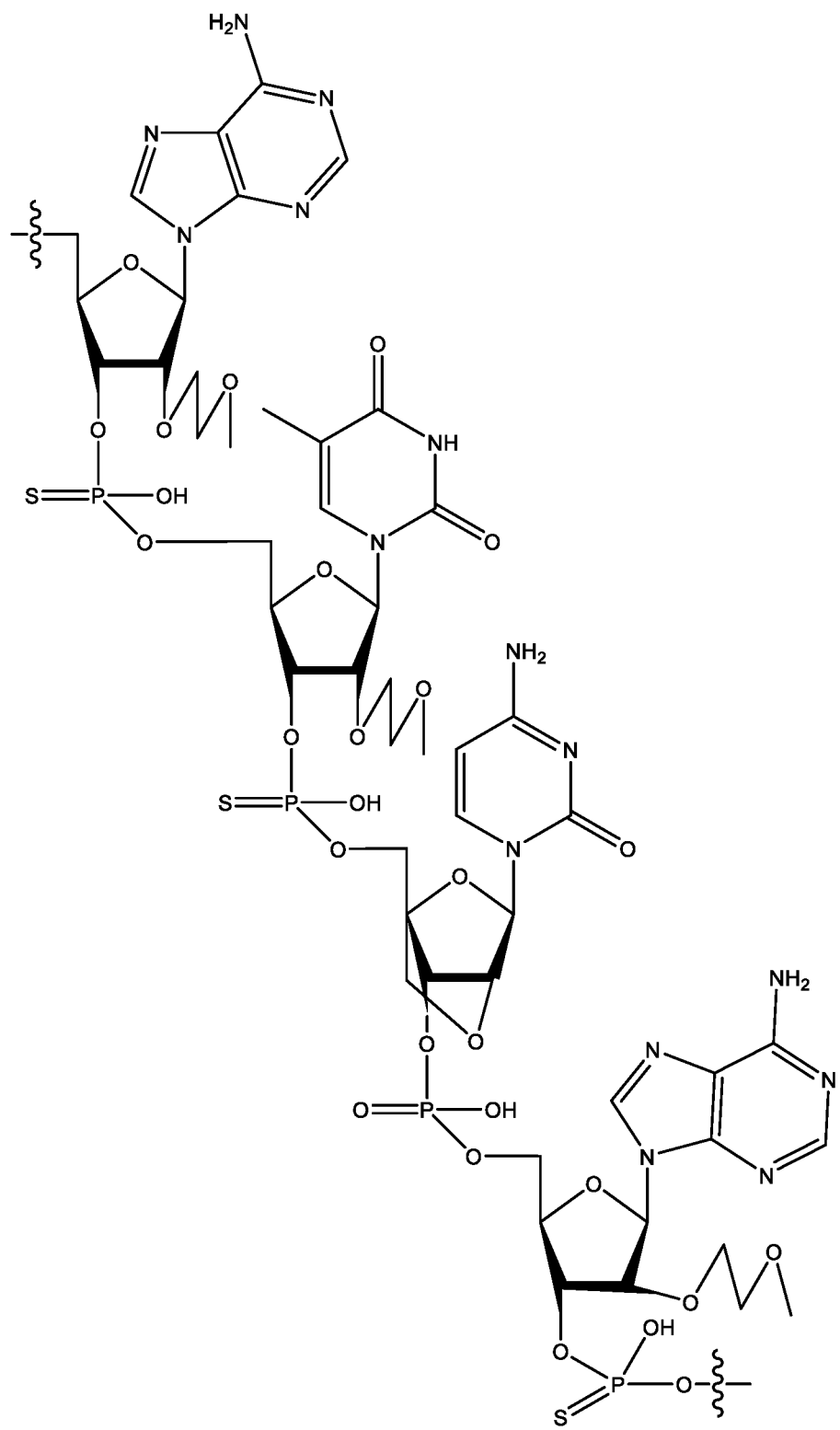
Figure 10C:
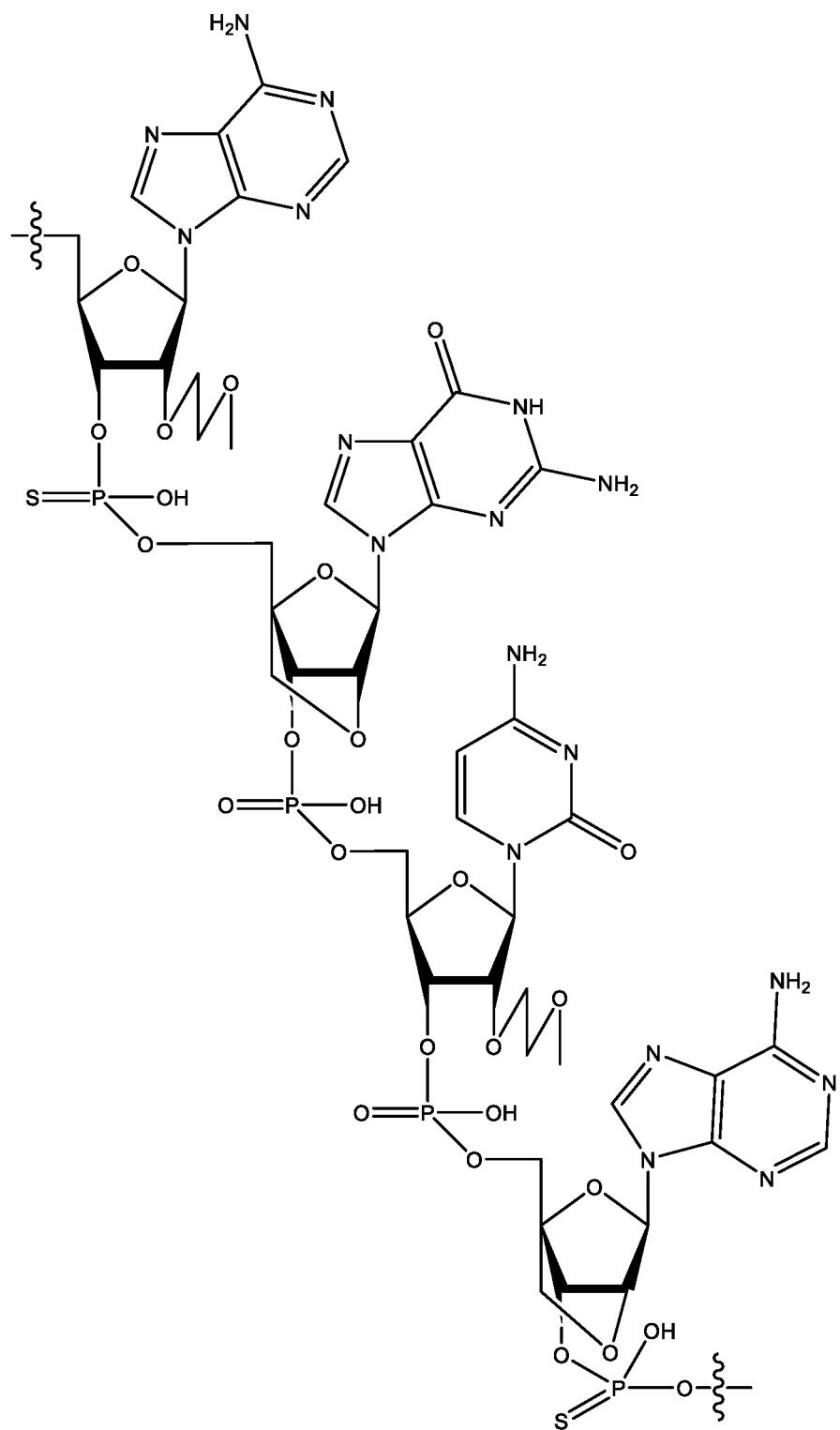
Figure 10C:
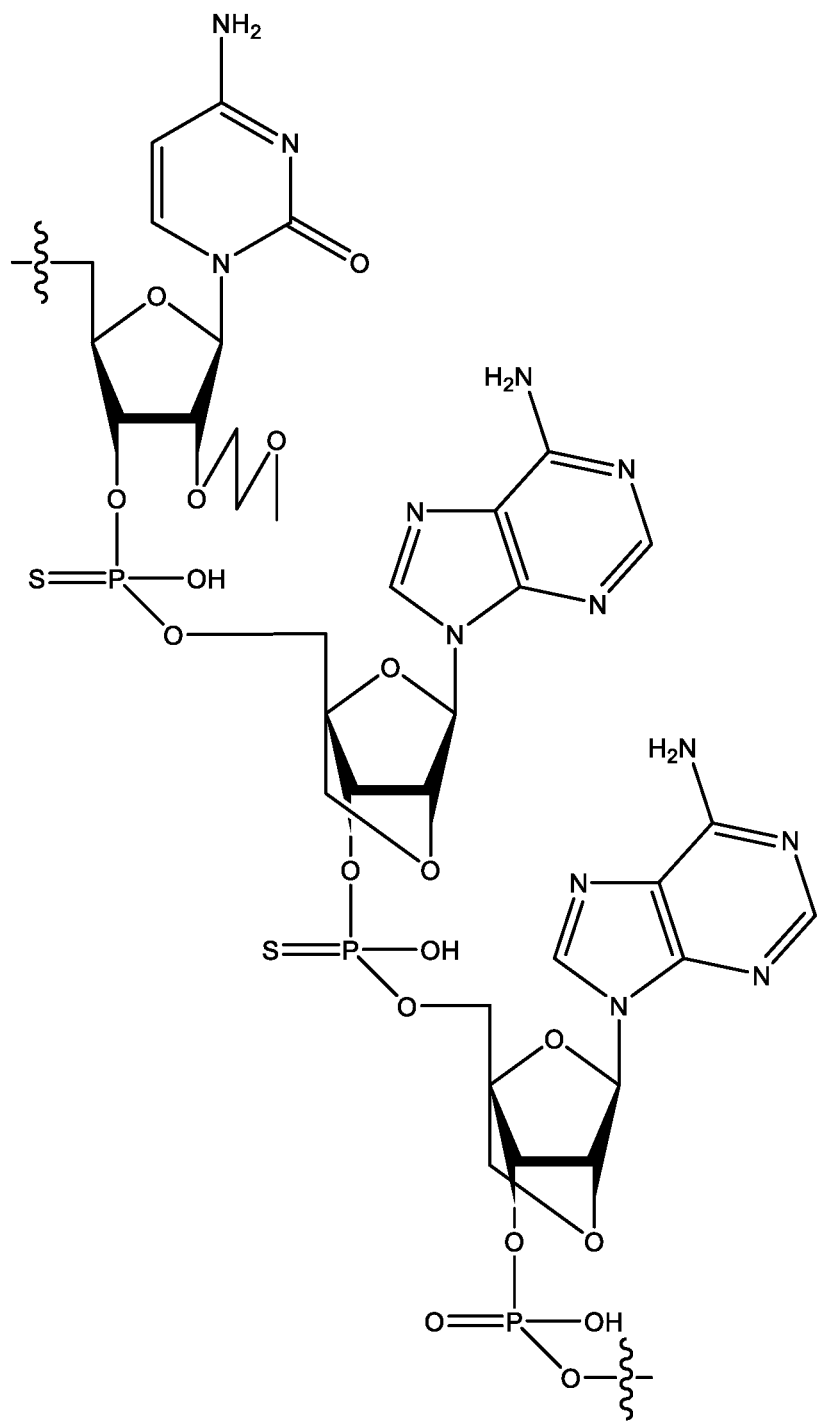
Figure 10C:
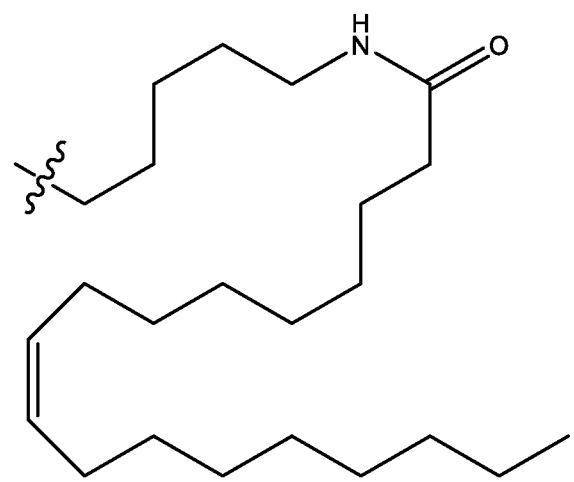

In all the antimiRs tested, we have always conjugated oleic acid either in 3' or 5' using a spacer that contains an amino group to form an amide linkage between the oleic acid and the oligonucleotide. The first spacer was the 6-aminohexyl group (NHC6 spacer) that was introduced both at the 3' and the 5'-ends. Next, we tested whether other types of spacer (NHC6, NHC3 or threoninol) and the addition of spacers of different sizes (either 3 or 6 carbon atoms) between the oligo sequence MD23b-2 V2 and the oleic acid (FIG. 8), could improve the effects of the conjugated resulting molecule on the levels of MBNL1 protein. We observed that all the antimiRs generated (4 in total in Table 7, Table 8 and FIG. 9), were able to produce upregulation of MBNL1 protein. Of note, the molecule conjugated using the threoninol was the most active as it reached the EC50 at the lowest concentration, but the molecule with the 6 carbons spacer (NHC6) was the one producing the most robust maximum upregulation of the protein. This data demonstrates that modifications in the spacer can further modulate the efficacy and pharmacodynamics of the oleic acid-conjugated antimiRs of the invention.

TABLE 7

| NAME | SEQUENCE |
|---|---|
| MD23b-2 V2 3'Ol | AbsTbs(5Mc)s(5Mc)sCmTbGmsgsCmsAbAm TbGbTmsGbsAb(NHC6)(Oleic Acid) |
| MD23b-2 V2 3'Ol (threoninol) | Abs Tbs(5Mc)s(5Mc)sCm TbGmsgsCmsAbAm TbGbTmsGbsAb(threoninol) (OleicAcid) |
| MD23b-2 V2 3'Ol (C6SSC6) (NHC6) | AbsTbs(5Mc)s(5Mc)sCmTbGmsgsCmsAbAmTbGbTmsGbsAb(C6SSC6)(NHC6) (OleicAcid) |
| MD23b-2 V2 3'Ol (C6SSC6) (NHC3) | Abs Tbs(5Mc)s(5Mc)sCmTbGmsgsCmsAbAmTbGbTmsGbsAb(C6SSC6)(NHC3) (OleicAcid) |

TABLE 8

| ASO | EC50 (μM) | Emax (maximum fold change) |
|---|---|---|
| MD23b-2 V2 3'Ol | 0.062 | 2.30 |
| MD23b-2 V2 3'Ol (C6SSC6) (NHC3) | 0.217 | 1.96 |
| MD23b-2 V2 3'Ol (C6SSC6) (NHC6) | 0.164 | 3.05 |
| MD23b-2 V2 3'Ol (Threoninol) | 0.007 | 1.98 |

Example 8

Although synthesis methods of oligonucleotides are widely known in the art, we provide herein an example of the synthesis of MD23b-2 V2 3'Ol, MD23b-2 V2 3'Ol is a 16 nt long oligonucleotide consisting of LNA, 2'-O-MOE and 2'-O-Me modified building blocks that are linked by phosphodiester or phosphorothioate linkages. Its 3' end is modified with an oleic acid moiety (FIG. 10). This oleic acid is introduced by coupling the activated carboxylic acid to a hexyl amino spacer at the 3'-end of a precursor oligonucleotide. The synthesis of the MD23b-2 V2 3'Ol is based on solid-phase synthesis using building blocks and spacers-GPG. This process consists of two main steps.

First, the synthesis of the unconjugated oligonucleotide (precursor) with sequence AbsTbs(5Mc)s(5Mc) sCmTbGmsgsCmsAbAmTbGbTmsGbsAb(NH2C6) (SEQ ID NO:160).

The first phosphoramidite considered as a building block in the chain is attached to the solid surface with a catalyzed condensation reaction. This step will be repeated as many times as the length of nucleotides of the final sequence. In this case, 16 times. Upon completion of the solid phase synthesis, the manufacture involves the following steps: cleavage and deprotection, purification, desalting Secondly, the oleic acid is conjugated. Once the desalted unconjugated oligonucleotide from the last step is conjugated with the oleic acid, it is purified, desalted and lyophilized.

Example 9

1.1 Quantification of MD23b-2 V2 3'Ol by ELISA

MD23b-2 V2 and MD23b-2 V2 3'Ol were used. A dose of 12 mg/kg of the compounds was administered intravenously to the HSA$^{LR}$ mice. After 14 days, all mice were euthanized, and their brain, kidney, liver, gastrocnemius, and quadriceps muscles were removed, weighed, and frozen for further processing. The experiments were conducted in a blinded manner by the investigator, who was unaware of the group assignment. Samples from brain, muscle (quadriceps and gastrocnemius), kidney and liver were collected during the necropsy procedure from all the experimental groups. Samples were weighed upon collection in gram units to a minimum of 3 decimal places. Each piece was placed in RNase-free tubes and snap frozen (e.g., 2 ml Eppendorf tube RNase-free).

1.1.1 Sample Preparation
1) Remove the tissues and wash them in phosphate-buffered saline.
2) Dry the tissues on absorbent paper and weigh them (20 mg per tissue; in the case of the brain take 30 mg per tissue).
3) Add the 100 μL of RIPA buffer supplemented with PhosSTOP EASYpack and Complete ULTRA Tablets, Mini, EASYpack (1 tablet of each per 10 mL of RIPA buffer) per each 10 mg of tissue.
4) Homogenize the tissues using a tissuelyser in 2 ml Eppendorf tubes for 20 s, 4 times at 5000 RPMs, or until the tissues are fully homogenized.
5) Incubate the homogenate at 55° C. overnight.
6) Centrifuge the homogenate at 15000 rpm for 15 min, aliquot the supernatant, and store it at −20° C. ready for analysis.

For the muscle lysate, 1/10 of the actual homogenate in oligonucleotide diluting buffer was used. If the samples were above the limit of quantification, then a dilution of 1:40 was applied. For the brain, 1/5 dilution was used, and for the liver and kidney a dilution of 1:400 was used.

1.1.2 Stock Preparation for Standard Curve

In the case of stock preparation for the standard curve. First, a stock of 20 UM of the MD23b-2 V2 3'Ol was made. For standard curve preparation, 1 μM concentration was used. So, the 20 μM stock was diluted in water for the final volume of 1 μM and stored in different aliquots. For each experiment, make the standard curve fresh, and for this it is necessary to heat the 1 UM stock each time at 65° C. for 15 minutes. On the other hand, after preparing the tissue homogenate, 55 μL of the homogenate was added in 5445 μL of compound diluting buffer to have the control tissue homogenate.

1.1.3 Standard Curve Preparation

For this, a control tissue homogenate is needed to prepare the standard dilution. Then, to prepare the serial dilution, 1 μM of the desired compound was denatured at 65° C. for 15 min and vortexed for 30 s at least. Then 32 μL of this denatured compound was diluted in 968 μL of control homogenate. This is the first point of the standard curve (32000 pM). Then for the next point, 500 μL of 32000 pM was diluted in 500 μL of compound diluting buffer (16000 pM). By this similar fashion 8000 pM, 4000 pM, 2000 pM, and 1000 pM were made.

TABLE 9

| ELISA design | | | | |
|---|---|---|---|---|
| Spiking solution | Volume of spiking solution (μL) | Volume of Dilution Buffer (μL) | Concentration | Standard |
| Stock | 32 | 968 | 32000 pM | STD 1 |
| STD 1 | 500 μL | 500 μL | 16000 pM | STD 2 |
| STD 2 | 500 μL | 500 μL | 8000 pM | STD 3 |
| STD 3 | 500 μL | 500 μL | 4000 pM | STD 4 |
| STD 4 | 500 μL | 500 μL | 2000 pM | STD 5 |
| STD 5 | 500 μL | 500 μL | 1000 pM | STD 6 |
| — | — | 500 μL | — | Blank |

1.1.4 QC

Three QC levels (L, M, H) in triplicates in each run Acceptance Criteria:
≥67% of QCs should be ±30% of the nominal (theoretical) values.

1.1.5 ELISA Protocol

The probe miR-23b TbsCsAsCbsAsTsTbsGsCsCbsAsGsGbsGsAsTb-Digoxigenin NHS ester (SEQ ID NO:111) (stock is 100 UM in water, and prepare 1 μM for this stock in water) need to be heated at 65° C. for 15 min and vortex for 30 s.

Prepare the sample homogenate and oligonucleotide serial dilution before starting the experiment.

Dilute the probe (1 μM) in the hybridization buffer at a 0.5 nM concentration.

Add 70 μL of each dilution of the desired compound in triplicate and in the case of sample homogenate add them in duplicate. Then add 70 μL of the probe at a 0.5 nM concentration.

Seal the plate with PCR film and incubate at 37° C. for 30 min (an important step for hybridization of the probe with the compound!)-until this step we can do it in a normal transparent 96-well plate.

Then immediately transfer 100 μL of the hybridized solution to the black NeutrAvidin coated plates.

Then again seal the plate with PCR film and incubate at 37° C. for 30 min (an important step for binding the biotin with the Avidin coated plate).

Prepare micrococcal nuclease in micrococcal nuclease dilution buffer (1.6 μL of nuclease+ 16 ml of the buffer) during the incubation step. This calculation is made for the whole plate.

Take out the liquid first, wash the plate 6 times with 100 μL of washing buffer, then dry the plate using an absorbent paper by keeping the plate upside down and add 150 μL of micrococcal nuclease per well (final amount of 30 U/well).

After adding the micrococcal nuclease seal the plate with PCR film and incubate the plate at 37° C. for 1 h (this step is sufficient to cleave at least 99% of the single-stranded probe).

Prepare the TBS buffer with 0.25% Tween 20 and the antibody (anti-digoxigenin antibody, Roche #11093274910), vortex them well, and leave them at RT. For the rest of the amount which you don't need you can keep in the freezer in aliquots.

Take out the liquid first, then wash the plate 6 times with 100 μL of washing buffer, dry the plate and add 150 μL of anti-digoxigenin antibody (conjugated with alkaline phosphatase) at 1/5,000 dilution in TBS buffer (with 0.25% v/v Tween 20).

Seal the plate with PCR film and incubate at 37° C. for 30 min.

To prepare the Attophos substrate, dilute 36 mg of powder (which came in the bottle) by adding 60 ml of the Attophos buffer and keep in the refrigerator protected from the light (preferably wrapped up with an aluminum foil).

Take out the liquid, wash the plate 6 times with 100 μL of washing buffer, dry the plate and add 150 μL of Attophos substrate (Diluted 1:1 ratio in Attophos buffer).

Seal the plate with PCR film, then wrap it with aluminum foil and incubate at room temperature (RT) for 40 minutes. Then to determine the fluorescence intensity Synergy H1 (Biotek) was used. 444 nm of excitation and 555 nm of emission were used. Perform serial readings at 60, 70, 80, and 90 minutes at a 1-sec delay per well.

TABLE 10

Mean values of MD23b-2 V2 3'Ol and MD23b-2 V2 (ng/g) in brain, gastrocnemius, quadriceps, kidney and liver.

| Test Item | Time Treatment (days) | Dose (mg/kg) | Tissue | Compound (ng/g) |
|---|---|---|---|---|
| MD23b-2 V2 3'Ol | 14 | 12 | Brain | 289.9 |
| MD23b-2 V2 3'Ol | 14 | 12 | Gastrocnemius | 25657.9 |
| MD23b-2 V2 3'Ol | 14 | 12 | Quadriceps | 15827.7 |
| MD23b-2 V2 3'Ol | 14 | 12 | Kidney | 74971.6 |
| MD23b-2 V2 3'Ol | 14 | 12 | Liver | 183881.1 |
| MD23b-2 V2 | 14 | 12 | Brain | 0.0 |
| MD23b-2 V2 | 14 | 12 | Gastrocnemius | 2705.2 |
| MD23b-2 V2 | 14 | 12 | Quadriceps | 1790.2 |
| MD23b-2 V2 | 14 | 12 | Kidney | 18840.3 |
| MD23b-2 V2 | 14 | 12 | Liver | 39570.1 |

TABLE 11

Fold Change of delivery efficiency MD23B-2 V2 3'OL vs MD23b-2 V2.

| Test Item | Time Treatment (days) | Dose (mg/kg) | Tissue | Fold Change of delivery efficiency MD23B-2 V2 3'OL vs MD23b-2 V2* |
|---|---|---|---|---|
| MD23b-2 V2 3'Ol | 14 | 12 | Brain | 290 |
| MD23b-2 V2 3'Ol | 14 | 12 | Gastrocnemius | 9.5 |
| MD23b-2 V2 3'Ol | 14 | 12 | Quadriceps | 8.8 |
| MD23b-2 V2 3'Ol | 14 | 12 | Kidney | 4.0 |
| MD23b-2 V2 3'Ol | 14 | 12 | Liver | 4.6 |

*The fold change has been calculated with respect to the amount of the compound MD23b-2 V2

Results and FIG. 11

We have observed the presence of the both compounds in muscle (gastrocnemius and quadriceps) as well as liver, and kidney 14 days after the administration. In all the tissues the control groups were below limit of quantification. While the compound MD23b-2 V2 3'Ol is the only one capable of reaching the brain. In terms of tissue delivery, the MD23b-2 V2 3'Ol compound outperforms MD23b-2 V2, as it is able to reach all tissues, including the gastrocnemius, quadriceps, liver, kidney, and brain, more efficiently. Although we detected a higher amount of MD23b-2 V2 3'Ol in all tissues, its delivery to the gastrocnemius and quadriceps muscles is 9.5 and 8.8 times higher, respectively, compared to MD23b-2 V2. In contrast, the delivery to kidney and liver is only 4 and 4.5 times higher, respectively, indicating an enhanced delivery to muscles compared to less relevant tissues in the disease. MD23b-2 V2 3'Ol manages to reach the brain while MD23b-2 V2 does not, which shows that conjugation with oleic acid favours its arrival in this tissue. With all this, we conclude that oleic acid improves the delivery of our compound, and above all, it improves it to tissues such as muscle and brain involved in the pathology.

Example 10: Determination of MD23b-2 V2 3'OL and MBNL1 Protein Levels in Non-Human Primate Brain The objective of this study was the determination of the exposure of the brain of the animals treated with MD23b-2 V2 3'OL was determined using Enzyme-Linked Immunosorbent Assay (ELISA). Furthermore, target engagement on the brain of treated animals was measured by quantification of Muscleblind-like type 1 (MBNL1) protein levels from the No Human Primate brain.

1. Experimental Design 1.1 Experimental Groups & Dosing

For these purposes, a total of 8 Cynomolgus monkeys (4 males and 4 females) approximately 24 to 50 months were distributed into 3 groups experimental group and further allocated in Phase 1 (Maximum Tolerated dose (MTD) Group Assignment) and, Phase 2 (Fixed Dose (FD) Group Assignment). During Phase 1 (maximum-tolerated dose [MTD] phase), one male and one female cynomolgus monkey of Asian origin were assigned to Group 1 and administered a single dose of MD23b-2 V2 3'Ol under non fasted conditions at 5, 10, 15, and 20 mg/kg intravenously (slow bolus [10 minutes]) on Days 1, 15, 29, and 43 of the MTD phase at a dose volume of 5 mL/kg in an ascending dose design.

Following completion of the MTD phase, three male and three female cynomolgus monkeys of Asian origin were assigned to Groups 2 and 3 in Phase 2 (fixed-dose phase) and administered vehicle (Phosphate buffered Solution [PBS, pH: 7.4]) or 20 mg/kg MD23b-2 V2 3'Ol intravenously (slow bolus [10 minutes]) under non fasted conditions on Days 1 and 22 of Phase 2 at a dose volume of 5 ml/kg.

On the day of sacrifice samples from brain were collected during the necropsy procedure
Group Assignment and Dose Levels

TABLE 12

Phase 1: Maximum Tolerated dose (MTD) Group Assignment

| Group Number | Group Description | Dosing days | Dose Level (mg/kg) | Dose Volume$^a$ (mL/kg) | Animals/Group Males | Animals/Group Females | Necropsy on Day 57 |
|---|---|---|---|---|---|---|---|
| 1 | Low | 1 | 5.0 | 5 | 1 | 1 | 1M/1 F |
|   | Mid | 15 | 10 | 5 |   |   |   |
|   | Intermediate | 29 | 15 | 5 |   |   |   |
|   | High | 43 | 20 | 5 |   |   |   |

$^a$Based on most recent individual body weight

TABLE 13

Phase 2: Fixed Dose (FD) Group Assignment

| Group Number | Group Description | Dose Level (mg/kg) | Dose Volume$^a$ (mL/kg) | Animals/Group Males | Animals/Group Females | Necropsy on Day 43 |
|---|---|---|---|---|---|---|
| 2 | Control | 0 | 5 | 1 | 1 | 1M/1 F |
| 3 | High | 20 | 5 | 2 | 2 | 2M/2 F |

$^a$Based on most recent individual body weight

2. Experimental Data 2.1 Experimental Procedures 2.1.1 Sample Collection

The brain of all animals from Groups 1 to 3 were collected for ELISA quantification, MBNL1 investigations and determination of potential off targets. Two weeks after the last administration for the animals from the phase 1 and 3 weeks after the end of the treatment period for animals from phase 2. Each piece was placed in a separate RNase-free Eppendorf tube, frozen in liquid nitrogen and stored at (−80±10° C.). A total 8 brain samples were generated.

2.1.2 ELISA Quantification 2.1.2.1 Sample Preparation

1) Remove the tissues and wash them in phosphate-buffered saline.
2) Dry the tissues on absorbent paper and weigh them (20 mg per tissue).
3) Add the 100 μL of RIPA buffer supplemented with PhosSTOP EASYpack and Complete ULTRA Tablets, Mini, EASYpack (1 tablet of each per 10 mL of RIPA buffer) per each 10 mg of tissue.
4) Homogenise the tissues using a tissuelyzer in 2 ml Eppendorf tubes for 20 s, 4 times at 5000 RPMs, or until the tissues are fully homogenized.
5) Incubate the homogenate at 55° C. overnight.
6) Centrifuge the homogenate at 15000 rpm for 15 min, aliquot the supernatant, and store it at −20° C. ready for analysis.

For the brain lysate, a 1/5 dilution of the actual homogenate (80 μL+320 μL of oligonucleotide diluting buffer) was used.

2.1.2.2 Stock Preparation for Standard Curve

In the case of stock preparation for the standard curve. First, make a stock of 20 UM of the MD23b-2 V2 3'Ol. This can be stored at −20° C. for a longer period. From this 20 μM stock, we can make several dilutions according to the need. For standard curve preparation, we need 1 μM. So, the 20 μM stock was diluted in water for the final volume of 1 UM and stored in different aliquots. For each experiment, we need to make the standard curve fresh and for that, we need to heat the 1 μM stock each time at 65° C. for 15 minutes. On the other hand, after preparing the tissue homogenate add 55 μL of it in 5445 compounds diluting buffer to have the control tissue homogenate.

2.1.2.3 Standard Curve Preparation

For this, we need control tissue homogenate to prepare the standard dilution. Then to prepare the serial dilution at first take 1 μM of your desired compound and denature them at 65° C. for 15 min and Vortex them for 30 s at least. Then take 16 UL of this denatured compound and dilute it in 984 μL of control homogenate. This is the first point of the standard curve (16000 pM). Then for the next point take 500 μL of 16000 PM and dilute it in 500 μL of PMO diluting buffer (8000 pM). By this similar fashion make 4000 pM, 2000 pM, 1000 pM, and 500 pM

TABLE 14

| Spiking solution | Volumen of spiking solution (μL) | Volumen of Dilution Buffer (μL) | Concentration | Standard |
|---|---|---|---|---|
| Stock | 16 | 984 | 16000 pM | STD 1 |
| STD 1 | 500 μL | 500 μL | 8000 pM | STD 2 |
| STD 2 | 500 μL | 500 μL | 4000 pM | STD 3 |
| STD 3 | 500 μL | 500 μL | 2000 pM | STD 4 |
| STD 4 | 500 μL | 500 μL | 1000 pM | STD 5 |
| STD 5 | 500 μL | 500 μL | 500 pM | STD 6 |
| — | — | 500 μL | — | Blank |

2.1.2.4 QC

Three QC levels (L, M, H) in triplicates in each run. Acceptance Criteria:
≥67% of QCs should be ±20% of the nominal (theoretical) values, and ≥50% of QCs per level should be ±20% of their nominal concentration 2.1.2.5 ELISA Protocol The probe miR-23b TbsCsAsCbsAsTsTbsGsCsCbsAsGsGbsGsAsTb-Digoxigenin NHS ester (SEQ ID NO: 111) (stock is 100 UM in water, and prepare 1 μM for this stock in water) need to be heated at 65° C. for 15 min and vortex for 30 s.
Prepare the sample homogenate and oligonucleotide serial dilution before starting the experiment
Dilute the probe (1 μM) in the hybridization buffer at 0.5 nM concentration
Add 70 μL of each dilution of the desired compound in triplicate and in the case of sample homogenate add them in duplicate. Then add 70 μL of the probe at 0.5 nM concentration Seal the plate with PCR film and incubate at 37° C. for 30 min (An important step for hybridization of the probe with the compound!)-until this step can we do it in a normal transparent 96-well plate Then immediately transfer 100 μL of the hybridized solution to the black NeutrAvidin coated plates Then again seal the plate with PCR film and incubate at 37° C. for 30 min (An important step for binding the biotin with the Avidin coated plate!)

Prepare micrococcal nuclease in micrococcal nuclease dilution buffer (1.6 L of nuclease+ 16 ml of the buffer) during the incubation step. This calculation is made for the whole plate.

Take out the liquid first, wash the plate 6 times with 100 μL of washing buffer, then dry the plate using an absorbent paper by keeping the plate upside down and add 150 μL of micrococcal nuclease per well (Final amount of 30 U/well) 1 After adding the micrococcal nuclease seal the plate with PCR film and incubate the plate at 37° C. for 1 h (This step is sufficient to cleave at least 99% of the single-stranded probe)

Prepare the TBS buffer with 0.25% Tween 20 and the antibody, vortex them well, and leave them at RT. For the rest amount which you don't need you can keep them in the freezer in aliquots.

Take out the liquid first, then wash the plate 6 times with 100 μL of washing buffer, dry the plate and add 150 μL of anti-digoxigenin antibody (conjugated with alkaline phosphatase) at 1/5,000 dilution in TBS buffer (with 0.25% v/v Tween 20).

Seal the plate with PCR film and incubate at 37° C. for 30 min

To prepare the Attophos substrate, dilute 36 mg of powder (which came in the bottle) by adding 60 ml of the Attophos buffer and keep them in the fridge protected from the light (preferably wrapped up with an aluminum foil).

Take out the liquid, wash the plate 6 times with 100 μL of washing buffer, dry the plate and add 150 μl of Attophos substrate (Diluted 1:1 ratio in Attophos buffer).

Seal the plate with PCR film, then wrap it with aluminum foil and incubate at room temperature (RT) for 40 minutes. Then to determine the fluorescence intensity Synergy H1 (Biotek) was used. 444 nm of excitation and 555 nm of emission were used. Perform serial readings at 40, 50, 60, 70, 80, and 90 minutes at a 1-sec delay per well.

2.1.2.6 Acceptance Criteria for the ELISA Assay

The accuracy of an analytical method describes the closeness of mean test results obtained by the method to the true value (concentration) of analytic. Accuracy is estimated by the relative error of measurement (RE %). The true values of the reference controls for both ELISA assays did not correspond with the theoretical concentration based only in calculation. Therefore, the nominal concentration for the controls would be calculated as the mean of the pool of all the references for each concentration level form all the analytical batches $$RE(\%) = \frac{(\text{Mean calculated concentration} - \text{Theoretical concentration})}{\text{Theoretical concentration}} * 100$$

The precision of an analytical method describes the closeness of individual measures of an analyte when the procedure is applied repeatedly to multiple aliquots of a single homogeneous volume of biological matrix. Precision is estimated by the coefficient of variation (CV %).

$$CV(\%) = \frac{\text{Standard Deviation}}{\text{Mean}} * 100$$

TABLE 15

| Acceptance Criteria | |
|---|---|
| Standard Curve | $R^2 \geq 0.95$ |
|  | Non-zero standards should be ± 25% of nominal (theoretical) concentrations, except at LLOQ and ULOQ where the calibrator should be ± 30% of the nominal concentrations in each validation run. |
|  | 75% and a minimum of five non-zero standard levels should meet the above criteria in each qualification run. |
| Low limit of quantification | 500 pM |
| CV for Reference Levels | CV ≤30% in at least two of three QC levels |
| CV for Samples | CV ≤30% |
| % Recovery at each level (RE) | 70-130% in at least two of three QC levels |

2.1.3 MBNL Determinations

2.1.3.1 Protein Extraction

NHP brain samples were mechanically disaggregated with a TissueLyser II (QIAGEN) and homogenized in RIPA Buffer (Thermo Scientific, Cat. No. 89900) supplemented with protease and phosphatase inhibitors (Roche, Cat. No. 11873580001 and 4906845001). Total protein was quantified with Pierce™ BCA Protein Assay Kit (Cat. No. 23225) using bovine serum albumin as standard.

2.1.3.2 Western Blot

For the immunodetection of the MBNL1 and GAPDH (internal control for normalization) proteins, 15 μg of total protein for each animal sample was denatured by heat treatment at 100° C. for 5 min, separated by electrophoresis on 12% SDS-PAGE gels and subsequently transferred to 0.45 μm nitrocellulose membranes (GE Healthcare). The membranes were blocked using 5% skim milk in PBS-T (8 mM Na2HPO4, 150 mM NaCl, 2 mM KH2PO4, 3 mM KCl, 1% Tween 20, pH 7.4) for 1 h. After blocking, the membranes were incubated with the primary anti-MBNL1 mouse antibody (1: 200, MB1a (4A8) (DSHB, Iowa City, Iowa)) overnight at 4° C. Incubation with the primary antibody was followed by incubation with horseradish peroxidase-conjugated anti-mouse secondary antibody (1: 3500, (HRP)-conjugated anti-Mouse-IgG secondary antibody, Sigma-Aldrich, Saint Louis, Missouri), during 1 h at room temperature. Finally, visualization was carried out using an enhanced chemiluminescence substrate (ECL, Pierce), and images were acquired using ImageQuant 800 Amersham equipment (GE Healthcare).

After the detection of the immunoreactive bands corresponding to MBNL1, the membranes were stripped to eliminate the antibodies used so far, and the bands corresponding to the GAPDH protein, used as a normalizer, were detected. This detection was carried out using the anti-GAPDH antibody conjugated with HRP (1:3500, clone G-9, Santa Cruz) after blocking (performed as described above). For HRP-conjugated anti-GAPDH antibody, incubation time lasted 1 h and was performed at room temperature. The analysis was performed in duplicate.

2.1.3.3 Quantification

All images were quantified using ImageJ the analysis software. The results for the amount of MBNL1 protein was first normalized to GAPDH for every sample, and this ratio was normalized to the average ratio of the untreated animals (Relative Protein Level).

3. Results

3.1 Determination of MD23b-2 V2 3′OL from NHP Brain

TABLE 16

Concentrations of MD23b-2 V2 3'OL (nM, ng/mg, ng/g) in Cynomolgus Monkey Brain 14 days (Group 1) and 21 days (Groups 2 and 3) after last treatment.

| Tissue | Group Assigment | Dose Levels | Conc ng/g |
|---|---|---|---|
| Brain | Phase I (MTD) | 5, 10, 15, 20 mg/kg | 2917.70 |
| Brain | Phase II (FD) | Control | BLQ |
| Brain | Phase II (FD) | 20 mg/kg | 740.50 |

8 samples from the 8 animals were analysed into 1 plate in 1 analytical run for the determination of MD23b-2 V2 3'OL by ELISA. All the samples were measured in triplicate. The analytical run met the acceptance criteria.

All the treated animals from phase I and phase II have showed some levels of test item during the analysis. Animals from the control group did not have quantifiable levels of MD23b-2 V2 3'OL in the brain.

All animals treated with 20 mg/kg during the fixed dose presented levels of test item in the all the brain tested. With respect the animals from the MTD, the male (P0001) presented levels above the limit of quantification.

3.2 MBNL1 Relative Levels

TABLE 17

MBNL1 relative levels. Mean values Phase I and Phase II.

| Tissue | Group Assignment | Dose Levels | Relative MBNL1 protein level | SD |
|---|---|---|---|---|
| Brain | Phase I (MTD) | 5, 10, 15, 20 mg/kg | 1.796 | 0.238 |
| Brain | Phase II (FD) | Control | 1.000 | 0.231 |
| Brain | Phase II (FD) | 20 mg/kg | 2.139 | 0.328 |

MBNL1 protein levels from group 1 were quantified in samples collected two weeks after the last administration. Results showed higher MBNL1 protein levels in the brain tested compared with samples from untreated animals (Table 18, FIG. 12). The protein level in brain was 2-fold higher than the control group. The test item generated a pharmacology effect in the brain that led to an increase of MBNL protein when compare with untreated animals and the increase was still present two and three weeks after the administration. The results were similar in males and females.

4. Discussion and Conclusions

Results from the quantification by ELISA showed that two and three weeks after the last intravenous administration of MD23b-2 V2 3'OL, the treated groups (group 1 and 3) have quantifiable levels of MD23b-2 V2 3'OL in the brain. In addition, treated animals have higher MBNL1 protein levels in the brain compared with untreated animals two and three weeks after the last administration. These results showed evidence of presence and activity of the test item in the brain of the animals treated with MD23b-2 V2 3'OL.

The invention claimed is:

1. An oligonucleotide molecule consisting of SEQ ID NOs: 22, 23, or 25, wherein the 3' terminal nucleotide in each of said SEQ ID NOs: 22, 23, and 25 is conjugated to a spacer molecule, wherein the spacer molecule is conjugated to an oleic acid, and wherein the spacer molecule is selected from the group consisting of NHC3, NHC5, NHC6, and threoninol.

2. The oligonucleotide molecule according to claim 1, consisting of SEQ ID NO: 3.

3. The oligonucleotide molecule according to claim 1, consisting of SEQ ID NO: 4.

4. The oligonucleotide molecule according to claim 1, consisting of SEQ ID NO: 7.

5. A pharmaceutical composition, comprising one or more oligonucleotide molecules as defined in claim 1, and a pharmaceutically acceptable carrier or excipient, or a combination thereof.

6. The pharmaceutical composition of claim 5, comprising an oligonucleotide molecule consisting of SEQ ID NO: 3.

7. The pharmaceutical composition of claim 5, comprising an oligonucleotide molecule consisting of SEQ ID NO: 4.

8. The pharmaceutical composition of claim 5, comprising an oligonucleotide molecule consisting of SEQ ID NO: 7.

9. A method of treating Myotonic dystrophy type 1 (DM1) in a subject, comprising administering the pharmaceutical composition of claim 5 to a subject in need thereof.

10. The method of claim 9, wherein the pharmaceutical composition comprises an oligonucleotide molecule consisting of SEQ ID NO: 3.

11. The method of claim 9, wherein the pharmaceutical composition comprises an oligonucleotide molecule consisting of SEQ ID NO: 4.

12. The method of claim 9, wherein the pharmaceutical composition comprises an oligonucleotide molecule consisting of SEQ ID NO: 7.

13. The oligonucleotide molecule of claim 1, wherein the oligonucleotide molecule is an antimiR.

14. A method of delivering the pharmaceutical composition of claim 5 to the muscles and/or CNS of a subject, comprising administering the pharmaceutical composition of claim 5 to the subject in need thereof.

15. The method of claim 14, wherein the pharmaceutical composition comprises an oligonucleotide molecule consisting of SEQ ID NO: 3.

16. The method of claim 14, wherein the pharmaceutical composition comprises an oligonucleotide molecule consisting of SEQ ID NO: 4.

17. The method of claim 14, wherein the pharmaceutical composition comprises an oligonucleotide molecule consisting of SEQ ID NO: 7.

* * * * *